United States Patent
Zhang et al.

(10) Patent No.: US 9,498,479 B2
(45) Date of Patent: Nov. 22, 2016

(54) DIHYDROPYRIMIDINE COMPOUNDS AND THEIR APPLICATION IN PHARMACEUTICALS

(71) Applicant: SUNSHINE LAKE PHARMA CO., LTD., Dongguan, Guangdong (CN)

(72) Inventors: Yingjun Zhang, Dongguan (CN); Xinchang Liu, Dongguan (CN); Zhifu Zou, Dongguan (CN); Jinsheng Liang, Dongguan (CN); Siegfried Goldmann, Wuppertal (DE); Qingyun Ren, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/022,562

(22) PCT Filed: Nov. 18, 2014

(86) PCT No.: PCT/CN2014/091444
§ 371 (c)(1),
(2) Date: Mar. 16, 2016

(87) PCT Pub. No.: WO2015/074546
PCT Pub. Date: May 28, 2015

(65) Prior Publication Data
US 2016/0206616 A1   Jul. 21, 2016

(30) Foreign Application Priority Data

Nov. 19, 2013 (CN) .......................... 2013 1 0590683
Mar. 23, 2014 (CN) .......................... 2014 1 0108925

(51) Int. Cl.
| | |
|---|---|
| *C07D 403/14* | (2006.01) |
| *A61K 31/506* | (2006.01) |
| *C07D 417/14* | (2006.01) |
| *A61K 45/06* | (2006.01) |
| *A61K 31/541* | (2006.01) |

(52) U.S. Cl.
CPC ........... *A61K 31/506* (2013.01); *A61K 31/541* (2013.01); *A61K 45/06* (2013.01); *C07D 403/14* (2013.01); *C07D 417/14* (2013.01)

(58) Field of Classification Search
CPC .............. C07D 403/14; C07D 417/14; A61K 31/506; A61K 31/541
USPC .......................... 544/60, 333; 514/227.8, 256
See application file for complete search history.

(56) References Cited

U.S. PATENT DOCUMENTS

| | | | |
|---|---|---|---|
| 5,250,531 A | 10/1993 | Cooper | |
| 6,057,332 A | 5/2000 | Michne et al. | |
| 6,218,538 B1 | 4/2001 | Downs et al. | |
| 6,436,943 B1 | 8/2002 | Stoltefuss et al. | |
| 6,503,913 B1 | 1/2003 | Goldmann et al. | |
| 6,696,451 B1 | 2/2004 | Stoltefuss et al. | |
| 7,074,784 B2 | 7/2006 | Goldmann et al. | |
| 7,157,461 B2 | 1/2007 | Murugesan et al. | |
| 8,106,196 B2 | 1/2012 | Li et al. | |
| 8,168,642 B2 | 5/2012 | Li et al. | |
| 8,329,902 B2 | 12/2012 | Li et al. | |
| RE44,987 E | 7/2014 | Goldmann et al. | |
| 8,802,669 B2 | 8/2014 | Li et al. | |

(Continued)

FOREIGN PATENT DOCUMENTS

| | | |
|---|---|---|
| CN | 101744823 B | 6/2010 |
| CN | 103664897 A | 3/2014 |

(Continued)

OTHER PUBLICATIONS

Bundgaard, Design of Prodrugs, p. 1, 1985.*
Silverman, Chapter 8: Prodrugs and Drug Delivery Systems, The Organic Chemistry of Drug Design and Drug Action, pp. 352-400 (1992).*

(Continued)

*Primary Examiner* — Deepak Rao
(74) *Attorney, Agent, or Firm* — Kam W. Law; Squire Patton Boggs (US) LLP

(57) ABSTRACT

Provided herein are dihydropyrimidine compounds and their pharmaceutical applications, especially for use in treating and preventing HBV diseases. Specifically, provided herein are compounds having Formula (I) or (Ia), or an enantiomer, a diastereoisomer, a tautomer, a hydrate, a solvate, or a pharmaceutically acceptable salt thereof, wherein the variables of the formulas are as defined in the specification. Also provided herein is the use of the compounds having Formula (I) or (Ia), or an enantiomer, a diastereoisomer, a tautomer, a hydrate, a solvate, or a pharmaceutically acceptable salt thereof for treating and preventing HBV diseases.

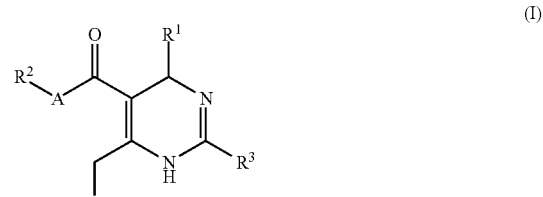

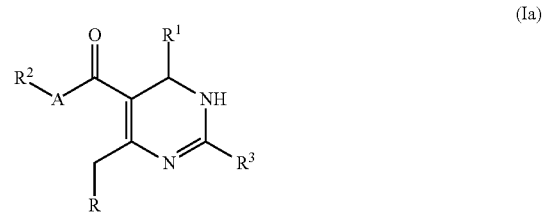

18 Claims, No Drawings

(56) References Cited

U.S. PATENT DOCUMENTS

| | | |
|---|---|---|
| 9,233,933 B2 | 1/2016 | Vandyck et al. |
| 2013/0267517 A1 | 10/2013 | Guo et al. |
| 2014/0343032 A1 | 11/2014 | Guo et al. |
| 2015/0031687 A1 | 1/2015 | Guo et al. |
| 2015/0152096 A1 | 6/2015 | Zhang et al. |
| 2015/0218182 A1 | 8/2015 | Zlotnick et al. |
| 2015/0292045 A1 | 10/2015 | Levrero et al. |

FOREIGN PATENT DOCUMENTS

| | | |
|---|---|---|
| CN | 103664899 A | 3/2014 |
| CN | 103664925 A | 3/2014 |
| EP | 0202654 A2 | 11/1986 |
| WO | WO0058302 A1 | 10/2000 |
| WO | WO0168639 A1 | 9/2001 |
| WO | WO0168641 A1 | 9/2001 |
| WO | WO0168642 A1 | 9/2001 |
| WO | WO0168647 A1 | 9/2001 |
| WO | WO2008154818 A1 | 12/2008 |
| WO | WO2008154819 A1 | 12/2008 |
| WO | WO2008154820 A1 | 12/2008 |
| WO | WO2010069147 A1 | 6/2010 |
| WO | WO2013019967 A1 | 2/2013 |
| WO | WO 2014/037480 * | 3/2014 |
| WO | WO 2014153459 A2 | 9/2014 |

OTHER PUBLICATIONS

Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. I: Principles and Practice, pp. 975-977, 1995.*
Gentile et al., Vertical transmission of hepatitis B virus: challenges and solutions, International Journal of Women's Health, 6: 605-611,2014.*
Halegoua-De Marzio et al., Then and now: The progress in hepatitis B treatment over the past 20 years, World Journal of Gastroenterology, 20(2): 401-413, Jan. 2014.*
Douglas, Jr. Introduction to Viral Diseases, Cecil Textbook of Medicine, 20th Edition, vol. 2, pp. 1739-1747, 1996.*
Eng. translation, CN, Mar. 26, 2014, Eng. translation of the abstract of CN 101744823.
Eng. translation, CN, Mar. 26, 2014, Eng. translation of the abstract of CN103664897.
Eng. translation, CN, Mar. 26, 2014, Eng. translation of the abstract of CN103664899.
Eng. translation, CN, Mar. 26, 2014, Eng. translation of the abstract of CN103664925.
ISR, Mar. 2015.
Written Opinion, Mar. 2015.

* cited by examiner

DIHYDROPYRIMIDINE COMPOUNDS AND THEIR APPLICATION IN PHARMACEUTICALS

CROSS-REFERENCE TO RELATED APPLICATIONS

This is a U.S. national stage application of the International Patent Application No. PCT/CN2014/091444, filed Nov. 18, 2014, which claims priorities to Chinese Patent Application No. 201310590683.6, filed Nov. 19, 2013, and No. 201410108925.8, filed Mar. 23, 2014, all of which are incorporated herein by reference in their entirety.

FIELD

The invention relates to dihydropyrimidine compounds and pharmaceutical compositions thereof, and further relates to uses of the compounds or the pharmaceutical compositions in the manufacture of a medicament, especially for use in preventing, managing, treating or lessening a viral disease or a HBV disease.

BACKGROUND

The hepatitis B virus belongs to the family of hepadnaviridae. It can cause acutely and/or persistently or progressively chronic diseases. Many other clinical manifestations in the pathological morphology are also caused by HBV—in particular chronic hepatitis, cirrhosis and hepatocellular carcinoma. Additionally, coinfection with hepatitis D virus may have adverse effects on the progress of the disease.

The conventional medicaments approved to be used for treating chronic hepatitis are interferon and lamivudine. However, the interferon has just moderate activity but has an adverse side reaction. Although lamivudine has good activity, its resistance develops rapidly during the treatment and relapse effects often appear after the treatment has stopped. The $IC_{50}$ value of lamivudine (3-TC) is 300 nM (*Science*, 2003, 299, 893-896).

Deres, et al, have reported heteroaryl-substituted dihydropyrimidine (HAP) compounds which were represented by Bay41-4109 and Bay39-5493, and these compounds play a role in blocking HBV replication by preventing the proper formation of viral core particles (nucleocapsids). Bay41-4109 has demonstrated better drug metabolic parameters in clinical study (*Science*, 2003, 299, 893-896). The study of these compounds' mechanism of action indicated that through reacting with 113-143 amino acid residues of a core protein, heteroaryl-substituted dihydropyrimidine compounds have changed the angle between dimers which can form nucleocapsids, and led to forming unstably expanded nucleocapsids, which accelerate the degradation of the core protein (*Biochem. Pharmacol.*, 2003, 66, 2273-2279).

New and effective antiviral compounds are urgently needed, especially for treating and/or preventing HBV infection.

SUMMARY

The invention relates to novel dihydropyrimidine compounds and pharmaceutical compositions, and their uses in the manufacture of a medicament for preventing, managing, treating or lessening a viral disease, especially hepatitis B (HBV) infection or a disease caused by hepatitis B infection.

In one aspect, provided herein are compounds having Formula (I) or (Ia), or an enantiomer, a diastereoisomer, a tautomer, a hydrate, a solvate, a prodrug, a stereoisomer, an N-oxide, or a pharmaceutically acceptable salt thereof,

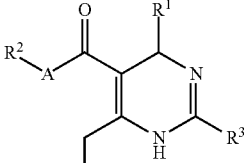

(I)

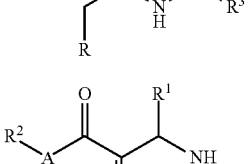

(Ia)

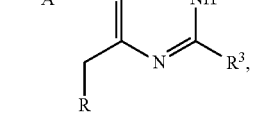

wherein
$R^1$ is $C_{6-10}$ aryl or $C_{1-9}$ heteroaryl;
$R^3$ is a 5-membered heteroaryl group;
A is a bond, —O—, —S— or —$NR^5$—;
R is

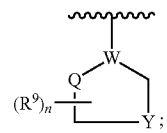

wherein, W is $CR^4$ or N;
each of $R^2$, $R^4$ and $R^5$ is independently hydrogen or $C_{1-4}$ alkyl;
Y is —$(CR^8R^{8a})_k$—$S(=O)_q$— or —$(CR^7R^6)_n$—;
Q is —$(CR^8R^{8a})_k$—;
each $R^7$ is independently hydrogen, F or alkyl;
each $R^6$ is independently F or alkyl;
or $R^6$ and $R^7$, together with the carbon atom to which they are attached, form —C(=$CH_2$)— or —C(=O)—;
each $R^8$ and $R^{8a}$ is independently hydrogen, cyano or alkyl;
each $R^9$ is independently —$(CR^{10}R^{10a})_t$—OH, triazolyl, tetrazolyl, —$(CR^{10}R^{10a})_m$—C(=O)O—$R^{11}$, —$(CR^{10}R^{10a})_k$—C(=O)O—$(CR^{10}R^{10a})_k$—OC(=O)O—$R^{11}$, —S(=O)$_q$O$R^{11}$, —$(CR^{10}R^{10a})_k$—S(=O)N($R^{11}$)$_2$, —$(CR^{10}R^{10a})_k$—C(=O)O—$(CR^{10}R^{10a})_k$—OC(=O)—$R^{11}$, —$(CR^{10}R^{10a})_k$—C(=O)O—$(CR^{10}R^{10a})_k$—C(=O)O—$R^{11}$, —$(CR^{10}R^{10a})_t$—N($R^{11}$)$_2$, —$(CR^{10}R^{10a})_t$—OC(=O)—$R^{11}$, —C(=O)O—$R^{11a}$ or —$(CR^{10}R^{10a})_k$—C(=O)N($R^{11}$)$_2$;
each $R^{10}$ and $R^{10a}$ is independently hydrogen, halogen, haloalkyl or alkyl, or $R^{10}$ and $R^{10a}$, together with the carbon atom to which they are attached, form cycloalkyl, heterocyclyl or —C(=O)—;
each $R^{11}$ is independently hydrogen, alkyl, alkoxy, hydroxy, alkyl-S(=O)$_q$—, aryl, heteroalyl, cycloalkyl, heterocyclyl, arylalkyl, heterocyclyl-S(=O)$_q$—, heteroaryl-S(=O)$_q$—, cycloalkyl-S(=O)$_q$— or aryl-S(=O)$_q$—;
$R^{11a}$ is alkyl, alkoxy, hydroxy, alkyl-S(=O)$_q$—, aryl, heteroalyl, cycloalkyl, heterocyclyl, arylalkyl, heterocyclyl-S(=O)$_q$—, heteroaryl-S(=O)$_q$—, cycloalkyl-S(=O)$_q$— or aryl-S(=O)$_q$—;

each n is independently 1, 2 or 3;

each t and m is independently 1, 2, 3 or 4;

each q is independently 1 or 2; and each k is independently 0, 1, 2, 3 or 4;

wherein each alkoxy, alkyl-S(=O)$_q$—, aryl, heteroaryl, arylalkyl, heterocyclyl-S(=O)$_q$—, heteroaryl-S(=O)$_q$—, cycloalkyl-S(=O)$_q$— and aryl-S(=O)$_q$— described in $R^{11}$ and $R^{11a}$, alkyl described in $R^6$, $R^7$, $R^8$, $R^{8a}$, $R^{10}$, $R^{10a}$, $R^{11a}$ and $R^{11}$, haloalkyl described in $R^{10}$ and $R^{11a}$, heterocyclyl and cycloalkyl described in $R^{10}$, $R^{10a}$, $R^{11a}$ and $R^{11}$, triazolyl and tetrazolyl described in $R^9$, a 5-membered heteroaryl group described in $R^3$, $C_{1-4}$ alkyl described in $R^1$, $R^4$ and $R^5$, and $C_{6-10}$ aryl and $C_{1-9}$ heteroaryl described in $R^1$, is optionally and independently substituted with one or more substituents independently selected from hydrogen, fluoro, chloro, bromo, iodo, oxo(=O), methylene(=CH$_2$), alkyl, alkoxy, cyano, hydroxy, nitro, alkylamino, amino, aryl, heteroaryl, heterocyclyl, cycloalkyl, trifluoromethyl, trifluoromethoxy, haloalkyl-substituted aryl, halogen-substituted aryl or trifluoromethylsulfonyl.

In some embodiments,
R is

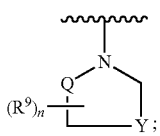

wherein Y is —(CR$^8$R$^{8a}$)$_k$—S(=O)$_q$— or —(CR$^7$R$^6$)$_n$—;

Q is —(CR$^8$R$^{8a}$)$_k$—;

each $R^7$ is independently hydrogen, $C_{1-4}$ alkyl or F;

each $R^6$ is independently F or $C_{1-4}$ alkyl;

or $R^6$ and $R^7$, together with the carbon atom to which they are attached, form —C(=CH$_2$)— or —C(=O)—;

each $R^8$ and $R^{8a}$ is independently hydrogen or $C_{1-4}$ alkyl;

each $R^9$ is independently —(CR$^{10}$R$^{10a}$)$_t$—OH, triazolyl, tetrazolyl, —(CR$^{10}$R$^{10a}$)$_m$—C(=O)O—R$^{11}$, —(CR$^{10}$R$^{10a}$)$_k$—C(=O)O—(CR$^{10}$R$^{10a}$)$_k$—OC(=O)O—R$^{11}$, —S(=O)$_q$OR$^{11}$, —(CR$^{10}$R$^{10a}$)$_k$—S(=O)N(R$^{11}$)$_2$, —(CR$^{10}$R$^{10a}$)$_k$—C(=O)O—(CR$^{10}$R$^{10a}$)$_k$—OC(=O)—R$^{11}$—(CR$^{10}$R$^{10a}$)$_k$—C(=O)O—(CR$^{10}$R$^{10a}$)$_k$—C(=O)—R$^{11}$, —(CR$^{10}$R$^{10a}$)$_t$—N(R$^{11}$)$_2$, —(CR$^{10}$R$^{10a}$)$_t$—OC(=O)—R$^{11}$, —C(=O)O—R$^{11a}$ or —(CR$^{10}$R$^{10a}$)$_k$—C(=O)N(R$^{11}$)$_2$;

each $R^{10}$ and $R^{10a}$ is independently hydrogen, halogen, $C_{1-4}$ haloalkyl or $C_{1-4}$ alkyl, or $R^{10}$ and $R^{10a}$, together with the carbon atom to which they are attached, form $C_{3-6}$ cycloalkyl, $C_{2-9}$ heterocyclyl or —C(=O)—;

each $R^{11}$ is independently hydrogen, $C_{1-6}$ alkyl, $C_{1-6}$alkoxy, $C_{1-6}$alkyl-S(=O)$_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-6}$-alkyl, $C_{2-9}$ heterocyclyl-S(=O)$_q$—, $C_{1-9}$ heteroaryl-S(=O)$_q$—, $C_{3-6}$ cycloalkyl-S(=O)$_q$— or $C_{6-10}$ aryl-S(=O)$_q$—; and $R^{11a}$ is $C_{1-6}$ alkyl, $C_{1-6}$ alkoxy, $C_{1-6}$ alkyl-S(=O)$_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-6}$-alkyl, $C_{2-9}$ heterocyclyl-S(=O)$_q$—, $C_{1-9}$ heteroaryl-S(=O)$_q$—, $C_{3-6}$ cycloalkyl-S(=O)$_q$— or $C_{6-10}$ aryl-S(=O)$_q$—.

In other embodiments, R is

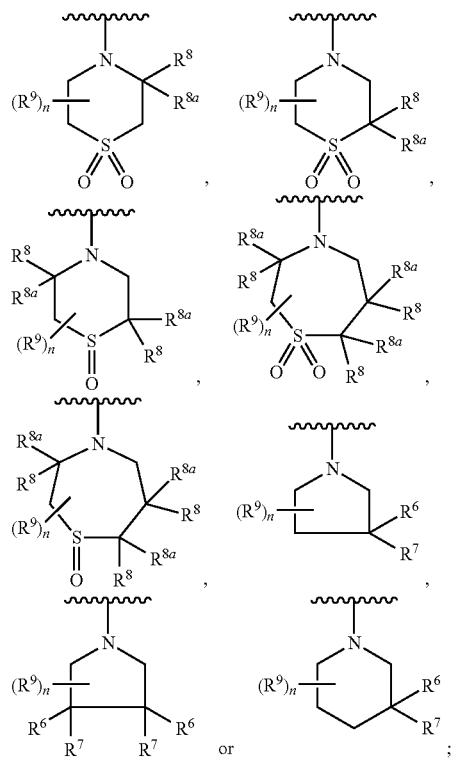

wherein each $R^7$ is independently hydrogen, methyl, ethyl or F;

each $R^6$ is independently F, methyl or ethyl;

or $R^6$ and $R^7$, together with the carbon atom to which they are attached, form —C(=CH$_2$)— or —C(=O)—; each $R^8$ and $R^{8a}$ is independently hydrogen, methyl, ethyl or propyl;

each $R^9$ is independently —(CR$^{10}$R$^{10a}$)$_t$—OH, triazolyl, tetrazolyl, —(CR$^{10}$R$^{10a}$)$_m$—C(=O)O—R$^{11}$, —(CR$^{10}$R$^{10a}$)$_k$—C(=O)O—(CR$^{10}$R$^{10a}$)$_k$—OC(=O)O—R$^{11}$, —S(=O)$_q$OR$^{11}$, —(CR$^{10}$R$^{10a}$)$_k$—S(=O)N(R$^{11}$)$_2$, —(CR$^{10}$R$^{10a}$)$_k$—C(=O)O—(CR$^{10}$R$^{10a}$)$_k$—OC(=O)—R$^{11}$, —(CR$^{10}$R$^{10a}$)$^k$—C(=O)O—(CR$^{10}$R$^{10a}$)$_k$—C(=O)O—R$^{11}$, —(CR$^{10}$R$^{10a}$)$_t$—N(R$^{11}$)$_2$, —(CR$^{10}$R$^{10a}$)$_t$—OC(=O)—R$^{11}$, —C(=O)O—R$^{11a}$ or —(CR$^{10}$R$^{10a}$)$_k$—C(=O)N(R$^{11}$)$_2$;

each $R^{10}$ and $R^{10a}$ is independently hydrogen, fluoro, chloro, bromo, iodo, trifluoromethyl, methyl, ethyl, propyl, or $R^{10}$ and $R^{10a}$, together with the carbon atom to which they are attached, form cyclopropyl, cyclobutyl, cyclopentyl, cyclohexyl or —C(=O)—;

each $R^{11}$ is independently hydrogen, $C_{1-4}$ alkyl, $C_{1-4}$ alkoxyl, $C_{1-4}$ alkyl-S(=O)$_2$—, phenyl, pyridyl, thiazolyl, furyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S(=O)$_2$—, cyclobutyl-S(=O)$_2$—, cyclopentyl-S(=O)$_2$—, cyclohexyl-S(=O)$_2$—, naphthyl-S(=O)$_2$— or phenyl-S(=O)$_2$—; and $R^{11a}$ is $C_{1-4}$ alkyl, $C_{1-4}$ alkoxyl, $C_{1-4}$ alkyl-S(=O)$_2$—, phenyl, pyridyl, thiazolyl, furyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl- $S(=O)_2$—, cyclobutyl-$S(=O)_2$—, cyclopentyl-$S(=O)_2$—, cyclohexyl-$S(=O)_2$—, naphthyl-$S(=O)_2$— or phenyl-$S(=O)_2$—.

In some embodiments,
$R^1$ is phenyl;
$R^3$ is thiazolyl or 1-methyl-1H-imidazolyl; and
each of $R^2$, $R^4$ and $R^5$ is independently hydrogen, methyl or ethyl;
wherein each thiazolyl and 1-methyl-1H-imidazolyl described in $R^3$, phenyl described in $R^1$, and methyl and ethyl described in $R^2$, $R^4$ and $R^5$, is optionally and independently substituted with one or more substituents independently selected from hydrogen, $C_{1-4}$ alkyl, fluoro, chloro or bromo.

In some embodiments, provided herein are compounds having Formula (II) or (IIa), or an enantiomer, a diastereoisomer, a tautomer, a hydrate, a solvate, a prodrug, a stereoisomer, an N-oxide or a pharmaceutically acceptable salt thereof,

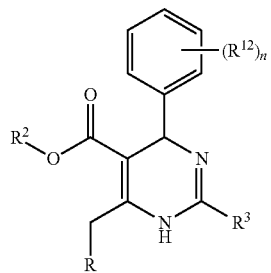

(II)

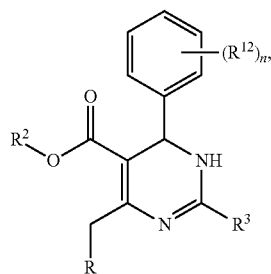

(IIa)

wherein
$R^2$ is hydrogen or $C_{1-4}$ alkyl;
$R^3$ is thiazolyl or 1-methyl-1H-imidazolyl;
R is

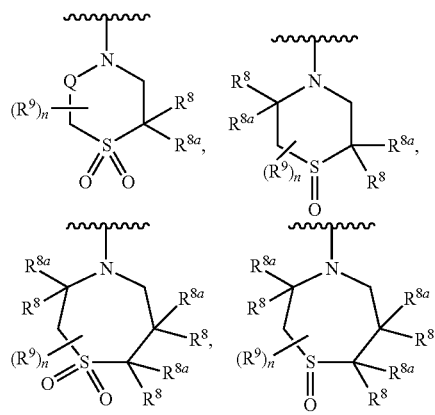

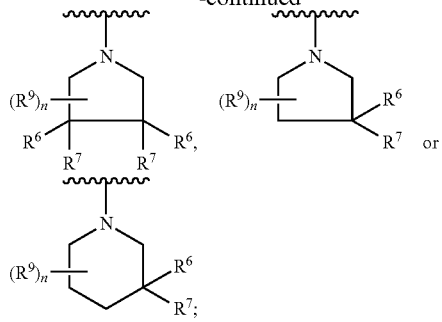

wherein each $R^7$ is independently hydrogen, $C_{1-4}$ alkyl or F;
each $R^6$ is independently F or $C_{1-4}$ alkyl;
or $R^6$ and $R^7$, together with the carbon atom to which they are attached, form -$C(=CH_2)$— or —$C(=O)$—;
Q is —$(CR^8R^{8a})_k$—;
each $R^8$ and $R^{8a}$ is independently hydrogen or $C_{1-4}$ alkyl;
each $R^9$ is independently —$(CR^{10}R^{10a})_t$—OH, triazolyl, tetrazolyl, —$(CR^{10}R^{10a})_m$—$C(=O)O$—$R^{11}$, —$(CR^{10}R^{10a})_k$—$C(=O)O$—$(CR^{10}R^{10a})_k$—$OC(=O)O$—$R^{11}$, —$S(=O)_q OR^{11}$, —$(CR^{10}R^{10a})_k$—$S(=O)N(R^{11})_2$, —$(CR^{10}R^{10a})_k$—$C(=O)O$—$(CR^{10}R^{10a})_k$—$OC(=O)$—$R^{11}$, —$(CR^{10}R^{10a})_k$—$C(=O)O$—$(CR^{10}R^{10a})_k$—$C(=O)$$O$—$R^{11}$, —$(CR^{10}R^{10a})_t$—$N(R^{11})_2$, —$(CR^{10}R^{10a})_t$—$OC(=O)$—$R^{11}$, —$C(=O)O$—$R^{11a}$ or —$(CR^{10}R^{10a})_k$—$C(=O)N(R^{11})_2$;
each $R^{10}$ and $R^{10a}$ is independently hydrogen, fluoro, chloro, bromo, iodo, $C_{1-4}$ haloalkyl or $C_{1-4}$ alkyl, or $R^{10}$ and $R^{10a}$, together with the carbon atom to which they are attached, form $C_{3-6}$ cycloalkyl or —$C(=O)$—;
each $R^{11}$ is independently hydrogen, $C_{1-4}$ alkyl, $C_{1-4}$ alkoxy, hydroxy, $C_{1-4}$ alkyl-$S(=O)_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-4}$-alkyl, $C_{2-9}$ heterocyclyl-$S(=O)_q$—, $C_{1-9}$ heteroaryl-$S(=O)_q$—, $C_{3-6}$cycloalkyl-$S(=O)_q$— or $C_{6-10}$ aryl-$S(=O)_q$—;
$R^{11a}$ is $C_{1-4}$ alkyl, $C_{1-4}$ alkoxy, hydroxy, $C_{1-4}$ alkyl-$S(=O)_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-4}$-alkyl, $C_{2-9}$ heterocyclyl-$S(=O)_q$—, $C_{1-9}$ heteroaryl-$S(=O)_q$—, $C_{3-6}$ cycloalkyl-$S(=O)_q$— or $C_{6-10}$ aryl-$S(=O)_q$—;
each $R^{12}$ is independently hydrogen, fluoro, chloro or bromo;
each n is independently 1, 2 or 3;
each t and m is independently 1, 2, 3 or 4;
each q is independently 1 or 2; and
each k is independently 0, 1, 2, 3 or 4.

In other embodiments, wherein R is

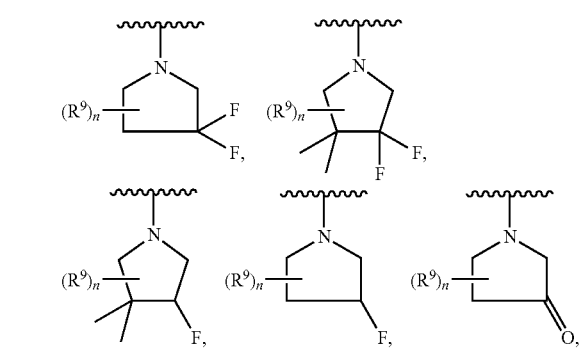

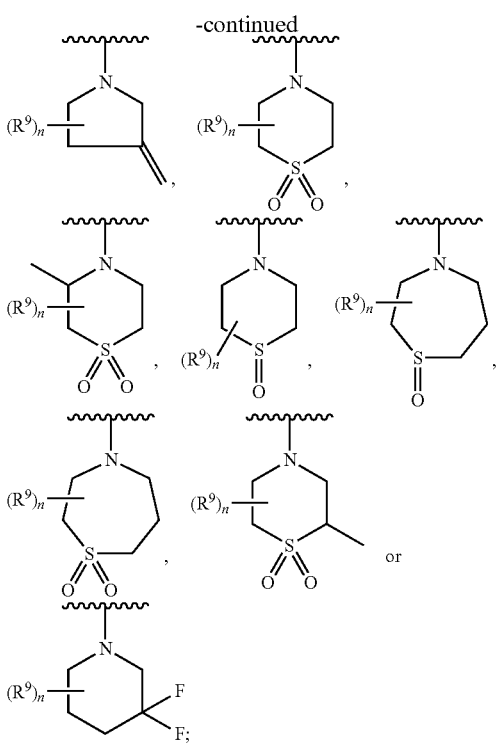

each $R^9$ is independently —$(CR^{10}R^{10a})_t$—OH, triazolyl, tetrazolyl, —$(CR^{10}R^{10a})_m$—C(=O)O—$R^{11}$, —$(CR^{10}R^{10a})_k$—C(=O)O—$(CR^{10}R^{10a})_k$—OC(=O)O—$R^{11}$, —S(=O)$_q$O$R^{11}$, —$(CR^{10}R^{10a})_k$—S(=O)N$(R^{11})_2$, —$(CR^{10}R^{10a})_k$—C(=O)O—$(CR^{10}R^{10a})_k$—OC(=O)—$R^{11}$, —$(CR^{10}R^{10a})_k$—C(=O)O—$(CR^{10}R^{10a})_k$—C(=O)O—$R^{11}$, —$(CR^{10}R^{10a})_t$—N$(R^{11})_2$, —$(CR^{10}R^{10a})_t$—OC(=O)—$R^{11}$, —C(=O)O—$R^{11a}$ or —$(CR^{10}R^{10a})_k$—C(=O)N$(R^{11})_2$;

each $R^{10}$ and $R^{10a}$ is independently hydrogen, fluoro, chloro, trifluoromethyl, methyl, ethyl, propyl, isopropyl, tert-butyl or n-butyl, or $R^{10}$ and $R^{10a}$ together with the carbon atom to which they are attached, form cyclopropyl, cyclobutyl, cyclopentyl, cyclohexyl or —C(=O)—;

each $R^{11}$ s independently hydrogen, methyl, ethyl, propyl, isopropyl, tert-butyl, n-butyl; methoxyl, ethoxy, propoxy, isopropoxy, tert-butoxy, n-butoxy, methyl-S(=O)$_2$—, ethyl-S(=O)$_2$—, propyl-S(=O)$_2$—, isopropyl-S(=O)$_2$—, pyridyl, thiazolyl, furyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S(=O)$_2$—, cyclobutyl-S(=O)$_2$—, cyclopentyl-S(=O)$_2$—, cyclohexyl-S(=O)$_2$—, naphthyl-S(=O)$_2$— or phenyl-S(=O)$_2$—; and $R^{11a}$ is methyl, ethyl, propyl, isopropyl, tert-butyl, n-butyl; methoxyl, ethoxy, propoxy, isopropoxy, tert-butoxy, n-butoxy, methyl-S(=O)$_2$—, ethyl-S(=O)$_2$—, propyl-S(=O)$_2$—, isopropyl-S(=O)$_2$—, pyridyl, thiazolyl, furyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S(=O)$_2$—, cyclobutyl-S(=O)$_2$—, cyclopentyl-S(=O)$_2$—, cyclohexyl-S(=O)$_2$—, naphthyl-S(=O)$_2$— or phenyl-S(=O)$_2$—.

In one aspect, provided herein is a pharmaceutical composition comprising the compound disclosed herein, and a pharmaceutically acceptable carrier, excipient, diluent, adjuvant, vehicle or a combination thereof.

In some embodiments, the pharmaceutical composition further comprises an anti-HBV agent.

In other embodiments, the anti-HBV agent is a HBV polymerase inhibitor, immunomodulator or interferon.

In still other embodiments, the anti-HBV agent comprises at least one selected from the group consisting of lamivudine, telbivudine, tenofovir, entecavir, adefovir, alfaferone, alloferon, celmoleukin, clevudine, emtricitabine, famciclovir, interferon, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, euforavac, ampligen, phosphazid, heplisav, interferon α-2b, levamisole, and propagermanium.

In another aspect, provided herein is use of the compound or the pharmaceutical composition in the manufacture of a medicament for preventing, managing, treating or lessening a viral disease or a HBV disease.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provided herein is the compound or the pharmaceutical composition in the manufacture of a medicament for use in preventing, managing, treating or lessening a viral disease or a HBV disease.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provided herein is a method for preventing, managing, treating or lessening a viral disease or a HBV disease comprising administering to a patient a therapeutically effective amount of the compound or the pharmaceutical composition.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provided herein is use of the compound or the pharmaceutical composition in the manufacture of a medicament for preventing, managing, treating or lessening a viral disease or a HBV disease in a patient, comprising administering to the patient a therapeutically effective amount of the compound or the composition disclosed herein.

In another aspect, provided herein are methods for preventing, managing, treating or lessening a viral disease or a HBV disease, which comprises administering a pharmaceutically effective amount of the compound disclosed herein to a patient.

In another aspect, provided herein are methods for preventing, managing, treating or lessening a viral disease or a HBV disease, which comprises administering a pharmaceutically effective amount of the pharmaceutical composition disclosed herein to a patient.

In another aspect, provided herein is use of the compound disclosed herein in the manufacture of a medicament for preventing, managing or treating a viral disease or a HBV disease and lessening the severity of a viral disease or a HBV disease.

In another aspect, provided herein is use of the pharmaceutical composition comprising the compound disclosed herein in the manufacture of a medicament for preventing, managing or treating a viral disease or a HBV disease and lessening the severity of a viral disease or a HBV disease in a patient.

In some embodiments, the organism is a mammal; in other embodiments, the organism is a human. In still other embodiments, the method further comprises contacting the kinase with a HBV therapeutic agent.

In another aspect, provided herein is a method of inhibiting HBV infection, comprising contacting the cell with an effective HBV inhibiting amount of a compound disclosed herein or a composition thereof. In other embodiments, the method further comprises contacting the cell with a HBV therapeutic agent.

In another aspect, provided herein is a method of treating HBV disease, the method comprises administering to a patient in need of such treatment an effective therapeutic amount of a compound disclosed herein or a composition thereof. In other embodiments, the method further comprises administering a HBV therapeutic agent.

In another aspect, provided herein is a method of inhibiting HBV infection, the method comprises administering to a patient in need of an effective therapeutic amount of a compound disclosed herein or a composition thereof. In other embodiments, the method further comprises administering a HBV therapeutic agent.

In another aspect, provided herein include methods of preparing, methods of separating, and methods of purifying compounds of Formula (I) or (Ia) and the specific compounds of the invention.

The foregoing merely summarizes certain aspects disclosed herein and is not intended to be limiting in nature. These aspects and other aspects and embodiments are described more fully below.

DETAILED DESCRIPTION DEFINITIONS AND GENERAL TERMINOLOGY

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

It is further appreciated that certain features of the invention, which are, for clarity, described in the context of separate embodiments, can also be provide in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes disclosed herein, the chemical elements are identified in accordance with the Periodic Table of the Elements, CAS version, and *the Handbook of Chemistry and Physics*, $75^{th}$ Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, New York: 2007, all of which are incorporated herein by reference in their entireties.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, "patient" refers to a human (including adults and children) or other animal. In one embodiment, "patient" refers to a human.

The term "comprising" is meant to be open ended, including the indicated component but not excluding other elements.

The term "Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

The term "Chiral" refers to molecules which have the property of non-superimposability of the mirror image partner, while the term "achiral" refers to molecules which are superimposable on their mirror image partner.

The term "Enantiomers" refer to two stereoisomers of a compound which are non-superimposable mirror images of one another.

The term "Diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

As described herein, compounds disclosed herein may optionally be substituted with one or more substituents, such as are illustrated above, specific compounds, or as exemplified by particular classes, subclasses, and species disclosed herein. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituents include, but are not limited to hydrogen, fluoro, chloro, bromo, iodo, oxo(=O), methylene(=$CH_2$), alkyl, alkoxy, cyano, hydroxy, thio, nitro, alkylamino, amino, aryl, arylalkyl, heteroaryl, heteroarylalkyl, heterocyclyl, heterocyclylalkyl, cycloalkyl, cycloalkylalkyl, trifluoromethyl, trifluoromethoxy, haloalkyl-substituted aryl, halogen-substituted aryl, or trifluoromethylsulfonyl, and the like.

At various places in the present specification, substituents of compounds disclosed herein are disclosed in groups or in ranges. It is specifically intended that the invention include each and every individual subcombination of the members of such groups and ranges. For example, the term "$C_{1-6}$alkyl group" refers to, respectively, discloses a methyl, ethyl, $C_3$ alkyl, $C_4$ alkyl, $C_5$ alkyl, $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched chain monovalent hydrocarbon radical of 1-20 carbon atoms, wherein the alkyl radical may be optionally substituted independently with one or more substituents described herein. Unless otherwise specified, alkyl groups contain 1-20 carbon atoms. In some embodiments, alkyl groups contain 1-10 carbon atoms. In other embodiments, alkyl groups contain 1-8 carbon atoms. In still other embodiments, alkyl groups contain 1-6 carbon atoms, and in yet other embodiments, alkyl groups contain 1-4 carbon atoms. In other embodiments, alkyl groups contain 1-3 carbon atoms. Some non-limiting examples of alkyl group include, but are not limited to, methyl (Me, —$CH_3$), ethyl (Et, —$CH_2CH_3$), 1-propyl (n-Pr, —$CH_2CH_2CH_3$), 2-propyl (i-Pr, —$CH(CH_3)_2$), 1-butyl (n-Bu, —$CH_2CH_2CH_2CH_3$), 2-methyl-1-propyl or isobutyl (i-Bu, —$CH_2CH(CH_3)_2$), 1-methylpropyl or sec-butyl (s-Bu, —$CH(CH_3)CH_2CH_3$), tert-butyl (t-Bu, —$C(CH_3)_3$), 1-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "haloalkyl" or "haloalkoxy" refers to an alkyl or alkoxy radical substituted with one or more halogen atoms (i.e., F, Cl, Br or I), which may be either the same or different. Wherein the alkyl and alkoxy groups are as defined herein. Some non-limiting examples of such radicals include trifluoromethyl, trifluoroethyl, trifluoromethoxy, and the like.

The term "alkenyl" refers to a linear or branched-chain monovalent hydrocarbon radical of two to twelve carbon atoms with at least one site of unsaturation, i.e., a carbon-carbon, sp$^2$ double bond, wherein the alkenyl radical may be optionally substituted with one or more substituents described herein, and includes radicals having "cis" and "trans" orientations, or alternatively, "E" and "Z" orientations. In some embodiments, alkenyl groups contain 2-8 carbon atoms. In other embodiments, alkenyl groups contain 2-6 carbon atoms. In still other embodiments, alkenyl groups include contain 2-4 carbon atoms. Examples include, but are not limited to, ethenyl or vinyl (—$CH=CH_2$), allyl (—$CH_2CH=CH_2$), and the like.

The term "cycloalkyl" or refers to a monovalent or multivalent, non-aromatic, saturated or partially unsaturated ring having 3 to 12 carbon atoms as a monocyclic, bicyclic, or tricyclic ring system, wherein the cycloalkyl radical may be optionally substituted with one or more substituents described herein. In some embodiments, a cycloalkyl contains 3 to 12 carbon atoms. In other embodiments, a cycloalkyl contains 3 to 8 carbon atoms, and in still other embodiments, a cycloalkyl contains 3 to 6 carbon atoms. Examples include, but are not limited to, cyclopropyl, cyclobutyl, cyclopentyl, cyclohexyl, suberyl, and the like.

The term "cycloalkylalkyl" refers to an alkyl radical substituted with one or more cycloalkyl groups, wherein the alkyl and cycloalkyl groups are as defined herein. Some non-limiting examples of such radicals include cyclopropylmethyl, cyclopropylethyl, cyclopropylpropyl, cyclobutylmethyl, cyclobutylethyl, cyclobutylpropyl, cyclopentylmethyl, cyclopentylethyl, cyclopentylpropyl, and the like.

The term "heterocycle", "heterocyclyl", or "heterocyclic ring" as used interchangeably herein refers to a saturated or partially unsaturated monocyclic, bicyclic or tricyclic ring containing 3-12 ring atoms of which at least one ring atom is selected from nitrogen, sulfur and oxygen. Wherein the heterocycle radical may be optionally substituted with one or more substituents described herein. Unless otherwise specified, heterocycle maybe carbon or nitrogen linked, and of which a —$CH_2$— group can optionally be replaced by a —$C(=O)$— group. Ring sulfur atoms may be optionally oxidized to form S-oxides. Ring nitrogen atoms maybe optionally oxidized to form N-oxides. In some embodiments, heterocyclyl may be $C_{2-10}$ heterocyclyl, which contain 2-10 carbon atoms and at least one heteroatoms selected from nitrogen, sulfur and oxygen; In other embodiments, heterocyclyl may be $C_{2-9}$ heterocyclyl, which contain 2-9 carbon atoms and at least one heteroatoms selected from nitrogen, sulfur and oxygen; In still other embodiments, heterocyclyl may be $C_{2-7}$ heterocyclyl, which contain 2-7 carbon atoms and at least one heteroatoms selected from nitrogen, sulfur and oxygen; In yet other embodiment, heterocyclyl may be $C_{2-5}$ heterocyclyl, which contain 2-5 carbon atoms and at least one heteroatoms selected from nitrogen, sulfur and oxygen. Some non-limiting examples of heterocyclic rings include pyrrolidinyl, tetrahydrofuranyl, tetrahydrothienyl, tetrahydropyrimidinyl, tetrahydropyranyl, piperidyl, morpholinyl, thiomorpholinyl, piperazinyl, homopiperazinyl, azetidinyl, oxetanyl, thietanyl, homopiperidinyl, glycidyl, 2-pyrrolinyl, dihydroindolinyl, pyrazolinyl, 1,1-dioxothiomorpholinyl, and the like. Some non-limited examples of heterocyclyl wherein —$CH_2$— group is replaced by —$C(O)$— moiety are 2-oxypyrrolidinyl, 2-piperidinonyl, 3-morphlinonyl, 3-thiomorpholinonyl, oxytetrahydropyrimidinyl, and the like.

The term "heterocyclylalkyl" or "heterocycloalkyl" refers to heterocycly attached to the rest of the molecule through alkyl, wherein the alkyl and heterocycly groups are as defined herein. The heterocyclylalkyl is optionally substituted with one or more substituents described herein. Some non-limiting examples of heterocyclylalkyl include pyrrol-2-ylmethyl, morpholin-4-ylmethyl, pyrrolidinylmethyl, piperidylmethyl, piperidylethyl, morpholinylmethyl, morpholinylethyl, and the like.

The term "halogen" refers to F, Cl, Br or I.

The term "alkoxy" refers to an alkyl group, as previously defined, attached to the rest of the molecule through an oxygen atom. Some non-limiting examples include methoxy (MeO, —OCH₃), ethyoxy (EtO, —OCH₂CH₃), 1-propoxy (n-PrO, n-propoxy, —OCH₂CH₂CH₃), 2-propoxy (i-PrO, i-propoxy, —OCH(CH₃)₂), 1-butoxy (n-BuO, n-butoxy, —OCH₂CH₂CH₂CH₃), 2-methyl-1-propoxy (i-BuO, i-butoxy, —OCH₂CH(CH₃)₂), 2-butoxy (s-BuO, s-butoxy, —OCH(CH₃)CH₂CH₃), 2-methyl-2-propoxy (t-BuO, t-butoxy, —OC(CH₃)₃), 1-pentoxy (n-pentoxy, —OCH₂CH₂CH₂CH₂CH₃), 2-pentoxy (—OCH(CH₃)CH₂CH₂CH₃), 3-pentoxy (—OCH(CH₂CH₃)₂), 2-methyl-2-butoxy (—OC(CH₃)₂CH₂CH₃), 3-methyl-2-butoxy (—OCH(CH₃)CH(CH₃)₂), 3-methyl-1-butoxy (—OCH₂CH₂CH(CH₃)₂), 2-methyl-1-butoxy (—OCH₂CH(CH₃)CH₂CH₃), and the like.

The term "aryl" refers to monocyclic, bicyclic and tricyclic carbocyclic ring systems having a total of six to fourteen ring members, or six to twelve ring members, or six to ten ring members. Wherein at least one ring in the system is aromatic, wherein each ring in the system contains 3 to 7 ring members and that has one or more points of attachment to the rest of the molecule. The term "aryl" may be used interchangeably with the term "aryl ring". Some non-limiting examples of aryl rings include phenyl, 2,3-dihydro-1H-indenyl, naphthyl, anthryl, and the like. The aryl is optionally substituted with one or more substituents described herein.

The term "arylalkyl" refers to aryl attached to the rest of the molecule through alkyl, wherein the alkyl and aryl groups are as defined herein. The arylalkyl is optionally substituted with one or more substituents described herein. Some non-limiting examples of arylalkyl include benzyl, phenylethyl, naphthylmethyl, and the like.

The term "heteroaryl" refers to monocyclic, bicyclic, and tricyclic ring systems having a total of 5 to 14 ring members, or 5 to 12 ring members, or 5 to 10 ring members or 5 to 6 ring members, wherein at least one ring in the system is aromatic, and at least one ring in the system contains one or more heteroatoms selected from nitrogen, sulfur and oxygen, wherein each ring in the system contains 5 to 7 ring members and that has a one or more points of attachment to the rest of the molecule. The term "heteroaryl" may be used interchangeably with the term "heteroaryl ring" or "heteroaromatic compound". In some embodiments, heteroaryl may be $C_{1-9}$ heteroaryl, which contains 1-9 carbon atoms and at least one heteroatom selected from nitrogen, sulfur and oxygen; In other embodiments, heteroaryl may be $C_{1-7}$ heteroaryl, which contains 1-7 carbon atoms and at least one heteroatom selected from nitrogen, sulfur and oxygen; In other embodiments, heteroaryl may be $C_{1-6}$ heteroaryl, which contains 1-6 carbon atoms and at least one heteroatom selected from nitrogen, sulfur and oxygen; In still other embodiment, heteroaryl may be $C_{1-5}$ heteroaryl, which contains 1-5 carbon atoms and at least one heteroatom selected from nitrogen, sulfur and oxygen; In yet other embodiment, heteroaryl may be $C_{1-4}$ heteroaryl, which contains 1-4 carbon atoms and at least one heteroatom selected from nitrogen, sulfur and oxygen; In other embodiment, heteroaryl may be $C_{1-3}$ heteroaryl, which contains 1-3 carbon atoms and at least one heteroatom selected from nitrogen, sulfur and oxygen. Some non-limiting examples of suitable heteroaryl rings include the following monocycles: furanyl (e.g., 2-furanyl, 3-furanyl), imidazolyl (e.g., N-imidazolyl, 1-methyl-1H-imidazolyl, 2-imidazolyl, 4-imidazolyl, 5-imidazolyl), 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), thiazolyl (e.g., 2-thiazolyl, 4-thiazolyl, 5-thiazolyl), tetrazolyl (e.g., 5-tetrazolyl), triazolyl (e.g., 2-triazolyl and 5-triazolyl), 2-thienyl, 3-thienyl, pyranyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, diazolyl, thiadiazolyl, triazinyl; and some following bicycles examples include, but are not limited to, benzothiazolyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl or 4-isoquinolinyl), and the like.

The term "heteroarylalkyl" refers to heteroaryl attached to the rest of the molecule through alkyl, wherein the alkyl and heteroaryl groups are as defined herein. The heteroarylalkyl radicals are optionally substituted with one or more substituents described herein. Some non-limiting examples of such radicals include pyridin-2-ylethyl, thiazol-2-ylmethyl, imidazol-2-ylethyl, pyrimidin-2-ylpropyl, and the like.

The term "alkyl-S(=O)$_q$—", "heterocyclyl-S(=O)$_q$—", "heteroaryl-S(=O)$_q$—", "cycloalkyl-S(=O)$_q$—" and "aryl-S(=O)$_q$—" refers to alkyl, heterocyclyl, heteroaryl, cycloalkyl and aryl attached to the rest of the molecule through sulfinyl (—S(=O)—) or sulfonyl (—S(=O)₂—), wherein the q, and alkyl, heterocyclyl, heteroaryl, cycloalkyl and aryl groups are as defined herein. Some non-limiting examples of such radicals include methylsulfinyl (—S(=O)CH₃), cyclopropyl-S(=O)₂—, cyclobutyl-S(=O)₂—, cyclopentyl-S(=O)₂—, cyclohexyl-S(=O)₂—, naphthyl-S(=O)₂—, phenyl-S(=O)₂—, methylsulfonyl (—S(=O)₂CH₃), and the like.

The term "alkylamino" refers to "N-alkylamino" and "N,N-dialkylamino" wherein amino groups are independently substituted with one alkyl radical or with two alkyl radicals, respectively, wherein the alkyl group is as defined herein. Some non-limiting examples of suitable alkylamino radicals include mono or dialkylamino such as N-methylamino, N-ethylamino, isopropylamino, propylamino, t-butylamino, n-butylamino, 1-methylpropylamino, n-pentylamino, n-hexylamino, N,N-dimethylamino, N,N-diethylamino, and the like.

The term "haloalkyl-substituted aryl" refers to aryl radical substituted with one or more haloalkyl radicals, wherein the haloalkyl and aryl groups are as defined herein. Some non-limiting examples of such radicals include 2-trifluoromethylphenyl, 3,5-bis(trifluoromethyl)phenyl, 3-trifluoromethylphenyl, 4-trifluoromethylphenyl, 2,6-bis(trifluoromethyl)phenyl, and the like.

The term "halogen-substituted aryl" refers to an aryl substituted with one or more halogen atoms, wherein the halogen atoms (halogen) and aryl groups are as defined herein. Some non-limiting examples of such radicals include fluorophenyl, difluorophenyl, trifluorophenyl, chlorophenyl, dichlorophenyl, trichlorophenyl, bromophenyl, tribromophenyl, dibromophenyl, fluorochlorophenyl, fluorobromophenyl, chorobromophenyl, and the like.

As described herein, a bond drawn from a substituent to the center of one ring within a ring system (as shown below) represents substitution of the substituent at any substitutable position on the rings. For example, Figure a represents possible substitution in any of the positions on the A ring and B ring, as shown in Figure b; Figure c, Figure d, Figure e; Figure f, Figure g and Figure h.

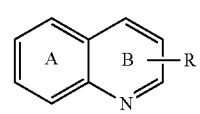

FIG a

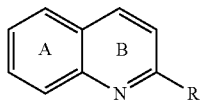
FIG b

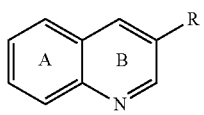
FIG c

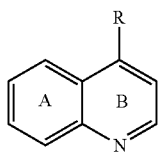
FIG d

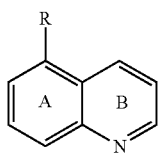
FIG e

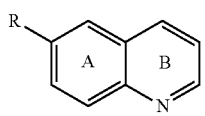
FIG f

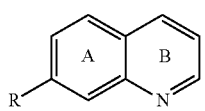
FIG g

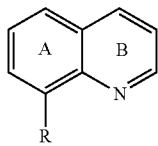
FIG h

Furthermore, what need to be explained is that the phrases "each . . . and . . . is independently", "each of . . . and . . . is independently" are used interchangeably. It should be broadly understood that the specific options expressed by the same symbol are variable independently of each other in different groups; or the specific options expressed by the same symbol are variable independently of each other in same groups. For example, figure p, specific options of multiple n are variable independently each other, and specific options of multiple $R^9$ are independently of each other.

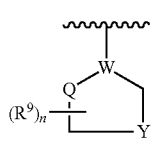
FIG p

As described herein, there are two attaching points within a system attaching to the rest of the molecule. For example, either E or E', as shown in Formula q, can attach to the rest of the molecule, i.e. if the molecular structure is reasonable, E and E' may be used interchangeably with each other.

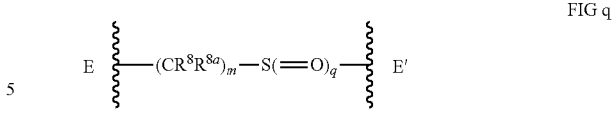
FIG q

As described herein, a double bond attached to the rest of the molecule by a wave bond (as shown Figure k) refers to (Z) double bond isomers or (E) double bond isomers, or a mixture of (Z) double bond isomers and (E) double bond isomers.

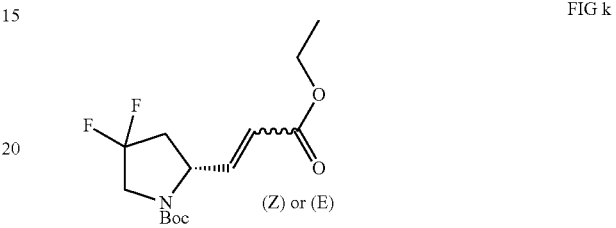
FIG k

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" refers to a compound that is transformed in vivo into a compound of Formula (I) or (Ia). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_{1-24}$) esters, acyloxymethyl esters, carbonates, carbamates and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., *Pro-drugs as Novel Delivery Systems*, Vol. 14 of the A.C.S. Symposium Series; Roche et al., ed., *Bioreversible Carriers in Drug Design*, American Pharmaceutical Association and Pergamon Press, 1987; Rautio et al., Prodrugs: Design and Clinical Applications, *Nature Review Drug Discovery*, 2008, 7, 255-270, and Hecker et al., Prodrugs of Phosphates and Phosphonates, *J Med. Chem.*, 2008, 51, 2328-2345, all of which are incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzyme cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow Parker, et al., McGraw-Hill Dictionary of Chemical Terms (1984) McGraw-Hill Book Company, New York and Eliel, et al., "*Stereochemistry of Organic Compounds*", John Wiley & Sons, Inc., New York, 1994.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

A "pharmaceutically acceptable salts" refers to organic or inorganic salts of a compound disclosed herein. Pharmaceutically acceptable salts are well known in the art. For example, Berge et al., describe pharmaceutically acceptable salts in detail in *J. Pharmacol Sci*, 1977, 66, 1-19, which is incorporated herein by reference. Some non-limiting examples of pharmaceutically acceptable salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, malic acid salt, 2-hydracrylic acid salt, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of solvents that form solvates include water, isopropanol, ethanol, methanol, DMSO, ethyl acetate, acetic acid, and ethanolamine. The term "hydrate" refers to the complex where the solvent molecule is water.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (Boc), benzyloxycarbonyl (Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H (deuterium, D), $^3$H, $^{11}$C, $^{13}$C, $^{14}$C, $^{15}$N, $^{17}$O, $^{18}$O, $^{18}$F, $^{31}$P, $^{32}$P, $^{35}$S, $^{36}$Cl, $^{125}$I.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^2$H and $^{13}$C are present. Such isotopically enriched compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, $d_6$-acetone, DMSO-$d_6$.

DESCRIPTION OF COMPOUNDS

The invention relates to novel dihydropyrimidine compounds and pharmaceutical compositions, and their application in the manufacture of a medicament for preventing, managing, treating or lessening a viral disease or a HBV disease, especially hepatitis B (HBV) infection or a disease caused by hepatitis B infection.

In one aspect, provided herein are compounds having Formula (I) or (Ia), or an enantiomer, a diastereoisomer, a tautomer, a hydrate, a solvate, a prodrug, a stereoisomer, an N-oxide, or a pharmaceutically acceptable salt thereof,

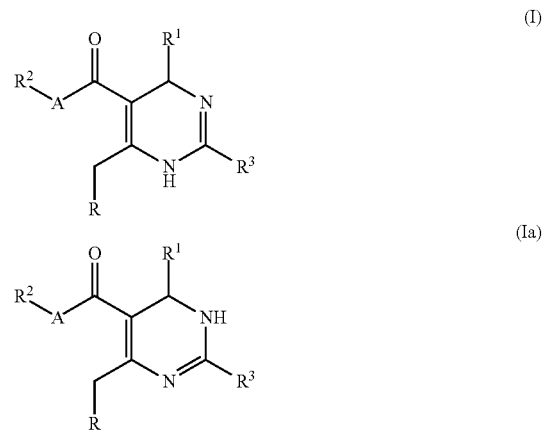

wherein
$R^1$ is $C_{6-10}$ aryl or $C_{1-9}$ heteroaryl;
$R^3$ is a 5-membered heteroaryl group;
A is a bond, —O—, —S— or —NR$^5$—;
R is

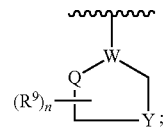

wherein, W is CR$^4$ or N;
each of R$^2$, R$^4$ and R$^5$ is independently hydrogen or $C_{1-4}$ alkyl;
Y is —(CR$^8$R$^{8a}$)$_k$—S(=O)$_q$— or —(CR$^7$R$^6$)$_n$—;
Q is —(CR$^8$R$^{8a}$)$_k$—;
each R$^7$ is independently hydrogen, F or alkyl;
each R$^6$ is independently F or alkyl;
or R$^6$ and R$^7$, together with the carbon atom to which they are attached, form —C(=CH$_2$)— or —C(=O)—;
each R$^8$ and R$^{8a}$ is independently hydrogen, cyano or alkyl;
each R$^9$ is independently —(CR$^{10}$R$^{10a}$)$_r$—OH, triazolyl, tetrazolyl, —(CR$^{10}$R$^{10a}$)$_m$—C(=O)O—R$^{11}$, —(CR$^{10}$R$^{10a}$)$_k$—C(=O)O—(CR$^{10}$R$^{10a}$)$_k$—OC(=O)O—R$^{11}$, —S(O)$_q$OR$^{11}$, —(CR$^{10}$R$^{10a}$)$_k$—S(=O)$_q$N(R$^{11}$)$_2$, —(CR$^{10}$R$^{10a}$)$_k$—C(=O)O—(CR$^{10}$R$^{10a}$)$_k$—OC(=O)—R$^{11}$, —(CR$^{10}$R$^{10a}$)$_k$—C(=O)O—(CR$^{10}$R$^{10a}$)$_k$—C(=O)O—R$^{11}$, —(CR$^{10}$R$^{10a}$)$_t$—N(R$^{11}$)$_2$, —(CR$^{10}$R$^{10a}$)$_t$—OC(=O)—R$^{11}$, —C(=O)O—R$^{11a}$ or —(CR$^{10}$R$^{10a}$)$_k$—C(=O)N(R$^{11}$)$_2$;
each R$^{10}$ and R$^{10a}$ is independently hydrogen, halogen, haloalkyl or alkyl, or R$^{10}$ and R$^{10a}$, together with the carbon atom to which they are attached, form cycloalkyl, heterocyclyl or —C(=O)—;
each R$^{11}$ is independently hydrogen, alkyl, alkoxy, hydroxy, alkyl-S(=O)$_q$—, aryl, heteroaryl, cycloalkyl, heterocyclyl, arylalkyl, heterocyclyl-S(=O)$_q$—, heteroaryl-S(=O)$_q$—, cycloalkyl-S(=O)$_q$— or aryl-S(=O)$_q$—;

$R^{11a}$ is alkyl, alkoxy, hydroxy, alkyl-$S(=O)_q$—, aryl, heteroaryl, cycloalkyl, heterocyclyl, arylalkyl, heterocyclyl-$S(=O)_q$—, heteroaryl-$S(=O)_q$—, cycloalkyl-$S(=O)_q$— or aryl-$S(=O)_q$—;

each n is independently 1, 2 or 3;
each t and m is independently 1, 2, 3 or 4;
each q is independently 1 or 2; and
each k is independently 0, 1, 2, 3 or 4;

wherein each alkoxy, alkyl-$S(=O)_q$—, aryl, heteroaryl, arylalkyl, heterocyclyl-$S(=O)_q$—, heteroaryl-$S(=O)_q$—, cycloalkyl-$S(=O)_q$— and aryl-$S(=O)_q$— described in $R^{11}$ and $R^{11a}$, alkyl described in $R^6$, $R^7$, $R^8$, $R^{8a}$, $R^{10}$, $R^{10a}$, $R^{11a}$ and $R^{11}$, haloalkyl described in $R^{10}$ and $R^{11a}$, heterocyclyl and cycloalkyl described in $R^{10}$, $R^{10a}$, $R^{11a}$ and $R^{11}$, triazolyl and tetrazolyl described in $R^9$, a 5-membered heteroaryl group described in $R^3$, $C_{1-4}$ alkyl described in $R^1$, $R^4$ and $R^5$, and $C_{6-10}$ aryl and $C_{1-9}$ heteroaryl described in $R^1$, is optionally and independently substituted with one or more substituents independently selected from hydrogen, fluoro, chloro, bromo, iodo, oxo(=O), methylene(=CH$_2$), alkyl, alkoxy, cyano, hydroxy, nitro, alkylamino, amino, aryl, heteroaryl, heterocyclyl, cycloalkyl, trifluoromethyl, trifluoromethoxy, haloalkyl-substituted aryl, halogen-substituted aryl or trifluoromethylsulfonyl.

In some embodiments,
R is

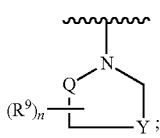

wherein Y is —$(CR^8R^{8a})_k$—$S(=O)_q$— or —$(CR^7R^6)_n$—;
Q is —$(CR^8R^{8a})_k$—;
each $R^7$ is independently hydrogen, $C_{1-4}$ alkyl or F;
each $R^6$ is independently F or $C_{1-4}$ alkyl;
or $R^6$ and $R^7$, together with the carbon atom to which they are attached, form —C(=CH$_2$)— or —C(=O)—;
each $R^8$ and $R^{8a}$ is independently hydrogen or $C_{1-4}$ alkyl;
each $R^9$ is independently —$(CR^{10}R^{10a})_t$—OH, triazolyl, tetrazolyl, —$(CR^{10}R^{10a})_m$—C(=O)O—$R^{11}$, —$(CR^{10}R^{10a})_k$—C(=O)O—$(CR^{10}R^{10a})_k$—OC(=O)—$R^{11}$, —$S(=O)_qOR^{11}$, —$(CR^{10}R^{10a})_k$—S(=O)N($R^{11}$)$_2$, —$(CR^{10}R^{10a})_k$—C(=O)O—$(CR^{10}R^{10a})_k$—OC(=O)—$R^1$—$(CR^{10}R^{10a})_k$—C(=O)O—$(CR^{10}R^{10a})_k$—C(=O)O—$R^{11}$, —$(CR^{10}R^{10a})_t$—N($R^{11}$)$_2$, —$(CR^{10}R^{10a})_t$—OC(=O)—$R^{11}$, —C(=O)O—$R^{11a}$ or —$(CR^{10}R^{10a})_k$—C(=O)N($R^{11}$)$_2$;

each $R^{10}$ and $R^{10a}$ is independently hydrogen, halogen, $C_{1-4}$ haloalkyl or $C_{1-4}$ alkyl, or $R^{10}$ and $R^{10a}$, together with the carbon atom to which they are attached, form $C_{3-6}$ cycloalkyl, $C_{2-9}$ heterocyclyl or —C(=O)—;

each $R^{11}$ is independently hydrogen, $C_{1-6}$ alkyl, $C_{1-6}$alkoxy, $C_{1-6}$alkyl-$S(=O)_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-6}$-alkyl, $C_{2-9}$ heterocyclyl-$S(=O)_q$—, $C_{1-9}$ heteroaryl-$S(=O)_q$—, $C_{3-6}$ cycloalkyl-$S(=O)_q$— or $C_{6-10}$ aryl-$S(=O)_q$—; and $R^{11a}$ is $C_{1-6}$ alkyl, $C_{1-6}$ alkoxy, $C_{1-6}$ alkyl-$S(=O)_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-6}$-alkyl, $C_{2-9}$ heterocyclyl-$S(=O)_q$—, $C_{1-9}$ heteroaryl-$S(=O)_q$—, $C_{3-6}$ cycloalkyl-$S(=O)_q$— or $C_{6-10}$ aryl-$S(=O)_q$—.

In other embodiments, wherein
R is

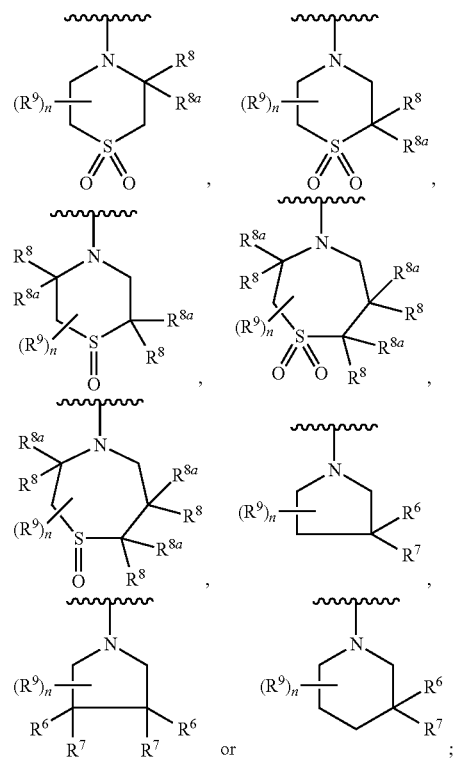

wherein, each $R^7$ is independently hydrogen, methyl, ethyl or F;
each $R^6$ is independently F, methyl or ethyl;
or $R^6$ and $R^7$, together with the carbon atom to which they are attached, form —C(=CH$_2$)— or —C(=O)—;
each $R^8$ and $R^{8a}$ is independently hydrogen, methyl, ethyl or propyl;
each $R^9$ is independently —$(CR^{10}R^{10a})_t$—OH, triazolyl, tetrazolyl, —$(CR^{10}R^{10a})_m$—C(=O)O—$R^{11}$, —$(CR^{10}R^{10a})_k$—C(=O)O—$(CR^{10}R^{10a})_k$—OC(=O)—$R^{11}$, —$S(=O)_qOR^{11}$, —$(CR^{10}R^{10a})_k$—S(=O)N($R^{11}$)$_2$, —$(CR^{10}R^{10a})_k$—C(=O)O—$(CR^{10}R^{10a})_k$—OC(=O)—$R^{11}$, —$(CR^{10}R^{11a})_k$—C(=O)O—$(CR^{10}R^{10a})_k$—C(=O)O—$R^{11}$, —$(CR^{10}R^{10a})_t$—N($R^{11}$)$_2$, —$(CR^{10}R^{10a})_t$—OC(=O)—$R^{11}$, —C(=O)O—$R^{11a}$ or —$(CR^{10}R^{10a})_k$—C(=O)N($R^{11}$)$_2$;

each $R^{10}$ and $R^{10a}$ is independently hydrogen, fluoro, chloro, bromo, iodo, trifluoromethyl, methyl, ethyl, propyl, or $R^{10}$ and $R^{10a}$, together with the carbon atom to which they are attached, form cyclopropyl, cyclobutyl, cyclopentyl, cyclohexyl or —C(=O)—;

each $R^{11}$ is independently hydrogen, $C_{1-4}$ alkyl, $C_{1-4}$ alkoxyl, $C_{1-4}$alkyl-$S(=O)_2$—, phenyl, pyridyl, thiazolyl, furyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-$S(=O)_2$—, cyclobutyl-$S(=O)_2$—, cyclopentyl-$S(=O)_2$—, cyclohexyl-$S(=O)_2$—, naphthyl-$S(=O)_2$— or phenyl-$S(=O)_2$—; and $R^{11a}$ is $C_{1-4}$ alkyl, $C_{1-4}$ alkoxyl, $C_{1-4}$ alkyl-$S(=O)_2$—, phenyl, pyridyl, thiazolyl, furyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S(=O)$_2$—, cyclobutyl-S(=O)$_2$—, cyclopentyl-S(=O)$_2$—, cyclohexyl-S(=O)$_2$—, naphthyl-S(=O)$_2$— or phenyl-S(=O)$_2$—.

In certain embodiments, wherein $R^1$ is phenyl;

$R^3$ is thiazolyl or 1-methyl-1H-imidazolyl; and each of $R^2$, $R^4$ and $R^5$ is independently hydrogen, methyl or ethyl;

wherein each thiazolyl and 1-methyl-1H-imidazolyl described in $R^3$, phenyl described in $R^1$, and methyl and ethyl described in $R^2$, $R^4$ and $R^5$, is optionally and independently substituted with one or more substituents independently selected from hydrogen, $C_{1-4}$ alkyl, fluoro, chloro or bromo.

In certain embodiments, provided herein are compounds having Formula (II) or (IIa) or an enantiomer, a diastereoisomer, a tautomer, a hydrate, a solvate, a prodrug, a stereoisomer, an N-oxide or a pharmaceutically acceptable salt thereof,

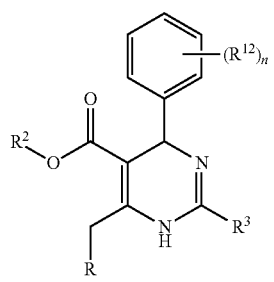
(II)

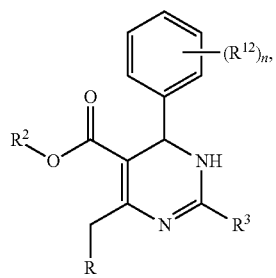
(IIa)

wherein $R^2$ is hydrogen or $C_{1-4}$ alkyl;

$R^3$ is thiazolyl or 1-methyl-1H-imidazolyl;

R is

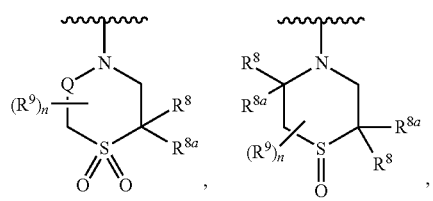

-continued

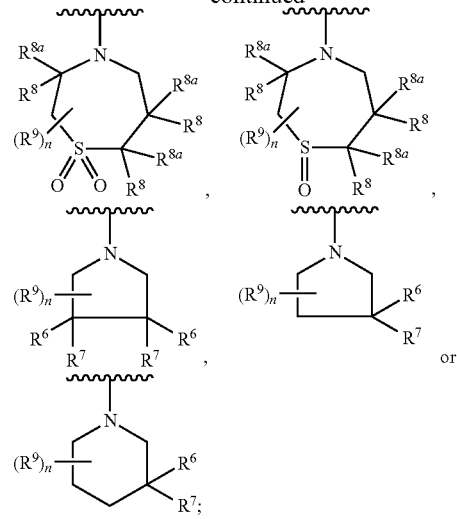

wherein each $R^7$ is independently hydrogen, $C_{1-4}$ alkyl or F;

each $R^6$ is independently F or $C_{1-4}$ alkyl;

or $R^6$ and $R^7$, together with the carbon atom to which they are attached, form —C(=CH$_2$)— or —C(=O)—;

Q is —(CR$^8$R$^{8a}$)$_k$—;

each $R^8$ and $R^{8a}$ is independently hydrogen or $C_{1-4}$ alkyl;

each $R^9$ is independently —(CR$^{10}$R$^{10a}$)$_t$—OH, triazolyl, tetrazolyl, —(CR$^{10}$R$^{10a}$)$_m$—C(=O)O—R$^1$, —(CR$^{10}$R$^{10a}$)$_k$—C(=O)O—(CR$^{10}$R$^{10a}$)$_k$—OC(=O)O—R$^{11}$, —S(=O)$_q$OR$^{11}$, —(CR$^{10}$R$^{11a}$)$_k$—S(=O)$_q$N(RU)$_2$, —(CR$^{10}$R$^{10a}$)$_k$—C(=O)O—(CR$^{10}$R$^{10a}$)$_k$—OC(=O)—R$^{11}$, —(CR$^{10}$R$^{10a}$)$_k$—C(=O)O—(CR$^{10}$R$^{10a}$)$_k$—C(=O)O—R$^{11}$, —(CR$^{10}$R$^{10a}$)$_t$—N(R$^{11}$)$_2$, —(CR$^{10}$R$^{10a}$)$_t$—OC(=O)—R$^{11}$, —C(=O)O—R$^{11a}$ or —(CR$^{10}$R$^{10a}$)$_k$—C(=O)N(R$^{11}$)$_2$;

each $R^{10}$ and $R^{10a}$ is independently hydrogen, fluoro, chloro, bromo, iodo, $C_{1-4}$ haloalkyl or $C_{1-4}$ alkyl, or $R^{10}$ and $R^{10a}$, together with the carbon atom to which they are attached, form $C_{3-6}$ cycloalkyl or —C(=O)—;

each $R^{11}$ is independently hydrogen, $C_{1-4}$ alkyl, $C_{1-4}$ alkoxy, hydroxy, $C_{1-4}$ alkyl-S(=O)$_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-4}$-alkyl, $C_{2-9}$ heterocyclyl-S(=O)$_q$—, $C_{1-9}$ heteroaryl-S(=O)$_q$—, $C_{3-6}$ cycloalkyl-S(=O)$_q$— or $C_{6-10}$ aryl-S(=O)$_q$—;

$R^{11a}$ is $C_{1-4}$ alkyl, $C_{1-4}$ alkoxy, hydroxy, $C_{1-4}$ alkyl-S(=O)$_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-4}$-alkyl, $C_{2-9}$ heterocyclyl-S(=O)$_q$—, $C_{2-9}$ heteroaryl-S(=O)$_q$—, $C_{3-6}$ cycloalkyl-S(=O)$_q$— or $C_{6-10}$ aryl-S(=O)$_q$—;

each $R^{12}$ is independently hydrogen, fluoro, chloro or bromo;

each n is independently 1, 2 or 3;

each t and m is independently 1, 2, 3 or 4;

each q is independently 1 or 2; and each k is independently 0, 1, 2, 3 or 4.

In other embodiments, wherein R is

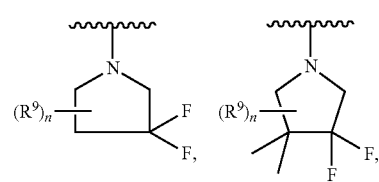

-continued

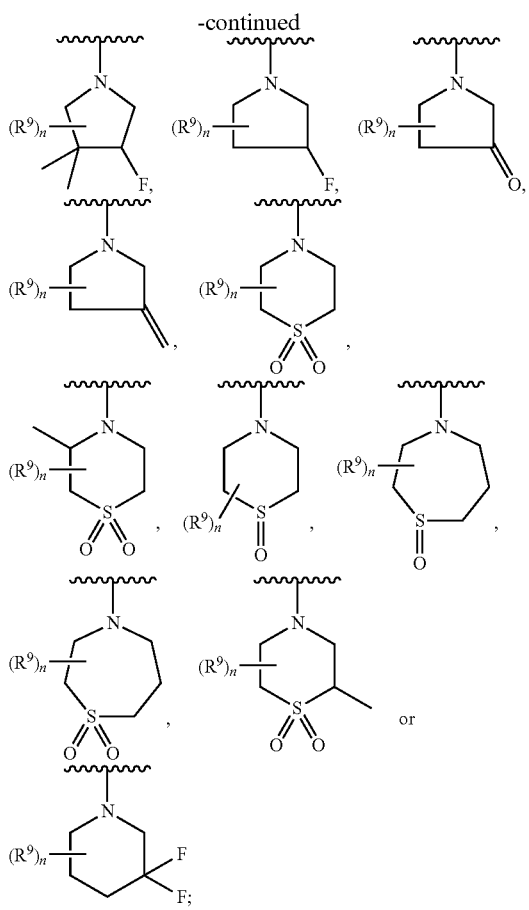

each $R^9$ is independently —$(CR^{10}R^{10a})_t$—OH, triazolyl, tetrazolyl, —$(CR^{10}R^{10a})_m$—C(=O)O—$R^{11}$, —$(CR^{10}R^{10a})_k$—C(=O)O—$(CR^{10}R^{10a})_k$—OC(=O)O—$R^{11}$, —S(=O)$_q$OR$^{11}$, —$(CR^{10}R^{10a})_k$—S(=O)$_q$N(R$^{11}$)$_2$, —$(CR^{10}R^{10a})_k$—C(=O)O—$(CR^{10}R^{10a})_k$—OC(=O)—$R^{11}$, —$(CR^{10}R^{10a})_k$—C(=O)O—$(CR^{10}R^{10a})_k$—C(=O)O—$R^{11}$, —$(CR^{10}R^{10a})_t$—N(R$^{11}$)$_2$, —$(CR^{10}R^{10a})_t$—OC(=O)—$R^{11}$, —C(=O)O—$R^{11a}$ or —$(CR^{10}R^{10a})_k$—C(=O)N(R$^{11}$)$_2$;

each $R^{10}$ and $R^{10a}$ is independently hydrogen, fluoro, chloro, trifluoromethyl, methyl, ethyl, propyl, isopropyl, tert-butyl or n-butyl, or $R^{10}$ and $R^{10a}$ together with the carbon atom to which they are attached, form cyclopropyl, cyclobutyl, cyclopentyl, cyclohexyl or —C(=O)—;

each $R^{11}$ is independently hydrogen, methyl, ethyl, propyl, isopropyl, tert-butyl, n-butyl; methoxyl, ethoxy, propoxy, isopropoxy, tert-butoxy, n-butoxy, methyl-S(=O)$_2$—, ethyl-S(=O)$_2$—, propyl-S(=O)$_2$—, isopropyl-S(=O)$_2$—, pyridyl, thiazolyl, furyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S(=O)$_2$—, cyclobutyl-S(=O)$_2$—, cyclopentyl-S(=O)$_2$—, cyclohexyl-S(=O)$_2$—, naphthyl-S(=O)$_2$— or phenyl-S(=O)$_2$—; and $R^{11a}$ is methyl, ethyl, propyl, isopropyl, tert-butyl, n-butyl; methoxyl, ethoxy, propoxy, isopropoxy, tert-butoxy, n-butoxy, methyl-S(=O)$_2$—, ethyl-S(=O)$_2$—, propyl-S(=O)$_2$—, isopropyl-S(=O)$_2$—, pyridyl, thiazolyl, furyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S(=O)$_2$—, cyclobutyl-S(=O)$_2$—, cyclopentyl-S(=O)$_2$—, cyclohexyl-S(=O)$_2$—, naphthyl-S(=O)$_2$— or phenyl-S(=O)$_2$—.

In other embodiments, provided herein is one of the compounds as follows, or an enantiomer, a diastereoisomer, a tautomer, a hydrate, a solvate, or a pharmaceutically acceptable salt thereof, and not limited to:

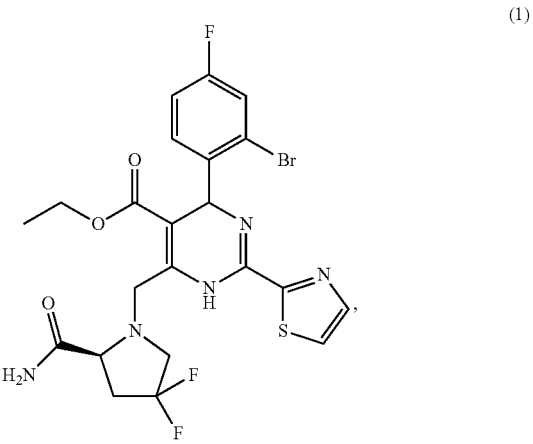

(1)

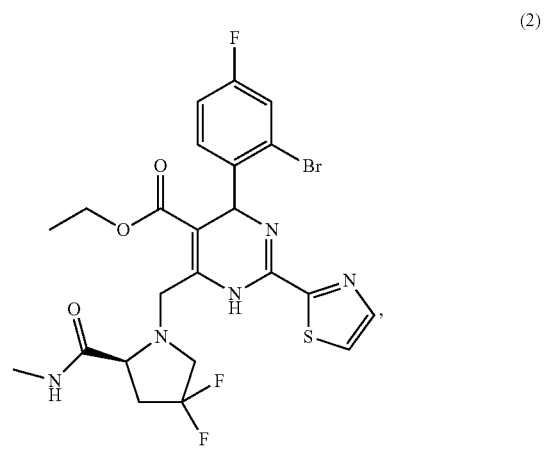

(2)

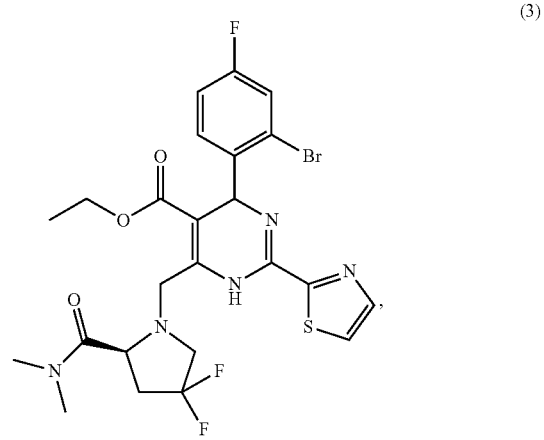

(3)

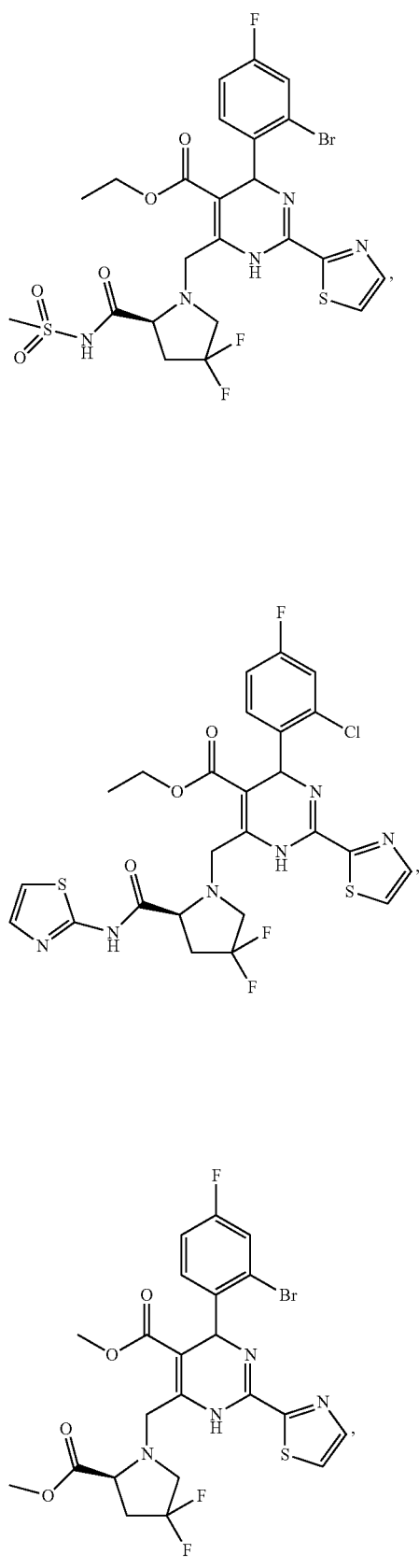
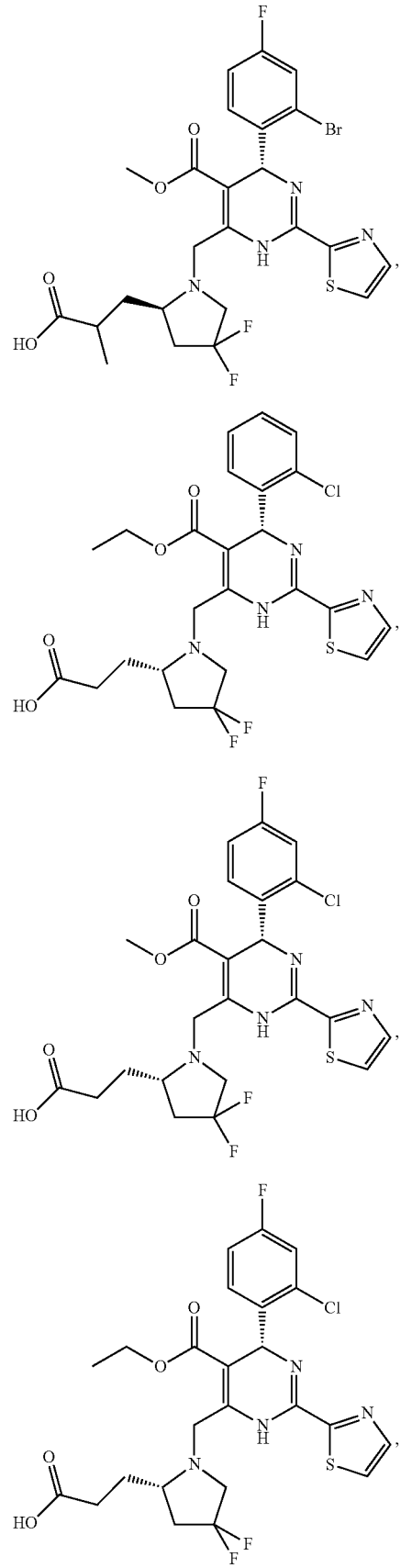

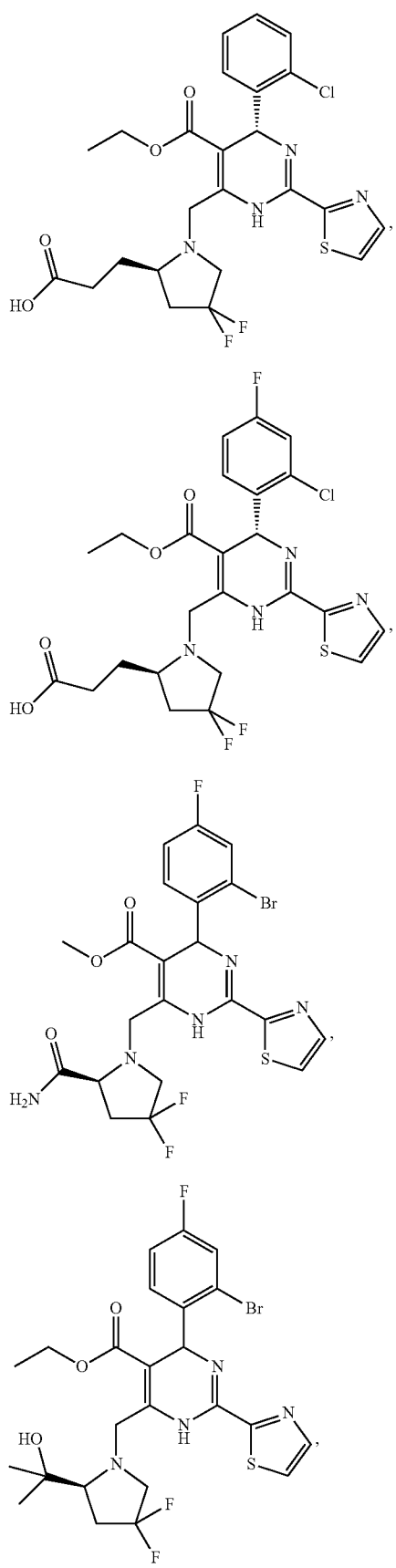
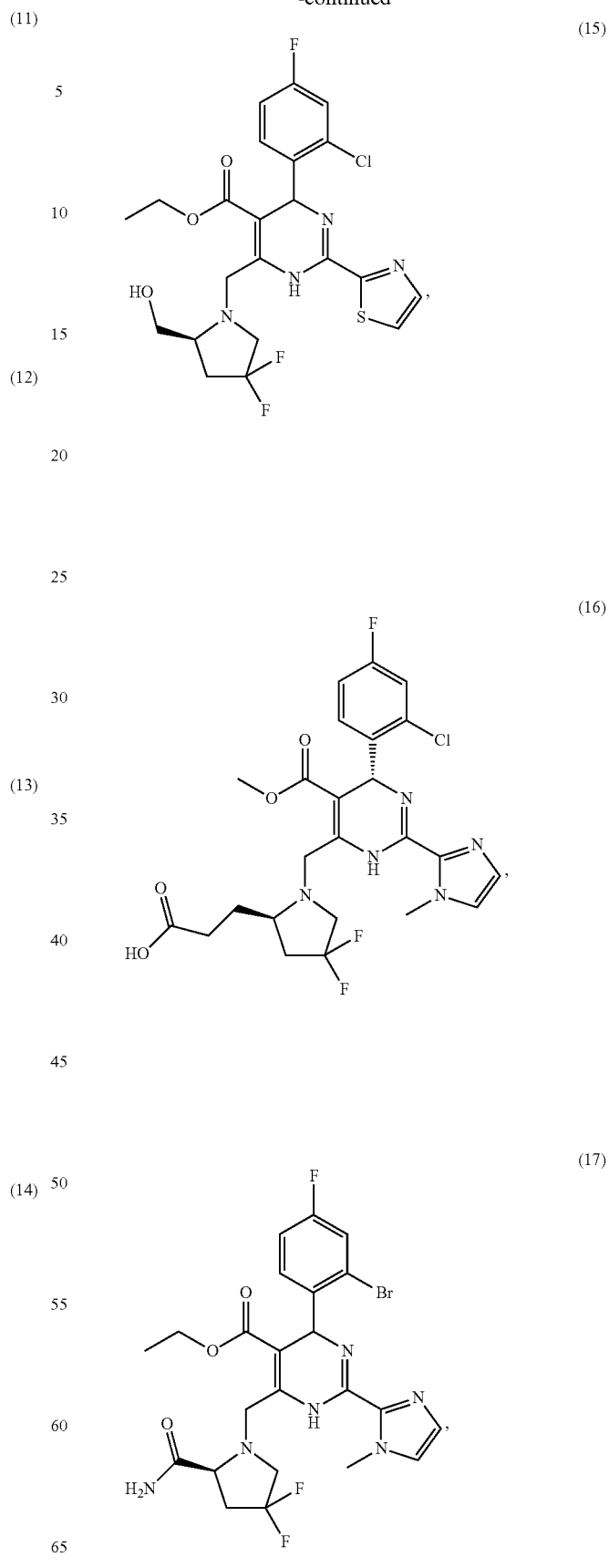

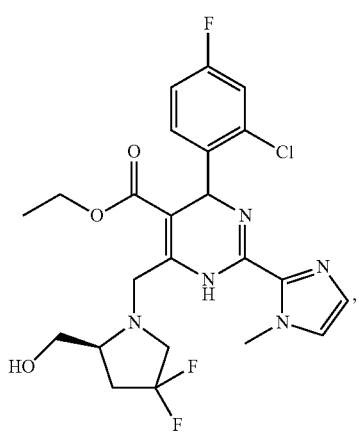
(18)
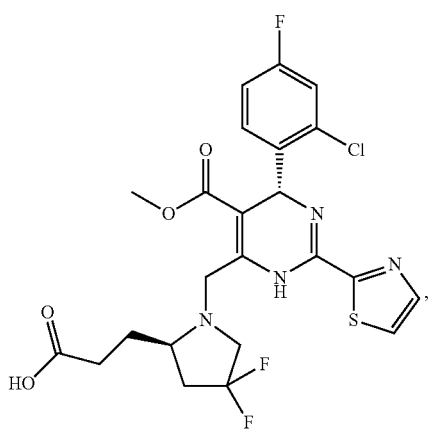
(19)
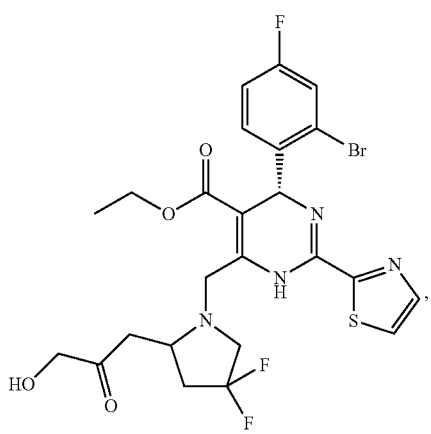
(20)
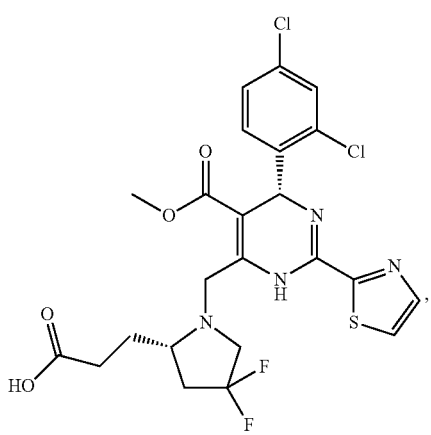
(21)

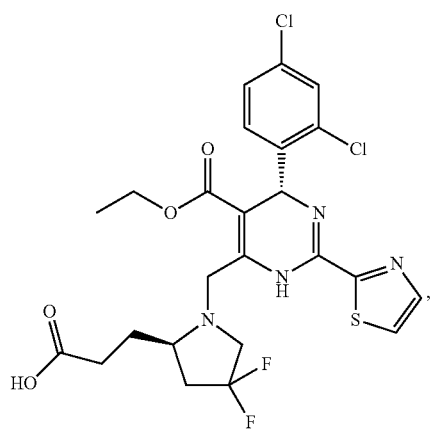
(24)
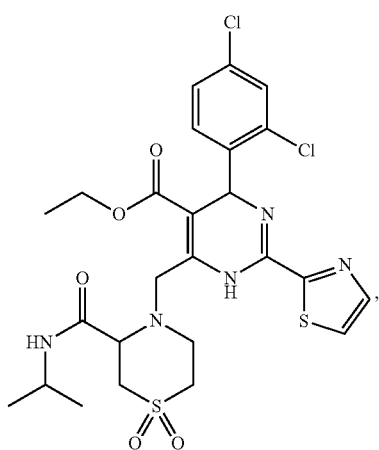
(27)
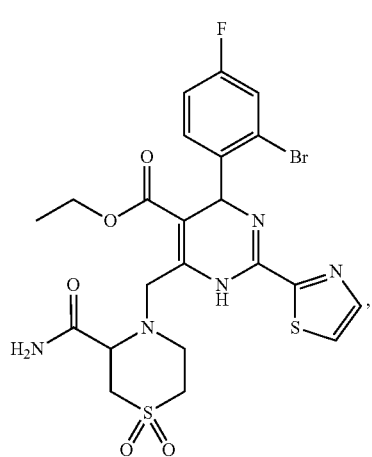
(25)
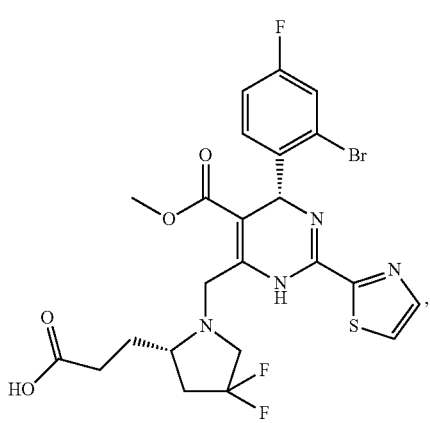
(28)
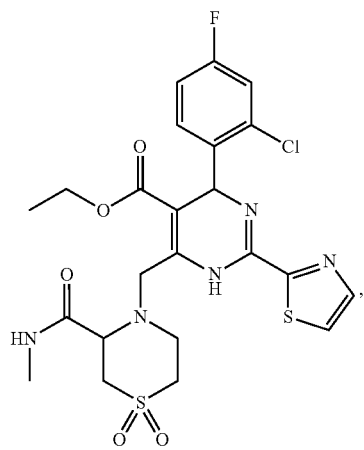
(26)
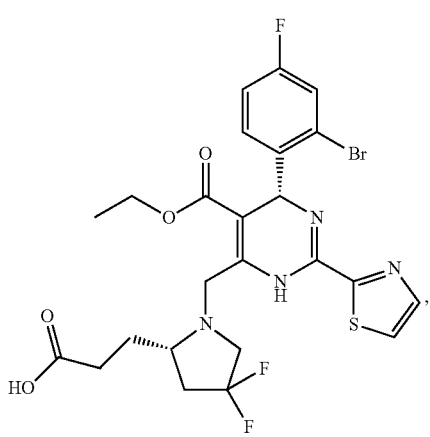
(29)

(30)
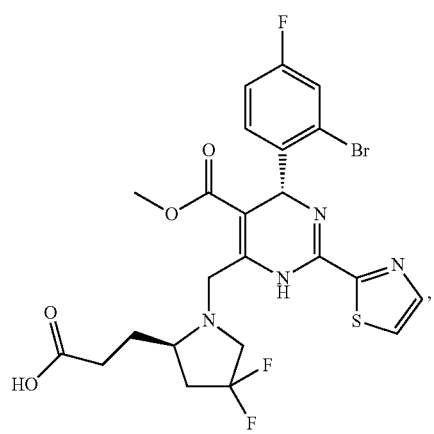
(31)
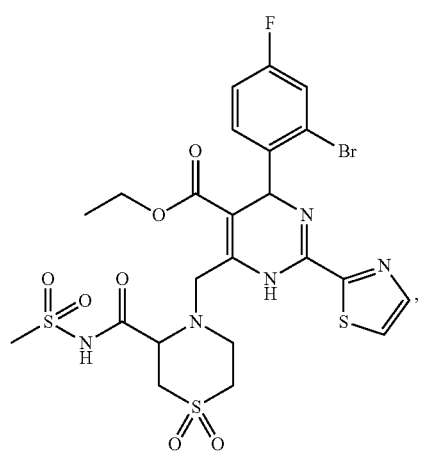
(32)
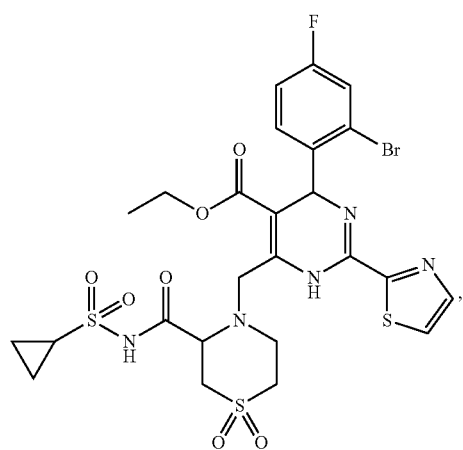
(33)
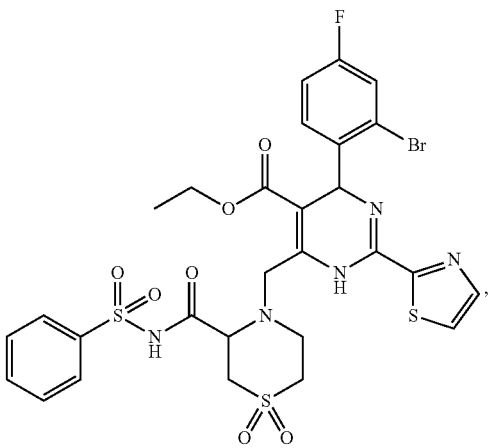
(34)
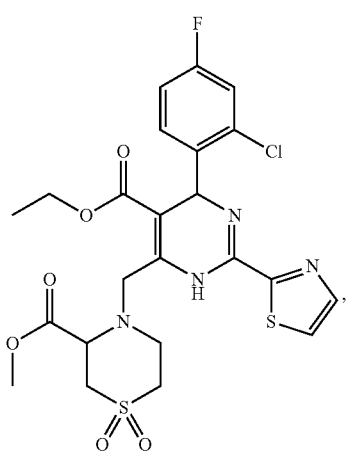
(35)
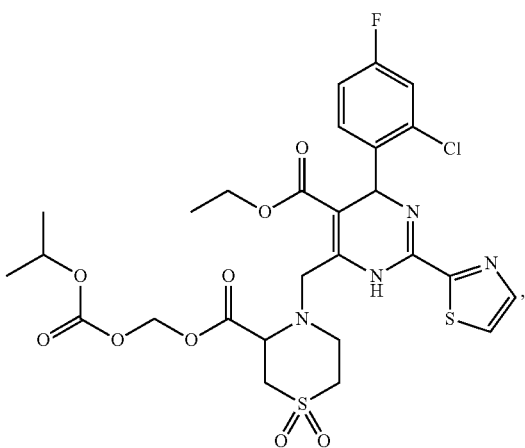

-continued
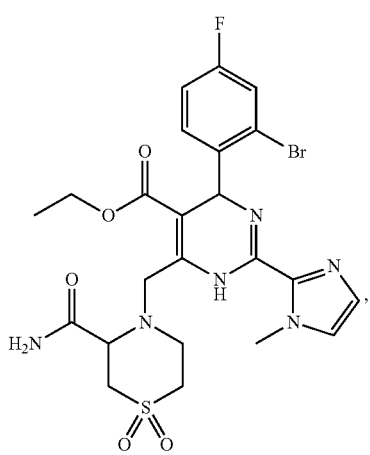
(36)
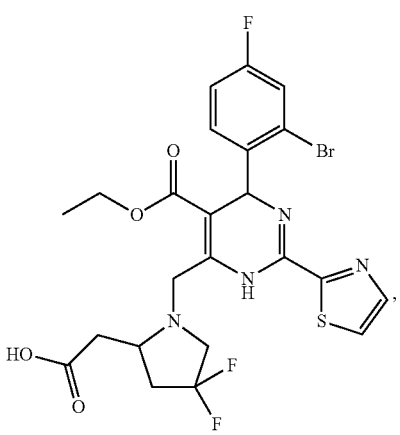
(39)
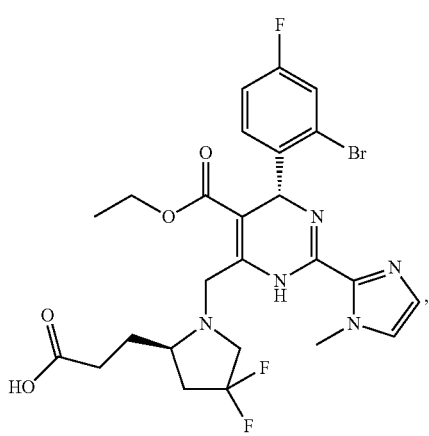
(37)
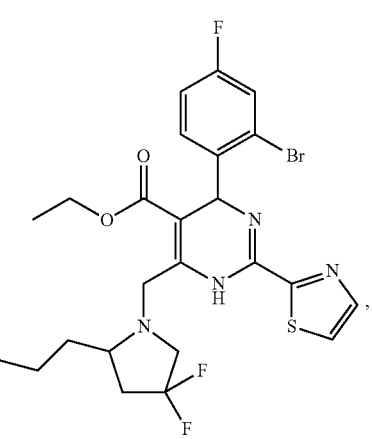
(40)
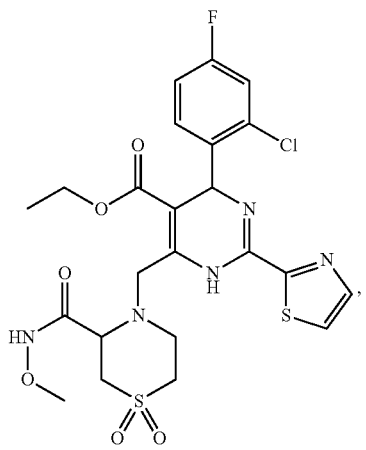
(38)
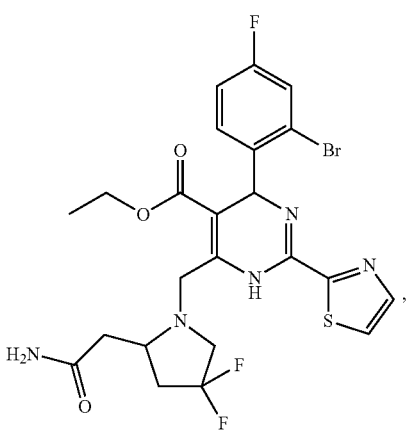
(41)

(42)
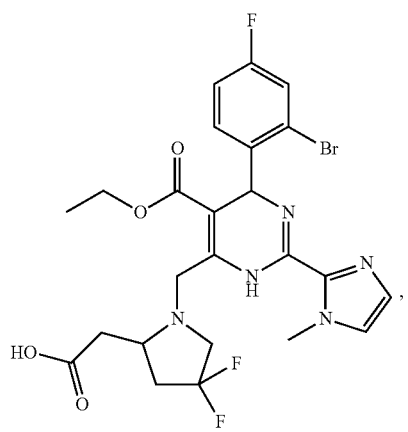
(43)
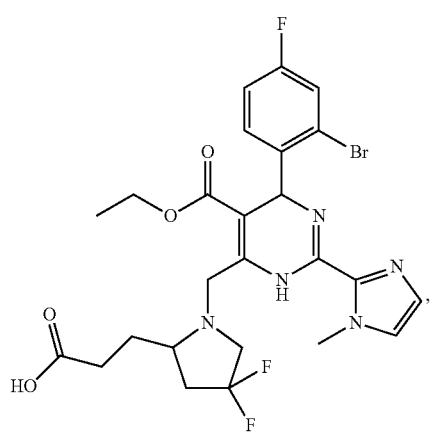
(44)
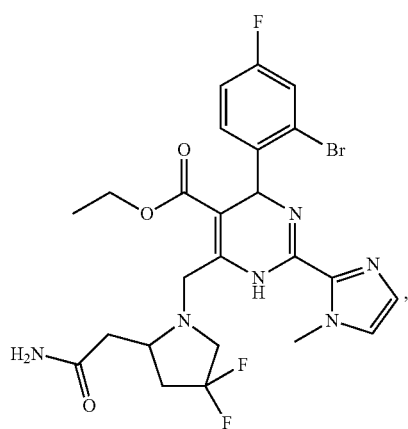
(45)
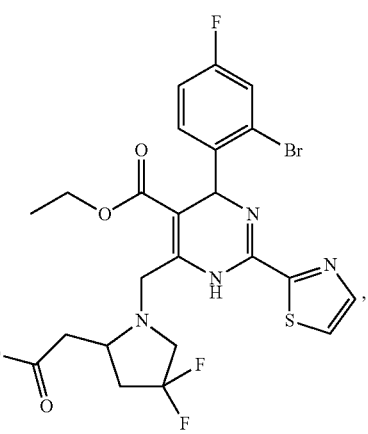
(46)
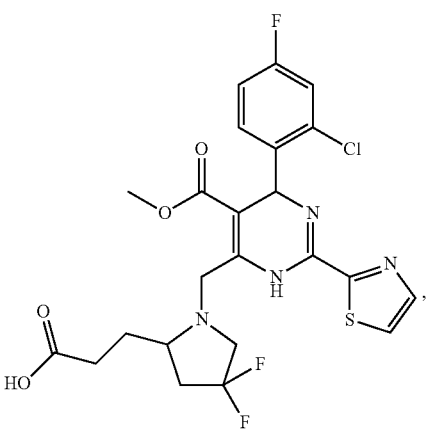
(47)
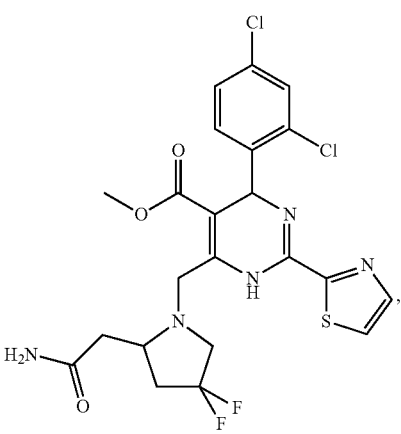

-continued
(48)
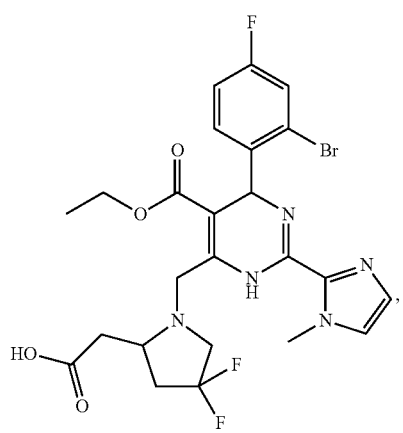
(51)
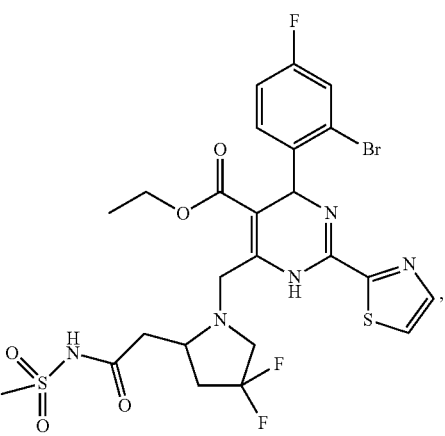
(49)
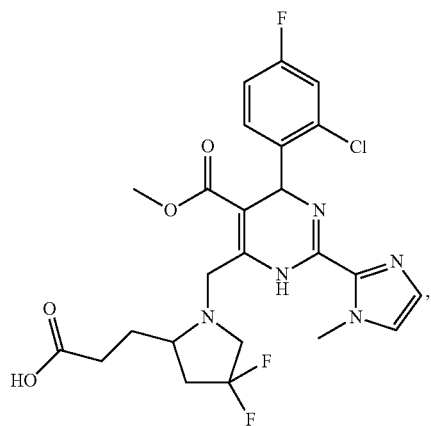
(52)
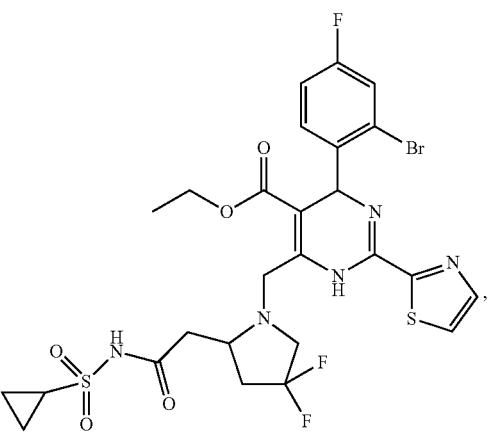
(50)
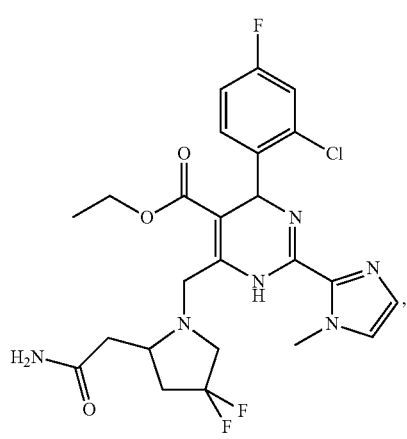
(53)
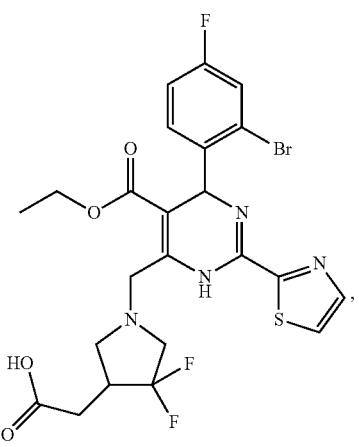

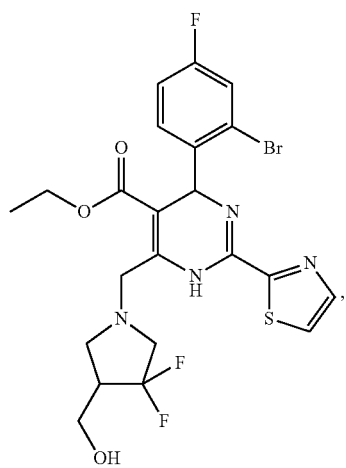
(54)
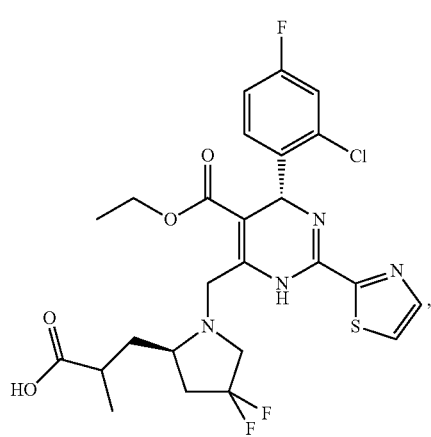
(55)
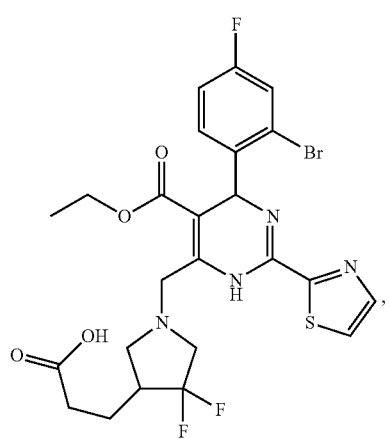
(56)
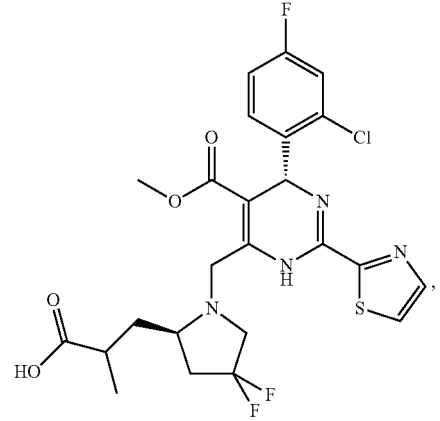
(57)
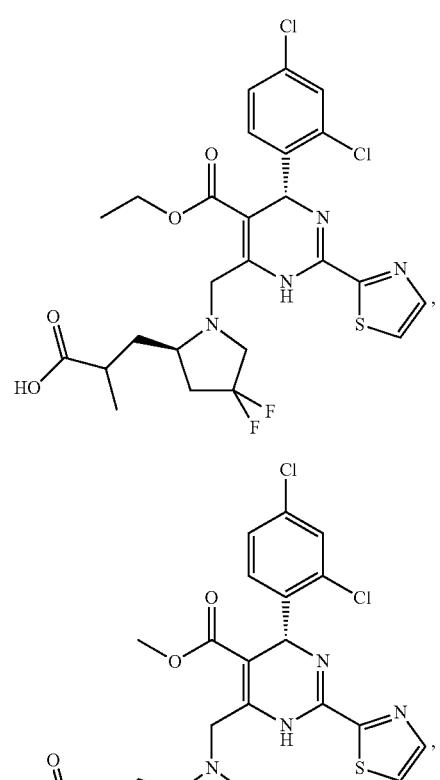
(58)
(59)
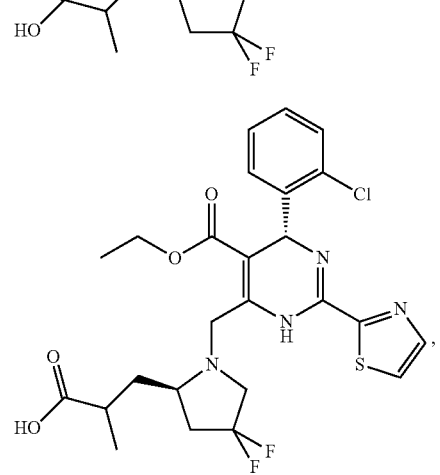
(60)

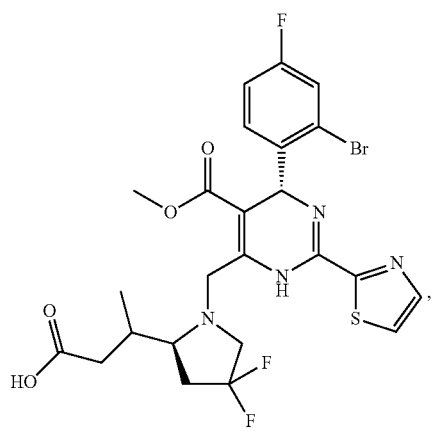
(61)
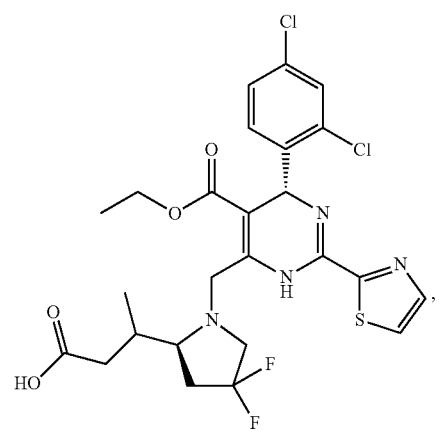
(64)
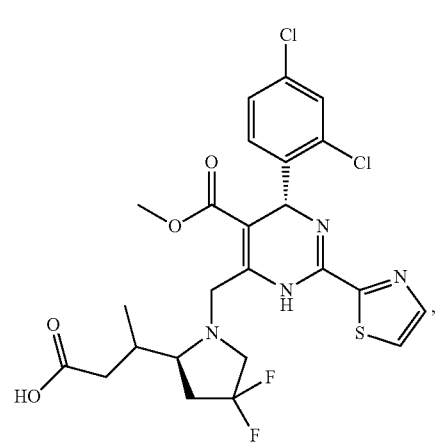
(65)
(62)
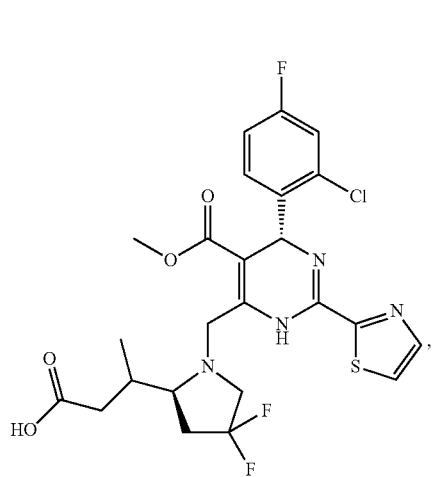
(63)
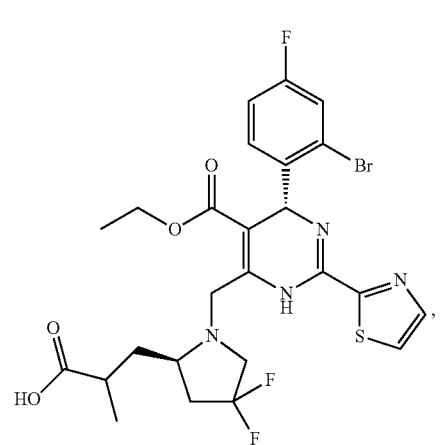
(66)

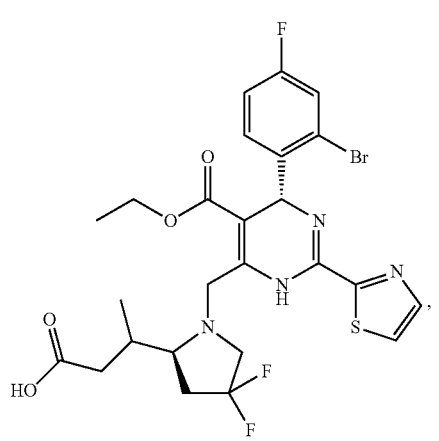
(67)
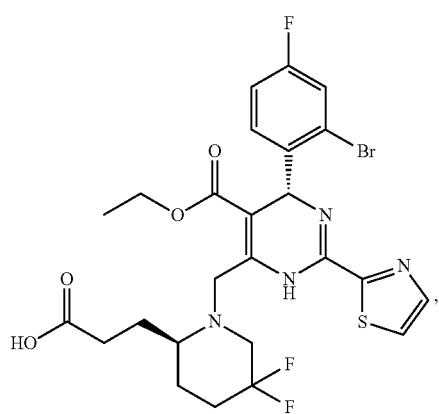
(68)
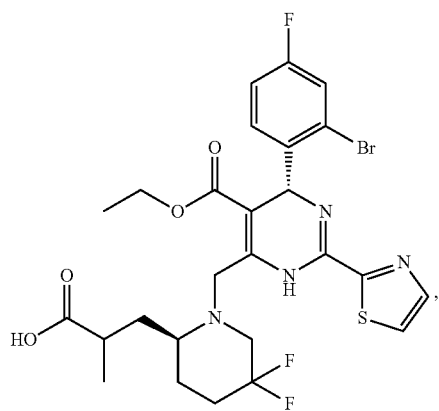
(69)
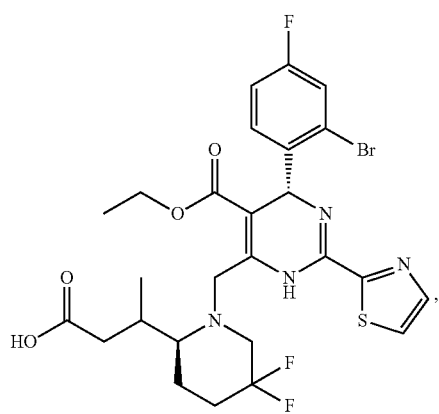
(70)
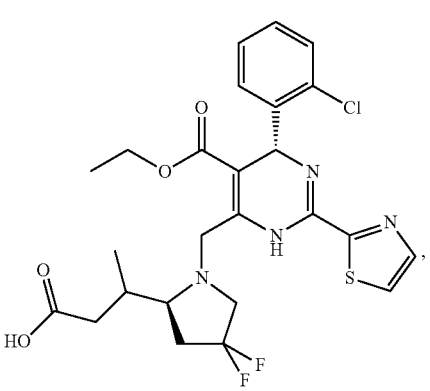
(71)
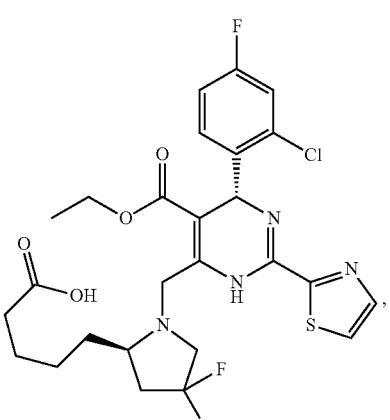
(72)
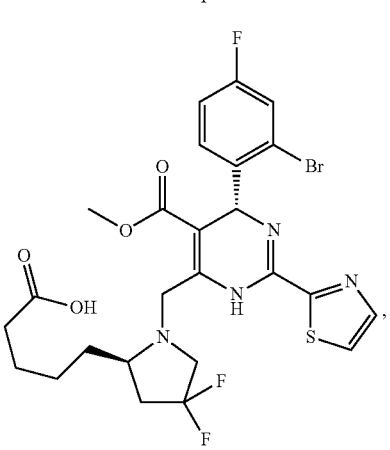
(73)
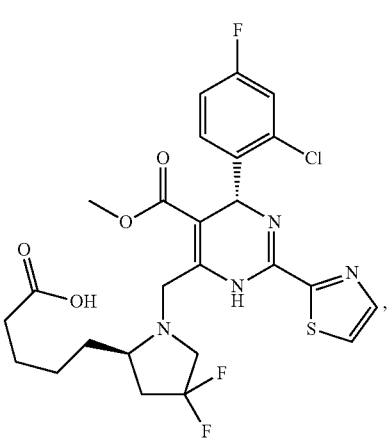
(74)

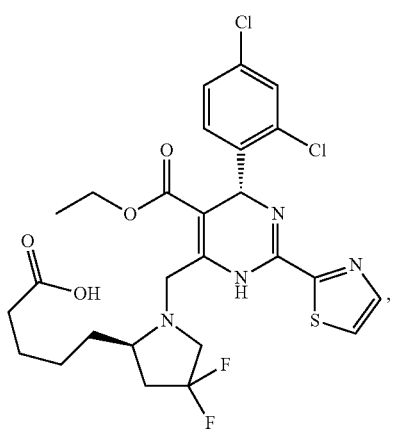
(75)
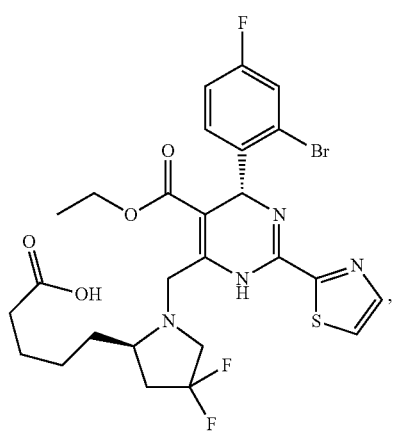
(78)
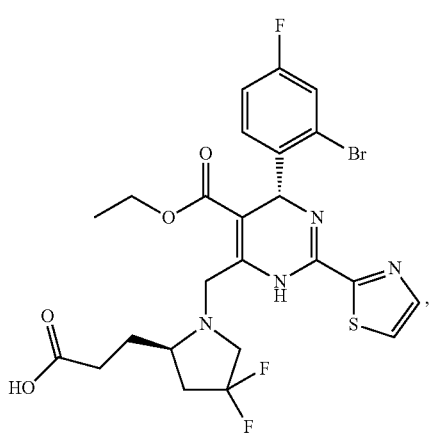
(76)
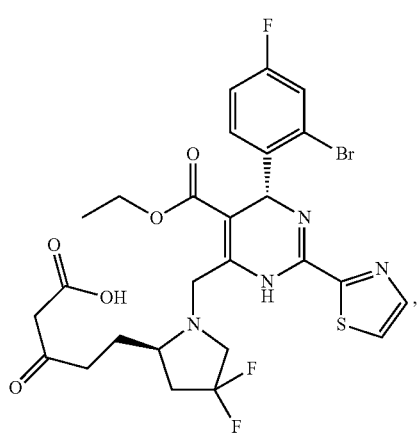
(79)
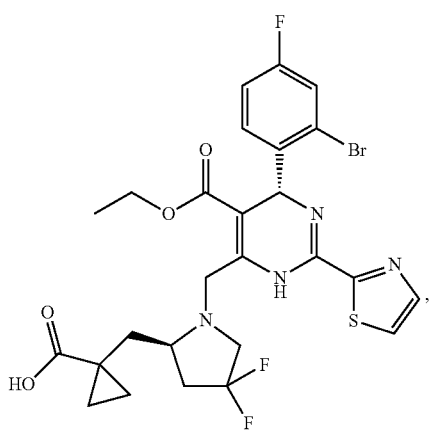
(77)
(80)

-continued
(81)
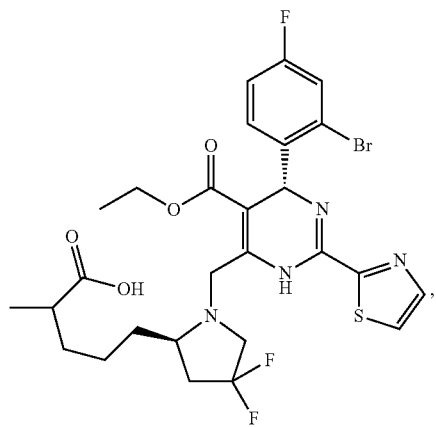
(82)
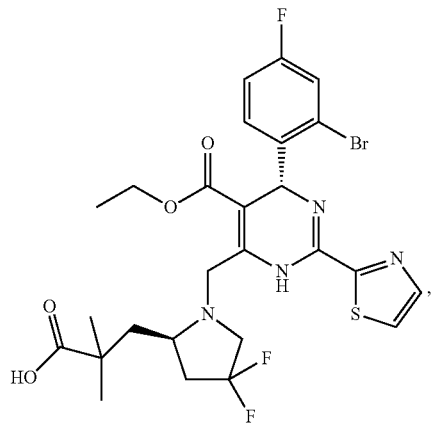
(83)
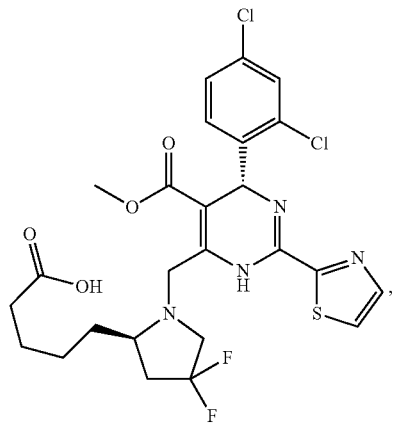
(84)
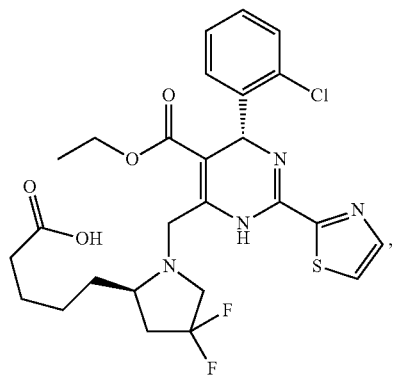
-continued
(85)
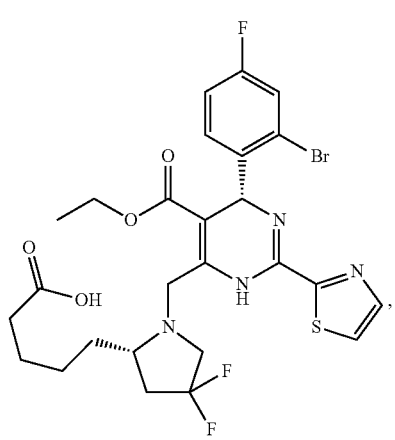
(86)
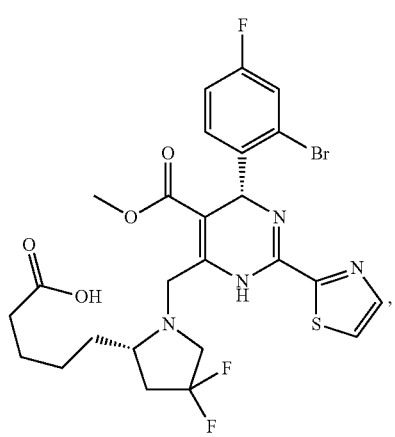
(87)
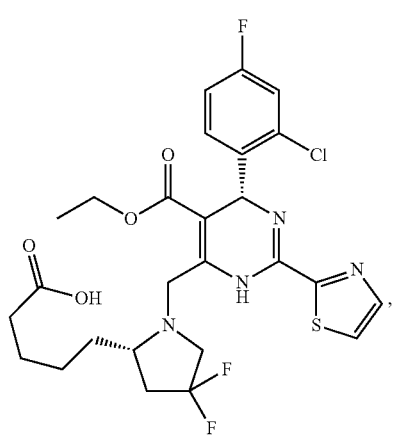

-continued
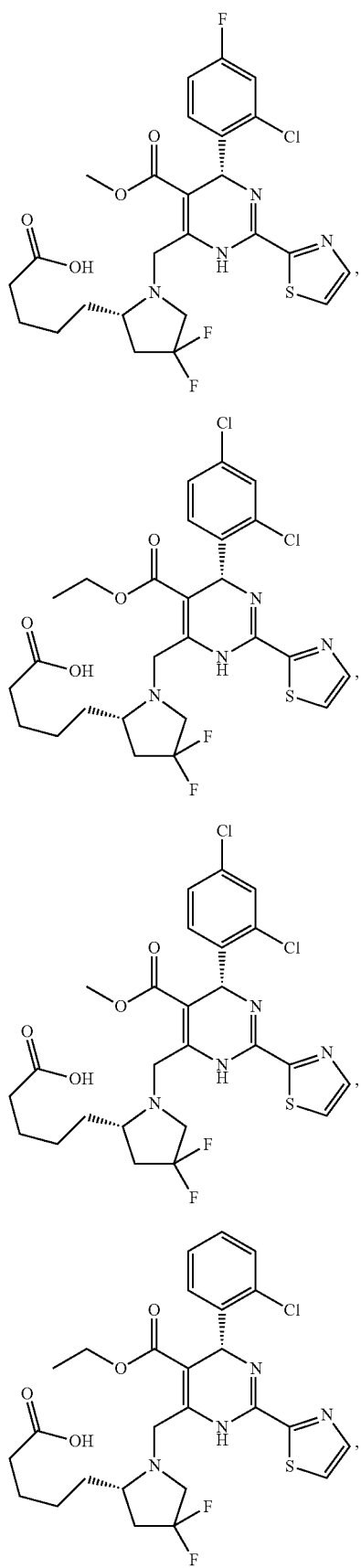
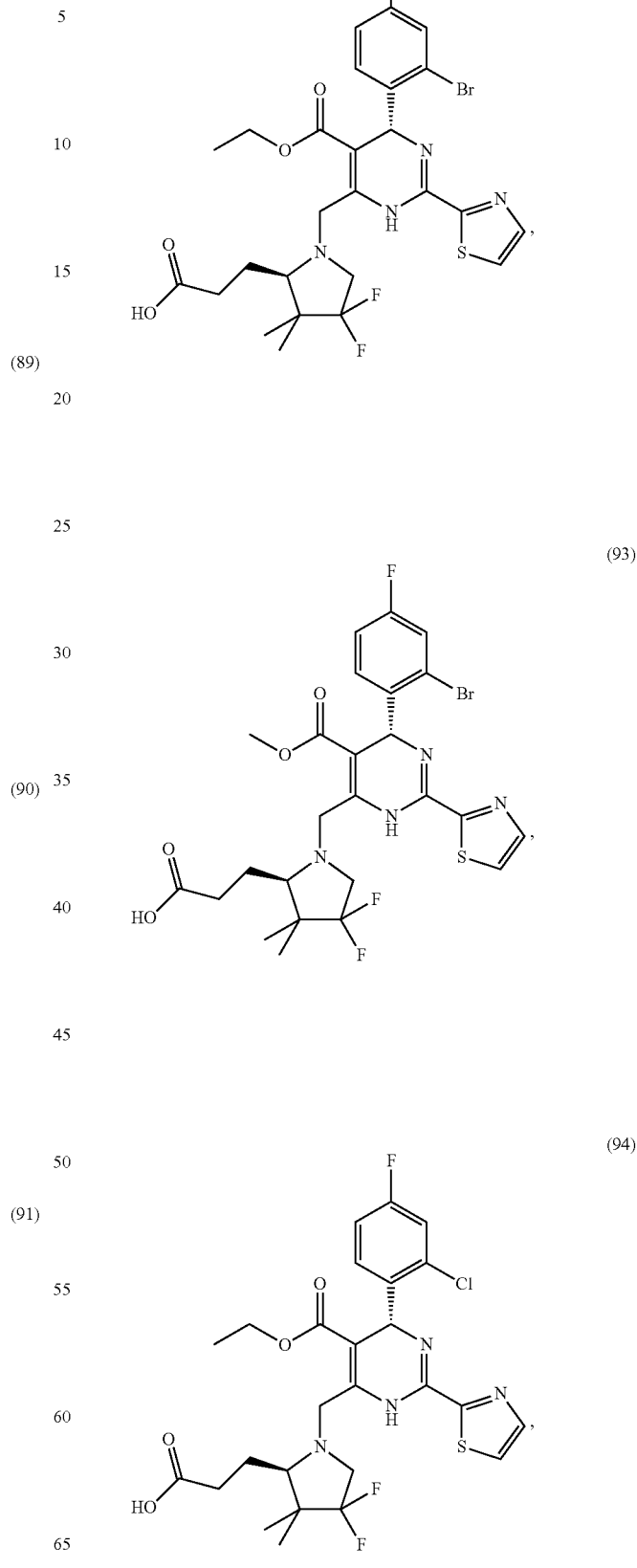

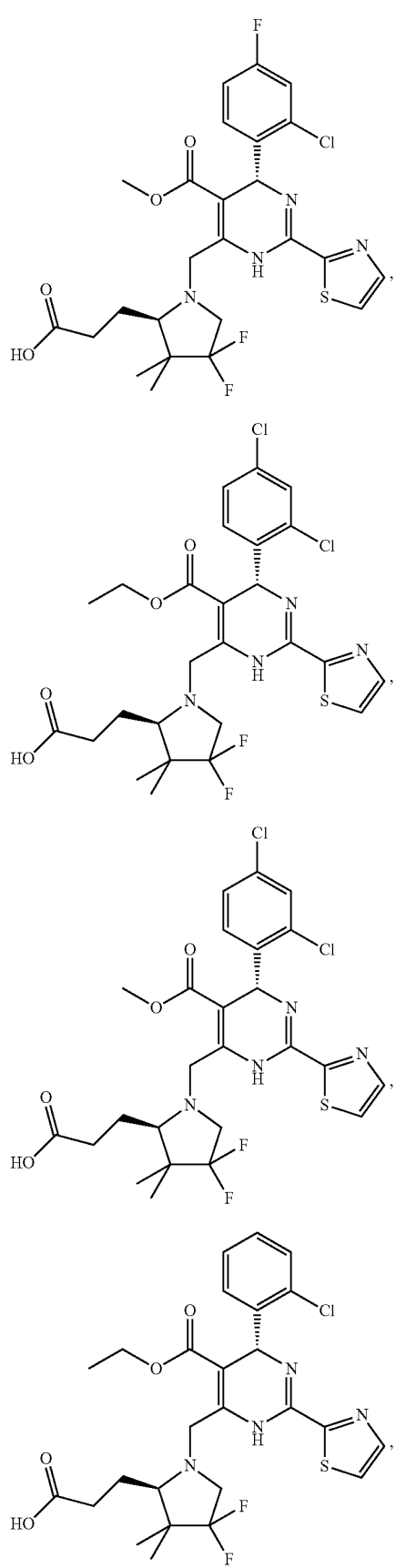

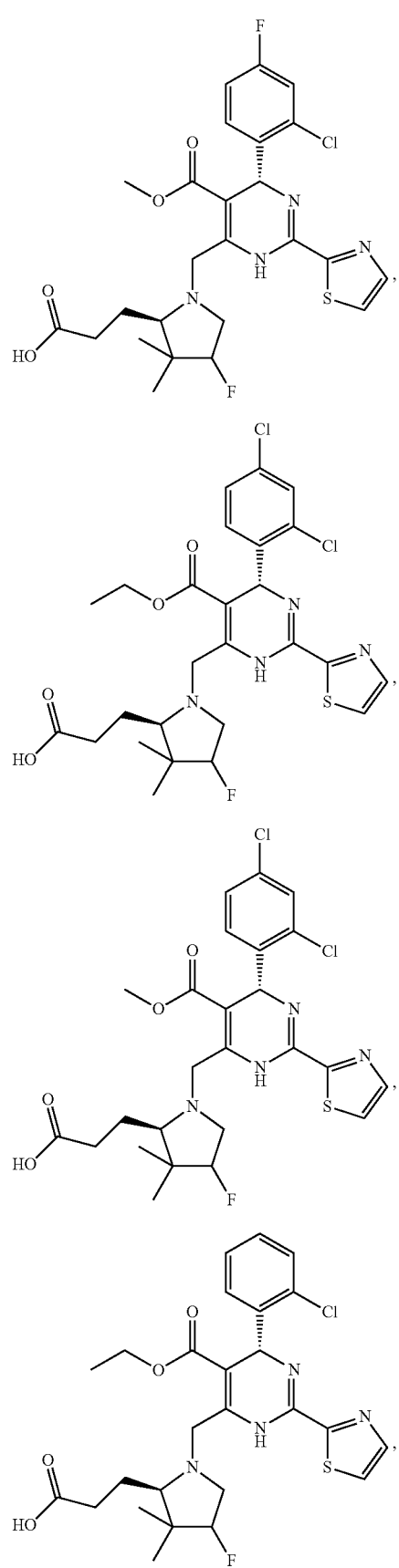
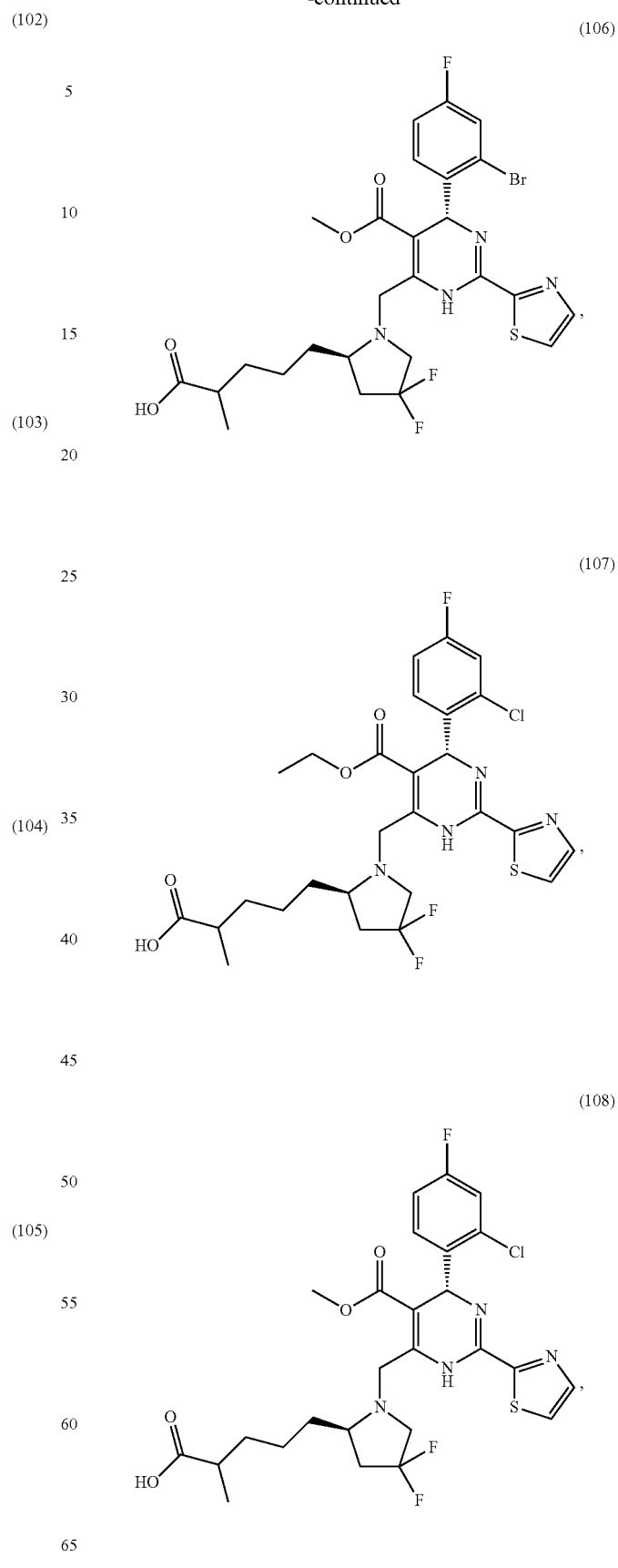

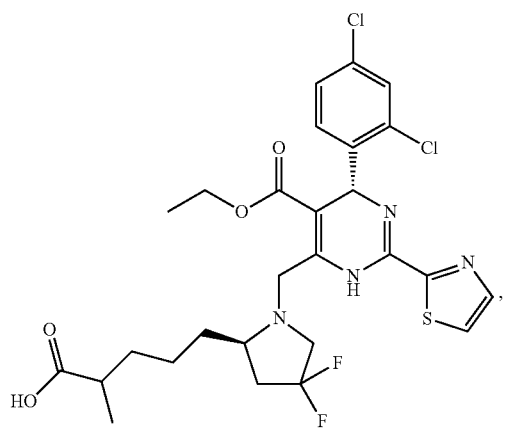
(109)
(110)
(111)
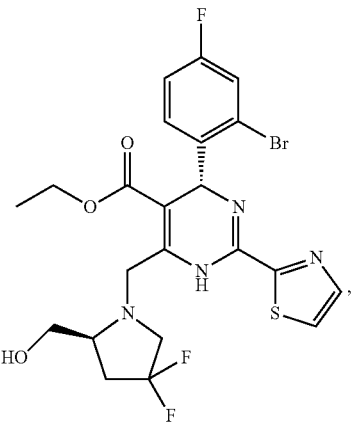
(112)
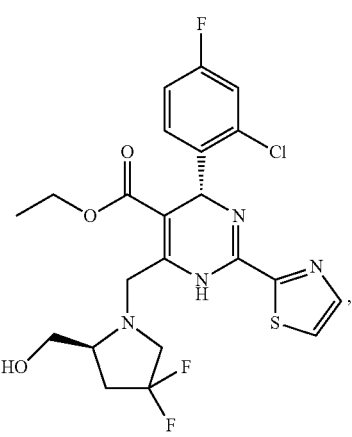
(113)
(114)

(115)
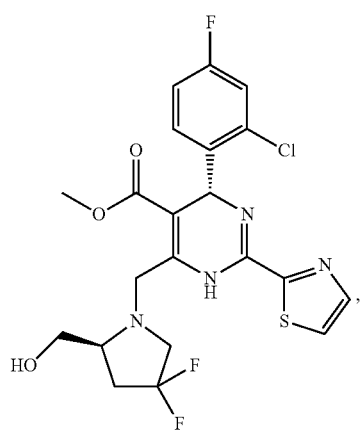
(116)
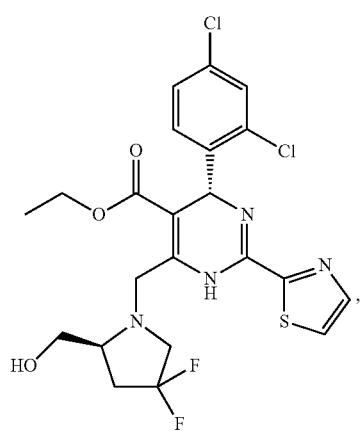
(117)
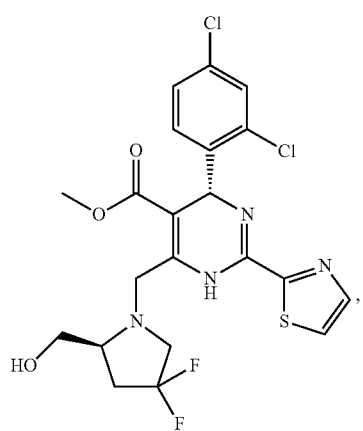
(118)
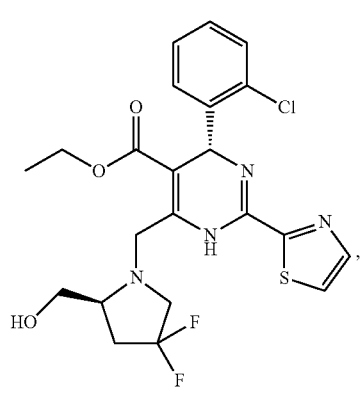
(119)
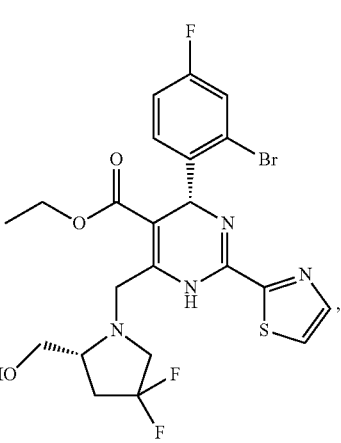
(120)
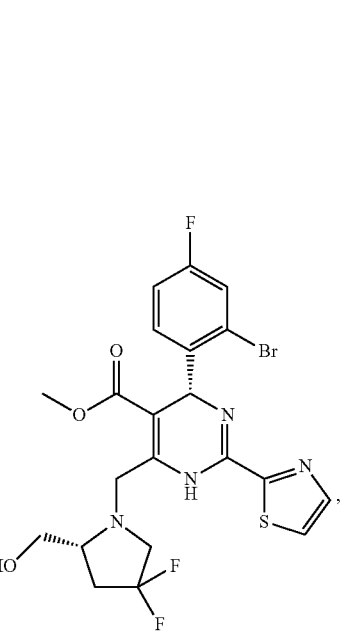
(121)
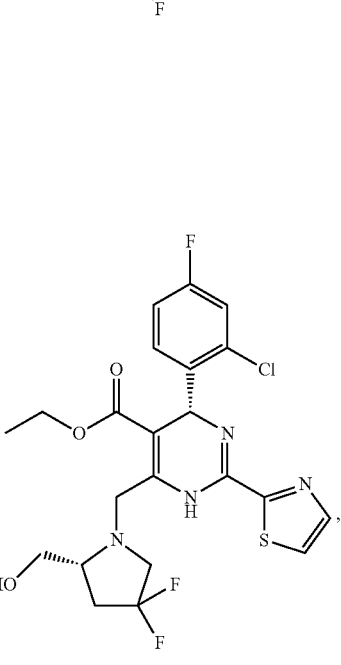

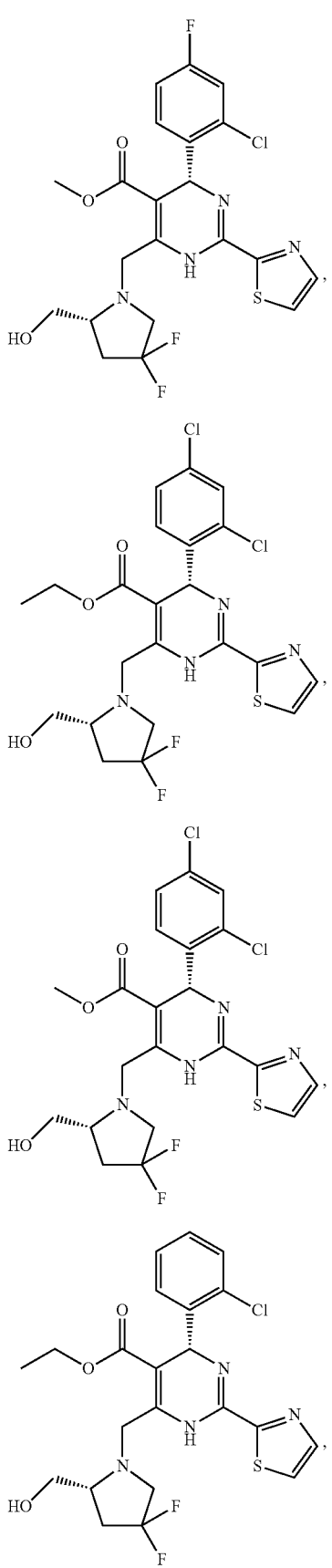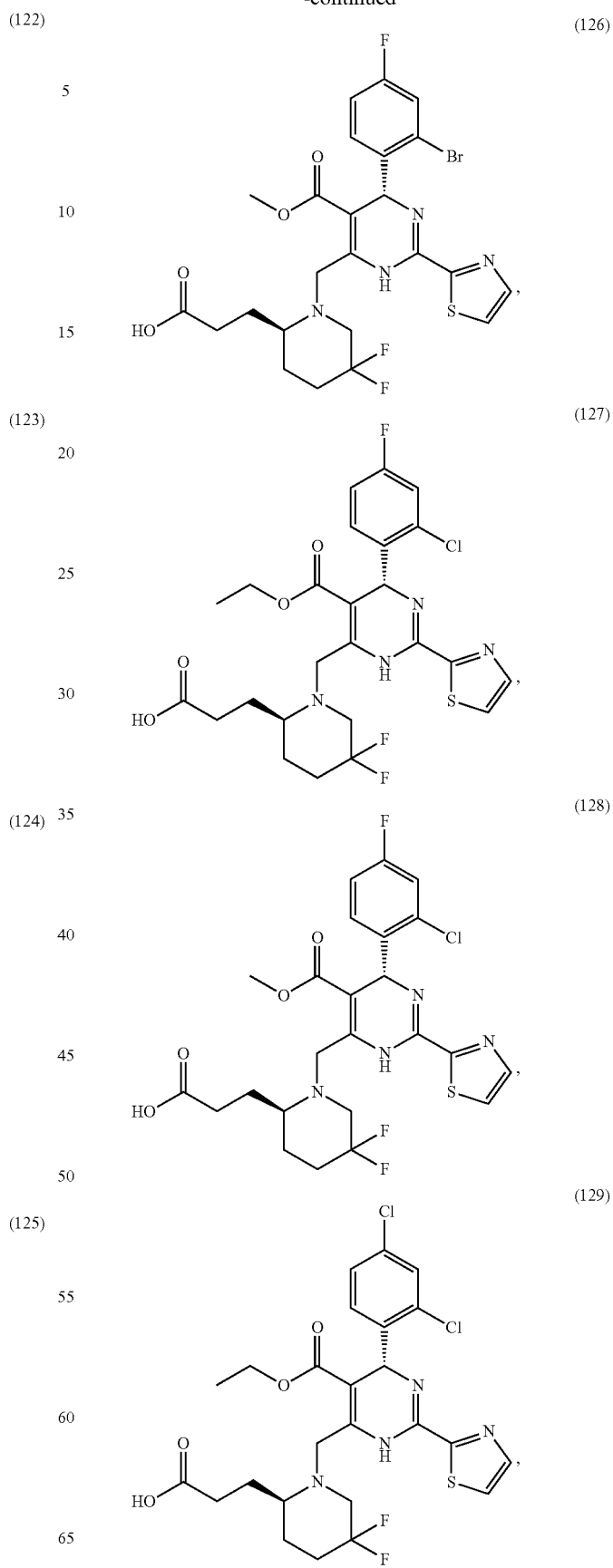

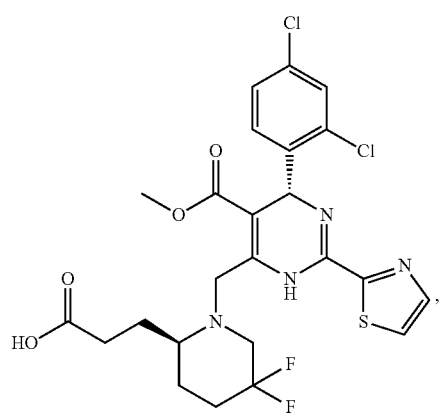
(130)
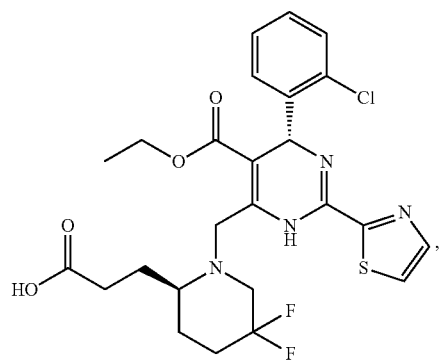
(131)
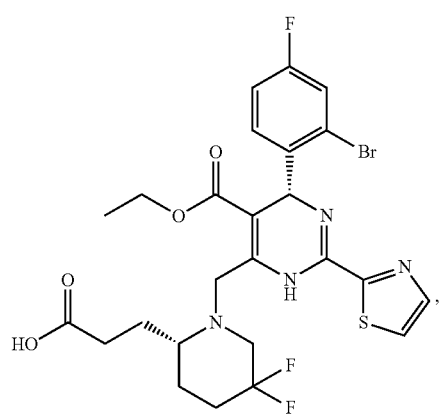
(132)
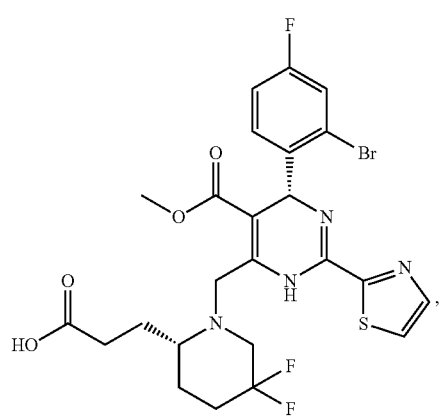
(133)
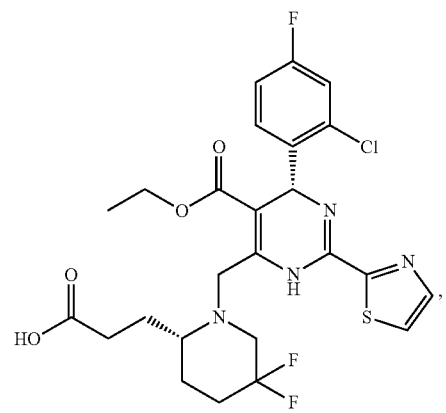
(134)
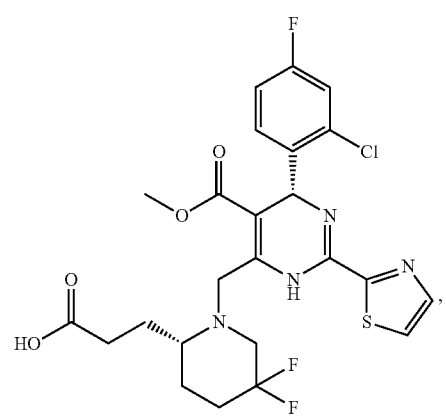
(135)
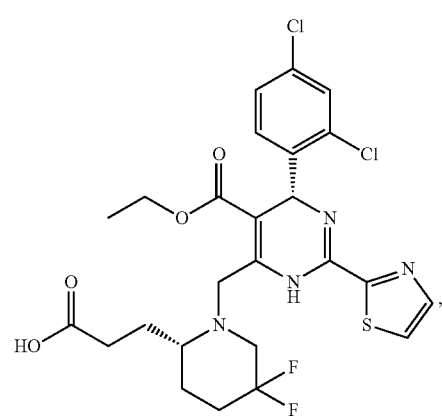
(136)
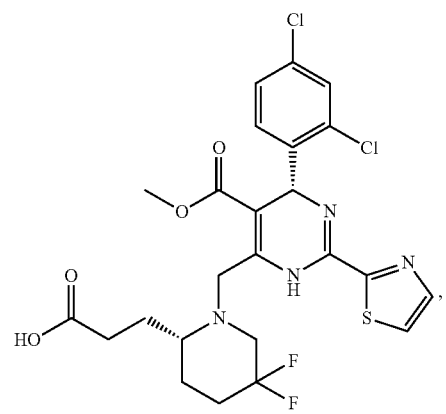
(137)

-continued
(138)
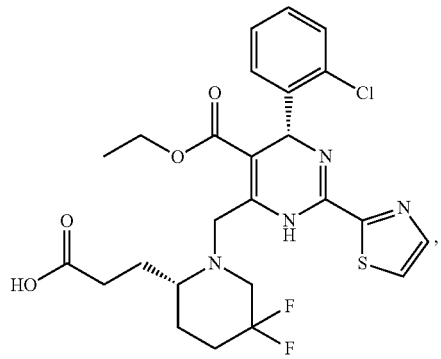
(139)
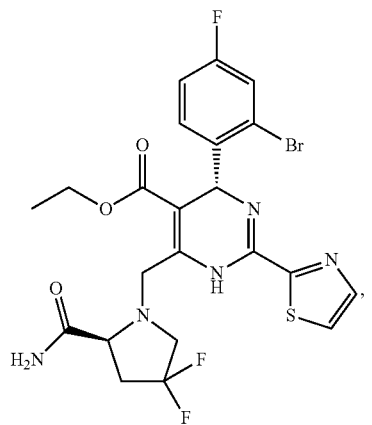
(140)
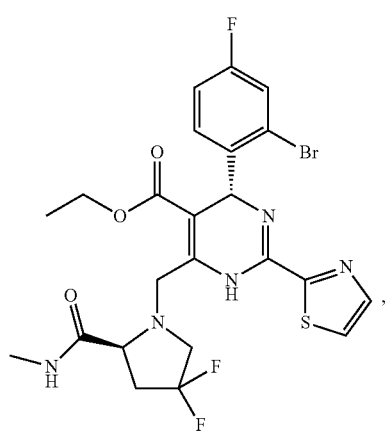
(141)
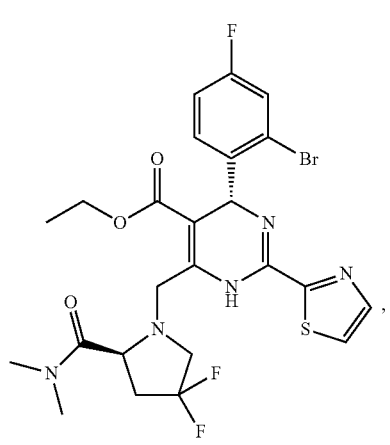
(142)
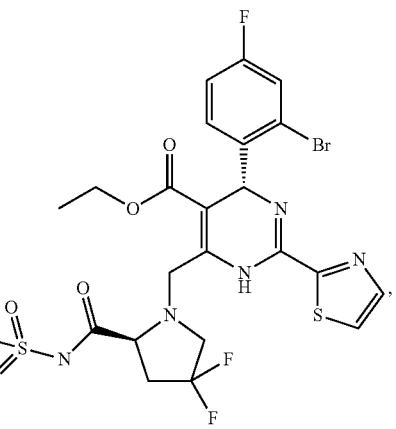
(143)
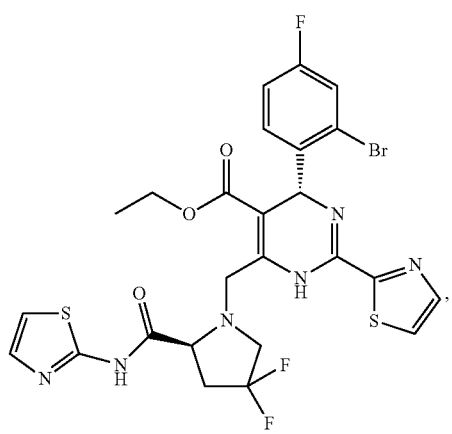
(144)
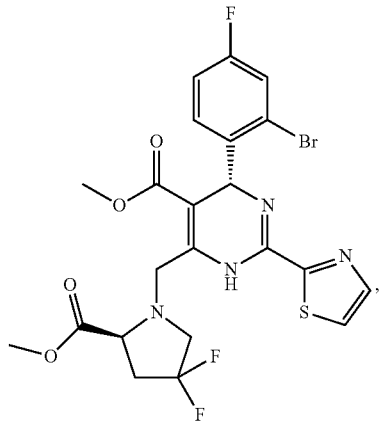

(145)
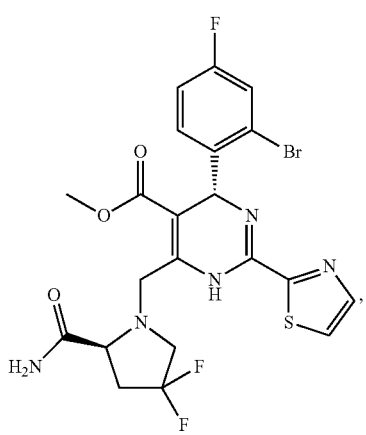
(146)
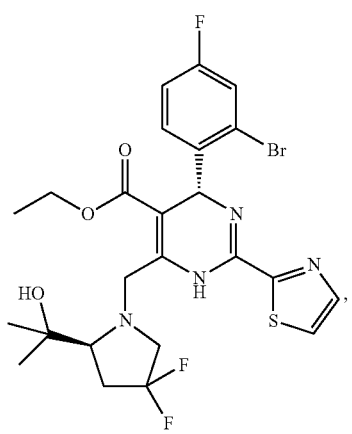
(147)
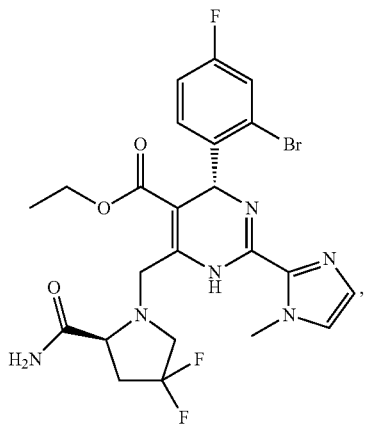
(148)
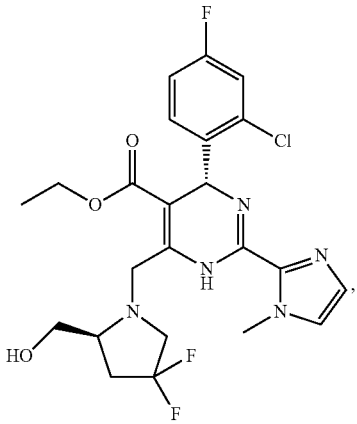
(149)
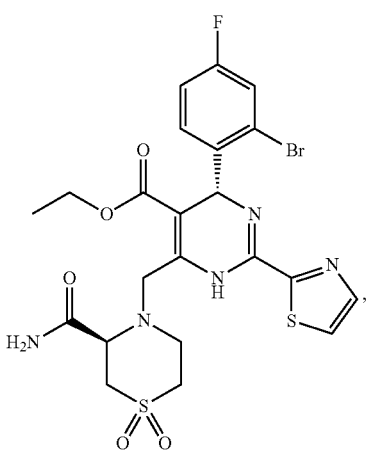
(150)
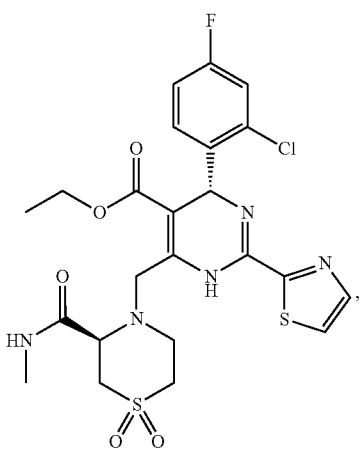

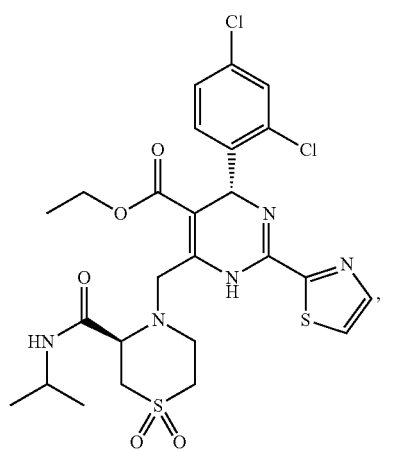
(151)
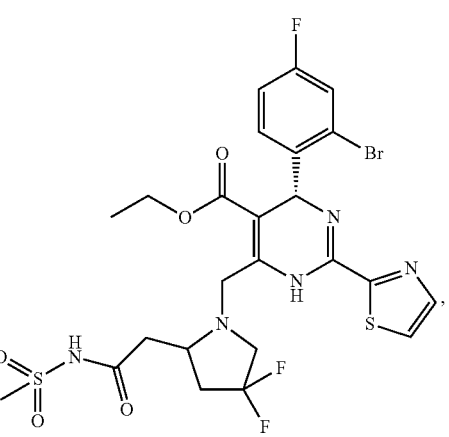
(154)
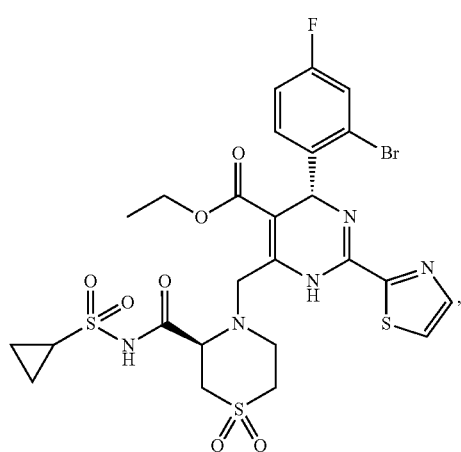
(152)
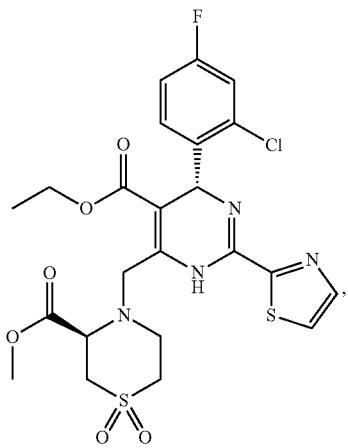
(155)
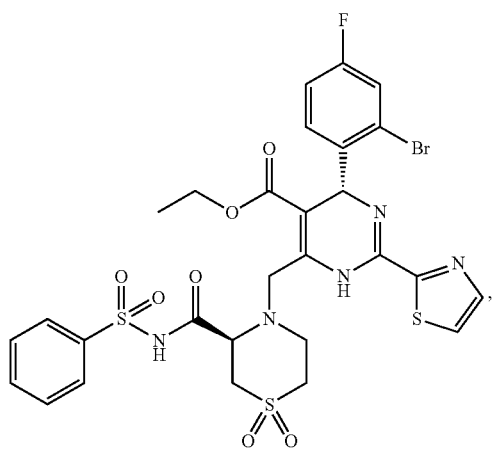
(153)
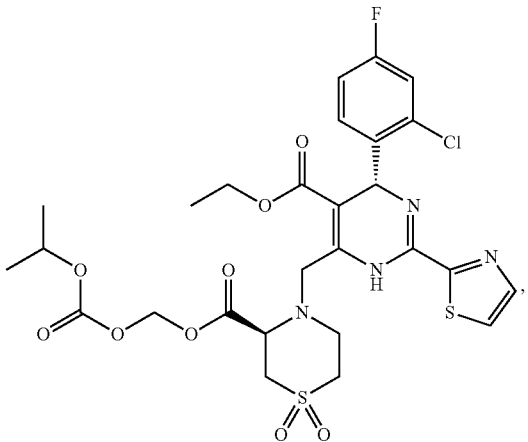
(156)

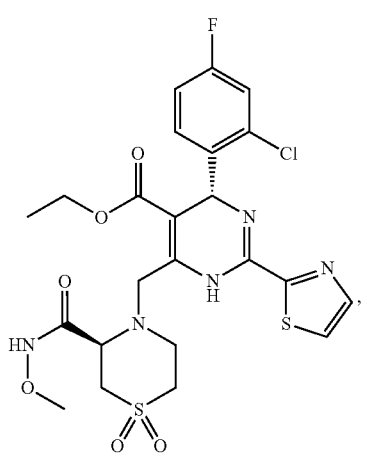
(157)
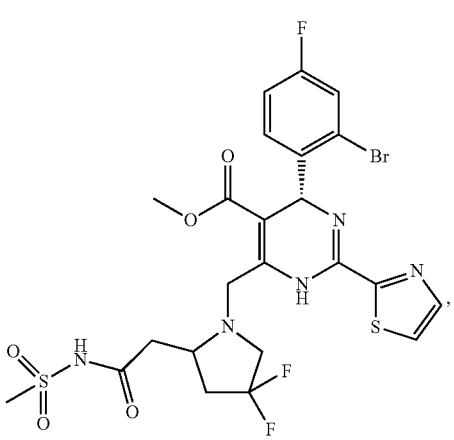
(160)
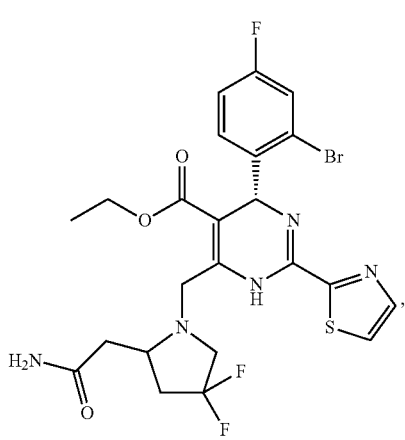
(158)
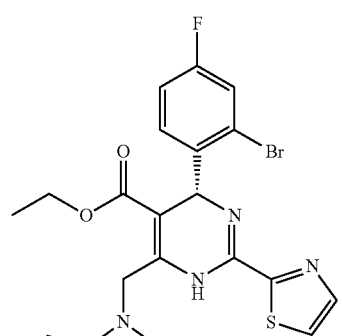
(161)
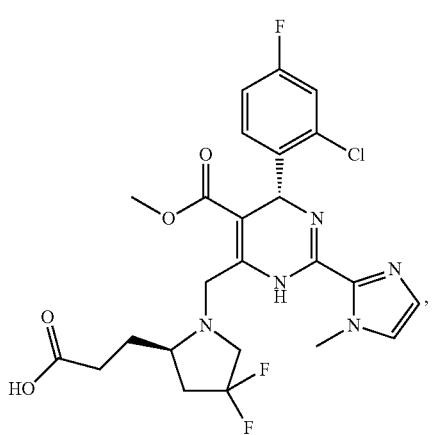
(159)
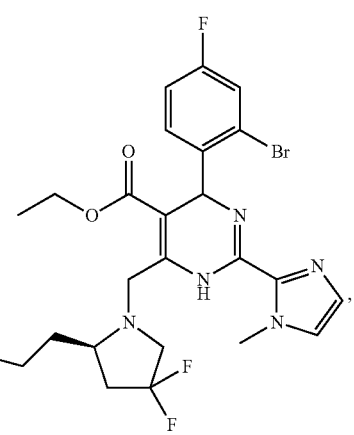
(162)

(163)
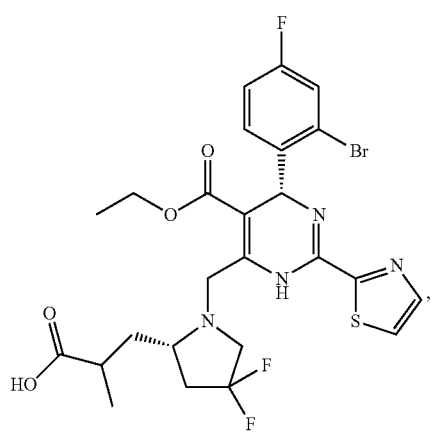
(164)
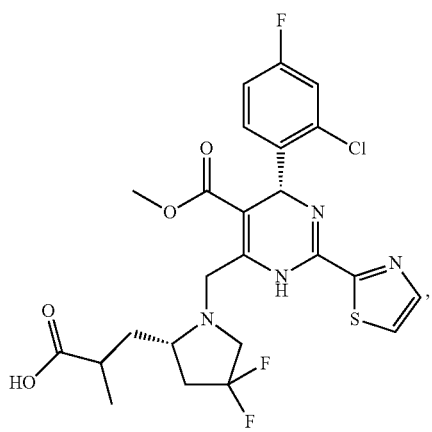
(165)
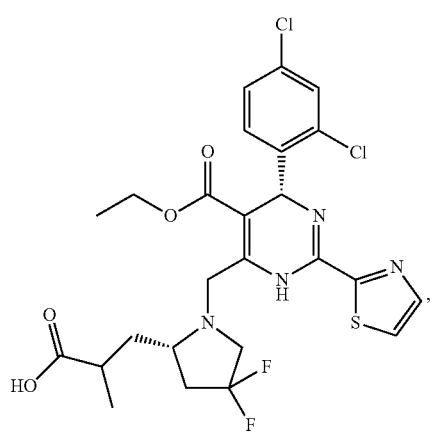
(166)
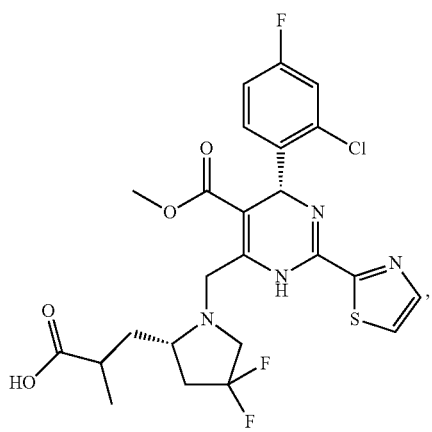
(167)
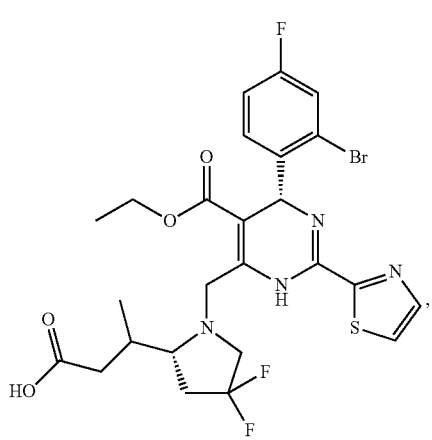
(168)

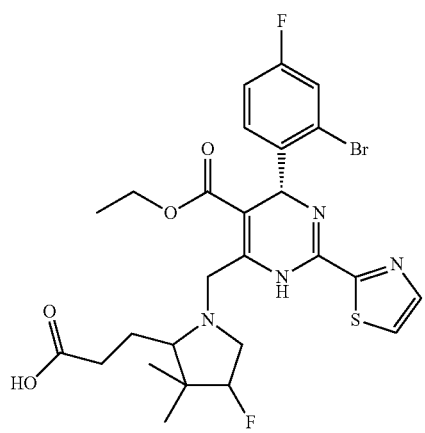
(169)
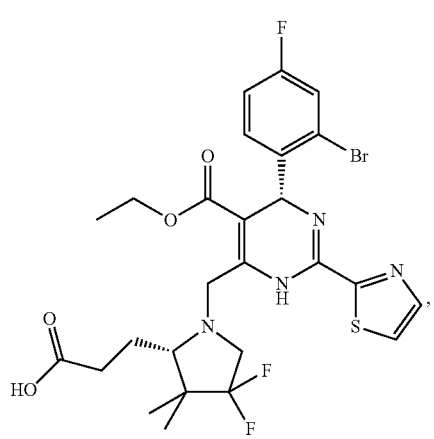
(170)
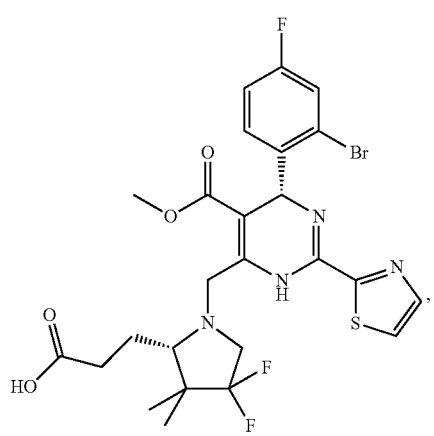
(171)
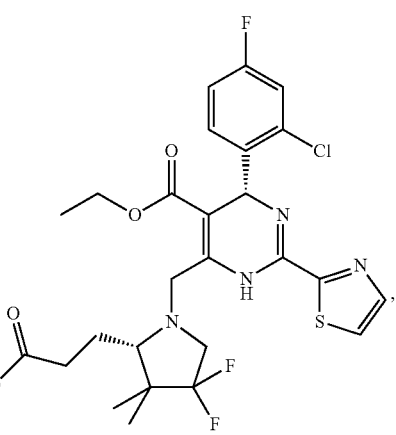
(172)
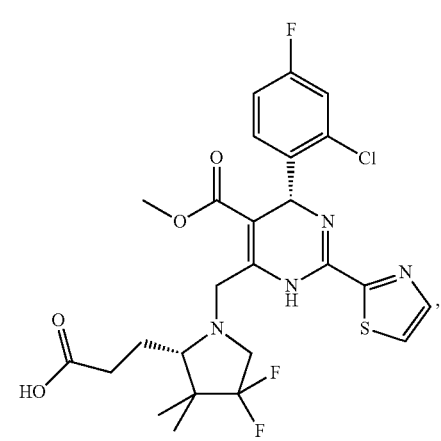
(173)
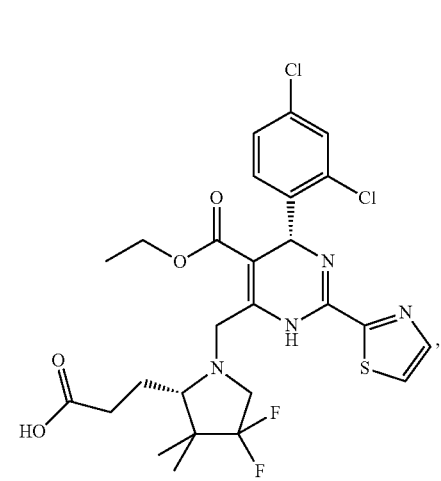
(174)

(175)
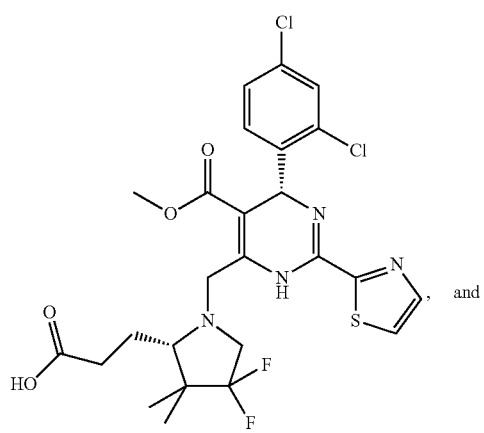
and
(176)
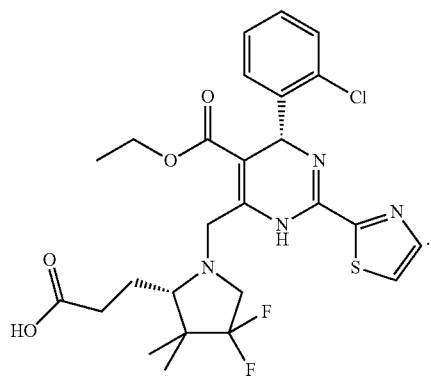
In another aspect, provided herein is one of the compounds as follows, or an enantiomer, a diastereoisomer, a tautomer, a hydrate, a solvate, or a pharmaceutically acceptable salt thereof, and not limited to:
(8-1)
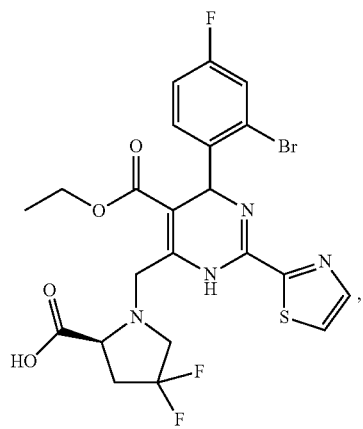
(8-2)
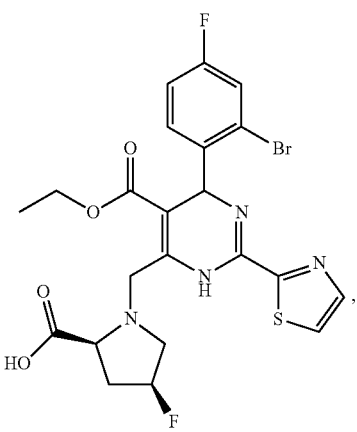
(8-3)
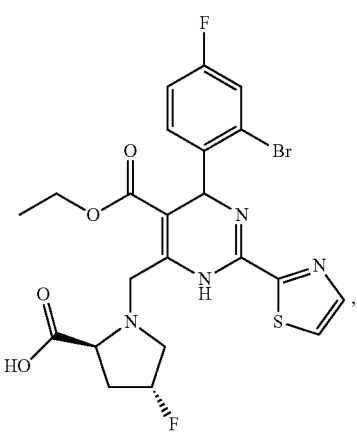
(8-4)
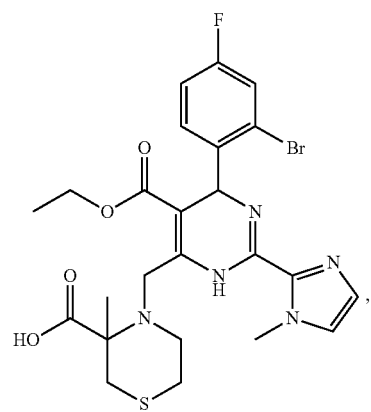

(8-5)
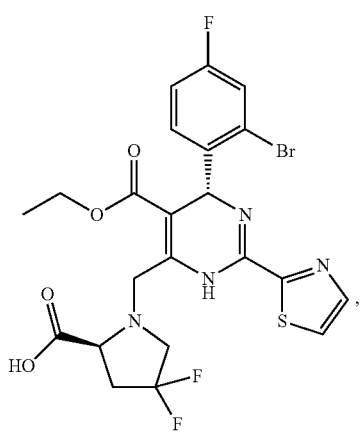
(8-8)
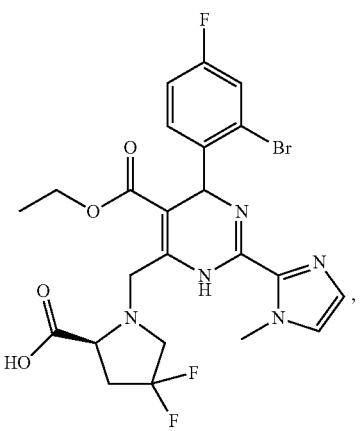
(8-6)
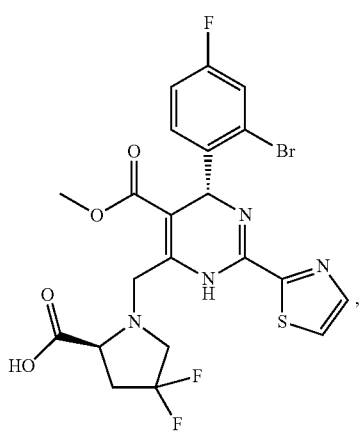
(8-9)
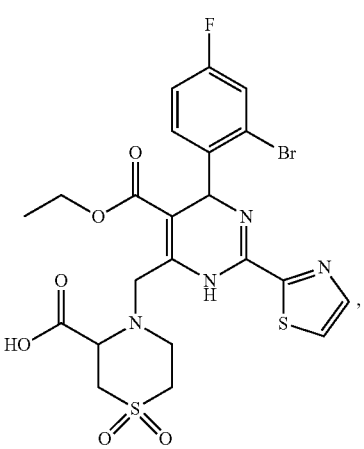
(8-7)
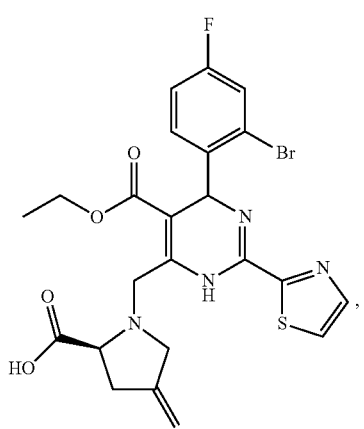
(8-10)
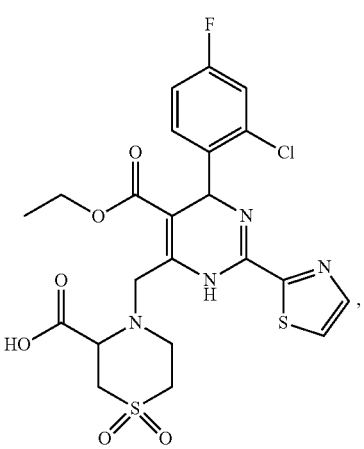

(8-11)
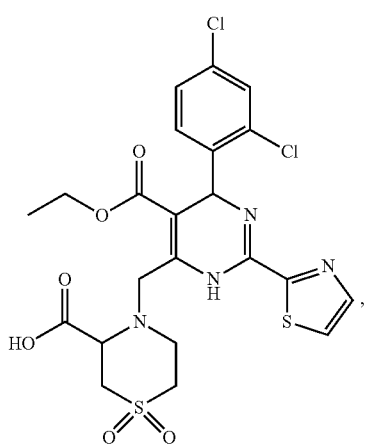
(8-12)
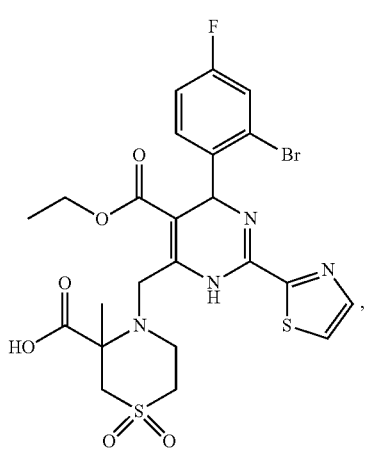
(8-13)
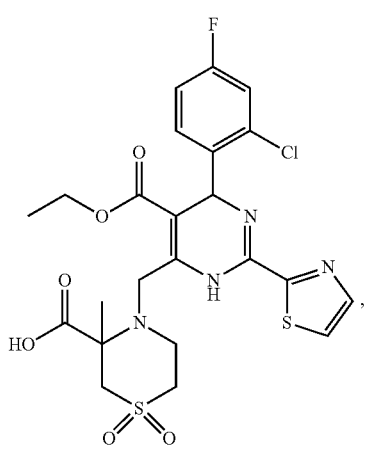
(8-14)
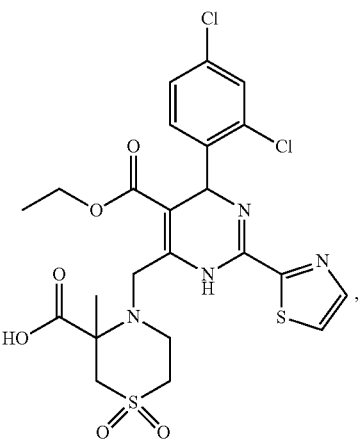
(8-15)
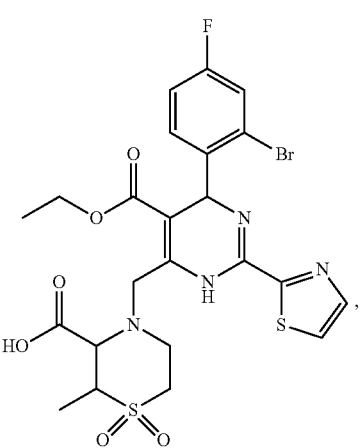
(8-16)
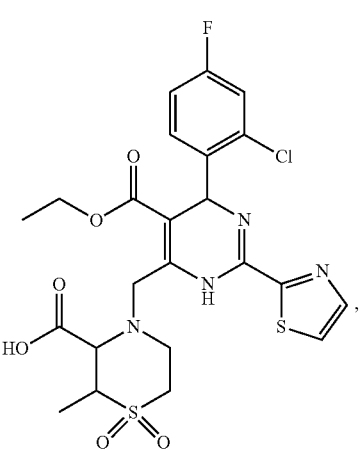

(8-17) 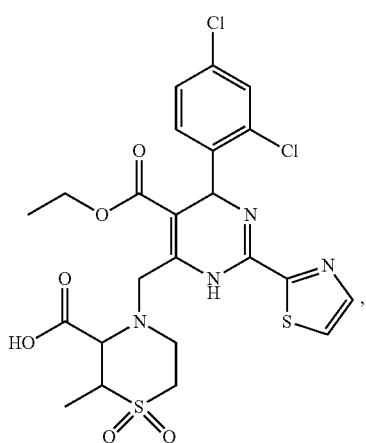
(8-20) 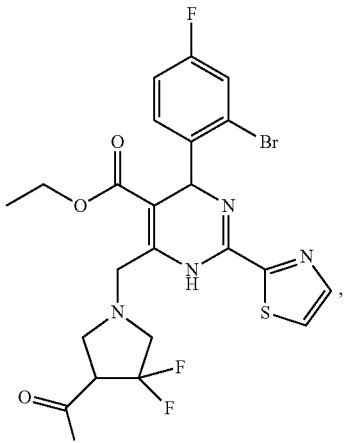
(8-18) 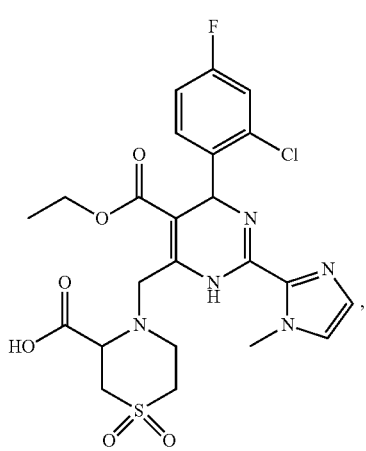
(8-21) 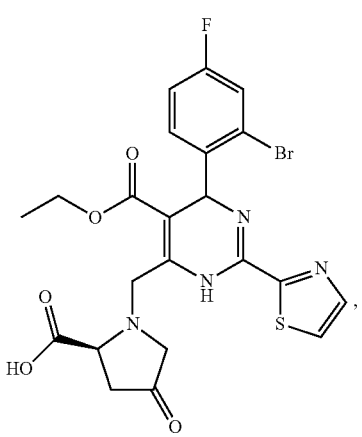
(8-19) 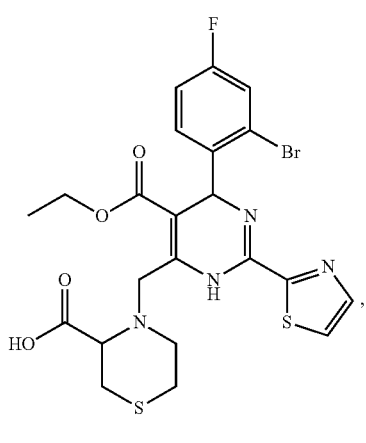
(8-22)

-continued
(8-23)
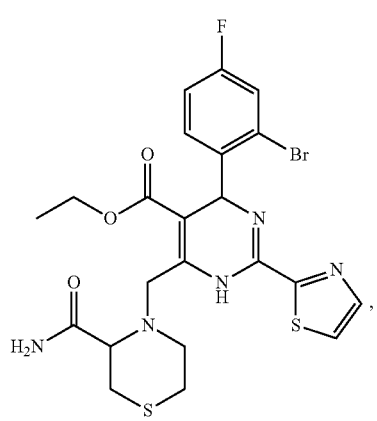
(8-24)
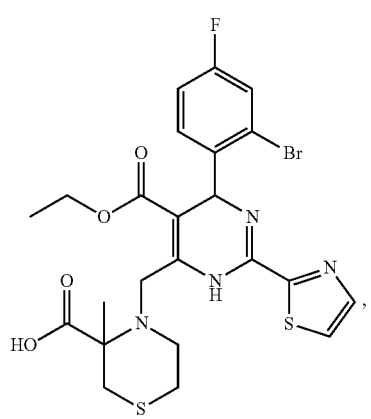
(8-25)
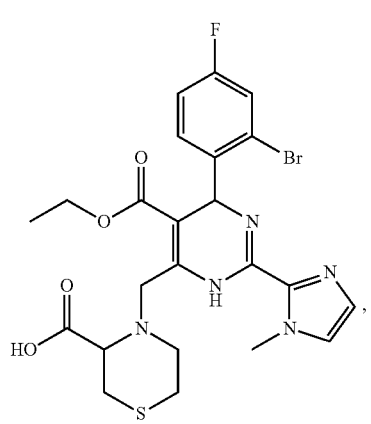
(8-26)
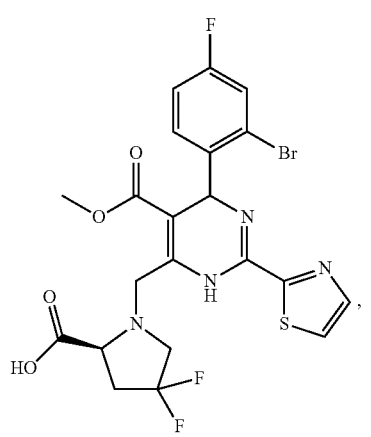
-continued
(8-27)
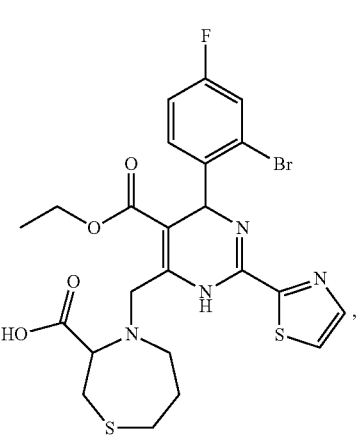
(8-28)
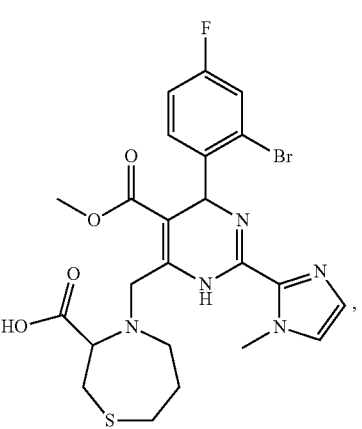
(8-29)
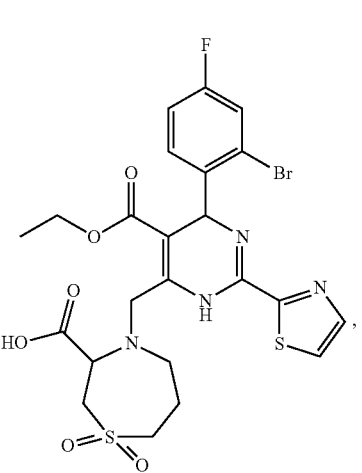

-continued
(8-30)
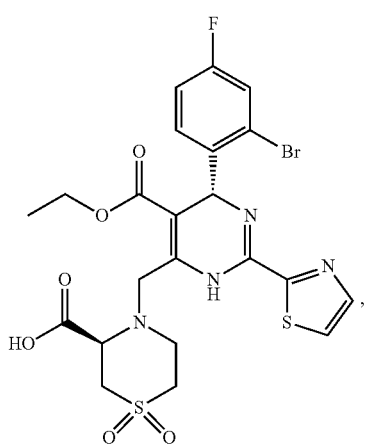
(8-31)
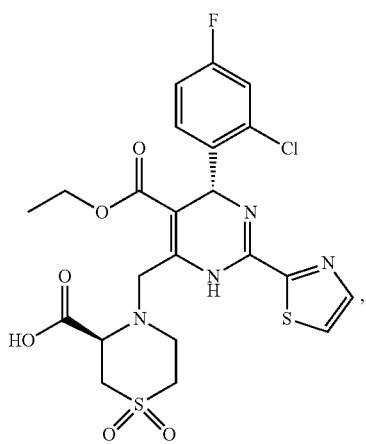
(8-32)
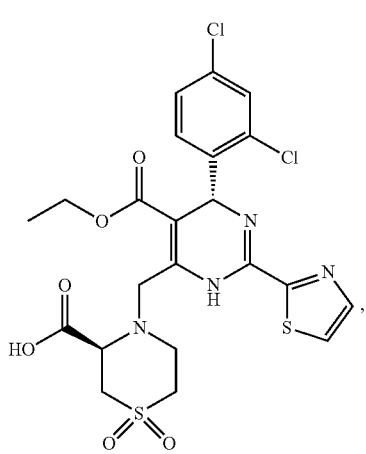
-continued
(8-33)
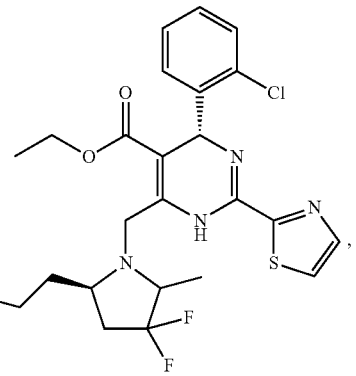
(8-34)
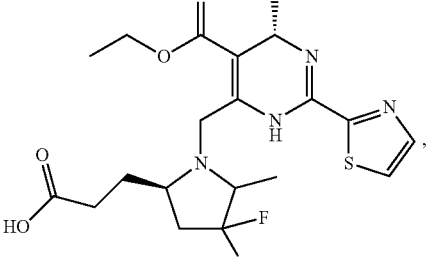
(8-35)
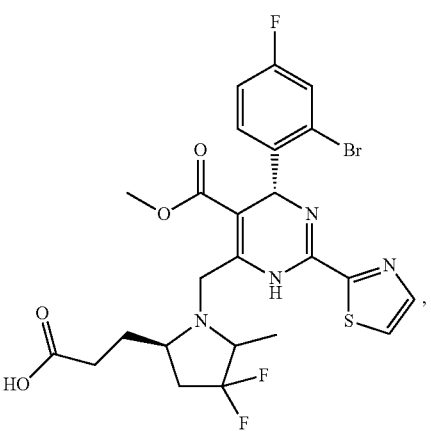

(8-36)
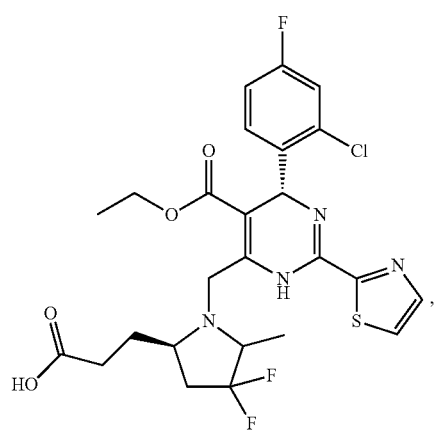
(8-37)
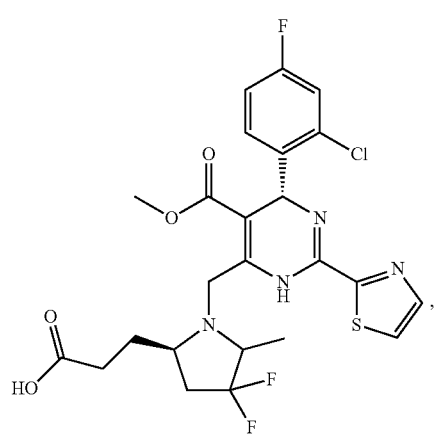
(8-38)
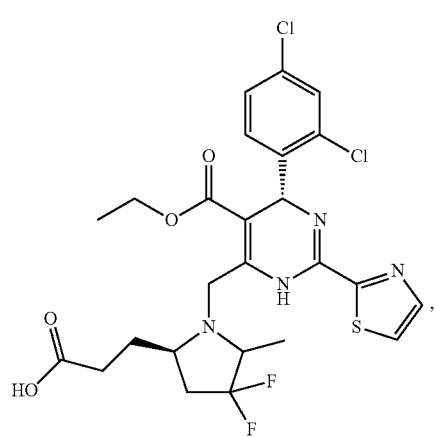
(8-39)
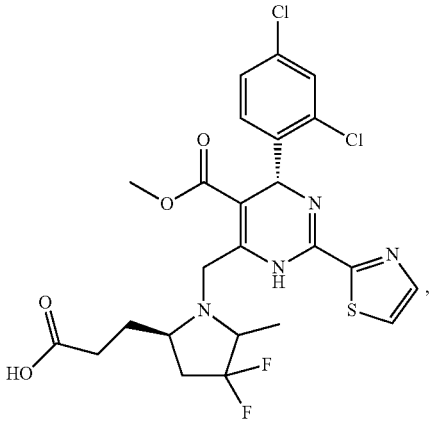
(8-40)
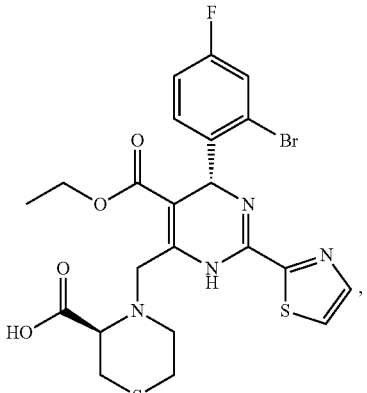
(8-41)
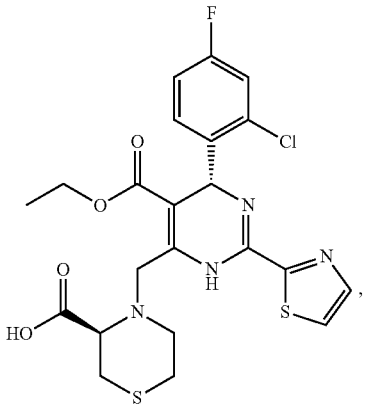
(8-42)
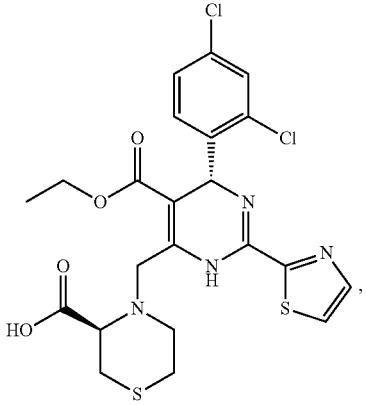

(8-43)
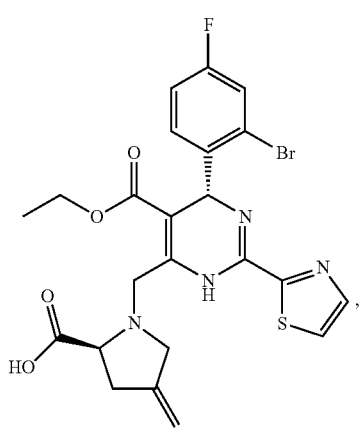
(8-44)
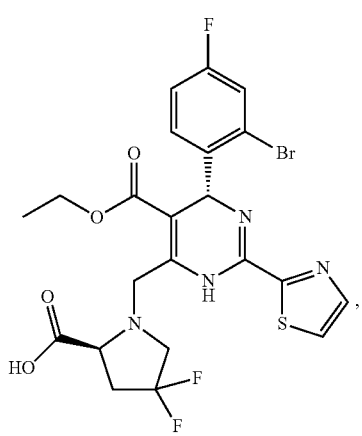
(8-45)
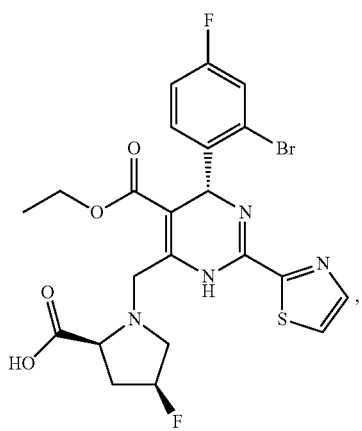
(8-46)
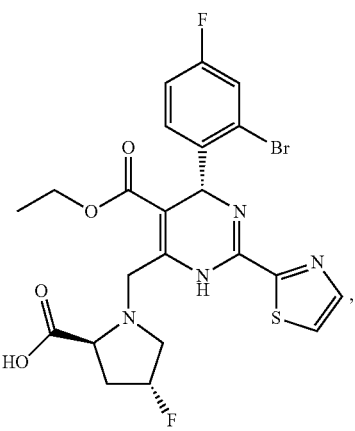
(8-47)
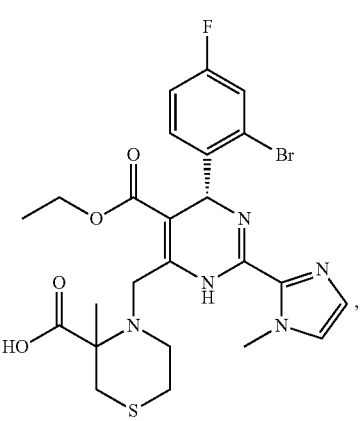
(8-48)
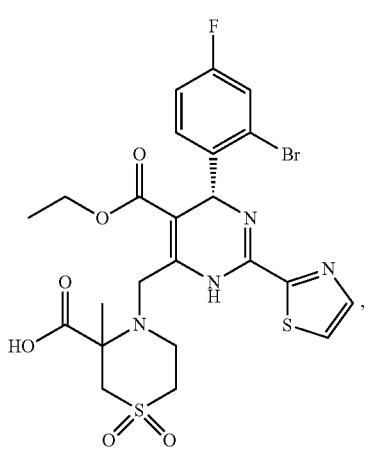

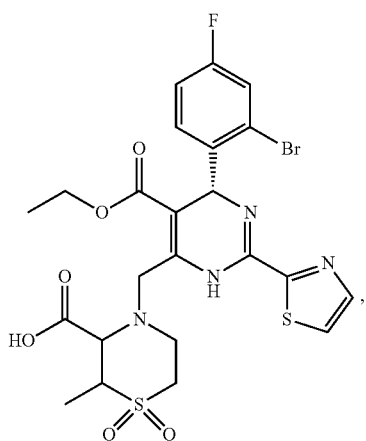
(8-49)
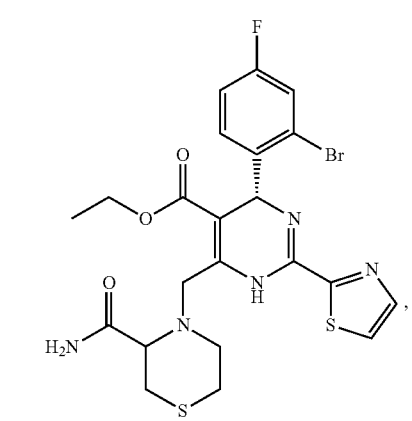
(8-52)
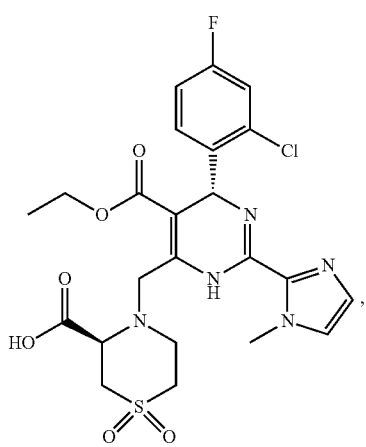
(8-50)
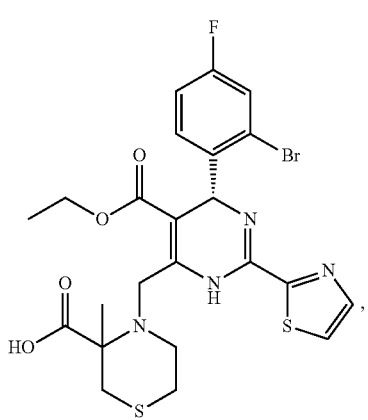
(8-53)
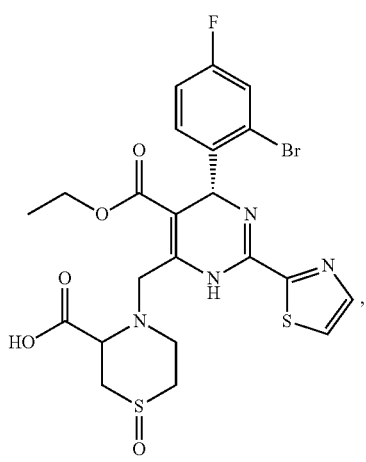
(8-51)
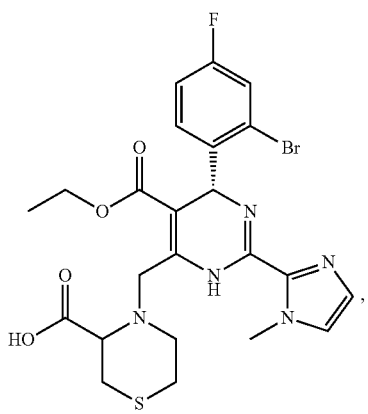
(8-54)

(8-55)

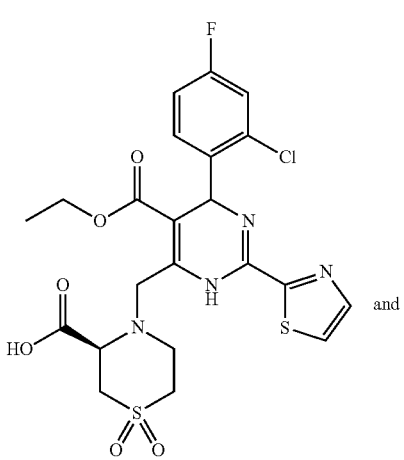

and (8-56)

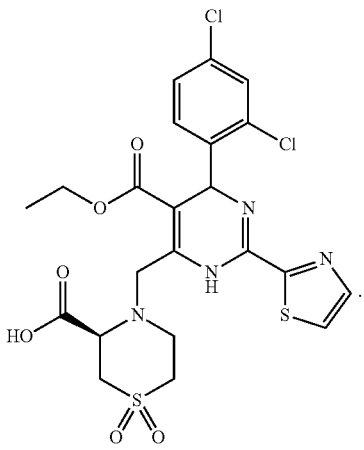

In one aspect, provided herein is a pharmaceutical composition comprising the compound disclosed herein, and a pharmaceutically acceptable carrier, excipient, diluent, adjuvant, vehicle or a combination thereof.

In certain embodiments, the pharmaceutical composition further comprises an anti-HBV agent.

In certain embodiments, the anti-HBV agent is a HBV polymerase inhibitor, immunomodulator or interferon.

In certain embodiments, the anti-HBV agent comprises at least one selected from the group consisting of lamivudine, telbivudine, tenofovir, entecavir, adefovir dipivoxil, alfaferone, alloferon, celmoleukin, clevudine, emtricitabine, famciclovir, feron, fepatect CP, intefen, interferon α-1b, interferon α, interferon α-2, interferon α-2a, interferon α-2b, interferon β-1a, interleukin-2, mivotilate, nitazoxanide, peginterferon alfa-2a, ribavirin, roferon-A, sizofiran, euforavac, rintatolimod, phosphazid, heplisav, levamisole, and propagermanium.

In another aspect, provided herein is use of the compound or the pharmaceutical composition in the manufacture of a medicament for preventing, managing, treating or lessening a viral disease or a HBV disease.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provised herein is the compound or the pharmaceutical composition in the manufacture of a medicament for use in preventing, managing, treating or lessening a viral disease or a HBV disease.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provided herein is to a method for preventing, managing, treating or lessening a viral disease or a HBV disease comprising administering to a patient a therapeutically effective amount of the compound or the pharmaceutical composition.

In some embodiments, the viral disease or HBV disease is hepatitis B infection or a disease caused by hepatitis B infection.

In other embodiments, the disease caused by hepatitis B infection is cirrhosis or hepatocellular carcinoma.

In another aspect, provided herein are methods for preventing, managing, treating or lessening a viral disease or a HBV disease, which comprises administering a pharmaceutically effective amount of the compound disclosed herein or the pharmaceutical composition disclosed herein to a patient.

In another aspect, provided herein are methods for preventing, managing, treating or lessening a viral disease or a HBV disease in a patient, which comprises administering a pharmaceutically effective amount of the compound disclosed herein to a patient.

In another aspect, provided herein are methods for preventing, managing, treating or lessening a viral disease or a HBV disease in a patient, which comprises administering a pharmaceutically effective amount of the pharmaceutical compositions disclosed herein to a patient.

In another aspect, provided herein is use of the compound disclosed herein in the manufacture of a medicament for preventing, managing, or treating a viral disease or a HBV disease, and lessening the severity of a viral disease or a HBV disease.

In another aspect, provided herein is use of the pharmaceutical composition disclosed herein in the manufacture of a medicament for preventing, managing, or treating a viral disease or a HBV disease, and lessening the severity of a viral disease or a HBV disease in a patient.

In some embodiments, the organism or patient is a mammal; in other embodiments, the organism or patient is a human. In still other embodiments, the method further comprises contacting the kinase or organism with a HBV therapeutic agent.

In another aspect, provided herein is a method of inhibiting HBV infection, comprising contacting a cell or a plurality of cells with an effective HBV inhibiting amount of a compound disclosed herein or a composition thereof. In other embodiments, the method further comprises contacting the cells with a HBV therapeutic agent.

In another aspect, provided herein is a method of treating HBV disease, the method comprises administering to a patient in need of such treatment an effective therapeutic amount of a compound disclosed herein or a composition thereof. In other embodiments, the method further comprises administering to the patient a HBV therapeutic agent.

In another aspect, provided herein is a method of inhibiting a HBV infection, the method comprises administering to a patient in need of an effective therapeutic amount of a compound disclosed herein or a composition disclosed herein. In other embodiments, the method further comprises administering to the patient a HBV therapeutic agent.

In another aspect, provided herein include methods of preparing, methods of separating, and methods of purifying the compounds of Formula (I) or (Ia) and a specific compound.

Provided herein includes the use of a compound disclosed herein, or a pharmaceutically acceptable salt thereof, in the manufacture of a medicament for inhibiting HBV infection effectively, including those described herein. The compounds disclosed herein are useful in the manufacture of a medicament for inhibiting HBV infection. The compounds disclosed herein are also useful in the manufacture of a medicament to attenuate, prevent, manage or treat disorders through inhibition of HBV. Also provided herein is a pharmaceutical composition comprising a therapeutically effective amount of a compound of Formula (I) or (Ia) and a specific compound in association with at least one pharmaceutically acceptable carrier, adjuvant or diluent.

Also provided herein is a method of inhibiting HBV disorders in a subject having or susceptible to such disorder, the method comprising treating the subject with a therapeutically effective amount of a compound of Formula (I) or (Ia) and a specific compound.

Unless otherwise stated, all stereoisomers, geometric isomers, tautomers, N-oxides, hydrates, solvates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The compounds disclosed herein also include salts of such compounds which are not necessarily pharmaceutically acceptable salts, and which may be useful as intermediates for preparing and/or purifying compounds of Formula (I) or (Ia) and/or for separating enantiomers of compounds of Formula (I) or (Ia) or and specific compounds.

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, malic acid, 2-hydroxy acrylic acid, lactic acid, citric acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid; a sulfonic acid, such as p-toluenesulfonic acid, benzenesulfonic acid, methanesulfonic acid, ethanesulfonic acid or trifluoromethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide, ammonium, a salt of $N^+(R^{14})_4$ or an alkaline earth metal hydroxide, and the like. Some non-limiting examples of suitable salts include organic salts derived from amino acids, such as glycine and arginine, ammonia (primary, secondary, and tertiary amines), salts of $N^+(R^{14})_4$, such as $R^{14}$ is H, $C_{1-4}$ alkyl, $C_{6-10}$ aryl or $C_{6-10}$ aryl-$C_{1-4}$-alkyl, and cyclic amines, such as piperidine, morpholine and piperazine, and inorganic salts derived from sodium, calcium, potassium, magnesium, manganese, iron, copper, zinc, aluminum, lithium, and the like. Further salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

Pharmaceutical Composition, Formulations, Uses and Administration of Compounds and Pharmaceutical Compositions The invention features pharmaceutical compositions that include a compound of Formula (I) or (Ia), a compound listed herein, or a compound named in Examples 1 to 44, and a pharmaceutically acceptable carrier, adjuvant, or excipient. The compound disclosed herein can inhibit HBV effectively, and is suitable for use in treating or lessening the diseases induced by viruses in a patient, especially acute and chronic persistent HBV infections. Chronic viral diseases induced by HBV can worsen the morbidity and the chronic HBV infection can cause liver cirrhosis and/or henatocellular carcinoma in many cases.

The compounds disclosed herein are suitable for the treatment of acute and chronic viral infections, particularly suitable for inhibiting HBV effectively. The compounds disclosed herein are suitable for use in treating or lessening the diseases induced by viruses in a patient, especially acute and chronic persistent HBV infections. Chronic viral diseases induced by HBV can worsen the morbidity and the chronic HBV infection can cause liver cirrhosis and/or henatocellular carcinoma in many cases.

The present invention includes pharmaceutical preparations which, besides nontoxic, inert pharmaceutically suitable carriers, comprise one or more compounds disclosed herein or a combination thereof or which consist of one or more active ingredients disclosed herein or a combination thereof.

The pharmaceutical preparations mentioned above may also comprise other active pharmaceutical ingredients apart from the compounds disclosed herein.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Troy et al., *Remington: The Science and Practice of Pharmacy*, 21st ed., 2005, Lippincott Williams & Wilkins, Philadelphia, and Swarbrick et al., *Encyclopedia of Pharmaceutical Technology*, eds. 1988-1999, Marcel Dekker, New York, all of each of which are herein incorporated by reference in their entireties, are disclosed various carriers used in formulating pharmaceutically acceptable compositions and known techniques for the preparation thereof. Except in so far as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some non-limiting examples of materials which can serve as pharmaceutically acceptable carriers include ion exchangers, aluminium, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants. As a matter of convenience, local anesthetics, preservatives, buffering agents and so on, can be dissolved in carriers directly.

The pharmaceutical composition comprising the compound disclosed herein may be administered in any of the following routes: orally, inhaled by spray, rectally, nasally, locally, vaginally, parenterally such as subcutaneous, intravenous, intramuscular, intraperitoneal, intrathecal, intraventricular, intrasternal, or intracranial injection or infusion, or administered with the aid of an explanted reservoir, wherein the administration routes by orally, intramuscular, intraperitoneal or intravenous injection are preferred.

The compound or the acceptable pharmaceutical composition comprising the compound disclosed herein may be administered in a unit dosage form. The dosage form may be in a liquid form, or a solid form. The liquid form includes true solution, colloids, particulates, emulsions, suspensions. Other dosage forms include tablets, capsules, dropping pills, aerosols, pills, powder, solutions, suspensions, emulsions, granules, suppositories, lyophilized powder for injection, clathrates, implants, patches, liniments, and the like.

Oral tablets and capsules may comprise excipients, e.g., binders such as syrup, Arabic gum, sorbitol, tragacanth, or polyvinylpyrrolidone; fillers such as lactose, sucrose, corn starch, calcium phosphate, sorbitol, aminoacetic acid; lubricants such as magnesium stearate, saponite, polyethylene glycol, silica, disintegrating agents such as potato starch, or acceptable moisturizing agents such as sodium lauryl sulfate. Tablets may be coated by using known methods in pharmaceutics.

Oral solution may be made as a suspension of water and oil, a solution, an emulsion, syrup or an elixir, or made as a dried product to which water or other medium is added before use. This liquid preparation may comprise conventional additives, e.g., suspending agents such sorbitol, cellulose methyl ether, glucose syrup, gelatin, hydroxyethyl cellulose, carboxymethyl cellulose, aluminum stearate gel, hydrogenated edible grease; emulsifying agents such as lecithin, sorbitan monooleate, Arabic gum; or non-aqueous carriers (possibly including edible oil), such as almond oil, grease such as glycerin, ethylene glycol, or ethanol; antiseptics such as methyl or propyl p-hydroxybenzoate, sorbic acid. If desired, a flavoring agent or a colorant may be added.

Suppository may comprise a conventional suppository substrate, such as cocoa butter or other glyceride.

For non-gastric administration, the liquid dosage form is usually made of the compound and a sterilized carrier. The preferred carrier is water. According to the carrier selected and the drug concentration, the compound can be dissolved in the carrier or made into a suspension. When making an injection solution, the compound is firstly dissolved in water, and then filtered and sterilized before being packaged into an enclosed bottle or ampoule.

For topical application on skin, the compound disclosed herein may be made into a suitable form of ointment, lotion or cream, wherein the active ingredient is suspended or dissolved in one or more carrier(s). Some non-limiting examples of the carriers used for an ointment include mineral oil, liquid vaseline, albolene, propylene glycol, polyoxyethylene, polyoxypropylene, emulsified wax, water, and the like; Some non-limiting examples of the carriers used for a lotion and a cream include mineral oil, sorbitan monostearic ester, tween 60, cetyl esters wax, hexadecylene aromatic alcohol, 2-octyl dodecanol, benzyl alcohol, water, and the like.

In general, it has been proved that, advantageously, whether in human medicine or in veterinary medicine, the total dose of the active compound disclosed herein is about 0.5 to 500 mg every 24 hours, preferably 1 to 100 mg per kg body weight. If appropriate, the drug is administrated by single dose for multiple times, to thereby achieve the desired effect. The amount of the active compound in a single dose is preferably about 1 to 80 mg, more preferably 1 to 50 mg per kg weight body. Nevertheless, the dose may also be varied according to the type and body weight of the object to be treated, the kind and extent of severity of diseases, the type of the preparation and the administration manner of the drug, and the administration period or the time interval.

In one aspect, provided herein is the pharmaceutical composition further comprising an anti-HBV agent. And the anti-HBV agent is a HBV polymerase inhibitor, immunomodulator or interferon.

The HBV agent is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, euforavac, veldona, rintatolimod, phosphazid, heplisav, interferon α-2b, levamisole or propagermanium and so on.

In another aspect, provided herein is use of a compound and the pharmaceutical composition in the manufacture of a medicament for preventing, managing, treating or lessening the HBV disease in a patient, comprising administering a pharmaceutically effective amount to a patient. The HBV disease is a hepatic disease caused by hepatitis B virus infection or hepatitis B infection, including acute hepatitis, chronic hepatitis, cirrhosis and hepatocellular carcinoma. The symptoms of acute hepatitis B virus infection may be asymptomatic or may be the same as acute hepatitis. A patient with chronic virus infection may develop active disease, which can progress to cirrhosis and liver cancer.

Those additional agents may be administered separately from the compound-containing composition, as part of a multiple dosage regimen. Alternatively, those agents may be part of a single dosage form, mixed together with the compound disclosed herein in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions disclosed herein will be no more than the amount that would normally be administered in a composition comprising that therapeutic agent as the only active agent. In other embodiment, the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound disclosed herein may act synergistically.

The compound disclosed herein exhibits a relatively strong antiviral effect. This kind of compound has unexpected antiviral activity to HBV, and thus is adapted to be used for treating various virus-caused diseases, in particular acute and chronic viral diseases caused by HBV may lead to various syndromes having different extents of severity. As well known, chronic HBV infection may lead to hepatic cirrhosis and/or liver cell carcinoma.

Examples of indications capable of being treated by the compound disclosed herein include: acute and chronic viral infections capable of leading to infectious hepatitis, such as HBV infection, and particularly preferred chronic HBV infection and acute HBV infection.

The invention further relates to the use of the compounds and compositions defined above for producing a medicament for the treatment and prophylaxis of the diseases described above, preferably of viral diseases, in particular of hepatitis B.

General Synthetic Procedures

If any differences between the chemical name and chemical structure in the specification, the chemical structure is dominant.

Generally, the compounds disclosed herein may be prepared by methods described herein, wherein the substituents are as defined for Formulas (I) or (Ia), above, except where further noted. The following non-limiting schemes and examples are presented to further exemplify the invention.

Persons skilled in the art will recognize that the chemical reactions described may be readily adapted to prepare other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (200-300 mesh) was purchased from Qingdao Ocean Chemical Factory. $^1H$ NMR spectra were recorded with a Bruker 400 MHz or 600 MHz spectrometer using $CDCl_3$, $d_6$-DMSO, $CD_3OD$ or $d_6$-acetone as solutions (reported in ppm), and using TMS (0 ppm) or chloroform (7.25 ppm) as the reference standard. When peak multiplicities are reported, the following abbreviations are used: s (singlet), s, s (singlet, singlet), d (doublet), t (triplet), m (multiplet), br (broadened), dd (doublet of doublets), ddd (doublet of doublet of doublets), dt (doublet of triplets), br.s (broadened singlet), ddt (doublet of doublet of triplets), dddd (doublet of doublet of doublet of doublets), td (triplet of doublets) and brs (broadened singlet). Coupling constants, when given, are reported in Hertz (Hz).

Low-resolution mass spectral (MS) data were determined on an Agilent 6320 Series LC-MS spectrometer equipped with G1312A binary pumps and a G1316A TCC (Temperature Control of Column, maintained at 30° C.). A G1329A autosampler and a G1315B DAD detector were used in the analysis, and an ESI source was used on the LC-MS spectrometer.

Low-resolution mass spectral (MS) data were determined on an Agilent 6120 Series LC-MS spectrometer equipped with G1311A quaternary pumps and a G1316A TCC (Temperature Control of Column, maintained at 30° C.). A G1329A autosampler and a G1315D DAD detector were used in the analysis, and an ESI source was used on the LC-MS spectrometer.

Both Spectrographs were equipped with an Agilent Zorbax SB-C18 (2.1×30 mm, 5 μm). Injection volume was decided by the sample concentration. The flow rate was 0.6 mL/min; the peak of HPLC was recorded with UV-Vis detection at 210/254 nm. The mobile phases consisted of a combination of A (0.1% formic acid in $CH_3CN$) and B (0.1% formic acid in $H_2O$). The conditions of gradient elution are described in Table 1:

TABLE 1

| Mobile phase conditions of gradient elution with low resolution mass spectrometry | | |
|---|---|---|
| t (min) | A (CH$_3$CN, 0.1% HCOOH) | B (H$_2$O, 0.1% HCOOH) |
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 μm), 10 min, 0.6 mL/min flow rate, a combination of A (0.1% formic acid in CH$_3$CN) and B (0.1% formic acid in H$_2$O) in gradient mode (5 to 95%). Column was operated at 40 OC.

Purification of compounds by preparative chromatography was implemented on Agilent 1260 Series high performance liquid chromatography (HPLC) with UV detection at 278 nm (Daicel CHIRALPAK IC, 10.0×250 mm, 5 μm), 40 min, 2.0 mL/min flow rate, n-hexand/ethanol (97/3, v/v). Column was operated at 30 OC.

The following abbreviations are used throughout the specification:
DCM, CH$_2$Cl$_2$ methylene chloride
DMSO-d$_6$ dimethyl-d$_6$ sulfoxide
Acetone-d$_6$ CD$_3$COCD$_3$
D$_2$O deuterium oxide
CDCl$_3$ chloroform-d
CCl$_4$ carbon tetrachloride
Boc tert-butyloxycarbonyl
PE petroleum ether
EtOAc, EA ethyl acetate
K$_2$CO$_3$ potassium carbonate
NaHSO$_3$ sodium bisulfite
NaHSO$_4$ sodium bisulfate
NaHCO$_3$ sodium bicarbonate
Na$_2$SO$_4$ sodium sulfate
Na$_2$S$_2$O$_3$ sodium thiosulfate
NBS N-bromosuccinimide
c concentration
g gram
v/v, v:v volume ratio
mm millimeter
nm nanometer
μm micron
min minute
mol mole
mmol millimole
mL milliliter
L liter
DAST Diethylaminosulfur trifluoride
CuI cuprous iodide
MeLi lithium methide
DMAP 4-dimethylaminopyridine
DCC N,N-dicyclohexylcarbodiimide
DMF N,N-dimethylformamide
LiAlH$_4$ lithium aluminum hydride
THF tetrahydrofuran
TFA trifluoroacetic acid
KMnO$_4$ potassium permanganate
EDCI, EDC 1-(3-dimethylaminopropyl)-3-ethylcarbodiimide hydrochloride
HOAT 1-hydroxy-7-azabenzotriazole
Pd/C, Pd—C palladium on carbon
LiOH.H$_2$O lithium hydroxide monohydrate
TMSCl chlorotrimethylsilane
LDA lithium diisopropylamide
CH$_3$OH, MeOH methanol
[a]$_D^{25}$ specific rotation, measuring temperature is 25° C., using d sodium light.
t$_{1/2}$ half-life period
AUC area under the curve
Vss apparent volume of distribution
CL clearance
F absolute bioavailability
T$_{max}$ time to peak
C$_{max}$ peak concentration
hr*ng/mL blood concentration*time Synthetic Techniques

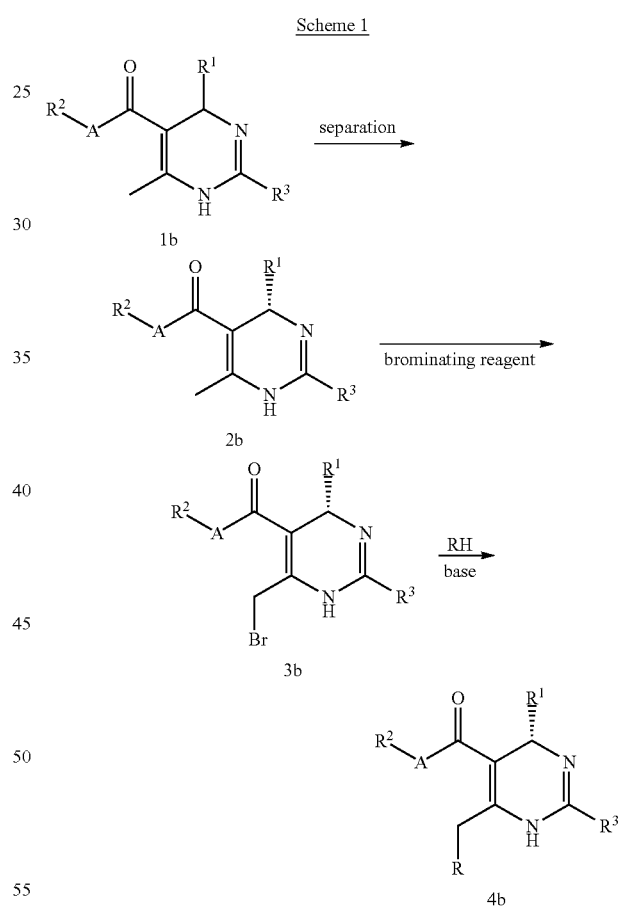

Scheme 1

The target compound 4b can be prepared by the process illustrated in scheme 1, wherein each R$^1$, R$^2$, R$^3$, A and R is as defined herein. Compound 2b can be prepared by separating compound 1b, and then bromination reaction of compound 2b with a brominating reagent to give compound 3b. Subsequently, compound 3b can react with RH under an alkaline condition to give the target compound 4b.

Scheme 2

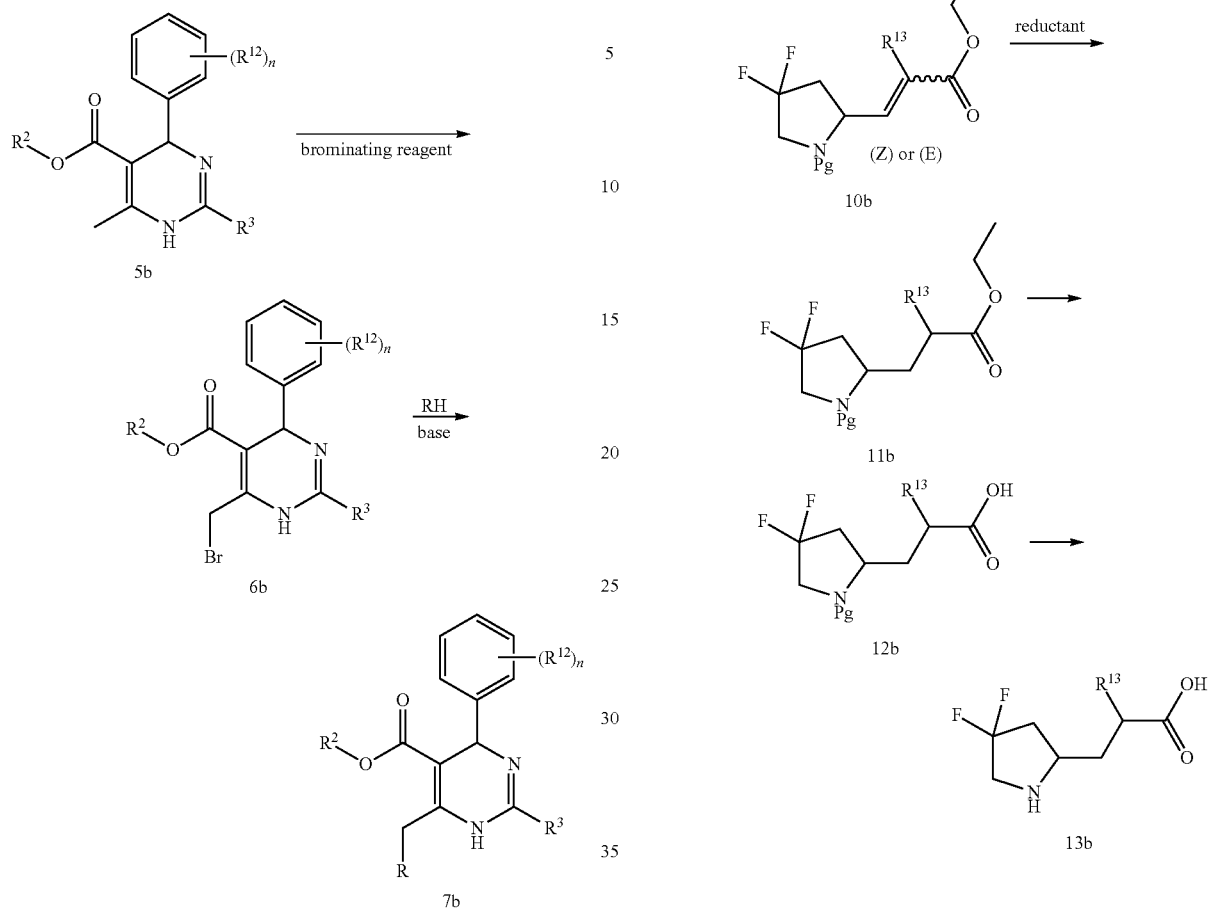

The target compound 7b can be prepared by the process illustrated in scheme 2, wherein each $R^{12}$, $R^2$, $R^3$ and R is as defined herein. Bromination reaction of compound 5b with brominating reagent to give compound 6b. Subsequently, compound 6b can react with RH under an alkaline condition to give the target compound 7b.

Scheme 3

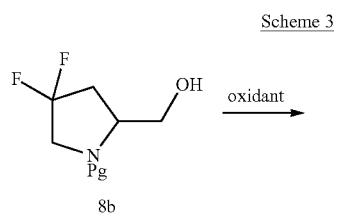

The target compound 13b can be prepared by the process illustrated in scheme 3, wherein $R^{13}$ is hydrogen or methyl. Pg is an amino protecting group, such as Boc, Fmoc, Cbz, and the like. Compound 8b can be converted to compound 9b in the presence of an oxidant (e.g. Dess-Martin periodinane). Wittig reaction of compound 9b with Wittig reagent to give compound 10b. Compound 10b can be reduced to afford compound 11b in the presence of a reductant, and then compound 11b can be converted to compound 12b by hydrolysis. Subsequently, the protecting group Pg of compound 12b can be removed to afford compound 13b.

Scheme 4

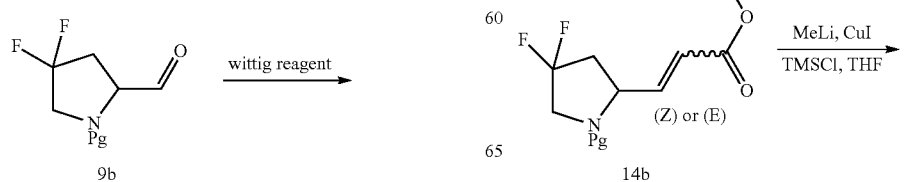

109
-continued

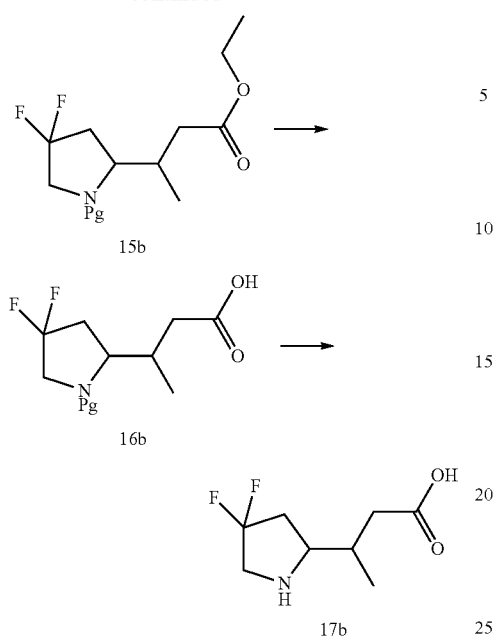

The target compound 17b can be prepared by the process illustrated in scheme 4, wherein Pg is an amino protecting group, such as Boc, Fmoc, Cbz, and the like. Compound 14b can be converted to compound 15b in the presence of CuI, MeLi and TMSCl, and then compound 15b can be converted to compound 16b by hydrolysis. Subsequently, the protecting group Pg of compound 16b can be removed to afford compound 17b.

Scheme 5

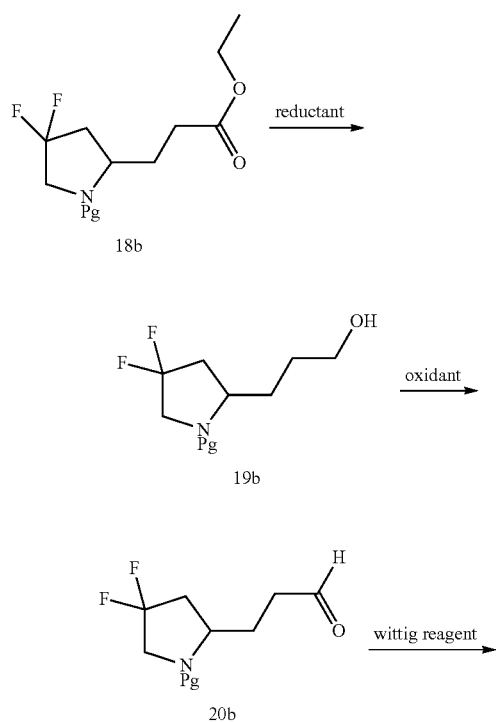

110
-continued

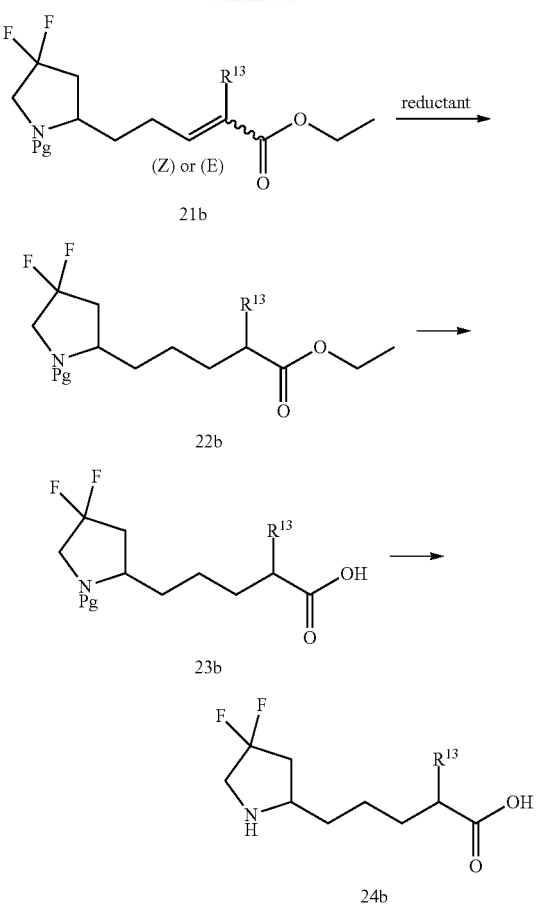

The target compound 24b can be prepared by the process illustrated in scheme 5, wherein $R^{13}$ is hydrogen or methyl. Pg is an amino protecting group, such as Boc, Fmoc, Cbz, and the like. Compound 18b can be converted to compound 19b in the presence of a reductant. Compound 19b can be converted to compound 20b in the presence of an oxidant (e.g. Dess-Martin periodinane). Wittig reaction of compound 20b with Wittig reagent to give compound 21b. Compound 21b can be reduced to afford compound 22b, and then compound 22b can be converted to compound 23b by hydrolysis. Subsequently, the protecting group Pg of compound 23b can be removed to afford compound 24b.

Scheme 6

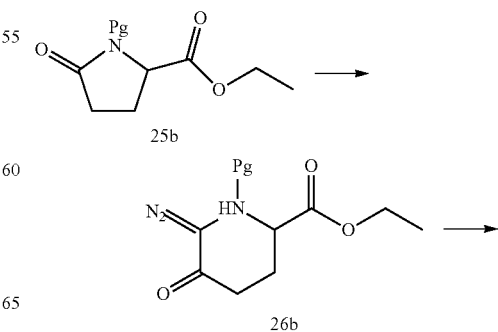

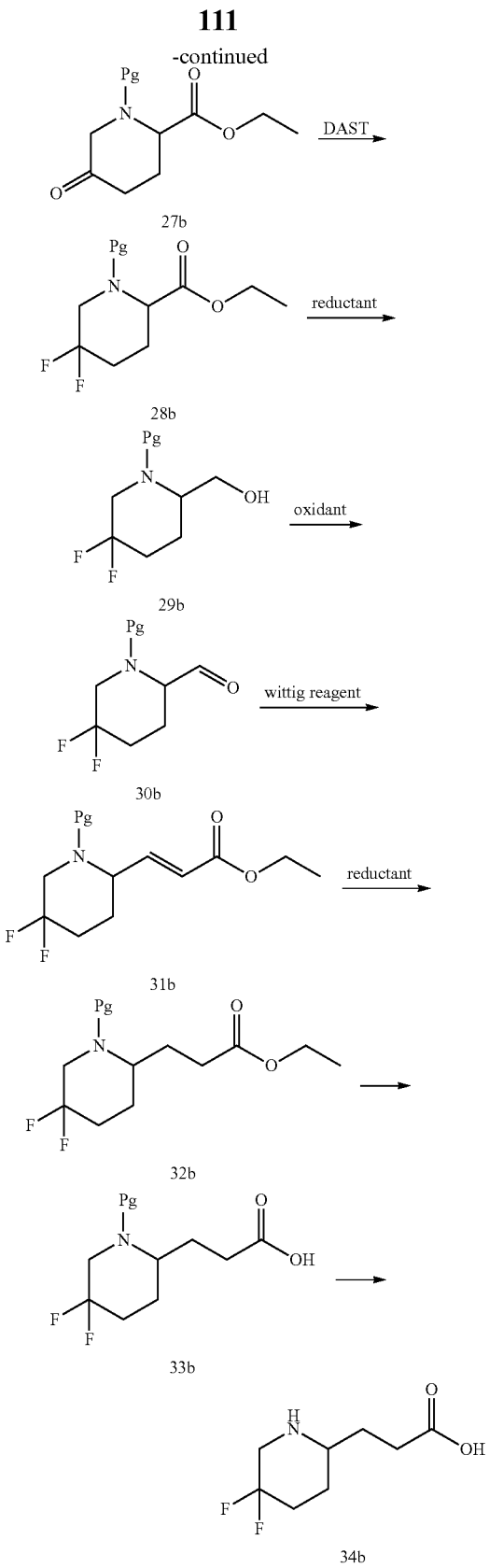

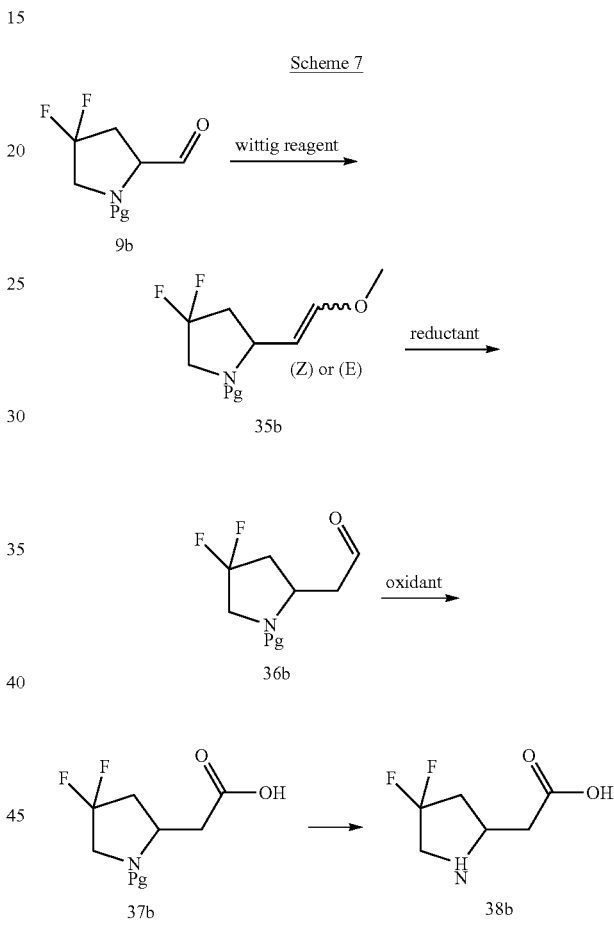

(trimethylsilyl)diazomethane and n-Butyllithium. Compound 26b can be converted to compound 27b in the presence of rhodium acetate. Compound 27b can react with DAST to give compound 28b. Compound 28b can be reduced to afford compound 29b in the presence of a reductant. Compound 29b can be converted to compound 30b in the presence of an oxidant (e.g. Dess-Martin periodinane). Compound 30b can react with Wittig reagent to give compound 31b. Compound 31b can be reduced to afford compound 32b, and then compound 32b can be converted to compound 33b by hydrolysis. Subsequently, the protecting group Pg of compound 33b can be removed to afford compound 34b.

The target compound 38b can be prepared by the process illustrated in scheme 7, wherein Pg is an amino protecting group, such as Boc, Fmoc, Cbz, and the like. Wittig reaction of compound 9b with Wittig reagent to give compound 35b. Compound 35b can be reduced to afford compound 36b in the presence of a reductant, and then compound 36b can be converted to compound 37b in the presence of an oxidant. Subsequently, the protecting group Pg of compound 37b can be removed to afford compound 38b.

The target compound 34b can be prepared by the process illustrated in scheme 6, wherein Pg is an amino protecting group, such as Boc, Fmoc, Cbz, and the like. Compound 25b can be converted to compound 26b in the presence of

EXAMPLES

The invention is illustrated further by the following examples, which are not be construed as limiting the invention in scope.

Example 1

(S)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidine-2-carboxylic acid

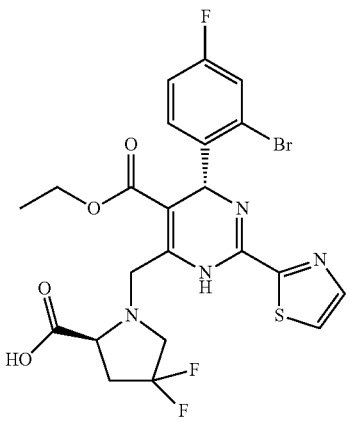 [SMILES: CCOC(=O)C1=C(CN2CC(F)(F)C[C@H]2C(=O)O)NC(c2nccs2)=N[C@H]1c1ccc(F)cc1Br]

Step 1) (R)-ethyl 4-(2-bromo-4-fluorophenyl)-6-methyl-2-(thiazol-2-yl)-1,4-dihydropyrimidine-5-carboxylate

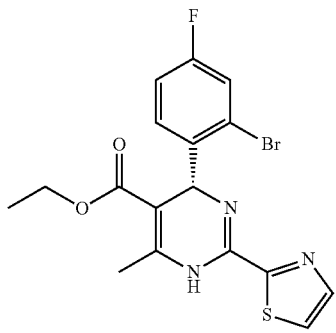

A solution of ethyl 4-(2-bromo-4-fluorophenyl)-6-methyl-2-(thizaol-2-yl)-1,4-dihydropyrimidin-5-carboxylate (5 g, 11.8 mmol, synthetic procedures refer to: WO2010069147A) in a mixture of MeOH and DCM (v/v=1/1, 20 mL) was separated by Preparative chromatography to give the title compound as a yellow solid (2 g, 40%).

The compound was characterized by the following spectroscopic data:

$[\alpha]_D^{25}$=−80.71 (c=0.3023 g/100 mL, MeOH);

MS (ESI, pos.ion) m/z: 424.0 [M+1]+; and $^1$H NMR (400 MHz, DMSO-$d_6$): δ 9.88 (s, 1H), 7.97 (d, 1H), 7.89 (d, 1H), 7.54 (dd, 1H), 7.35 (dd, 1H), 7.23 (td, 1H), 5.96 (s, 1H), 3.93 (q, 2H), 2.46 (s, 3H), 1.03 (t, 3H).

Step 2) (R)-ethyl 4-(2-bromo-4-fluorophenyl)-6-(bromomethyl)-2-(thiazol-2-yl)-1,4-dihydropyrimidine-5-carboxylate

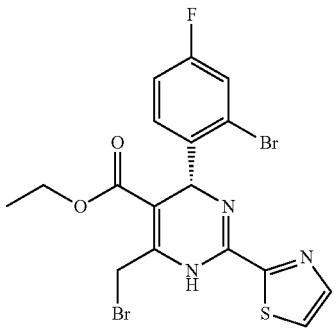 [SMILES: CCOC(=O)C1=C(CBr)NC(c2nccs2)=N[C@H]1c1ccc(F)cc1Br]

To a mixture of (R)-ethyl 4-(2-bromo-4-fluorophenyl)-6-methyl-2-(thiazol-2-yl)-1,4-dihydropyrimidine-5-carboxylate (1 g, 2.4 mmol) and CCl$_4$ (20 mL) was added NBS (0.47 g, 2.64 mmol) at 76° C. The reaction mixture was stirred at 76° C. for 30 min. After the reaction was finished, the mixture was cooled and concentrated in vacuo. The residue was purified by silica column chromatography (PE/EtOAc (v/v)=5/1) to give the title compound as a yellow solid (0.85 g, 70%). The compound was characterized by the following spectroscopic data:

MS (ESI, pos.ion) m/z: 503.9 [M+H]+; and $^1$H NMR (600 MHz, DMSO-$d_6$): δ 10.23 (s, 1H), 8.01 (d, 1H), 7.98 (d, 1H), 7.62 (dd, 1H), 7.42 (dd, 1H), 7.29 (td, 1H), 6.01 (s, 1H), 4.79 (br, 2H), 4.01 (q, 2H), 1.08 (t, 3H).

Step 3) (S)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidine-2-carboxylic acid

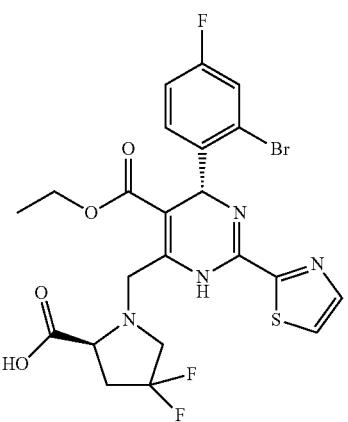 [SMILES: CCOC(=O)C1=C(CN2CC(F)(F)C[C@H]2C(=O)O)NC(c2nccs2)=N[C@H]1c1ccc(F)cc1Br]

To a flask were added (R)-ethyl 4-(2-bromo-4-fluorophenyl)-6-(bromomethyl)-2-(thiazol-2-yl)-1,4-dihydropyrimidine-5-carboxylate (0.56 g, 1.1 mmol), (S)-4,4-difluoropyrrolidine-2-carboxylic acid trifluoroacetic acid salt (0.58 g, 2.2 mmol, synthetic procedures refer to: Tetrahedron letters, 1998, 39(10), 1169-1172), potassium carbonate (0.3 g, 2.2 mmol) and anhydrous ethyl alcohol (20 mL). The mixture was stirred at 30 OC for 24 hours under N$_2$, and then filtered.

The filtrate was concentrated in vacuo. The residue was purified by silica column chromatography (DCM/CH$_3$OH (V/V)=15/1) to give the title compound as a light yellow solid (0.15 g, 24%). The compound was characterized by the following spectroscopic data:

MS (ESI, pos.ion) m/z: 573.0 [M+H]$_+$; and $^1$H NMR (600 MHz, DMSO-d$_6$): δ 9.98 (br, 1H), 8.03 (d, 1H), 8.00 (d, 1H), 7.61 (dd, 1H), 7.48 (dd, 1H), 7.28 (td, 1H), 6.02 (s, 1H), 4.35 (d, 1H), 4.13 (d, 1H), 4.01-3.94 (m, 3H), 3.61-3.51 (m, 1H), 3.25-3.19 (m, 1H), 3.10-3.04 (m, 1H), 2.86-2.68 (m, 1H), 1.20 (t, 3H).

Example 2

(R)-4-(((R)-6-(2-bromo-4-fluorophenyl)-5-(ethoxycarbonyl)-2-(thiazol-2-yl)-3,6-dihydropyrimidin-4-yl)methyl)thiomorpholine-3-carboxylic acid 1,1-dioxide

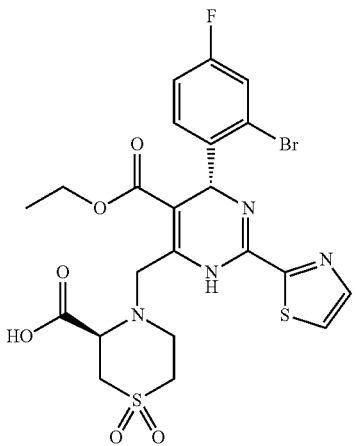

To a flask were added (R)-ethyl 4-(2-bromo-4-fluorophenyl)-6-(bromomethyl)-2-(thiazol-2-yl)-1,4-dihydropyrimidine-5-carboxylate (0.56 g, 1.1 mmol), (R)-thiomorpholine-3-carboxylic acid 1,1-dioxide (0.4 g, 2.2 mmol, synthetic procedures refer to: Acta Chemica Scandinavica, 1994: 48: 517-525), potassium carbonate (0.3 g, 2.2 mmol) and anhydrous ethyl alcohol (20 mL). The mixture was stirred at 30 OC for 24 hours under N$_2$. After the reaction was finished, the reaction was filtered, and the filtrate was concentrated in vacuo. The residue was purified by silica column chromatography (DCM/CH$_3$OH (V/V)=10/1) to give the title compound as a light yellow solid (0.2 g, 30%).

The compound was characterized by the following spectroscopic data:

MS (ESI, pos.ion) m/z: 601.0 [M+H]$^+$; and $^1$H NMR (600 MHz, DMSO-d$_6$): δ 11.07 (br, 1H), 10.19 (br, 1H), 8.00 (d, 1H), 7.92 (d, 1H), 7.56 (dd, 1H), 7.41 (dd, 1H), 7.21 (td, 1H), 6.01 (s, 1H), 4.55 (dd, 1H), 4.11 (br, 1H), 3.99-3.89 (m, 3H), 3.55-3.35 (m, 3H), 3.23-2.97 (m, 3H), 1.06 (t, 3H).

Example 3

(3R)-4-((6-(2-chloro-4-fluorophenyl)-5-(ethoxycarbonyl)-2-(thiazol-2-yl)-3,6-dihydropyrimidin-4-yl)methyl)thiomorpholine-3-carboxylic acid 1,1-dioxide

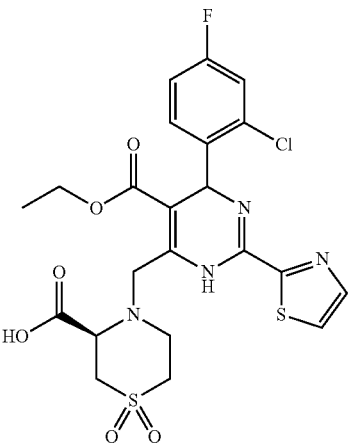 [SMILES: CCOC(=O)C1=C(CN2CCS(=O)(=O)C[C@H]2C(=O)O)NC(c2nccs2)=NC1c1ccc(F)cc1Cl]

A mixture of ethyl 6-(bromomethyl)-4-(2-chloro-4-fluorophenyl)-2-(thiazol-2-yl)-1,4-dihydropyrimidine-5-carboxylate (1.24 g, 2.7 mmol, synthetic procedures refer to: WO2010069147A), K$_2$CO$_3$ (0.66 g, 4.8 mmol), anhydrous ethanol (60 mL) and (R)-thiomorpholine-3-carboxylic acid 1,1-dioxide (0.43 g, 2.4 mmol) was stirred at 25° C. for 24 hours. After the reaction was finished, the reaction mixture was filtered, and the filtrate was concentrated in vacuo. The residue was purified by silica column chromatography (DCM/CH$_3$OH (V/V)=15/1) to give the title compound as a yellow solid (0.16 g, 12%). The compound was characterized by the following spectroscopic data:

MS (ESI, pos.ion) m/z: 557.1[M+H]$_+$; and $^1$H NMR (600 MHz, DMSO-d$_6$): δ 13.03 (brs, 1H), 9.73 (brs, 1H), 8.03 (d, 1H), 7.97 (d, 1H), 7.47-7.43 (m, 2H), 7.19 (td, 1H), 6.05 (s, 1H), 4.55 (dd, 1H), 4.40-4.24 (m, 2H), 4.11-3.93 (m, 3H), 3.65-3.40 (m, 3H), 3.25-3.15 (m, 2H), 1.06 (t, 3H).

Example 4

(3R)-4-((6-(2,4-dichlorophenyl)-5-(ethoxycarbonyl)-2-(thiazol-2-yl)-3,6-dihydropyrimidin-4-yl)methyl)thiomorpholine-3-carboxylic acid 1,1-dioxide

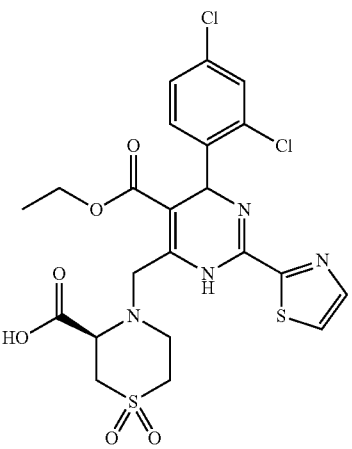 [SMILES: CCOC(=O)C1=C(CN2CCS(=O)(=O)C[C@H]2C(=O)O)NC(c2nccs2)=NC1c1ccc(Cl)cc1Cl]

A mixture of ethyl 6-(bromomethyl)-4-(2,4-dichlorophenyl)-2-(thiazol-2-yl)-1,4-dihydropyrimidine-5-carboxylate (1.35 g, 3.4 mmol, synthetic procedures refer to: WO2010069147A), K$_2$CO$_3$ (0.88 g, 6.2 mmol), (R)-thiomorpholine-3-carboxylic acid 1,1-dioxide (0.55 g, 3.1 mmol) and anhydrous ethanol (60 mL) was stirred at 35° C. for 24 hours. After the reaction was finished, the reaction mixture was filtered, and the filtrate was concentrated. The residue was purified by silica column chromatography (DCM/CH$_3$OH (V/V)=50/1) to give the title compound as a yellow solid (0.15 g, 8.4%). The compound was characterized by the spectroscopic data:

MS (ESI, pos.ion) m/z: 573.1[M+H]$^+$;

$^1$H NMR (600 MHz, DMSO-d$_6$): δ 10.49 (br, 1H), 7.99 (br, 1H), 7.92 (d, 1H), 7.73-7.60 (m, 2H), 7.42-7.40 (m, 1H), 6.05 (s, 1H), 4.52 (d, 1H), 4.38 (d, 1H), 4.18-4.13 (m, 1H), 3.99-3.93 (m, 3H), 3.55-3.40 (m, 3H), 3.20-3.05 (m, 2H), 1.05 (t, 3H).

Example 5

2-(1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)acetic acid

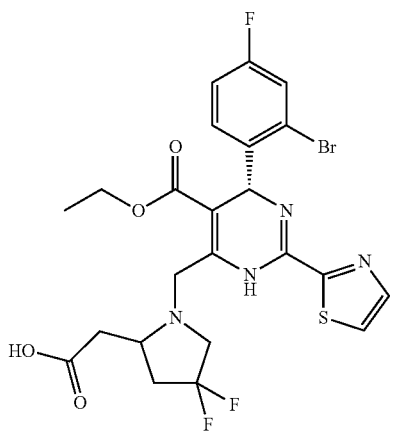 [SMILES: CCOC(=O)C1=C(CN2CC(F)(F)CC2CC(=O)O)NC(c2nccs2)=N[C@H]1c1ccc(F)cc1Br]

Step 1) (S)-tert-butyl 4,4-difluoro-2-formylpyrrolidine-1-carboxylate

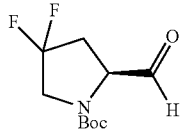

To a solution of (S)-tert-butyl 4,4-difluoro-2-(hydroxymethyl)pyrrolidine-1-carboxylate (10 g, 42.2 mmol) in DCM (200 mL) was added Dess-Martin periodinane (21.5 g, 50.6 mmol) at 0° C. After the addition, the reaction mixture was stirred 0° C. for 3 hours. After the reaction was finished, the reaction was quenched with saturated aqueous NaHCO$_3$ solution (200 mL). The separated organic phase was washed with saturated aqueous NaHCO$_3$ solution (200 mL) and saturated brine (200 mL), dried with anhydrous Na$_2$SO$_4$ and concentrated in vacuo. The residue was purified by silica column chromatography (PE/EtOAc (v/v)=2/1) to give the title compound as light yellow oil (5.6 g, 56%). The compound was characterized by the following spectroscopic data:

MS (ESI, pos.ion) m/z: 180.1 [M+H-56]$^+$.

Step 2) tert-butyl 4,4-difluoro-2-(2-methoxyvinyl)pyrrolidine-1-carboxylate

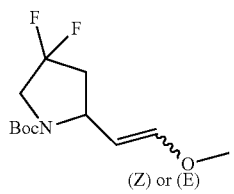 [SMILES: COC=CC1CC(F)(F)CN1C(=O)OC(C)(C)C]

A mixture of (methoxymethyl)triphenylphosphonium chloride (19.0 g, 55.4 mmol), anhydrous THF (200 mL) and potassium tert-butoxide (7.4 g, 60.94 mmol) was stirred at 50° C. under N$_2$ for 2 hours. The mixture was cooled to 25° C. and then a solution of (S)-tert-butyl 4,4-difluoro-2-formylpyrrolidine-1-carboxylate (4.5 g, 19.14 mmol) in anhydrous THF (15 mL) was added dropwise. After the addition, the resulted mixture was stirred at 25° C. for 12 hours. After the reaction was finished, the reaction was quenched with water (200 mL) and then extracted with EtOAc (300 mL×2). The combined organic phases were washed with brine (300 mL×2), dried over anhydrous Na$_2$SO$_4$, filtered, and concentrated in vacuo. The residue was purified by silica column chromatography (PE/EtOAc (v/v)=8/1) to give the title compound as light yellow oil (3.0 g, 59.64%). The compound was characterized by the following spectroscopic data:

MS (ESI, pos.ion) m/z: 164.1 [M+H-100]$^+$; and $^1$H NMR (400 MHz, CDCl$_3$): δ 6.55-5.92 (m, 1H), 4.96-4.68 (m, 1H), 4.55-4.36 (m, 1H), 3.85-3.66 (m, 2H), −3.63-3.55 (s, s, 3H), 2.70-2.44 (m, 1H), 2.27-2.08 (m, 1H), 1.47 (s, 9H).

Step 3) tert-butyl 4,4-difluoro-2-(2-oxoethyl)pyrrolidine-1-carboxylate

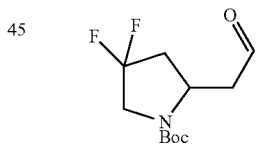

A mixture of tert-butyl 4,4-difluoro-2-(2-methoxyvinyl)pyrrolidine-1-carboxylate (1.0 g, 3.8 mmol), acetonitrile (40 mL) and TFA aqueous solution (5%, 8 mL) was stirred at 25° C. 12 hours. After the reaction was finished, the reaction was quenched with saturated aqueous sodium bicarbonate solution (100 mL) and the mixture was extracted with EtOAc (150 mL×2). The combined organic phases were washed with saturated aqueous sodium bicarbonate solution (100 mL×2) and saturated brine (100 mL×2) in turn, dried over anhydrous Na$_2$SO$_4$, filtered, and concentrated in vacuo to give the title compound as brownness oil (1.0 g) which was used directly for next step without further purification. The compound was characterized by the following spectroscopic data:

$^1$H NMR (400 MHz, CDCl$_3$): δ 9.78 (s, 1H), 4.46 (s, 1H), 3.90-3.64 (m, 2H), 3.23-2.91 (m, 1H), 2.80-2.54 (m, 2H), 2.27-2.08 (m, 1H), 1.47 (s, 9H).

Step 4) 2-(1-(tert-butoxycarbonyl)-4,4-difluoropyrrolidin-2-yl)acetic acid

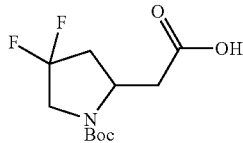

To a mixture of tert-butyl 4,4-difluoro-2-(2-oxoethyl) pyrrolidine-1-carboxylate (1.0 g, 4.02 mmol), acetone (2 mL) was added aqueous KMnO₄ solution (1 mol/L, 10 mL) at 0° C. The reaction mixture was stirred at 25° C. for 2 hours. After the reaction was finished, the reaction was quenched with saturated aqueous NaHSO₃ solution (50 mL). The resulting mixture was extracted with EtOAc (100 mL×2). The combined organic phases dried over anhydrous Na₂SO₄, filtered, and concentrated in vacuo to give the title compound as brownness oil (0.8 g, 75.5%). The compound was characterized by the following spectroscopic data:

MS (ESI, pos.ion) m/z: 166.1 [M+H-100]$^+$.

Step 5) 2-(4,4-difluoropyrrolidin-2-yl)acetic acid hydrochloride

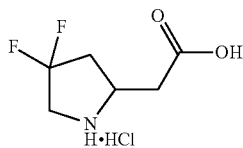

A mixture of 2-(1-(tert-butoxycarbonyl)-4,4-difluoropyrrolidin-2-yl)acetic acid (0.2 g, 0.75 mmol) and HCl in EtOAc (4 mol/L, 20 ml) was stirred at 25° C. for 2 hours. After the reaction was finished, the mixture was concentrated in vacuo to give the title compound as puce oil (0.15 g, 99%) which was used directly for next step without further purification. The compound was characterized by the following spectroscopic data:

MS (ESI, pos.ion) m/z: 166.1 [M+H]$^+$.

Step 6) 2-(1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)acetic acid

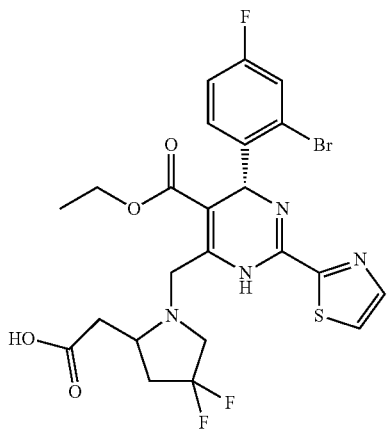 [SMILES: CCOC(=O)C1=C(CN2CC(F)(F)CC2CC(=O)O)NC(c2nccs2)=N[C@H]1c1ccc(F)cc1Br]

A mixture of 2-(4,4-difluoropyrrolidin-2-yl)acetic acid hydrochloride (0.15 g, 0.74 mmol), (R)-ethyl 4-(2-bromo-4-fluorophenyl)-6-(bromomethyl)-2-(thiazol-2-yl)-1,4-dihydropyrimidine-5-carboxylate (0.46 g, 0.92 mmol), K₂CO₃ (0.47 g, 3.36 mmol) and anhydrous ethanol (10 mL) was stirred at 25° C. under N₂ for 12 hours. After the reaction was finished, the reaction mixture was filtered, and the filtrate was concentrated in vacuo. The residue was purified by silica column chromatography (DCM/CH₃OH (V/V)=10/1) to give the title compound as a yellow solid (0.15 g, 34.24%). The compound was characterized by the following spectroscopic data:

MS (ESI, pos.ion) m/z: 587.0 [M+H]$^+$; and
$^1$H NMR (400 MHz, DMSO-d₆): δ 12.46 (s, 1H), 9.63 (s, 1H), 8.09-7.87 (m, 2H), 7.58 (d, 1H), 7.50-7.34 (m, 1H), 7.23 (d, 1H), 6.02 (s, 1H), 4.40-4.10 (m, 2H), 4.02-3.95 (m, 2H), 3.57 (d, 2H), 3.19 (s, 1H), 3.00-2.78 (m, 1H), 2.70 (d, 1H), 2.42 (dd, 1H), 2.20 (s, 1H), 1.06 (t, 3H).

Example 6

3-((R)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)propanoic acid

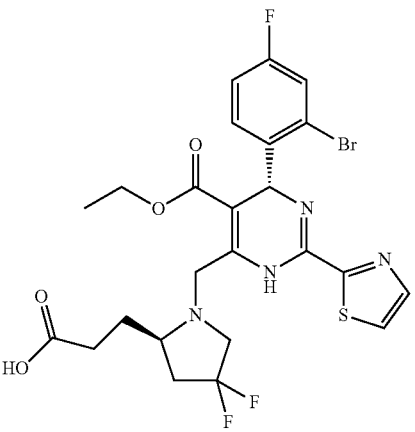 [SMILES: CCOC(=O)C1=C(CN2CC(F)(F)C[C@H]2CCC(=O)O)NC(c2nccs2)=N[C@H]1c1ccc(F)cc1Br]

Step 1) (S)-tert-butyl 2-(3-ethoxy-3-oxoprop-1-en-1-yl)-4,4-difluoropyrrolidine-1-carboxylate

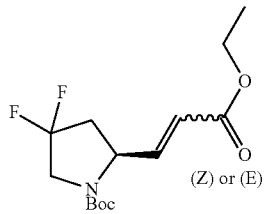 [SMILES: CCOC(=O)C=C[C@@H]1CC(F)(F)CN1C(=O)OC(C)(C)C]

(Z) or (E)

A mixture of (S)-tert-butyl 4,4-difluoro-2-formylpyrrolidine-1-carboxylate (4.84 g, 20.57 mmol), DCM (120 mL) and ethyl (triphenylphosphoranylidene)acetate (8.59 g, 24.69 mmol) was stirred at 25° C. for 12 hours. After the reaction was finished, the reaction mixture was concentrated in vacuo. The residue was purified by silica column chromatography (PE/EtOAc (V/V)=3/1) to give the title compound as light yellow oil (3.96 g, 63.1%). The compound was characterized by the following spectroscopic data:

MS (ESI, pos.ion) m/z: 206 [M+H-100]+; 250 [M+H-56]+; and $^1$H NMR (600 MHz, CDCl$_3$): δ 6.83 (m, 1H), 5.91 (d, 1H), 4.65 (d, 1H), 4.22 (d, 2H), 3.86 (s, 1H), 3.73 (m, 1H), 2.66 (d, 1H), 2.26 (dd, 1H), 1.45 (d, 9H), 1.31 (t, 3H).

Step 2) (R)-tert-butyl-2-(3-ethoxy-3-oxopropyl)-4,4-difluoropyrrolidine-1-carboxylate

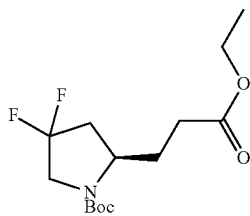 [SMILES: CCOC(=O)CC[C@@H]1CC(F)(F)CN1C(=O)OC(C)(C)C]

A mixture of (S)-tert-butyl 2-(3-ethoxy-3-oxoprop-1-en-1-yl)-4,4-difluoropyrrolidine-1-carboxylate (0.5 g, 1.8 mmol), ethanol (10 mL) and Pd/C (10%, 60 mg) was stirred under H$_2$ at 25° C. for 12 hours. After the reaction was finished, the reaction mixture was filtered. The filtrate was concentrated in vacuo to give the title compound as colourless oil (0.45 g, 89.5%). The compound was characterized by the following spectroscopic data:

$^1$H NMR (600 MHz, CDCl$_3$): δ 4.15 (dd, 2H), 3.98-3.82 (m, 1H), 3.77 (t, 1H), 3.62 (dd, 1H), 2.61-2.43 (m, 1H), 2.40-2.26 (m, 2H), 2.19-2.07 (m, 2H), 1.91-1.83 (m, 1H), 1.49 (s, 9H), 1.28 (t, 3H).

Step 3) (R)-3-(1-(tert-butoxycarbonyl)-4,4-difluoropyrrolidin-2-yl)propanoic acid

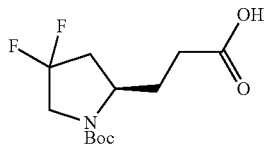 [SMILES: CC(C)(C)OC(=O)N1CC(F)(F)C[C@H]1CCC(=O)O]

A mixture of (R)-tert-butyl 2-(3-ethoxy-3-oxopropyl)-4,4-difluoropyrrolidine-1-carboxylate (0.45 g, 1.46 mmol) in ethanol (10 mL) was added aqueous LiOH.H$_2$O solution (LiOH.H$_2$O (0.62 g, 14.7 mmol) in 10 mL of water) was stirred at 25° C. for 1 hour and concerned in vacuo. Then to the residue was added water (15 mL). The resulting mixture was extracted with EtOAc (25 mL×2). The organic phase was discarded. To the water phase was added EtOAc (50 mL) and the resulting mixture was adjusted to pH 4-6 with concentrated hydrochloric acid, then the separated organic phase was washed with saturated brine (25 mL×2), dried over anhydrous Na$_2$SO$_4$, filtered, and concentrated in vacuo to give the title compound as light yellow oil (0.25 g, 61.1%). The compound was characterized by the following spectroscopic data:

MS (ESI, pos.ion) m/z: 180 [M+H-100]+; 224 [M+H-56]+; and $^1$H NMR (600 MHz, CDCl$_3$): δ 4.30-4.09 (m, 1H), 4.02-3.78 (m, 1H), 3.69-3.56 (m, 1H), 2.61-2.48 (m, 1H), 2.47-2.35 (m, 1H), 2.22-2.09 (m, 1H), 1.92-1.79 (m, 1H), 1.49 (s, 9H).

Step 4) (R)-3-(4,4-difluoropyrrolidin-2-yl)propanoic acid hydrochloride

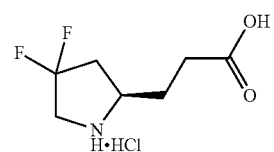

A mixture of (R)-3-(1-(tert-butoxycarbonyl)-4,4-difluoropyrrolidin-2-yl)propanoic acid (0.25 g, 0.90 mmol) and a solution of HCl in EtOAc (4 mol/L, 5 mL) was stirred at 25° C. for 2 hours. The reaction mixture was concentrated in vacuo to give the title compound as white powder (0.15 g, 77.9%). The compound was characterized by the following spectroscopic data:

MS (ESI, pos.ion) m/z: 180.1 [M+H]+; and $^1$H NMR (600 MHz, DMSO-d$_6$): δ 10.21 (br, 1H), 3.80-3.73 (m, 2H), 3.66-3.59 (m, 1H), 2.74-2.67 (m, 1H), 2.43-2.40 (m, 2H), 2.33-2.23 (m, 1H), 2.05-1.95 (m, 2H).

Step 5) 3-((R)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)propanoic acid

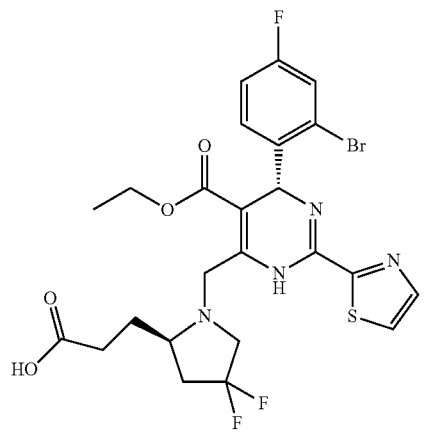 [SMILES: CCOC(=O)C1=C(CN2CC(F)(F)C[C@H]2CCC(=O)O)NC(c2nccs2)=N[C@H]1c1ccc(F)cc1Br]

A mixture of (R)-3-(4,4-difluoropyrrolidin-2-yl)propanoic acid hydrochloride (0.18 g, 0.84 mmol), (R)-ethyl4-(2-bromo-4-fluorophenyl)-6-(bromomethyl)-2-(thiazol-2-yl)-1,4-dihydropyrimidine-5-carboxylate (0.47 g, 0.92 mmol), K$_2$CO$_3$ (0.46 g, 3.36 mmol) and anhydrous ethanol (10 mL) was stirred at 25° C. for 12 hours under nitrogen protection. After the reaction was finished, the reaction mixture was filtered, and the filtrate was concentrated in vacuo. The residue was purified by silica column chromatography (DCM/CH$_3$OH (V/V)=25/1) to give the title compound as a yellow solid (0.4 g, 79.2%). The compound was characterized by the following spectroscopic data:

MS (ESI, pos.ion) m/z: 601.1 [M+H]+; and

¹H NMR (600 MHz, DMSO-d₆): δ 12.08 (s, 1H), 9.51 (s, 1H), 8.01 (d, 1H), 7.93 (d, 1H), 7.57 (dd, 1H), 7.41 (dd, 1H), 7.24 (td, 1H), 6.01 (s, 1H), 4.12 (dd, 2H), 3.97 (q, 2H), 3.61-3.52 (m, 1H), 3.04-2.96 (m, 2H), 2.58-2.56 (m, 1H), 2.35-2.20 (m, 2H), 2.12-1.98 (m, 1H), 1.93-1.90 (m, 1H), 1.56-1.48 (m, 1H), 1.06 (t, 3H).

Example 7

3-((2R)-1-((6-(2-bromo-4-fluorophenyl)-5-(ethoxycarbonyl)-2-(1-methyl-1H-imidazol-2-yl)-3,6-dihydropyrimidin-4-yl)methyl)-4,4-difluoropyrrolidin-2-yl)propanoic acid

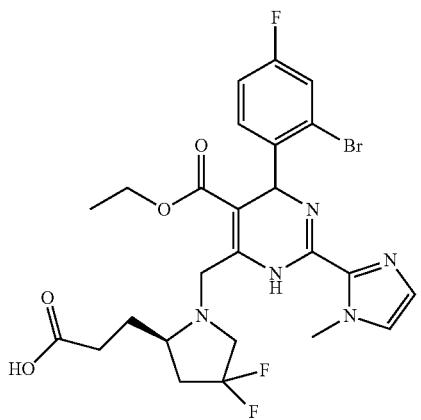 [SMILES: CCOC(=O)C1=C(CN2CC(F)(F)C[C@H]2CCC(=O)O)NC(c2nccn2C)=NC1c1ccc(F)cc1Br]

A mixture of (R)-3-(4,4-difluoropyrrolidin-2-yl)propanoic acid hydrochloride (0.1 g, 0.46 mmol), ethyl 4-(2-bromo-4-fluorophenyl)-6-(bromomethyl)-2-(1-methyl-1H-imidazol-2-yl)-1,4-dihydropyrimidine-5-carboxylate (0.26 g, 0.51 mmol), K₂CO₃ (0.13 g, 0.94 mmol), ethanol (3 mL) and DMF (1.5 mL) was stirred at 25 OC under nitrogen protection for 12 hours. After the reaction was finished, the reaction mixture was filtered, and the filtrate was concentrated in vacuo. The residue was purified by silica column chromatography (DCM/CH₃OH (V/V)=15/1) to give the title compound as a yellow solid (0.15 g, 56%). The compound was characterized by the following spectroscopic data:

MS (ESI, pos.ion) m/z: 598.0 [M+H]+; and

¹H NMR (400 MHz, DMSO-d₆): δ 12.18 (s, 1H), 9.54 (s, s, 1H), 7.59-7.56 (m, 1H), 7.37-7.26 (m, 2H), 7.25-7.14 (m, 1H), 7.02 (s, 1H), 6.01 (s, s, 1H), 4.21-4.09 (m, 2H), 4.04-3.92 (m, 2H), 3.89-3.88 (s, s, 3H), 3.58-3.37 (m, 1H), 3.07-2.78 (m, 1H), 2.56-2.51 (m, 1H), 2.38-2.12 (m, 2H), 2.15-1.85 (m, 2H), 1.66-1.44 (m, 1H), 1.09-1.05 (m, 3H).

Example 8

3-((R)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)-2-methylpropanoic acid

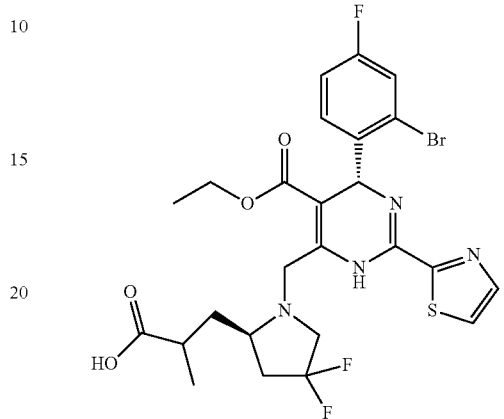

Step 1) (S)-tert-butyl 4,4-difluoro-2-(3-methoxy-2-methyl-3-oxoprop-1-en-1-yl)pyrrolidine-1-carboxylate

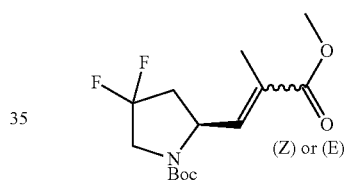

The title compound was prepared by the procedure described in step 6 of Example 1 using (S)-tert-butyl 4,4-difluoro-2-formylpyrrolidine-1-carboxylate (2.6 g, 11.06 mmol), DCM (120 mL) and methyl 2-(triphenylphosphoranylidene)propanoate (4.24 g, 12.17 mmol) to give the title compound as light yellow oil (1.6 g, 47.3%). The compound was characterized by the following spectroscopic data:

MS (ESI, pos.ion) m/z: 250.1[M+H-56]+.

Step 2) (2R)-tert-butyl 4,4-difluoro-2-(3-methoxy-2-methyl-3-oxopropyl)pyrrolidine-1-carboxylate

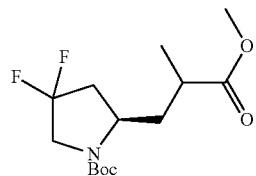 [SMILES: COC(=O)C(C)C[C@@H]1CC(F)(F)CN1C(=O)OC(C)(C)C]

The title compound was prepared by the procedure described in step 6 of Example 2 using (S)-tert-butyl 4,4-difluoro-2-(3-methoxy-2-methyl-3-oxoprop-1-en-1-yl)pyrrolidine-1-carboxylate (1.6 g, 5.24 mmol), methanol (10 mL) and Pd/C (10%, 0.2 g) to give the title compound as colourless oil (1.4 g, 87.5%). The compound was characterized by the following spectroscopic data:

MS (ESI, pos.ion) m/z: 208 [M+H-100]+; 252 [M+H-56]+.

Step 3) 3-((R)-1-(tert-butoxycarbonyl)-4,4-difluoro-pyrrolidin-2-yl)-2-methylpropanoic acid

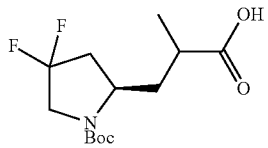 [SMILES: CC(C[C@@H]1CC(F)(F)CN1C(=O)OC(C)(C)C)C(=O)O]

The title compound was prepared by the procedure described in step 6 of Example 3 using (2R)-tert-butyl 4,4-difluoro-2-(3-methoxy-2-methyl-3-oxopropyl)pyrrolidine-1-carboxylate (1.4 g, 4.55 mmol), ethanol (50 mL) and aqueous LiOH.H$_2$O solution (LiOH.H$_2$O (1.9 g, 45.3 mmol) in 50 mL of water to give the title compound as light yellow oil (1.1 g, 82.7%). The compound was characterized by the following spectroscopic data:

MS (ESI, pos.ion) m/z: 194 [M+H-100]+; 238 [M+H-56]$^+$.

Step 4) 3-((R)-4,4-difluoropyrrolidin-2-yl)-2-methylpropanoic acid hydrochloride

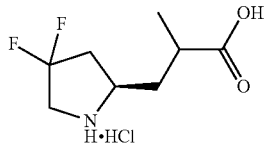

The title compound was prepared by the procedure described in step 6 of Example 4 using 3-((R)-1-(tert-butoxycarbonyl)-4,4-difluoropyrrolidin-2-yl)-2-methylpropanoic acid (1.1 g, 3.75 mmol) and a solution of HCl in EtOAc (4 mol/L, 80 mL) to give the title compound as light brownness goo (0.69 g, 80%). The compound was characterized by the following spectroscopic data:

MS (ESI, pos.ion) m/z: 194.2 [M+H]$^+$.

Step 5) 3-(1-(((R)-6-(2-bromo-4-fluorophenyl)-5-(ethoxycarbonyl)-2-(thiazol-2-yl)-3,6-dihydropy-rimidin-4-yl)methyl)-4,4-difluoropyrrolidin-2-yl)-2-methylpropanoic acid

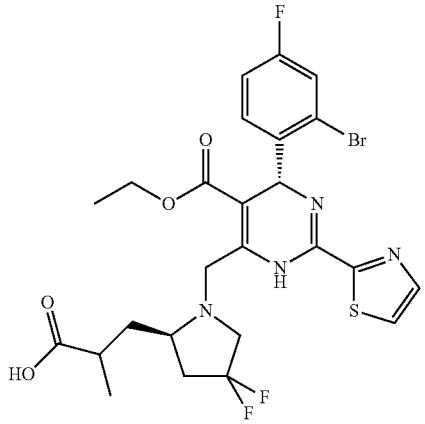 [SMILES: CCOC(=O)C1=C(CN2CC(F)(F)C[C@H]2CC(C)C(=O)O)NC(c2nccs2)=N[C@H]1c1ccc(F)cc1Br]

The title compound was prepared by the procedure described in Example 2 using 3-((R)-4,4-difluoropyrrolidin-2-yl)-2-methylpropanoic acid hydrochloride (0.81 g, 3.75 mmol), (R)-ethyl 4-(2-bromo-4-fluorophenyl)-6-(bromomethyl)-2-(thiazol-2-yl)-1,4- dihydropyrimidine-5-carboxylate (2.07 g, 4.12 mmol), K$_2$CO$_3$ (1.54 g, 11.19 mmol) and anhydrous ethanol (40 mL) to give the title compound as a yellow solid (1.63 g, 70.6%). The compound was characterized by the following spectroscopic data:

MS (ESI, pos.ion) m/z: 616 [M+H]$^+$;
$^1$H NMR (400 MHz, DMSO-d$_6$): δ 8.05-8.01 (m, 2H), 7.58 (dd, 1H), 7.47 (dd, 1H), 7.26 (td, 1H), 6.01 (s, 1H), 4.51 (d, 1H), 4.22 (t, 1H), 4.00 (q, 2H), 3.89 (br, 1H), 3.55-3.42 (m, 2H), 2.79-2.69 (m, 1H), 2.47-2.36 (m, 1H), 2.30-2.14 (m, 1H), 2.02-1.86 (m, 1H), 1.55-1.45 (m, 1H), 1.15-1.09 (m, 6H).

Example 9

3-((S)-1-(((R)-6-(2-bromo-4-fluorophenyl)-5-(ethoxycarbonyl)-2-(thiazol-2-yl)-3,6-dihydropy-rimidin-4-yl)methyl)-4,4-difluoropyrrolidin-2-yl) butanoic acid

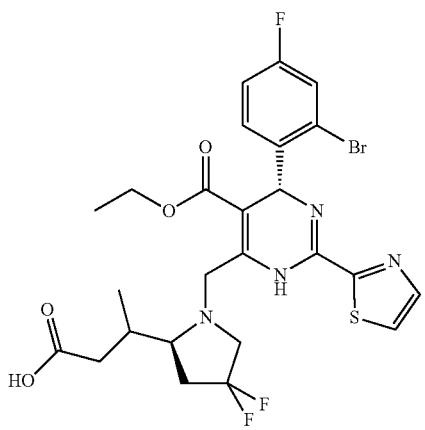 [SMILES: CCOC(=O)C1=C(CN2CC(F)(F)C[C@H]2C(C)CC(=O)O)NC(c2nccs2)=N[C@H]1c1ccc(F)cc1Br]

Step 1) (2S)-tert-butyl 2-(4-ethoxy-4-oxobutan-2-yl)-4,4-difluoropyrrolidine-1-carboxylate

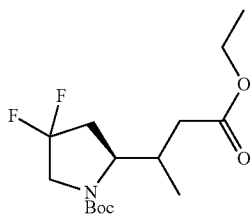 [SMILES: CCOC(=O)CC(C)[C@@H]1CC(F)(F)CN1C(=O)OC(C)(C)C]

To a mixture of CuI (960 mg, 5.05 mmol) and anhydrous THF (100 mL) was added a solution of MeLi in THF (1.6 mol/L, 6.3 mL) at 0° C. under nitrogen. The reaction mixture was stirred at this temperature for 1 hour. Then the mixture was cooled to −78° C. and TMSCl (283 mg, 2.62 mmol) and (S)-tert-butyl 2-(3-ethoxy-3-oxoprop-1-en-1-yl)-4,4-difluoropyrrolidine-1-carboxylate were added in turn at −78° C. The resulted mixture was stirred at −78° C. for 2 hours and then stirred at 25° C. for 1 hour. After the reaction was finished, the reaction was quenched with saturated ammonium chloride (50 mL). The resulted mixture was extracted with EtOAc (50 mL×2). The combined organic phases were washed with saturated brine (30 mL×2), dried with anhydrous Na$_2$SO$_4$ and concentrated in vacuo. The residue was purified by silica column chromatography (PE/EtOAc (V/V)=8/1) to give the title compound as light yellow oil (500 mg, 59.4%). The compound was characterized by the following spectroscopic data:

MS (ESI, pos.ion) m/z: 222 [M+H-100]$^+$.

Step 2) 3-((S)-1-(tert-butoxycarbonyl)-4,4-difluoro-pyrrolidin-2-yl)butanoic acid

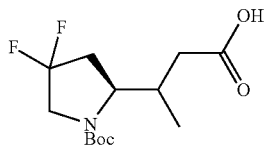

The title compound was prepared by the procedure described in step 3 of Example 6 using (2S)-tert-butyl 2-(4-ethoxy-4-oxobutan-2-yl)-4,4-difluoropyrrolidine-1-carboxylate (500 mg, 1.55 mmol), ethanol (10 mL) and aqueous LiOH.H$_2$O solution (LiOH.H$_2$O (0.65 g) in 10 mL of water) to give the title compound as light yellow oil (320 mg, 70.1%). The compound was characterized by the following spectroscopic data:

MS (ESI, pos.ion) m/z: 194 [M+H-100]+; 238 [M+H-56].

Step 3) 3-((S)-4,4-difluoropyrrolidin-2-yl)butanoic acid hydrochloride

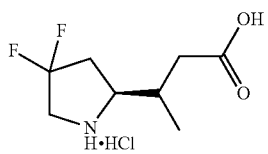

The title compound was prepared by the procedure described in step 4 of Example 6 using 3-((S)-1-(tert-butoxycarbonyl)-4,4-difluoropyrrolidin-2-yl)butanoic acid (320 mg, 1.09 mmol) and HCl in EtOAc (4 mol/L, 2 mL) to give the title compound as light brownness oil (0.19 g, 76%) The compound was characterized by the following spectroscopic data:

MS (ESI, pos.ion) m/z: 194.1 [M+H]+.

Step 4) 3-((S)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)butanoic acid

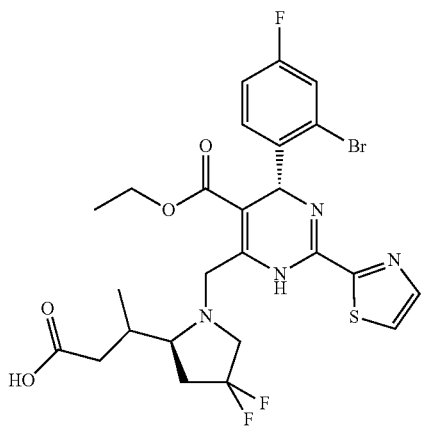 [SMILES: CCOC(=O)C1=C(CN2CC(F)(F)C[C@H]2C(C)CC(=O)O)NC(c2nccs2)=N[C@H]1c1ccc(F)cc1Br]

The title compound was prepared by the procedure described in Example 2 using 3-((S)-4,4-difluoropyrrolidin-2-yl)butanoic acid hydrochloride (250 mg, 1.09 mmol), (R)-ethyl4-(2-bromo-4-fluorophenyl)-6-(bromomethyl)-2-(thiazol-2-yl)-1,4-dihydropyrimidine-5-carboxylate (0.66 g, 1.31 mmol), K$_2$CO$_3$ (0.45 g, 3.27 mmol), and anhydrous ethanol (10 mL) to give the title compound as a yellow solid (0.1 g, 14.6%). The compound was characterized by the following spectroscopic data:

MS (ESI, pos.ion) m/z: 615.0 [M+H]+; and
$^1$H NMR (600 MHz, DMSO-d$_6$): δ 11.97 (s, 1H), 9.47 (s, 1H), 8.11-7.82 (m, 2H), 7.58 (dd, 1H), 7.42 (dd, 1H), 7.24 (td, 1H), 6.00 (s, 1H), 4.20-4.10 (m, 2H), 3.96 (q, 2H), 3.75-3.65 (m, 1H), 3.13-3.01 (m, 2H), 2.67 (d, 1H), 2.37-2.25 (m, 2H), 2.11-2.06 (m, 1H), 2.00-1.95 (m, 1H), 1.06 (t, 3H), 0.89 (d, 3H).

Example 10

(R)-4-(((R)-6-(2-chloro-4-fluorophenyl)-5-(ethoxycarbonyl)-2-(thiazol-2-yl)-3,6-dihydropyrimidin-4-yl)methyl)thiomorpholine-3-carboxylic acid 1,1-dioxide

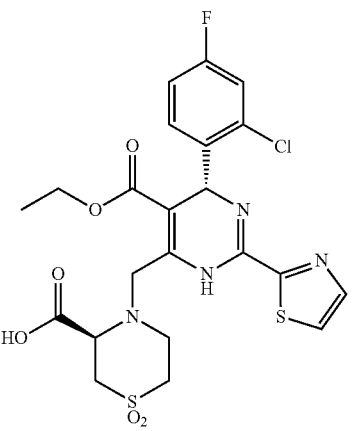 [SMILES: CCOC(=O)C1=C(CN2CCS(=O)(=O)C[C@H]2C(=O)O)NC(c2nccs2)=N[C@H]1c1ccc(F)cc1Cl]

Step 1) (R)-ethyl 4-(2-chloro-4-fluorophenyl)-6-methyl-2-(thiazol-2-yl)-1,4-dihydropyrimidine-5-carboxylate

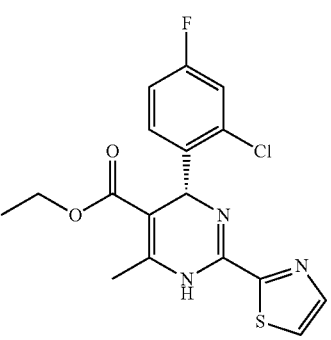 [SMILES: CCOC(=O)C1=C(C)NC(c2nccs2)=N[C@H]1c1ccc(F)cc1Cl]

The title compound was prepared by the procedure described in step 1 of Example 1 using ethyl 4-(2-chloro-4-fluorophenyl)-6-methyl-2- (thiazol-2-yl)-1,4-dihydropyrimidine-5-carboxylate (5 g, 13.2 mmol) to give the title compound as a yellow solid (2.1 g, 42%). The compound was characterized by the following spectroscopic data:

[a]$_D^{25}$=−59.6 (c=0.3020 g/100 mL, MeOH);

MS (ESI, pos.ion) m/z: 380.2 [M+H]$^+$; and $^1$H NMR (600 MHz, DMSO-d$_6$): δ 9.92 (s, 1H), 7.97 (d, 1H), 7.90 (d, 1H), 7.41 (dd, 1H), 7.37 (dd, 1H), 7.19 (td, 1H), 6.00 (s, 1H), 3.93 (q, 2H), 2.46 (s, 3H), 1.03 (t, 3H).

Step 2) (R)-ethyl 6-(bromomethyl)-4-(2-chloro-4-fluorophenyl)-2-(thiazol-2-yl)-1,4-dihydropyrimidine-5-carboxylate

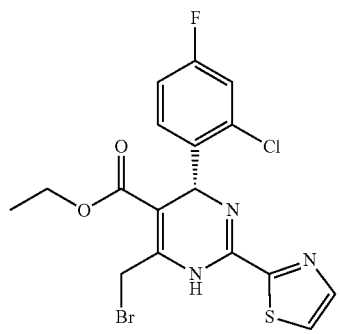 [SMILES: CCOC(=O)C1=C(CBr)NC(c2nccs2)=N[C@H]1c1ccc(F)cc1Cl]

The title compound was prepared by the procedure described in step 2 of Example 1 using (R)-ethyl 4-(2-chloro-4-fluorophenyl)-6-methyl-2-(thiazol-2-yl)-1,4-dihydropyrimidine-5-carboxylate (0.91 g, 2.4 mmol), CCl$_4$ (20 mL) and NBS (0.47 g, 2.64 mmol) to give the title compound as a yellow solid (0.8 g, 73%). The compound was characterized by the following spectroscopic data:

MS (ESI, pos.ion) m/z: 457.9 [M+H]$^+$; and $^1$H NMR (400 MHz, DMSO-d$_6$): δ 9.67 (s, 1H), 8.01 (d, 1H), 7.97 (br, 1H), 7.44-7.41 (m, 2H), 7.22 (td, 1H), 5.99 (s, 1H), 4.83 (br, 2H), 4.02 (q, 2H), 1.07 (t, 3H).

Step 3) (R)-4-(((R)-6-(2-chloro-4-fluorophenyl)-5-(ethoxycarbonyl)-2-(thiazol-2-yl)-3,6-dihydropyrimidin-4-yl)methyl)thiomorpholine-3-carboxylic acid 1,1-dioxide

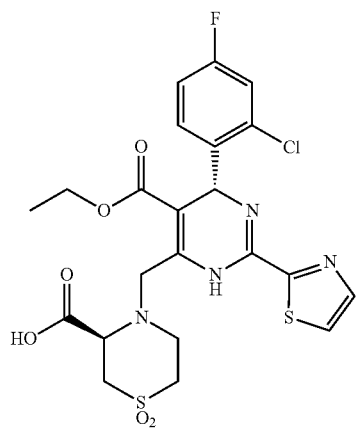

The title compound was prepared by the procedure described in Example 2 using (R)-ethyl 6-(bromomethyl)-4-(2-chloro-4-fluorophenyl)-2-(thiazol-2-yl)-1,4-dihydropyrimidine-5-carboxylate (1.24 g, 2.7 mmol), (R)-thiomorpholine-3-carboxylic acid 1,1-dioxide (0.43 g, 2.4 mmol), K$_2$CO$_3$ (0.75 g, 5.4 mmol) and anhydrous ethanol (25 mL) to give the title compound as a yellow solid (0.16 g, 12%). The compound was characterized by the following spectroscopic data:

MS (ESI, pos.ion) m/z: 557.1[M+H]$^+$; and $^1$H NMR (600 MHz, DMSO-d$_6$): δ 13.03 (br, 1H), 9.73 (br, 1H), 8.03 (d, 1H), 7.97 (d, 1H), 7.47-7.43 (m, 2H), 7.19 (td, 1H), 6.05 (s, 1H), 4.55 (dd, 1H), 4.40-4.24 (m, 2H), 4.11-3.93 (m, 3H), 3.65-3.40 (m, 3H), 3.25-3.15 (m, 2H), 1.06 (t, 3H).

Example 11

(R)-4-(((R)-6-(2,4-dichlorophenyl)-5-(ethoxycarbonyl)-2-(thiazol-2-yl)-3,6-dihydropyrimidin-4-yl)methyl)thiomorpholine-3-carboxylic acid 1,1-dioxide

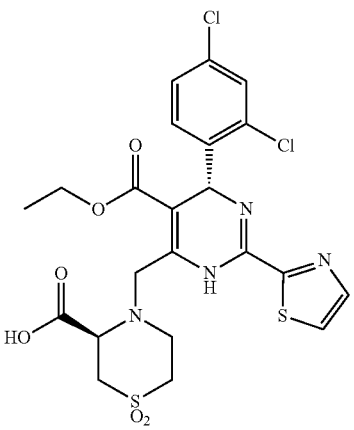

Step 1) (R)-ethyl 4-(2,4-dichlorophenyl)-6-methyl-2-(thiazol-2-yl)-1,4-dihydropyrimidine-5-carboxylate

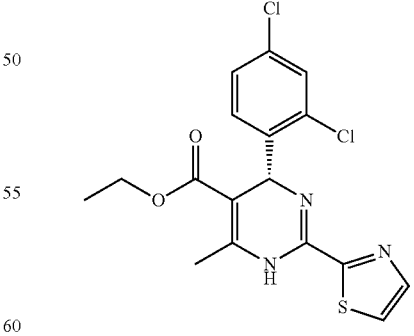

The title compound was prepared by the procedure described in step 1 of Example 1 using ethyl 4-(2,4-dichlorophenyl)-6-methyl-2-(thiazol-2-yl)-1,4-dihydropyrimidine-5-carboxylate (5 g, 12.6 mmol) to give the title compound as a yellow solid (1.9 g, 38%). The compound was characterized by the following spectroscopic data:

[a]$_D^{25}$=−39.07 (c=0.3032 g/100 mL, MeOH);
MS (ESI, pos.ion) m/z: 396.1 [M+H]$^+$; and
$^1$H NMR (400 MHz, DMSO-d$_6$): δ 9.93 (s, 1H), 7.97 (d, 1H), 7.90 (d, 1H), 7.58 (d, 1H), 7.41 (dd, 1H), 7.35 (d, 1H), 6.00 (s, 1H), 3.93 (q, 2H), 2.46 (s, 3H), 1.03 (t, 3H).

Step 2) (R)-ethyl 6-(bromomethyl)-4-(2,4-dichlorophenyl)-2-(thiazol-2-yl)-1,4-dihydropyrimidine-5-carboxylate

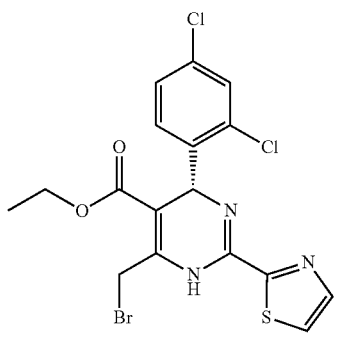 [SMILES: CCOC(=O)C1=C(CBr)NC(c2nccs2)=N[C@H]1c1ccc(Cl)cc1Cl]

The title compound was prepared by the procedure described in step 2 of Example 1 using (R)-ethyl 4-(2,4-dichlorophenyl)-6-methyl-2-(thiazol-2-yl)-1,4-dihydropyrimidine-5-carboxylate (0.95 g, 2.4 mmol), CCl$_4$ (20 mL) and NBS (0.47 g, 2.64 mmol) to give the title compound as a yellow solid (0.74 g, 65%). The compound was characterized by the following spectroscopic data:

MS (ESI, pos.ion) m/z: 475.6 [M+H]$^+$; and
$^1$H NMR (600 MHz, DMSO-d$_6$): δ 8.03 (d, 1H), 7.98 (d, 1H), 7.66-7.62 (m, 1H), 7.47-7.35 (m, 2H), 5.99 (s, 1H), 4.82 (br, 2H), 4.02 (q, 2H), 1.09 (t, 3H).

Step 3) (R)-4-(((R)-6-(2,4-dichlorophenyl)-5-(ethoxycarbonyl)-2-(thiazol-2-yl)-3,6-dihydropyrimidin-4-yl)methyl)thiomorpholine-3-carboxylic acid 1,1-dioxide

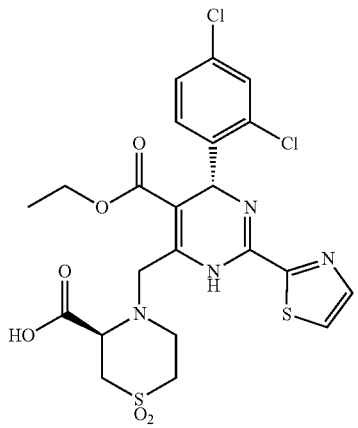 [SMILES: CCOC(=O)C1=C(CN2CCS(=O)(=O)C[C@H]2C(=O)O)NC(c2nccs2)=N[C@H]1c1ccc(Cl)cc1Cl]

The title compound was prepared by the procedure described in Example 2 using (R)-ethyl 6-(bromomethyl)-4-(2,4-dichlorophenyl)-2-(thiazol-2-yl)-1,4-dihydropyrimidine-5-carboxylate (1.35 g, 3.4 mmol), (R)-thiomorpholine-3-carboxylic acid 1,1-dioxide (0.55 g, 3.1 mmol), K$_2$CO$_3$ (0.94 g, 6.8 mmol) and anhydrous ethanol (25 mL) to give the title compound as a yellow solid (0.15 g, 8.4%). The compound was characterized by the following spectroscopic data:

MS (ESI, pos.ion) m/z: 573.1[M+H]$^+$; and
$^1$H NMR (600 MHz, DMSO-d$_6$): δ 10.49 (br, 1H), 7.99 (br, 1H), 7.92 (d, 1H), 7.73-7.60 (m, 2H), 7.42-7.40 (m, 1H), 6.05 (s, 1H), 4.52 (d, 1H), 4.38 (d, 1H), 4.18-4.13 (m, 1H), 3.99-3.93 (m, 3H), 3.55-3.40 (m, 3H), 3.20-3.05 (m, 2H), 1.05 (t, 3H).

Example 12

3-((R)-1-(((R)-6-(2-chloro-4-fluorophenyl)-5-(ethoxycarbonyl)-2-(thiazol-2-yl)-3,6-dihydropyrimidin-4-yl)methyl)-4,4-difluoropyrrolidin-2-yl)propanoic acid

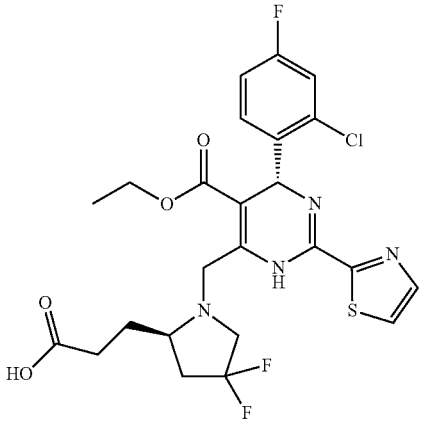 [SMILES: CCOC(=O)C1=C(CN2CC(F)(F)C[C@H]2CCC(=O)O)NC(c2nccs2)=N[C@H]1c1ccc(F)cc1Cl]

The title compound was prepared by the procedure described in Example 2 using (R)-3-(4,4-difluoropyrrolidin-2-yl)propanoic acid hydrochloride (0.11 g, 0.51 mmol), (R)-methyl 6-(bromomethyl)-4-(2-chloro-4-fluorophenyl)-2-(thiazol-2-yl)-1,4-dihydropyrimidine-5-carboxylate (0.21 g, 0.46 mmol), potassium carbonate (0.13 g, 0.94 mmol) and anhydrous ethyl alcohol (10 mL) to give the title compound as a yellow solid (0.13 g, 50%). The compound was characterized by the following spectroscopic data:

MS (ESI, pos.ion) m/z: 556.9 [M+H]$^+$; and
$^1$H NMR (400 MHz, DMSO-d$_6$): δ 12.08 (s, 1H), 9.52 (s, 1H), 7.99 (d, 1H), 7.92 (d, 1H), 7.44-7.40 (m, 2H), 7.19 (td, 1H), 6.03 (s, 1H), 4.13 (dd, 2H), 3.97 (q, 2H), 3.60-3.52 (m, 1H), 3.06-2.96 (m, 2H), 2.59-2.56 (m, 1H), 2.36-2.20 (m, 2H), 2.13-1.99 (m, 1H), 1.93-1.88 (m, 1H), 1.57-1.44 (m, 1H), 1.05 (t, 3H).

Example 13

3-((R)-1-(((R)-6-(2,4-dichlorophenyl)-5-(ethoxycarbonyl)-2-(thiazol-2-yl)-3,6-dihydropyrimidin-4-yl)methyl)-4,4-difluoropyrrolidin-2-yl)propanoic acid

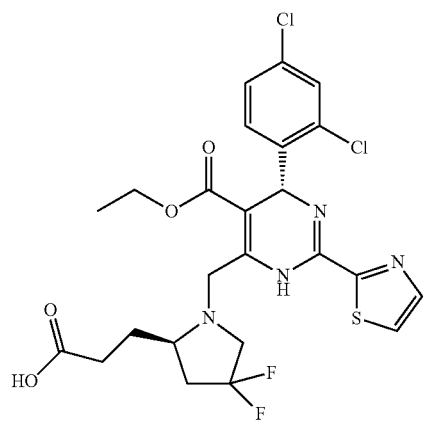 [SMILES: CCOC(=O)C1=C(CN2CC(F)(F)C[C@H]2CCC(=O)O)NC(c2nccs2)=N[C@H]1c1ccc(Cl)cc1Cl]

The title compound was prepared by the procedure described in Example 2 using (R)-3-(4,4-difluoropyrrolidin-2-yl)propanoic acid hydrochloride (0.12 g, 0.56 mmol), (R)-methyl 6-(bromomethyl)-4-(2,4-dichlorophenyl)-2-(thiazol-2-yl)-1,4-dihydropyrimidine-5-carboxylate (0.21 g, 0.44 mmol), potassium carbonate (0.12 g, 0.87 mmol) and anhydrous ethyl alcohol (10 mL) to give the title compound as a yellow solid (0.18 g, 72%). The compound was characterized by the following spectroscopic data:

MS (ESI, pos.ion) m/z: 573.3 [M+H]$^+$; and $^1$H NMR (400 MHz, DMSO-d$_6$): δ 12.05 (s, 1H), 9.52 (s, 1H), 8.00 (d, 1H), 7.94 (d, 1H), 7.60 (br, 1H), 7.41 (br, 2H), 6.04 (s, 1H), 4.14 (dd, 2H), 3.97 (q, 2H), 3.57-3.49 (m, 1H), 3.07-2.97 (m, 2H), 2.58-2.54 (m, 1H), 2.34-2.21 (m, 2H), 2.18-2.03 (m, 1H), 1.95-1.91 (m, 1H), 1.60-1.49 (m, 1H), 1.06 (t, 3H).

Example 14

3-((R)-1-(((R)-6-(2-bromo-4-fluorophenyl)-5-(methoxycarbonyl)-2-(thiazol-2-yl)-3,6-dihydropyrimidin-4-yl)methyl)-4,4-difluoropyrrolidin-2-yl)propanoic acid

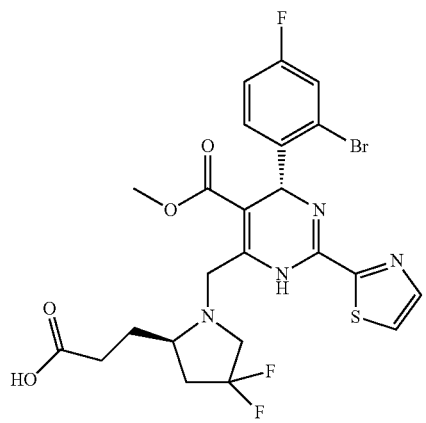

Step 1) (R)-methyl 4-(2-bromo-4-fluorophenyl)-6-methyl-2-(thiazol-2-yl)-1,4-dihydropyrimidine-5-carboxylate

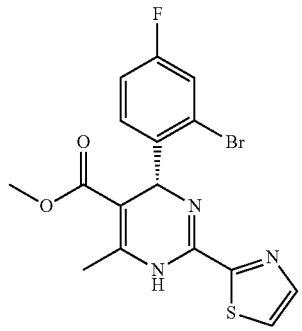 [SMILES: COC(=O)C1=C(C)NC(c2nccs2)=N[C@H]1c1ccc(F)cc1Br]

The title compound was prepared by the procedure described in step 1 of Example 1 using methyl 4-(2-bromo-4-fluorophenyl)-6-methyl-2-(thiazol-2-yl)-1,4-dihydropyrimidine-5-carboxylate (5 g, 12.2 mmol, synthetic procedures refer to: WO2008154817A) to give the title compound as a yellow solid (2 g, 40%). The compound was characterized by the following spectroscopic data:

[a]$_D^{25}$=−86.04 (c=0.3022 g/100 mL, MeOH);

MS (ESI, pos.ion) m/z: 410.0 [M+H]$^+$; and $^1$H NMR (400 MHz, DMSO-d$_6$): δ 7.79 (d, 1H), 7.67 (d, 1H), 7.42 (dd, 1H), 7.36 (dd, 1H), 7.15 (td, 1H), 5.85 (s, 1H), 3.40 (s, 3H), 2.33 (s, 3H).

Step 2) (R)-methyl 4-(2-bromo-4-fluorophenyl)-6-(bromomethyl)-2-(thiazol-2-yl)-1,4-dihydropyrimidine-5-carboxylate

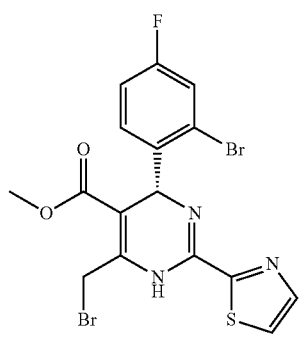 [SMILES: COC(=O)C1=C(CBr)NC(c2nccs2)=N[C@H]1c1ccc(F)cc1Br]

The title compound was prepared by the procedure described in step 2 of Example 1 using (R)-methyl 4-(2-bromo-4-fluorophenyl)-6-methyl-2-(thiazol-2-yl)-1,4-dihydropyrimidine-5-carboxylate (0.98 g, 2.4 mmol), CCl$_4$ (20 mL) and NBS (0.47 g, 2.64 mmol) to give the title compound as a yellow solid (0.8 g, 68%). The compound was characterized by the following spectroscopic data:

MS (ESI, pos.ion) m/z: 489.9[M+H]$^+$; and $^1$H NMR (400 MHz, CDCl$_3$): δ 7.87 (d, 1H), 7.54 (d, 1H), 7.40 (dd, 1H), 7.35 (dd, 1H), 7.03 (td, 1H), 6.11 (s, 1H), 4.97 (d, 1H), 4.64 (d, 1H), 3.69 (s, 3H).

Step 3) 3-((R)-1-(((R)-6-(2-bromo-4-fluorophenyl)-5-(methoxycarbonyl)-2-(thiazol-2-yl)-3,6-dihydropyrimidin-4-yl)methyl)-4,4-difluoropyrrolidin-2-yl)propanoic acid

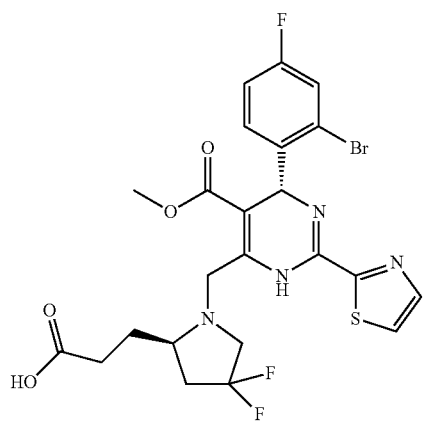

The title compound was prepared by the procedure described in Example 2 using (R)-3-(4,4-difluoropyrrolidin-2-yl)propanoic acid hydrochloride (0.1 g, 0.46 mmol), (R)-methyl 4-(2-bromo-4-fluorophenyl)-6-(bromomethyl)-2-(thiazol-2-yl)-1,4-dihydropyrimidine-5-carboxylate (0.2 g, 0.41 mmol), potassium carbonate (0.06 g, 0.4 mmol) and anhydrous ethyl alcohol (10 mL) to give the title compound as a yellow solid (0.1 g, 40%). The compound was characterized by the following spectroscopic data:

MS (ESI, pos.ion) m/z: 587.2 [M+H]$^+$; and $^1$H NMR (400 MHz, DMSO-d$_6$): δ 11.03 (s, 1H), 9.57 (s, 1H), 7.99 (d, 1H), 7.92 (d, 1H), 7.55 (dd, 1H), 7.39 (dd, 1H), 7.23 (td, 1H), 6.00 (s, 1H), 4.14 (dd, 2H), 3.62-3.54 (m, 1H), 3.53 (s, 3H), 3.05-2.96 (m, 2H), 2.57-2.56 (m, 1H), 2.36-2.20 (m, 2H), 2.13-1.98 (m, 1H), 1.95-1.90 (m, 1H), 1.56-1.46 (m, 1H).

Example 15

3-((R)-1-(((R)-6-(2-chloro-4-fluorophenyl)-5-(methoxycarbonyl)-2-(thiazol-2-yl)-3,6-dihydropyrimidin-4-yl)methyl)-4,4-difluoropyrrolidin-2-yl)propanoic acid

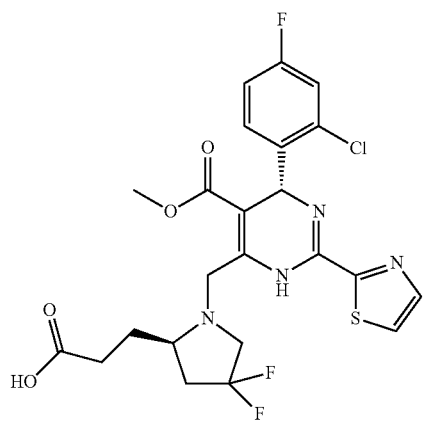 [SMILES: COC(=O)C1=C(CN2CC(F)(F)C[C@H]2CCC(=O)O)NC(c2nccs2)=N[C@H]1c1ccc(F)cc1Cl]

Step 1) (R)-methyl 4-(2-chloro-4-fluorophenyl)-6-methyl-2-(thiazol-2-yl)-1,4-dihydropyrimidine-5-carboxylate

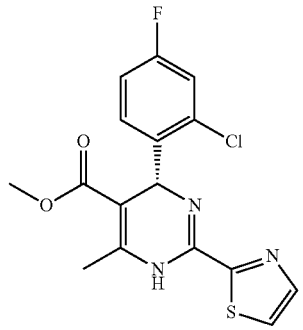 [SMILES: COC(=O)C1=C(C)NC(c2nccs2)=N[C@H]1c1ccc(Cl)cc1Cl]

The title compound was prepared by the procedure described in step 1 of Example 1 using methyl 4-(2-chloro-4-fluorophenyl)-6-methyl-2-(thiazol-2-yl)-1,4-dihydropyrimidine-5-carboxylate (5 g, 13.7 mmol, synthetic procedures refer to: WO2008154818A) to give the title compound as a yellow solid (2.1 g, 42%). The compound was characterized by the following spectroscopic data:

[a]$_D^{25}$=−81.49 (c=0.5031 g/100 mL, MeOH);

MS (ESI, pos.ion) m/z: 366.1 [M+H]$^+$; and $^1$H NMR (400 MHz, DMSO-d$_6$): δ 7.81 (d, 1H), 7.68 (d, 1H), 7.36 (dd, 1H), 7.29 (dd, 1H), 7.11 (td, 1H), 5.90 (s, 1H), 3.41 (s, 3H), 2.34 (s, 3H).

Step 2) (R)-methyl 6-(bromomethyl)-4-(2-chloro-4-fluorophenyl)-2-(thiazol-2-yl)-1,4-dihydropyrimidine-5-carboxylate

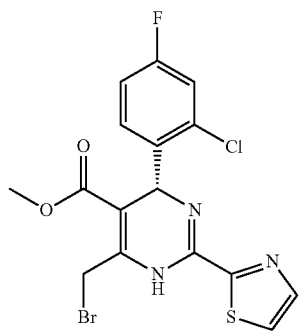 [SMILES: COC(=O)C1=C(CBr)NC(c2nccs2)=N[C@H]1c1ccc(Cl)cc1Cl]

The title compound was prepared by the procedure described in step 2 of Example 1 using (R)-methyl 4-(2-chloro-4-fluorophenyl)-6-methyl-2-(thiazol-2-yl)-1,4-dihydropyrimidine-5-carboxylate (0.88 g, 2.4 mmol), CCl$_4$ (20 mL) and NBS (0.47 g, 2.64 mmol) to give the title compound as a yellow solid (0.78 g, 73%). The compound was characterized by the following spectroscopic data:

MS (ESI, pos.ion) m/z: 445.6 [M+H]$^+$; and $^1$H NMR (600 MHz, DMSO-d$_6$): δ 8.02 (d, 1H), 7.96 (br, 1H), 7.46-7.40 (m, 2H), 7.22 (td, 1H), 5.98 (s, 1H), 4.83 (br, 2H), 3.57 (s, 3H).

Step 3) 3-((R)-1-(((R)-6-(2-chloro-4-fluorophenyl)-5-(methoxycarbonyl)-2-(thiazol-2-yl)-3,6-dihydropyrimidin-4-yl)methyl)-4,4-difluoropyrrolidin-2-yl)propanoic acid

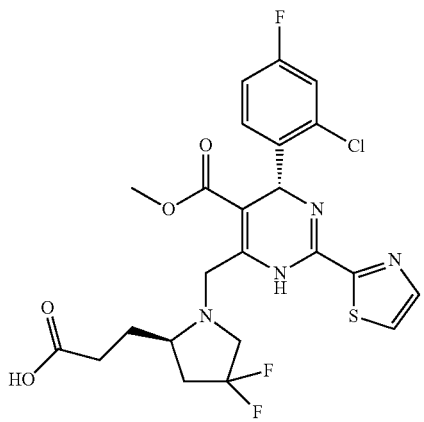 [SMILES: COC(=O)C1=C(CN2CC(F)(F)C[C@H]2CCC(=O)O)NC(c2nccs2)=N[C@H]1c1ccc(Cl)cc1Cl]

The title compound was prepared by the procedure described in Example 2 using (R)-3-(4,4-difluoropyrrolidin-2-yl)propanoic acid hydrochloride (0.15 g, 0.72 mmol), (R)-methyl 6-(bromomethyl)-4-(2-chloro-4-fluorophenyl)-2-(thiazol-2-yl)-1,4-dihydropyrimidine-5-carboxylate (0.31 g, 0.63 mmol), potassium carbonate (0.1 g, 0.7 mmol) and anhydrous ethyl alcohol (10 mL) to give the title compound as a yellow solid (0.26 g, 75%). The compound was characterized by the following spectroscopic data:

MS (ESI, pos.ion) m/z: 543.0 [M+H]+; and $^1$H NMR (400 MHz, DMSO-d$_6$): δ 12.07 (br, 1H), 9.55 (s, 1H), 7.99 (d, 1H), 7.92 (d, 1H), 7.43-7.39 (m, 2H), 7.18 (td, 1H), 6.03 (s, 1H), 4.15 (d, 1H), 4.09 (d, 1H), 3.56-3.54 (m, 1H), 3.53 (s, 3H), 3.05-2.95 (m, 2H), 2.48-2.46 (m, 1H), 2.36-2.17 (m, 2H), 2.15-2.02 (m, 1H), 1.97-1.85 (m, 1H), 1.59-1.50 (m, 1H).

Example 16

3-((R)-1-(((R)-6-(2,4-dichlorophenyl)-5-(methoxycarbonyl)-2-(thiazol-2-yl)-3,6-dihydropyrimidin-4-yl)methyl)-4,4-difluoropyrrolidin-2-yl)propanoic acid

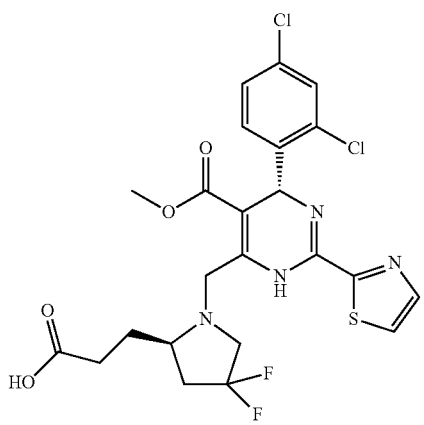

Step 1) (R)-methyl 4-(2,4-dichlorophenyl)-6-methyl-2-(thiazol-2-yl)-1,4-dihydropyrimidine-5-carboxylate

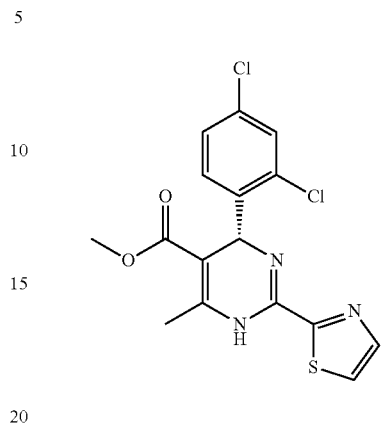

The title compound was prepared by the procedure described in step 1 of Example 1 using ethyl methyl 4-(2,4-dichlorophenyl)-6-methyl-2-(thiazol-2-yl)-1,4-dihydropyrimidine-5-carboxylate (5 g, 13.1 mmol, synthetic procedures refer to: WO0008154820A) to give the title compound as a yellow solid (1.9 g, 38%). The compound was characterized by the following spectroscopic data:

[a]$^1$=−46.08 (c=0.3038 g/100 mL, MeOH);

MS (ESI, pos.ion) m/z: 382.1 [M+H]+; and $^1$H NMR (400 MHz, DMSO-d$_6$): δ 9.99 (s, 1H), 7.98 (d, 1H), 7.90 (d, 1H), 7.59 (d, 1H), 7.40 (dd, 1H), 7.33 (d, 1H), 5.98 (s, 1H), 3.49 (s, 3H), 2.47 (s, 3H).

Step 2) (R)-methyl 6-(bromomethyl)-4-(2,4-dichlorophenyl)-2-(thiazol-2-yl)-1,4-dihydropyrimidine-5-carboxylate

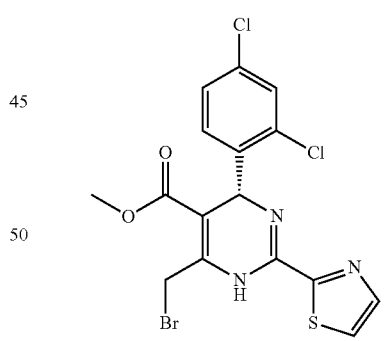

The title compound was prepared by the procedure described in step 2 of Example 1 using (R)-methyl 4-(2,4-dichlorophenyl)-6-methyl-2-(thiazol-2-yl)-1,4-dihydropyrimidine-5-carboxylate (0.92 g, 2.4 mmol), CCl$_4$ (20 mL) and NBS (0.47 g, 2.64 mmol) to give the title compound as a yellow solid (0.72 g, 65%). The compound was characterized by the following spectroscopic data:

MS (ESI, pos.ion) m/z: 459.9 [M+H]+; and $^1$H NMR (600 MHz, DMSO-d$_6$): δ 9.91 (s, 1H), 8.01 (d, 1H), 7.96 (d, 1H), 7.62 (br, 1H), 7.40 (br, 2H), 6.01 (s, 1H), 4.86 (br, 2H), 3.56 (s, 3H).

Step 3) 3-((R)-1-(((R)-6-(2,4-dichlorophenyl)-5-(methoxycarbonyl)-2-(thiazol-2-yl)-3,6-dihydropyrimidin-4-yl)methyl)-4,4-difluoropyrrolidin-2-yl)propanoic acid

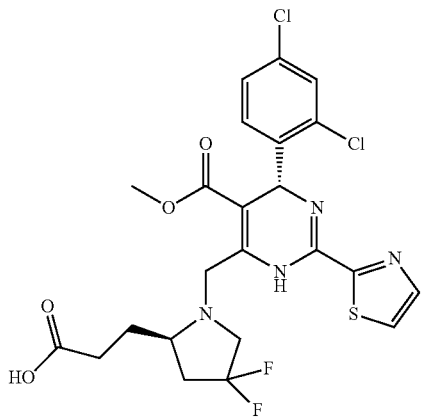

The title compound was prepared by the procedure described in Example 2 using (R)-3-(4,4-difluoropyrrolidin-2-yl)propanoic acid hydrochloride (0.13 g, 0.6 mmol), (R)-methyl 6-(bromomethyl)-4-(2,4-dichlorophenyl)-2-(thiazol-2-yl)-1,4-dihydropyrimidine-5-carboxylate (0.25 g, 0.54 mmol), potassium carbonate (0.1 g, 0.7 mmol) and anhydrous ethyl alcohol (10 mL) to give the title compound as a yellow solid (0.11 g, 38%). The compound was characterized by the following spectroscopic data:

MS (ESI, pos.ion) m/z: 559.0 [M+H]+; and
$^1$H NMR (400 MHz, DMSO-d$_6$): δ 11.07 (br, 1H), 9.56 (s, 1H), 7.99 (d, 1H), 7.92 (d, 1H), 7.60 (br, 1H), 7.39 (br, 2H), 6.02 (s, 1H), 4.14 (dd, 2H), 3.52 (s, 3H), 3.08-2.94 (m, 3H), 2.55-2.53 (m, 1H), 2.30-2.19 (m, 2H), 2.12-1.99 (m, 1H), 1.95-1.84 (m, 1H), 1.60-1.46 (m, 1H).

Example 17

3-((S)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)propanoic acid

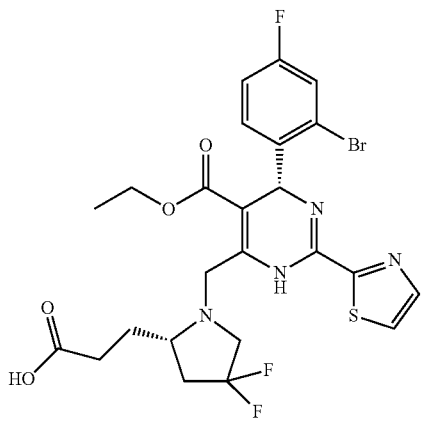 [SMILES: CCOC(=O)C1=C(CN2CC(F)(F)C[C@@H]2CCC(=O)O)NC(c2nccs2)=N[C@H]1c1ccc(F)cc1Br]

Step 1) (R)-tert-butyl 4,4-difluoro-2-formylpyrrolidine-1-carboxylate

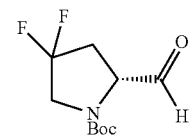

The title compound was prepared by the procedure described in step 5 of Example 1 using (R)-tert-butyl 4,4-difluoro-2-(hydroxymethyl)pyrrolidine-1-carboxylate (10 g, 42.2 mmol), DCM (200 mL) and Dess-Martin periodinane (21.5 g, 50.6 mmol) to give the title compound as light yellow oil (4.8 g, 48%). The compound was characterized by the following spectroscopic data:

MS (ESI, pos.ion) m/z: 180.1 [M+H-56]+.

Step 2) (R)-tert-butyl 2-(3-ethoxy-3-oxoprop-1-en-1-yl)-4,4-difluoropyrrolidine-1-carboxylate

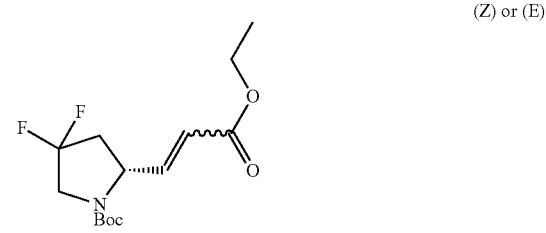 [SMILES: CCOC(=O)C=C[C@H]1CC(F)(F)CN1C(=O)OC(C)(C)C]

The title compound was prepared by the procedure described in step 6 of Example 1 using (R)-tert-butyl 4,4-difluoro-2-formylpyrrolidine-1-carboxylate (4.84 g, 20.57 mmol), DCM (120 mL) and ethyl (triphenylphosphoranylidene)acetate (8.59 g, 24.69 mmol) to give the title compound as light yellow oil (3.83 g, 61%). The compound was characterized by the following spectroscopic data:

MS (ESI, pos.ion) m/z: 206.0 [M+H-100]+.

Step 3) (S)-tert-butyl 2-(3-ethoxy-3-oxopropyl)-4,4-difluoropyrrolidine-1-carboxylate

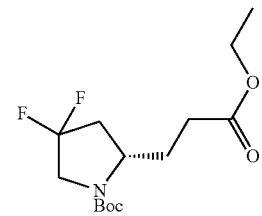

The title compound was prepared by the procedure described in step 6 of Example 2 using (R)-tert-butyl 2-(3-ethoxy-3-oxoprop-1-en-1-yl)-4,4-difluoropyrrolidine-1-carboxylate (3.8 g, 12.4 mmol), methanol (80 mL) and Pd/C (10%, 0.38 g) to give the title compound as colourless oil (3.3 g, 86%). The compound was characterized by the following spectroscopic data:

MS (ESI, pos.ion) m/z: 208.1 [M+H-100]+.

Step 4) (S)-3-(1-(tert-butoxycarbonyl)-4,4-difluoro-pyrrolidin-2-yl)propanoic-acid

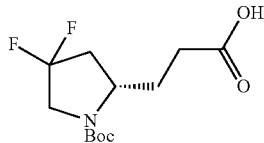

The title compound was prepared by the procedure described in step 6 of Example 3 using (S)-tert-butyl-2-(3-ethoxy-3-oxopropyl)-4,4-difluoropyrrolidine-1-carboxylate (3.2 g, 10.4 mmol), ethanol (32 mL) and aqueous $LiOH \cdot H_2O$ solution ($LiOH \cdot H_2O$ (2.2 g, 52.1 mmol) in 32 mL of water to give the title compound as sandy beige oil (2.53 g, 87%). The compound was characterized by the following spectroscopic data:

MS (ESI, pos.ion) m/z: 224.1 [M+H-56]$^+$.

Step 5) (S)-3-(4,4-difluoropyrrolidin-2-yl)propanoic acid hydrochloride

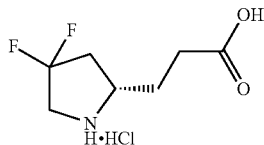

The title compound was prepared by the procedure described in step 6 of Example 4 using (S)-3-(1-(tert-butoxycarbonyl)-4,4-difluoropyrrolidin-2-yl)propanoic-acid (2.5 g, 9 mmol) and HCl in EtOAc (4 mol/L, 50 mL) to give the title compound as a white solid (1.6 g, 83%). The compound was characterized by the following spectroscopic data:

MS (ESI, pos.ion) m/z: 180.2 [M+H]$^+$; and
$^1$H NMR (600 MHz, D$_2$O): δ 4.00-3.94 (m, 1H), 3.82 (dd, 1H), 3.72 (dd, 1H), 2.83-2.76 (m, 1H), 2.57-2.47 (m, 2H), 2.39-2.32 (m, 1H), 2.16-2.03 (m, 2H).

Step 6) 3-((S)-1-(((R)-6-(2-bromo-4-fluorophenyl)-5-(ethoxycarbonyl)-2-(thiazol-2-yl)-3,6-dihydropy-rimidin-4-yl)methyl)-4,4-difluoropyrrolidin-2-yl)propanoic acid

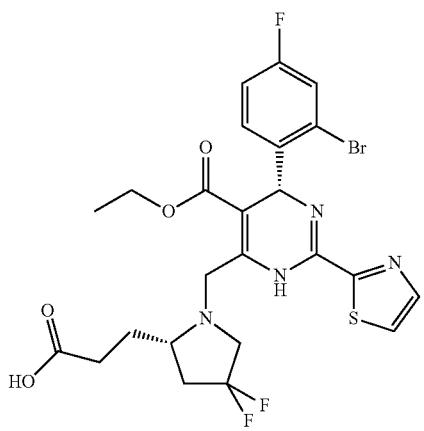 [SMILES: CCOC(=O)C1=C(CN2CC(F)(F)C[C@@H]2CCC(=O)O)NC(c2nccs2)=N[C@H]1c1ccc(F)cc1Br]

The title compound was prepared by the procedure described in Example 2 using (S)-3-(4,4-difluoropyrrolidin-2-yl)propanoic acid hydrochloride (0.18 g, 0.84 mmol), (R)-ethyl 4-(2-bromo-4-fluorophenyl)-6-(bromomethyl)-2-(thiazol-2-yl)-1,4-dihydropyrimidine-5-carboxylate (0.47 g, 0.92 mmol), potassium carbonate (0.46 g, 3.36 mmol) and anhydrous ethyl alcohol (10 mL) to give the title compound as a yellow solid (0.28 g, 55%). The compound was characterized by the following spectroscopic data:

MS (ESI, pos.ion) m/z: 601.2 [M+H]$^+$; and
$^1$H NMR (400 MHz, CDCl$_3$): δ 12.19 (br, 1H), 9.46 (s, 1H), 7.86 (d, 1H), 7.50 (d, 1H), 7.37-7.33 (m, 2H), 7.00 (td, 1H), 6.19 (s, 1H), 4.52 (d, 1H), 4.14-4.03 (m, 2H), 3.65 (d, 1H), 3.31-3.23 (m, 2H), 3.02-2.91 (m, 1H), 2.57-2.25 (m, 5H), 1.79-1.74 (m, 1H), 1.16 (t, 3H).

Example 18

3-((S)-1-(((R)-6-(2-bromo-4-fluorophenyl)-5-(methoxycarbonyl)-2-(thiazol-2-yl)-3,6-dihydropy-rimidin-4-yl)methyl)-4,4-difluoropyrrolidin-2-yl)propanoic acid

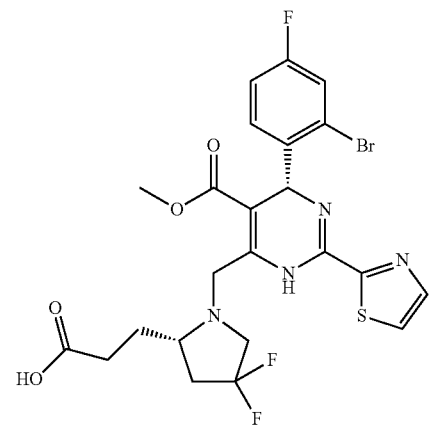

The title compound was prepared by the procedure described in Example 2 using (S)-3-(4,4-difluoropyrrolidin-2-yl)propanoic acid hydrochloride (0.22 g, 1 mmol), (R)-methyl 4-(2-bromo-4-fluorophenyl)-6-(bromomethyl)-2-(thiazol-2-yl)-1,4-dihydropyrimidine-5-carboxylate (0.49 g, 1 mmol), potassium carbonate (0.14 g, 1 mmol) and anhydrous ethyl alcohol (10 mL) to give the title compound as a yellow solid (0.29 g, 49%). The compound was characterized by the following spectroscopic data:

MS (ESI, pos.ion) m/z: 587.2 [M+H]$^+$; and
$^1$H NMR (400 MHz, CDCl$_3$): δ 12.15 (br, 1H), 9.47 (s, 1H), 7.85 (d, 1H), 7.51 (d, 1H), 7.38-7.33 (m, 2H), 7.01 (td, 1H), 6.17 (s, 1H), 4.50 (d, 1H), 3.66 (d, 1H), 3.55 (s, 3H), 3.33-3.23 (m, 2H), 3.04-2.92 (m, 1H), 2.58-2.25 (m, 5H), 1.78-1.74 (m, 1H).

Example 19

3-((S)-1-(((R)-6-(2-chloro-4-fluorophenyl)-5-(ethoxycarbonyl)-2-(thiazol-2-yl)-3,6-dihydropyrimidin-4-yl)methyl)-4,4-difluoropyrrolidin-2-yl)propanoic acid

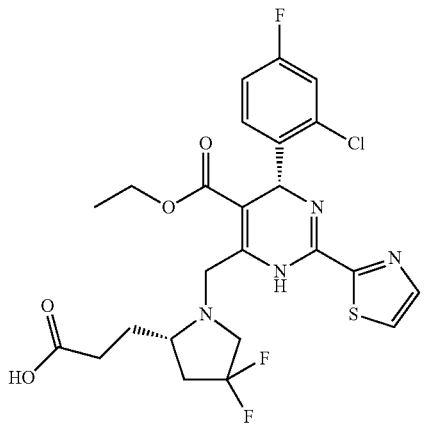 [SMILES: CCOC(=O)C1=C(CN2CC(F)(F)C[C@@H]2CCC(=O)O)NC(c2nccs2)=N[C@H]1c1ccc(F)cc1Cl]

The title compound was prepared by the procedure described in Example 2 using (S)-3-(4,4-difluoropyrrolidin-2-yl)propanoic acid hydrochloride (0.22 g, 1 mmol), (R)-ethyl 6-(bromomethyl)-4-(2-chloro-4-fluorophenyl)-2-(thiazol-2-yl)-1,4-dihydropyrimidine-5-carboxylate (0.46 g, 1 mmol), potassium carbonate (0.28 g, 2 mmol) and anhydrous ethyl alcohol (10 mL) to give the title compound as a yellow solid (0.31 g, 56%). The compound was characterized by the following spectroscopic data:

MS (ESI, pos.ion) m/z: 557.2 [M+H]$^+$; and $^1$H NMR (400 MHz, DMSO-d$_6$): δ 12.16 (br, 1H), 9.45 (s, 1H), 8.00 (d, 1H), 7.94 (d, 1H), 7.47-7.41 (m, 2H), 7.18 (td, 1H), 6.06 (s, 1H), 4.12 (dd, 2H), 4.00-3.93 (m, 2H), 3.46-3.38 (m, 1H), 3.01-2.85 (m, 2H), 2.60-2.53 (m, 1H), 2.40-2.23 (m, 2H), 2.15-1.99 (m, 2H), 1.66-1.56 (m, 1H), 1.05 (t, 3H).

Example 20

3-((S)-1-(((R)-6-(2-chloro-4-fluorophenyl)-5-(methoxycarbonyl)-2-(thiazol-2-yl)-3,6-dihydropyrimidin-4-yl)methyl)-4,4-difluoropyrrolidin-2-yl)propanoic acid

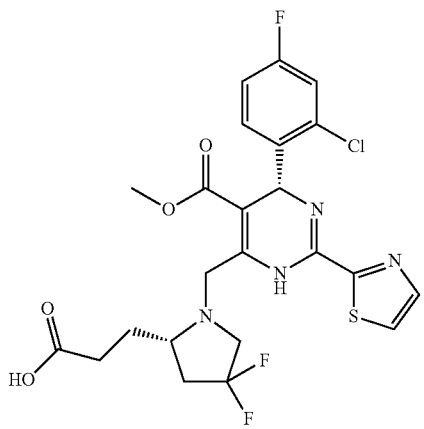 [SMILES: COC(=O)C1=C(CN2CC(F)(F)C[C@@H]2CCC(=O)O)NC(c2nccs2)=N[C@H]1c1ccc(F)cc1Cl]

The title compound was prepared by the procedure described in Example 2 using (S)-3-(4,4-difluoropyrrolidin-2-yl)propanoic acid hydrochloride (0.22 g, 1 mmol), (R)-methyl 6-(bromomethyl)-4-(2-chloro-4-fluorophenyl)-2-(thiazol-2-yl)-1,4-dihydropyrimidine-5-carboxylate (0.45 g, 1 mmol), potassium carbonate (0.14 g, 1 mmol) and anhydrous ethyl alcohol (10 mL) to give the title compound as a yellow solid (0.23 g, 43%). The compound was characterized by the following spectroscopic data:

MS (ESI, pos.ion) m/z: 543.0 [M+H]$^+$; and $^1$H NMR (400 MHz, DMSO-d$_6$): δ 12.06 (br, 1H), 9.56 (s, 1H), 8.01 (d, 1H), 7.94 (d, 1H), 7.44-7.40 (m, 2H), 7.16 (td, 1H), 6.05 (s, 1H), 4.13 (d, 1H), 4.09 (d, 1H), 3.57-3.54 (m, 1H), 3.52 (s, 3H), 3.06-2.96 (m, 2H), 2.47-2.45 (m, 1H), 2.37-2.17 (m, 2H), 2.16-2.02 (m, 1H), 1.98-1.85 (m, 1H), 1.60-1.51 (m, 1H).

Example 21

3-((S)-1-(((R)-6-(2,4-dichlorophenyl)-5-(ethoxycarbonyl)-2-(thiazol-2-yl)-3,6-dihydropyrimidin-4-yl)methyl)-4,4-difluoropyrrolidin-2-yl)propanoic acid

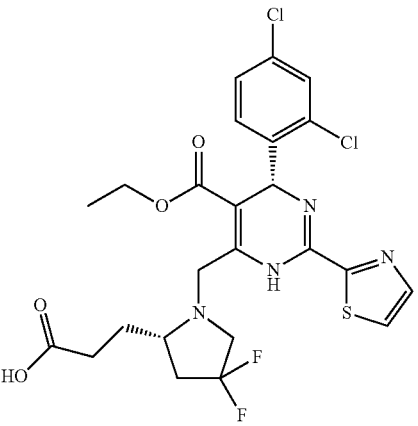 [SMILES: CCOC(=O)C1=C(CN2CC(F)(F)C[C@@H]2CCC(=O)O)NC(c2nccs2)=N[C@H]1c1ccc(Cl)cc1Cl]

The title compound was prepared by the procedure described in Example 2 using (S)-3-(4,4-difluoropyrrolidin-2-yl)propanoic acid hydrochloride (0.22 g, 1 mmol), (R)-ethyl 6-(bromomethyl)-4-(2,4-dichlorophenyl)-2-(thiazol-2-yl)-1,4-dihydropyrimidine-5-carboxylate (0.48 g, 1 mmol), potassium carbonate (0.28 g, 2 mmol) and anhydrous ethyl alcohol (10 mL) to give the title compound as a yellow solid (0.35 g, 62%). The compound was characterized by the following spectroscopic data:

MS (ESI, pos.ion) m/z: 573.2[M+H]$^+$; and $^1$H NMR (400 MHz, DMSO-d$_6$): δ 12.17 (s, 1H), 9.47 (s, 1H), 8.00 (d, 1H), 7.94 (d, 1H), 7.60 (br, 1H), 7.45-7.37 (m, 2H), 6.06 (s, 1H), 4.15 (dd, 2H), 3.96 (q, 2H), 3.47-3.39 (m, 1H), 3.01-2.86 (m, 2H), 2.59-2.53 (m, 1H), 2.38-2.25 (m, 2H), 2.15-2.01 (m, 2H), 1.65-1.55 (m, 1H), 1.05 (t, 3H).

Example 22

3-((S)-1-(((R)-6-(2,4-dichlorophenyl)-5-(methoxycarbonyl)-2-(thiazol-2-yl)-3,6-dihydropyrimidin-4-yl)methyl)-4,4-difluoropyrrolidin-2-yl)propanoic acid

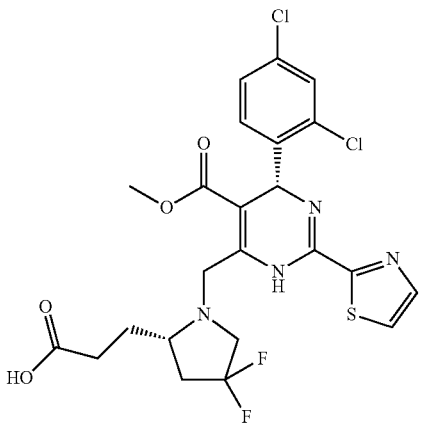 [SMILES: COC(=O)C1=C(CN2CC(F)(F)C[C@@H]2CCC(=O)O)NC(c2nccs2)=N[C@H]1c1ccc(Cl)cc1Cl]

The title compound was prepared by the procedure described in Example 2 using (S)-3-(4,4-difluoropyrrolidin-2-yl)propanoic acid hydrochloride (0.22 g, 1 mmol), (R)-methyl 6-(bromomethyl)-4-(2,4-dichlorophenyl)-2-(thiazol-2-yl)-1,4-dihydropyrimidine-5-carboxylate (0.46 g, 1 mmol), potassium carbonate (0.14 g, 1 mmol) and anhydrous ethyl alcohol (10 mL) to give the title compound as a yellow solid (0.26 g, 47%). The compound was characterized by the following spectroscopic data:

MS (ESI, pos.ion) m/z: 558.6[M+H]+; and $^1$H NMR (400 MHz, DMSO-d$_6$): δ 12.15 (s, 1H), 9.52 (s, 1H), 8.00 (d, 1H), 7.94 (d, 1H), 7.60 (s, 1H), 7.41 (br, 2H), 6.05 (s, 1H), 4.13 (dd, 2H), 3.52 (s, 3H), 3.47-3.39 (m, 1H), 3.01-2.87 (m, 2H), 2.59-2.53 (m, 1H), 2.37-2.25 (m, 2H), 2.15-2.02 (m, 2H), 1.64-1.55 (m, 1H).

Example 23

3-((R)-1-(((R)-6-(2-bromo-4-fluorophenyl)-5-(methoxycarbonyl)-2-(thiazol-2-yl)-3,6-dihydropyrimidin-4-yl)methyl)-4,4-difluoropyrrolidin-2-yl)-2-methylpropanoic acid

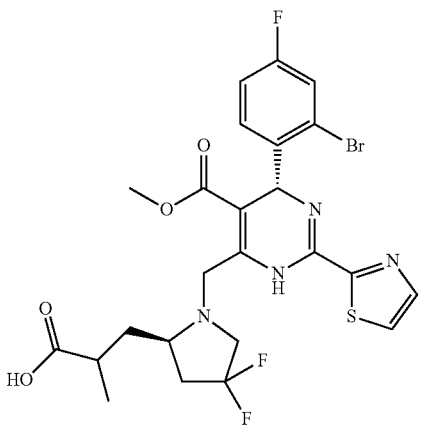 [SMILES: COC(=O)C1=C(CN2CC(F)(F)C[C@H]2CC(C)C(=O)O)NC(c2nccs2)=N[C@H]1c1ccc(F)cc1Br]

The title compound was prepared by the procedure described in Example 2 using 3-((R)-4,4-difluoropyrrolidin-2-yl)-2-methylpropanoic acid hydrochloride (0.23 g, 1 mmol), (R)-methyl 4-(2-bromo-4-fluorophenyl)-6-(bromomethyl)-2-(thiazol-2-yl)-1,4-dihydropyrimidine-5-carboxylate (0.49 g, 1 mmol), potassium carbonate (0.14 g, 1 mmol) and anhydrous ethyl alcohol (10 mL) to give the title compound as a yellow solid (0.23 g, 39%). The compound was characterized by the following spectroscopic data:

MS (ESI, pos.ion) m/z: 600.7 [M+H]+; and $^1$H NMR (400 MHz, DMSO-d$_6$): δ 8.01 (d, 1H), 7.93 (d, 1H), 7.56 (dd, 1H), 7.44 (dd, 1H), 7.24 (td, 1H), 6.02 (s, 1H), 4.49 (d, 1H), 4.20 (t, 1H), 3.90 (br, 1H), 3.59 (s, 3H), 3.56-3.43 (m, 2H), 2.80-2.70 (m, 1H), 2.46-2.35 (m, 1H), 2.31-2.14 (m, 1H), 2.03-1.87 (m, 1H), 1.57-1.46 (m, 1H), 1.13 (d, 3H).

Example 24

3-((R)-1-(((R)-6-(2-chloro-4-fluorophenyl)-5-(ethoxycarbonyl)-2-(thiazol-2-yl)-3,6-dihydropyrimidin-4-yl)methyl)-4,4-difluoropyrrolidin-2-yl)-2-methylpropanoic acid

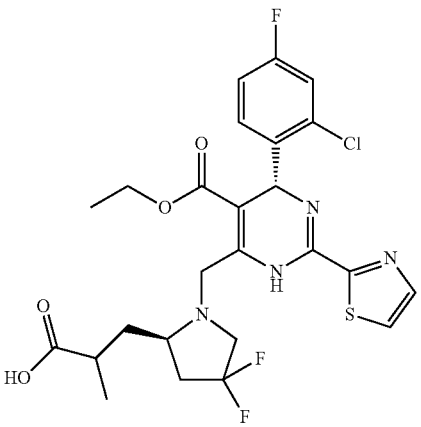 [SMILES: CCOC(=O)C1=C(CN2CC(F)(F)C[C@H]2CC(C)C(=O)O)NC(c2nccs2)=N[C@H]1c1ccc(F)cc1Cl]

The title compound was prepared by the procedure described in Example 2 using 3-((R)-4,4-difluoropyrrolidin-2-yl)-2-methylpropanoic acid hydrochloride (0.1 g, 0.44 mmol), (R)-ethyl 6-(bromomethyl)-4-(2-chloro-4-fluorophenyl)-2-(thiazol-2-yl)-1,4-dihydropyrimidine-5-carboxylate (0.31 g, 0.68 mmol), potassium carbonate (0.12 g, 0.87 mmol) and anhydrous ethyl alcohol (10 mL) to give the title compound as a yellow solid (0.11 g, 45%). The compound was characterized by the following spectroscopic data:

MS (ESI, pos.ion) m/z: 571.2 [M+H]+; and $^1$H NMR (400 MHz, DMSO-d$_6$): δ 9.49 (s, 1H), 8.00 (d, 1H), 7.92 (d, 1H), 7.48-7.38 (m, 2H), 7.18 (td, 1H), 6.04 (s, 1H), 4.53 (d, 1H), 4.19 (t, 1H), 4.02 (q, 2H), 3.90 (br, 1H), 3.52-3.42 (m, 2H), 2.77-2.68 (m, 1H), 2.48-2.36 (m, 1H), 2.31-2.14 (m, 1H), 2.04-1.87 (m, 1H), 1.54-1.45 (m, 1H), 1.16-1.09 (m, 6H).

Example 25

3-((R)-1-(((R)-6-(2-chloro-4-fluorophenyl)-5-(methoxycarbonyl)-2-(thiazol-2-yl)-3,6-dihydropyrimidin-4-yl)methyl)-4,4-difluoropyrrolidin-2-yl)-2-methylpropanoic acid

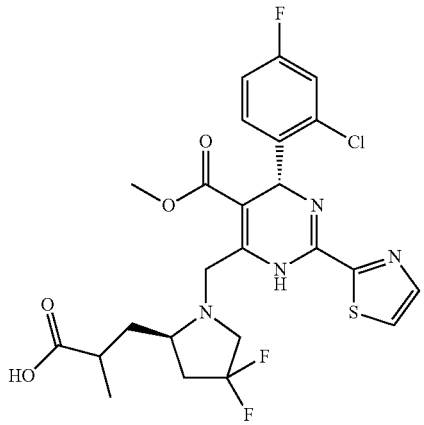 [SMILES: COC(=O)C1=C(CN2CC(F)(F)C[C@H]2CC(C)C(=O)O)NC(c2nccs2)=N[C@H]1c1ccc(F)cc1Cl]

The title compound was prepared by the procedure described in Example 2 using 3-((R)-4,4-difluoropyrrolidin-2-yl)-2-methylpropanoic acid hydrochloride (0.23 g, 1 mmol), (R)-methyl 6-(bromomethyl)-4-(2-chloro-4-fluorophenyl)-2-(thiazol-2-yl)-1,4-dihydropyrimidine-5-carboxylate (0.44 g, 1 mmol), potassium carbonate (0.14 g, 1 mmol) and anhydrous ethyl alcohol (10 mL) to give the title compound as a yellow solid (0.23 g, 41%). The compound was characterized by the following spectroscopic data:

MS (ESI, pos.ion) m/z: 556.7 [M+H]$^+$; and $^1$H NMR (400 MHz, DMSO-d$_6$): δ 9.54 (s, 1H), 7.99 (d, 1H), 7.91 (d, 1H), 7.43-7.35 (m, 2H), 7.17 (td, 1H), 6.02 (s, 1H), 4.47 (d, 1H), 4.21 (t, 1H), 3.92 (br, 1H), 3.52 (s, 3H), 3.50-3.40 (m, 2H), 2.81-2.71 (m, 1H), 2.49-2.37 (m, 1H), 2.33-2.17 (m, 1H), 2.03-1.85 (m, 1H), 1.58-1.46 (m, 1H), 1.12 (d, 3H).

Example 26

3-((R)-1-(((R)-6-(2,4-dichlorophenyl)-5-(ethoxycarbonyl)-2-(thiazol-2-yl)-3,6-dihydropyrimidin-4-yl)methyl)-4,4-difluoropyrrolidin-2-yl)-2-methylpropanoic acid

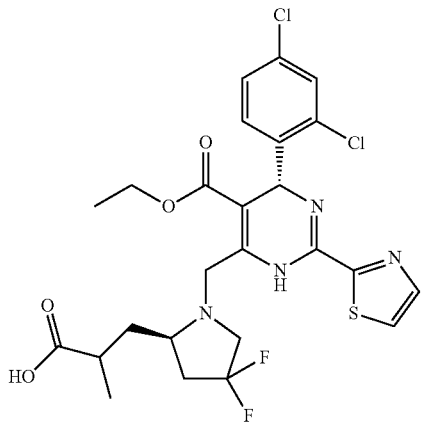 [SMILES: CCOC(=O)C1=C(CN2CC(F)(F)C[C@H]2CC(C)C(=O)O)NC(c2nccs2)=N[C@H]1c1ccc(Cl)cc1Cl]

The title compound was prepared by the procedure described in Example 2 using 3-((R)-4,4-difluoropyrrolidin-2-yl)-2-methylpropanoic acid hydrochloride (0.23 g, 1 mmol), (R)-ethyl 6-(bromomethyl)-4-(2,4-dichlorophenyl)-2-(thiazol-2-yl)-1,4-dihydropyrimidine-5-carboxylate (0.48 g, 1 mmol), potassium carbonate (0.28 g, 2 mmol) and anhydrous ethyl alcohol (10 mL) to give the title compound as a yellow solid (0.31 g, 53%). The compound was characterized by the following spectroscopic data:

MS (ESI, pos.ion) m/z: 587.2 [M+H]$^+$; and $^1$H NMR (400 MHz, DMSO-d$_6$): δ 9.50 (s, 1H), 8.01 (d, 1H), 7.93 (d, 1H), 7.60 (br, 1H), 7.40 (br, 2H), 6.03 (s, 1H), 4.17-4.01 (m, 3H), 3.97 (q, 2H), 3.20-2.95 (m, 2H), 2.65-2.59 (m, 1H), 2.39-2.29 (m, 1H), 2.08-2.02 (m, 1H), 1.75-1.60 (m, 1H), 1.55-1.45 (m, 1H), 1.10-0.95 (m, 6H).

Example 27

3-((R)-1-(((R)-6-(2,4-dichlorophenyl)-5-(methoxycarbonyl)-2-(thiazol-2-yl)-3,6-dihydropyrimidin-4-yl)methyl)-4,4-difluoropyrrolidin-2-yl)-2-methylpropanoic acid

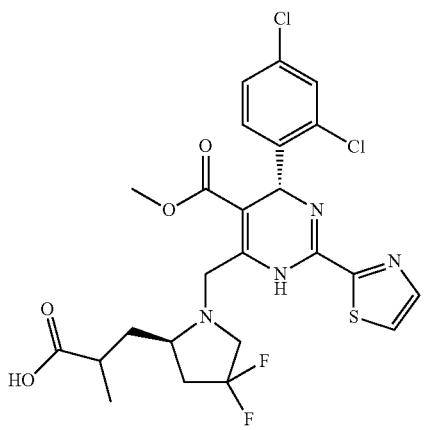 [SMILES: COC(=O)C1=C(CN2CC(F)(F)C[C@H]2CC(C)C(=O)O)NC(c2nccs2)=N[C@H]1c1ccc(Cl)cc1Cl]

The title compound was prepared by the procedure described in Example 2 using 3-((R)-4,4-difluoropyrrolidin-2-yl)-2-methylpropanoic acid hydrochloride (0.23 g, 1 mmol), (R)-methyl 6-(bromomethyl)-4-(2,4-dichlorophenyl)-2-(thiazol-2-yl)-1,4-dihydropyrimidine-5-carboxylate (0.46 g, 1 mmol), potassium carbonate (0.14 g, 1 mmol) and anhydrous ethyl alcohol (10 mL) to give the title compound as a yellow solid (0.25 g, 44%). The compound was characterized by the following spectroscopic data:

MS (ESI, pos.ion) m/z: 572.6 [M+H]$^+$; and $^1$H NMR (400 MHz, DMSO-d$_6$): δ 9.55 (s, 1H), 8.00 (d, 1H), 7.92 (d, 1H), 7.58 (br, 1H), 7.38 (br, 2H), 6.02 (s, 1H), 4.15-4.05 (m, 3H), 3.52 (s, 3H), 3.21-2.98 (m, 2H), 2.63-2.58 (m, 1H), 2.37-2.29 (m, 1H), 2.09-2.02 (m, 1H), 1.77-1.62 (m, 1H), 1.56-1.46 (m, 1H), 1.13 (d, 3H).

Example 28

3-((S)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)-2-methylpropanoic acid

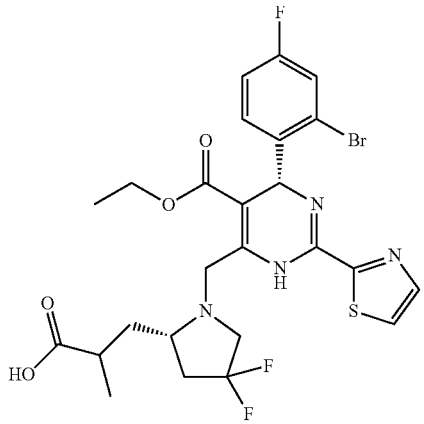 [SMILES: CCOC(=O)C1=C(CN2CC(F)(F)C[C@@H]2CC(C)C(=O)O)NC(c2nccs2)=N[C@H]1c1ccc(F)cc1Br]

Step 1) (R)-tert-butyl 4,4-difluoro-2-(3-methoxy-2-methyl-3-oxoprop-1-en-1-yl)pyrrolidine-1-carboxylate

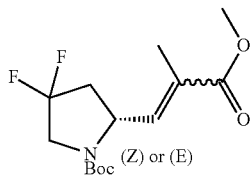

The title compound was prepared by the procedure described in step 6 of Example 1 using (R)-tert-butyl 4,4-difluoro-2-formylpyrrolidine-1-carboxylate (2.6 g, 11.06 mmol), DCM (120 mL) and Methyl 2-(triphenylphosphoranylidene)propanoate (4.24 g, 12.17 mmol) to give the title compound as yellow oil (1.9 g, 56%). The compound was characterized by the following spectroscopic data:
MS (ESI, pos.ion) m/z: 206.1 [M+H-100]$^+$.

Step 2) (2S)-tert-butyl 4,4-difluoro-2-(3-methoxy-2-methyl-3-oxopropyl)pyrrolidine-1-carboxylate

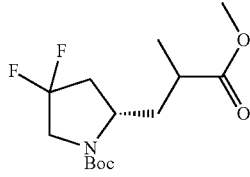 [SMILES: COC(=O)C(C)C[C@H]1CC(F)(F)CN1C(=O)OC(C)(C)C]

The title compound was prepared by the procedure described in step 6 of Example 2 using (R)-tert-butyl 4,4-difluoro-2-(3-methoxy-2-methyl-3-oxoprop-1-en-1-yl)pyrrolidine-1-carboxylate (1.6 g, 5.24 mmol), methanol (10 mL) and Pd/C (10%, 0.2 g) to give the title compound as colourless oil (1.38 g, 85.7%). The compound was characterized by the following spectroscopic data:
MS (ESI, pos.ion) m/z: 252.2 [M+H-56].

Step 3) 3-((S)-1-(tert-butoxycarbonyl)-4,4-difluoropyrrolidin-2-yl)-2-methylpropanoic acid

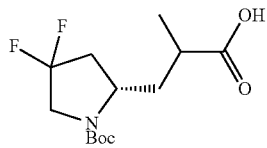 [SMILES: CC(C[C@H]1CC(F)(F)CN1C(=O)OC(C)(C)C)C(=O)O]

The title compound was prepared by the procedure described in step 6 of Example 3 using (2S)-tert-butyl 4,4-difluoro-2-(3-methoxy-2-methyl-3-oxopropyl)pyrrolidine-1-carboxylate (1.4 g, 4.55 mmol), ethanol (50 mL) and aqueous LiOH.H$_2$O solution (LiOH.H$_2$O (1.9 g, 45.3 mmol) in 50 mL of water) to give the title compound as light yellow oil (1.2 g, 90%). The compound was characterized by the following spectroscopic data:
MS (ESI, pos.ion) m/z: 194.1 [M+H-100]$^+$.

Step 4) 3-((S)-4,4-difluoropyrrolidin-2-yl)-2-methylpropanoic acid hydrochloride

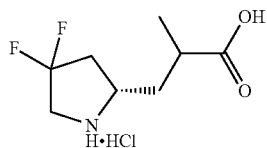

The title compound was prepared by the procedure described in step 6 of Example 4 using 3-((S)-1-(tert-butoxycarbonyl)-4,4-difluoropyrrolidin-2-yl)-2-methylpropanoic acid (1.1 g, 3.75 mmol) and HCl in EtOAc (4 mol/L, 10 mL) to give the title compound as light brownness goo (0.71 g, 83%). The compound was characterized by the following spectroscopic data:
MS (ESI, pos.ion) m/z: 194.2 [M+H]$^+$.

Step 5) 3-((S)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)-2-methylpropanoic acid

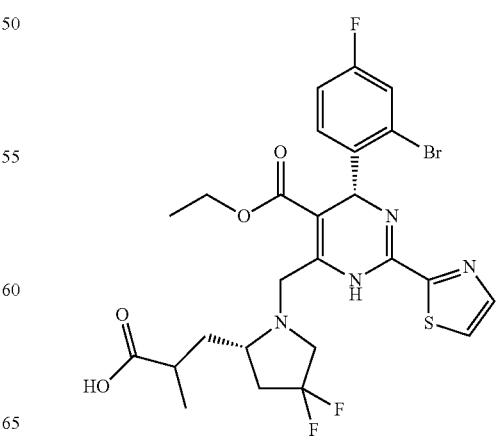

The title compound was prepared by the procedure described in Example 2 using 3-((S)-4,4-difluoropyrrolidin-2-yl)-2-methylpropanoic acid hydrochloride (0.86 g, 3.75 mmol), ((R)-ethyl 4-(2-bromo-4-fluorophenyl)-6-(bromomethyl)-2-(thiazol-2-yl)-1,4-dihydropyrimidine-5-carboxylate (2.07 g, 4.12 mmol), potassium carbonate (1.54 g, 11.19 mmol) and anhydrous ethyl alcohol (40 mL) to give the title compound as a yellow solid (1.36 g, 59%). The compound was characterized by the following spectroscopic data:

MS (ESI, pos.ion) m/z: 615.1 [M+H]$^+$; and $^1$H NMR (400 MHz, DMSO-d$_6$): δ 8.04 (d, 1H), 7.96 (d, 1H), 7.60 (dd, 1H), 7.51 (dd, 1H), 7.20 (td, 1H), 6.02 (s, 1H), 4.48 (d, 1H), 4.20 (t, 1H), 3.98 (q, 2H), 3.88 (br, 1H), 3.56-3.43 (m, 2H), 2.82-2.71 (m, 1H), 2.48-2.37 (m, 1H), 2.31-2.13 (m, 1H), 2.05-1.88 (m, 1H), 1.57-1.46 (m, 1H), 1.13-1.09 (m, 6H).

Example 29

3-((S)-1-(((R)-6-(2-chloro-4-fluorophenyl)-5-(ethoxycarbonyl)-2-(thiazol-2-yl)-3,6-dihydropyrimidin-4-yl)methyl)-4,4-difluoropyrrolidin-2-yl)-2-methylpropanoic acid

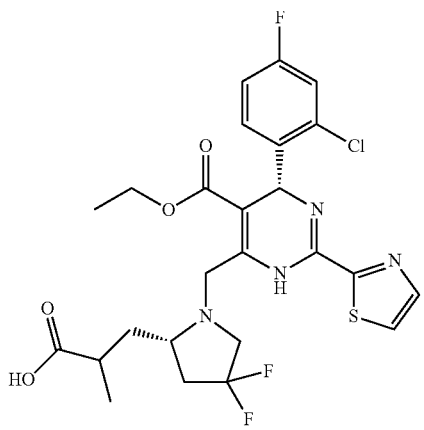 [SMILES: CCOC(=O)C1=C(CN2CC(F)(F)C[C@@H]2CC(C)C(=O)O)NC(c2nccs2)=N[C@H]1c1ccc(F)cc1Cl]

The title compound was prepared by the procedure described in Example 2 using 3-((S)-4,4-difluoropyrrolidin-2-yl)-2-methylpropanoic acid hydrochloride (0.2 g, 0.87 mmol), (R)-ethyl 6-(bromomethyl)-4-(2-chloro-4-fluorophenyl)-2-(thiazol-2-yl)-1,4-dihydropyrimidine-5-carboxylate (0.4 g, 0.87 mmol), potassium carbonate (0.24 g, 1.74 mmol) and anhydrous ethyl alcohol (8 mL) to give the title compound as a yellow solid (0.23 g, 47%). The compound was characterized by the following spectroscopic data:

MS (ESI, pos.ion) m/z: 571.1 [M+H]$^+$; and $^1$H NMR (400 MHz, DMSO-d$_6$): δ 8.03 (d, 1H), 7.94 (d, 1H), 7.46-7.39 (m, 2H), 7.19 (td, 1H), 6.02 (s, 1H), 4.51 (d, 1H), 4.18 (t, 1H), 4.01 (q, 2H), 3.92 (br, 1H), 3.54-3.41 (m, 2H), 2.79-2.69 (m, 1H), 2.48-2.36 (m, 1H), 2.33-2.15 (m, 1H), 2.07-1.85 (m, 1H), 1.56-1.45 (m, 1H), 1.18-1.09 (m, 6H).

Example 30

3-((S)-1-(((R)-6-(2,4-dichlorophenyl)-5-(ethoxycarbonyl)-2-(thiazol-2-yl)-3,6-dihydropyrimidin-4-yl)methyl)-4,4-difluoropyrrolidin-2-yl)-2-methylpropanoic acid

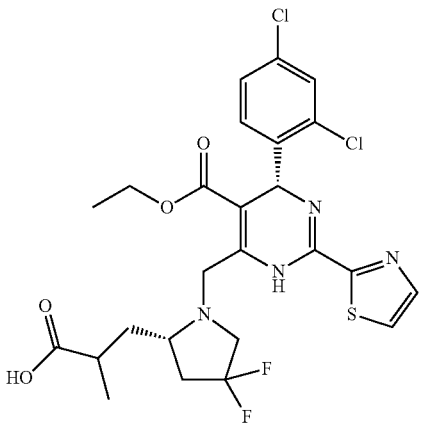

The title compound was prepared by the procedure described in Example 2 using 3-((S)-4,4-difluoropyrrolidin-2-yl)-2-methylpropanoic acid hydrochloride (0.23 g, 1 mmol), (R)-ethyl 6-(bromomethyl)-4-(2,4-dichlorophenyl)-2-(thiazol-2-yl)-1,4-dihydropyrimidine-5-carboxylate (0.48 g, 1 mmol), potassium carbonate (0.28 g, 2 mmol) and anhydrous ethyl alcohol (10 mL) to give the title compound as a yellow solid (0.33 g, 57%). The compound was characterized by the following spectroscopic data:

MS (ESI, pos.ion) m/z: 586.7 [M+H]$^+$; and $^1$H NMR (400 MHz, DMSO-d$_6$): δ 8.03 (d, 1H), 7.94 (d, 1H), 7.61 (br, 1H), 7.39 (br, 2H), 6.01 (s, 1H), 4.18-4.03 (m, 3H), 3.98 (q, 2H), 3.22-2.96 (m, 2H), 2.68-2.59 (m, 1H), 2.39-2.27 (m, 1H), 2.06-2.02 (m, 1H), 1.79-1.60 (m, 1H), 1.58-1.45 (m, 1H), 1.13-0.97 (m, 6H).

Example 31

3-((S)-1-(((R)-6-(2-chloro-4-fluorophenyl)-5-(methoxycarbonyl)-2-(thiazol-2-yl)-3,6-dihydropyrimidin-4-yl)methyl)-4,4-difluoropyrrolidin-2-yl)-2-methylpropanoic acid

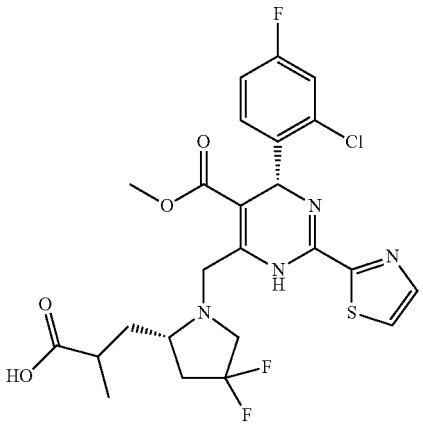 [SMILES: COC(=O)C1=C(CN2CC(F)(F)C[C@@H]2CC(C)C(=O)O)NC(c2nccs2)=N[C@H]1c1ccc(F)cc1Cl]

The title compound was prepared by the procedure described in Example 2 using 3-((S)-4,4-difluoropyrrolidin-2-yl)-2-methylpropanoic acid hydrochloride (0.23 g, 1 mmol), (R)-methyl 6-(bromomethyl)-4-(2-chloro-4-fluorophenyl)-2-(thiazol-2-yl)-1,4-dihydropyrimidine-5-carboxylate (0.44 g, 1 mmol), potassium carbonate (0.14 g, 1 mmol) and anhydrous ethyl alcohol (9 mL) to give the title compound as a yellow solid (0.21 g, 37%). The compound was characterized by the following spectroscopic data:

MS (ESI, pos.ion) m/z: 556.7 [M+H]$^+$; and $^1$H NMR (400 MHz, DMSO-d$_6$): δ 8.01 (d, 1H), 7.92 (d, 1H), 7.45-7.38 (m, 2H), 7.18 (td, 1H), 6.01 (s, 1H), 4.48 (d, 1H), 4.20 (t, 1H), 3.94 (br, 1H), 3.53 (s, 3H), 3.49-3.41 (m, 2H), 2.82-2.71 (m, 1H), 2.47-2.37 (m, 1H), 2.35-2.18 (m, 1H), 2.05-1.87 (m, 1H), 1.58-1.45 (m, 1H), 1.11 (d, 3H).

Example 32

3-((S)-1-(((R)-6-(2-chloro-4-fluorophenyl)-5-(ethoxycarbonyl)-2-(thiazol-2-yl)-3,6-dihydropyrimidin-4-yl)methyl)-4,4-difluoropyrrolidin-2-yl)butanoic acid

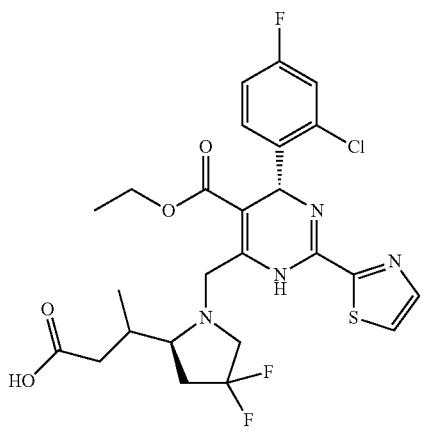 [SMILES: CCOC(=O)C1=C(CN2CC(F)(F)C[C@H]2C(C)CC(=O)O)NC(c2nccs2)=N[C@H]1c1ccc(F)cc1Cl]

The title compound was prepared by the procedure described in Example 2 using 3-((S)-4,4-difluoropyrrolidin-2-yl)butanoic acid hydrochloride (0.23 g, 1 mmol), (R)-ethyl 6-(bromomethyl)-4-(2-chloro-4-fluorophenyl)-2-(thiazol-2-yl)-1,4-dihydropyrimidine-5-carboxylate (0.46 g, 1 mmol), potassium carbonate (0.28 g, 2 mmol) and anhydrous ethyl alcohol (10 mL) to give the title compound as a yellow solid (0.12 g, 21%). The compound was characterized by the following spectroscopic data:

MS (ESI, pos.ion) m/z: 571.1 [M+H]$^+$; and $^1$H NMR (600 MHz, DMSO-d$_6$): δ 7.98 (d, 1H), 7.91 (d, 1H), 7.53-7.38 (m, 2H), 7.20 (td, 1H), 6.01 (s, 1H), 4.22-4.12 (m, 2H), 3.99 (q, 2H), 3.77-3.66 (m, 1H), 3.15-3.05 (m, 2H), 2.69 (d, 1H), 2.35-2.25 (m, 2H), 2.10-2.06 (m, 1H), 2.01-1.96 (m, 1H), 1.07 (t, 3H), 0.91 (d, 3H).

Example 33

3-((S)-1-(((R)-6-(2,4-dichlorophenyl)-5-(ethoxycarbonyl)-2-(thiazol-2-yl)-3,6-dihydropyrimidin-4-yl)methyl)-4,4-difluoropyrrolidin-2-yl)butanoic acid

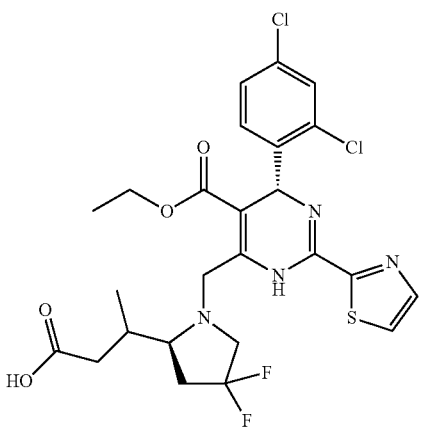

The title compound was prepared by the procedure described in Example 2 using 3-((S)-4,4-difluoropyrrolidin-2-yl)butanoic acid hydrochloride (0.23 g, 1 mmol), (R)-ethyl 6-(bromomethyl)-4-(2,4-dichlorophenyl)-2-(thiazol-2-yl)-1,4-dihydropyrimidine-5-carboxylate (0.48 g, 1 mmol), potassium carbonate (0.28 g, 2 mmol) and anhydrous ethyl alcohol (10 mL) to give the title compound as a yellow solid (0.15 g, 25%). The compound was characterized by the following spectroscopic data:

MS (ESI, pos.ion) m/z: 587.1 [M+H]$^+$; and $^1$H NMR (600 MHz, DMSO-d$_6$): δ 11.93 (s, 1H), 9.51 (s, 1H), 8.00 (d, 1H), 7.92 (d, 1H), 7.58 (br, 1H), 7.41 (br, 2H), 6.02 (s, 1H), 4.21-4.13 (m, 2H), 3.98 (q, 2H), 3.77-3.65 (m, 1H), 3.15-3.04 (m, 2H), 2.68 (d, 1H), 2.36-2.27 (m, 2H), 2.13-2.07 (m, 1H), 2.01-1.95 (m, 1H), 1.07 (t, 3H), 0.91 (d, 3H).

Example 34

3-((S)-1-(((R)-6-(2-chloro-4-fluorophenyl)-5-(methoxycarbonyl)-2-(thiazol-2-yl)-3,6-dihydropyrimidin-4-yl)methyl)-4,4-difluoropyrrolidin-2-yl)butanoic acid

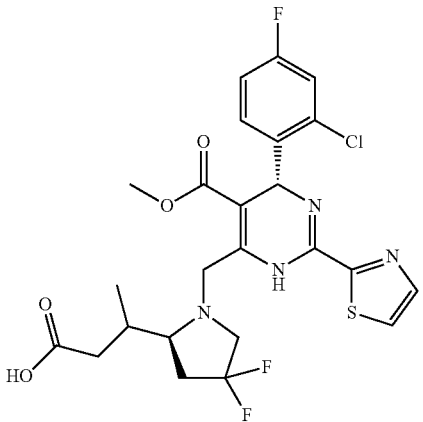 [SMILES: COC(=O)C1=C(CN2CC(F)(F)C[C@H]2C(C)CC(=O)O)NC(c2nccs2)=N[C@H]1c1ccc(F)cc1Cl]

The title compound was prepared by the procedure described in Example 2 using 3-((S)-4,4-difluoropyrrolidin-2-yl)butanoic acid hydrochloride (0.23 g, 1 mmol), (R)-methyl 6-(bromomethyl)-4-(2-chloro-4-fluorophenyl)-2-(thiazol-2-yl)-1,4-dihydropyrimidine-5-carboxylate (0.44 g, 1 mmol), potassium carbonate (0.14 g, 1 mmol) and anhydrous ethyl alcohol (10 mL) to give the title compound as a yellow solid (0.1 g, 18%). The compound was characterized by the following spectroscopic data:

MS (ESI, pos.ion) m/z: 557.1 [M+H]+; and $^1$H NMR (600 MHz, DMSO-d$_6$): δ 8.02 (d, 2H), 7.96 (d, 1H), 7.55-7.39 (m, 2H), 7.21 (td, 1H), 5.99 (s, 1H), 4.22-4.12 (m, 2H), 3.74-3.66 (m, 1H), 3.51 (s, 3H), 3.18-3.07 (m, 2H), 2.67 (d, 1H), 2.33-2.25 (m, 2H), 2.12-2.08 (m, 1H), 2.01-1.94 (m, 1H), 0.91 (d, 3H).

Example 35

3-((R)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)butanoic acid

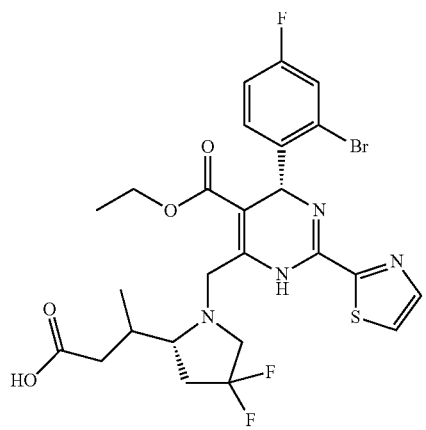 [SMILES: CCOC(=O)C1=C(CN2CC(F)(F)C[C@@H]2C(C)CC(=O)O)NC(c2nccs2)=N[C@H]1c1ccc(F)cc1Br]

Step 1) (2R)-tert-butyl 2-(4-ethoxy-4-oxobutan-2-yl)-4,4-difluoropyrrolidine-1-carboxylate

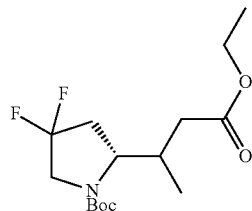 [SMILES: CCOC(=O)CC(C)[C@H]1CC(F)(F)CN1C(=O)OC(C)(C)C]

The title compound was prepared by the procedure described in step 1 Example 9 using CuI (0.96 g, 5.05 mmol), anhydrous THF (100 mL), a solution of MeLi in THF (1.6 mol/L, 6.3 mL) and (R)-tert-butyl 2-(3-ethoxy-3-oxoprop-1-en-1-yl)-4,4-difluoropyrrolidine-1-carboxylate (0.8 g, 2.62 mmol) in THF (8 mL) to give the title compound as light yellow oil (0.45 g, 54%). The compound was characterized by the following spectroscopic data:

MS (ESI, pos.ion) m/z: 222.1 [M+H-100]+.

Step 2) 3-((R)-1-(tert-butoxycarbonyl)-4,4-difluoropyrrolidin-2-yl)butanoic acid

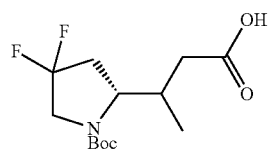 [SMILES: CC(CC(=O)O)[C@H]1CC(F)(F)CN1C(=O)OC(C)(C)C]

The title compound was prepared by the procedure described in step 6 of Example 3 using (2R)-tert-butyl 2-(4-ethoxy-4-oxobutan-2-yl)-4,4-difluoropyrrolidine-1-carboxylate (0.5 g, 1.55 mmol), ethanol (10 mL) and aqueous LiOH.H$_2$O solution (LiOH.H$_2$O (0.65 g) in 10 mL of water) to give the title compound as light yellow oil (0.38 g, 84%). The compound was characterized by the following spectroscopic data:

MS (ESI, pos.ion) m/z: 194.2 [M+H-100]+.

Step 3) 3-((R)-4,4-difluoropyrrolidin-2-yl)butanoic acid hydrochloride

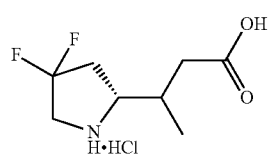

The title compound was prepared by the procedure described in step 6 of Example 4 using 3-((R)-1-(tert-butoxycarbonyl)-4,4-difluoropyrrolidin-2-yl)butanoic acid (0.35 g, 1.2 mmol) and HCl in EtOAc (4 mol/L, 2.5 mL) to give the title compound as light brownness goo (0.23 g, 82%). The compound was characterized by the following spectroscopic data:

MS (ESI, pos.ion) m/z: 194.1 [M+H]+.

Step 4) 3-((R)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)butanoic acid

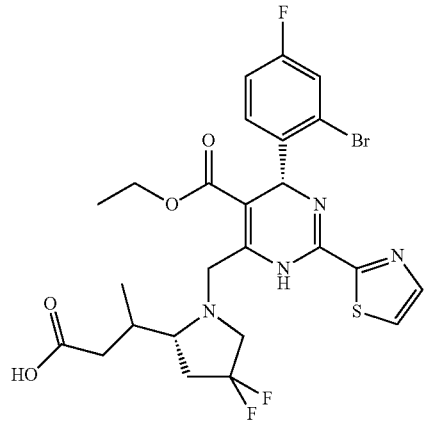 [SMILES: CCOC(=O)C1=C(CN2CC(F)(F)C[C@@H]2C(C)CC(=O)O)NC(c2nccs2)=N[C@H]1c1ccc(F)cc1Br]

The title compound was prepared by the procedure described in Example 2 using 3-((R)-4,4-difluoropyrrolidin-2-yl)butanoic acid hydrochloride (0.23 g, 1 mmol), (R)-ethyl 4-(2-bromo-4-fluorophenyl)-6-(bromomethyl)-2-(thiazol-2-yl)-1,4-dihydropyrimidine-5-carboxylate (0.5 g, 1 mmol), potassium carbonate (0.28 g, 2 mmol) and anhydrous ethyl alcohol (10 mL) to give the title compound as a yellow solid (0.14 g, 22%). The compound was characterized by the following spectroscopic data:

MS (ESI, pos.ion) m/z: 614.7 [M+H]$^+$; and $^1$H NMR (600 MHz, DMSO-d$_6$): δ 8.03 (d, 1H), 7.92 (d, 1H), 7.60 (dd, 1H), 7.41 (dd, 1H), 7.22 (td, 1H), 6.02 (s, 1H), 4.18-4.10 (m, 2H), 3.98 (q, 2H), 3.74-3.63 (m, 1H), 3.15-3.01 (m, 2H), 2.69 (d, 1H), 2.35-2.25 (m, 2H), 2.12-2.06 (m, 1H), 2.03-1.92 (m, 1H), 1.08 (t, 3H), 0.87 (d, 3H).

Example 36

3-((R)-1-(((R)-6-(2-chloro-4-fluorophenyl)-5-(methoxycarbonyl)-2-(thiazol-2-yl)-3,6-dihydropyrimidin-4-yl)methyl)-4,4-difluoropyrrolidin-2-yl)butanoic acid

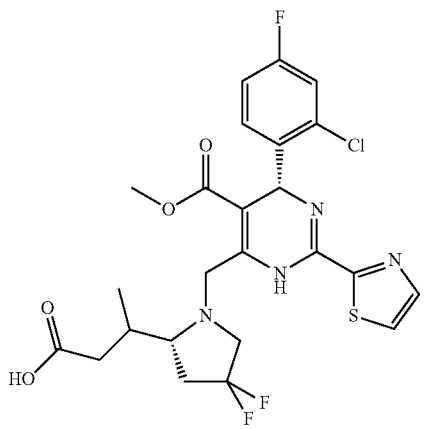 [SMILES: COC(=O)C1=C(CN2CC(F)(F)C[C@@H]2C(C)CC(=O)O)NC(c2nccs2)=N[C@H]1c1ccc(F)cc1Cl]

The title compound was prepared by the procedure described in Example 2 using 3-((R)-4,4-difluoropyrrolidin-2-yl)butanoic acid hydrochloride (0.23 g, 1 mmol), (R)-methyl 6-(bromomethyl)-4-(2-chloro-4-fluorophenyl)-2-(thiazol-2-yl)-1,4-dihydropyrimidine-5-carboxylate (0.44 g, 1 mmol), potassium carbonate (0.14 g, 1 mmol) and anhydrous ethyl alcohol (10 mL) to give the title compound as a yellow solid (0.1 g, 18%). The compound was characterized by the following spectroscopic data:

MS (ESI, pos.ion) m/z: 557.1 [M+H]$^+$; and $^1$H NMR (600 MHz, DMSO-d$_6$): δ 8.01 (d, 2H), 7.94 (d, 1H), 7.56-7.38 (m, 2H), 7.18 (td, 1H), 6.03 (s, 1H), 4.19-4.11 (m, 2H), 3.75-3.67 (m, 1H), 3.50 (s, 3H), 3.15-3.04 (m, 2H), 2.66 (d, 1H), 2.35-2.25 (m, 2H), 2.12-2.08 (m, 1H), 2.04-1.96 (m, 1H), 0.92 (d, 3H).

Example 37

5-((R)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)pentanoic acid

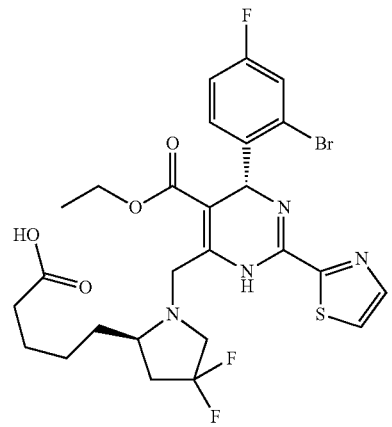 [SMILES: CCOC(=O)C1=C(CN2CC(F)(F)C[C@H]2CCCCC(=O)O)NC(c2nccs2)=N[C@H]1c1ccc(F)cc1Br]

Step 1) (R)-tert-butyl 4,4-difluoro-2-(3-hydroxypropyl)pyrrolidine-1-carboxylate

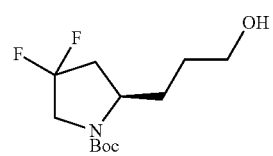 [SMILES: CC(C)(C)OC(=O)N1CC(F)(F)C[C@H]1CCCO]

To a mixture of (R)-tert-butyl 2-(3-ethoxy-3-oxopropyl)-4,4-difluoropyrrolidine-1-carboxylate (1.0 g, 3.25 mmol) and anhydrous THF (150 mL) was added LiAlH$_4$ (0.14 g, 3.58 mmol) at 0° C. After addition, the reaction mixture was stirred for 30 minutes. After the reaction was finished, to the mixture was added saturated aqueous NaHSO$_4$ solution (20 mL). The resulted mixture was filtered, and the filtrate was extracted with EtOAc (100 mL×2). The combined organic phases were dried with anhydrous Na$_2$SO$_4$ and concentrated in vacuo. The residue was purified by silica column chromatography (PE/EtOAc (V/V)=3/1) to give the title compound as light yellow oil (0.86 g, 99.7%). The compound was characterized by the following spectroscopic data:

MS (ESI, pos.ion) m/z: 210.2 [M+H-56]$^+$.

Step 2) (R)-tert-butyl 4,4-difluoro-2-(3-oxopropyl)pyrrolidine-1-carboxylate

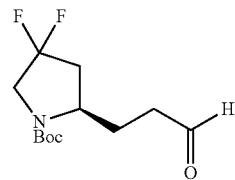 [SMILES: CC(C)(C)OC(=O)N1CC(F)(F)C[C@H]1CCC=O]

The title compound was prepared by the procedure described in step 5 of Example 1 using (R)-tert-butyl 4,4-difluoro-2-(3-hydroxypropyl)pyrrolidine-1-carboxylate (3 g, 11.3 mmol), Dess-Martin periodinane (5.75 g, 13.56 mmol) and DCM (60 mL) as starting materials to give the title compound as yellow oil (2.32 g, 78%). The compound was characterized by the following spectroscopic data:

MS (ESI, pos.ion) m/z: 208.1 [M+H-56]⁺.

Step 3) (R)-tert-butyl 2-(5-ethoxy-5-oxopent-3-en-1-yl)-4,4-difluoropyrrolidine-1-carboxylate

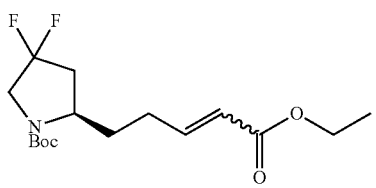

(Z) or (E)

The title compound was prepared by the procedure described in step 6 of Example 1 using (R)-tert-butyl 4,4-difluoro-2-(3-oxopropyl)pyrrolidine-1-carboxylate (2.98 g, 11.3 mmol), Ethyl (triphenylphosphoranylidene)acetate (3.94 g, 11.3 mmol) and DCM (60 mL) to give the title compound as colorless oil (2.64 g, 70%). The compound was characterized by the following spectroscopic data:

MS (ESI, pos.ion) m/z: 234.1 [M+H-100]⁺.

Step 4) (R)-tert-butyl 2-(5-ethoxy-5-oxopentyl)-4,4-difluoropyrrolidine-1-carboxylate

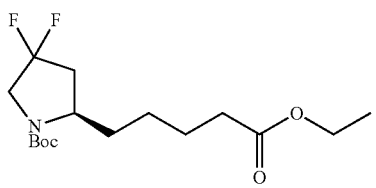 [SMILES: CCOC(=O)CCCC[C@@H]1CC(F)(F)CN1C(=O)OC(C)(C)C]

The title compound was prepared by the procedure described in step 6 of Example 2 using (R)-tert-butyl 2-(5-ethoxy-5-oxopent-3-en-1-yl)-4,4-difluoropyrrolidine-1-carboxylate (2.64 g, 7.92 mmol), Pd/C (10%, 0.5 g) and ethanol (60 mL) as starting materials to give the title compound as colourless oil (2.4 g, 90%). The compound was characterized by the following spectroscopic data:

MS (ESI, pos.ion) m/z: 236.3 [M+H-100]⁺.

Step 5) (R)-5-(1-(tert-butoxycarbonyl)-4,4-difluoropyrrolidin-2-yl)pentanoic acid

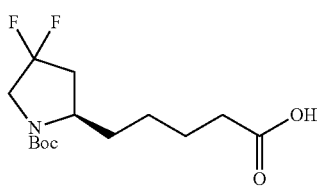 [SMILES: CC(C)(C)OC(=O)N1CC(F)(F)C[C@H]1CCCCC(=O)O]

The title compound was prepared by the procedure described in step 6 of Example 3 using (R)-tert-butyl 2-(5-ethoxy-5-oxopentyl)-4,4-difluoropyrrolidine-1-carboxylate (2.4 g, 7.2 mmol), ethanol (24 mL) and a solution of LiOH.H₂O (3.02 g, 72 mmol) in water (24 mL) as starting materials to give the title compound as light colorless oil (2.08 g, 94%). The compound was characterized by the following spectroscopic data:

MS (ESI, pos.ion) m/z: 208.1 [M+H-100]⁺.

Step 6) (R)-5-(4,4-difluoropyrrolidin-2-yl)pentanoic acid hydrochloride

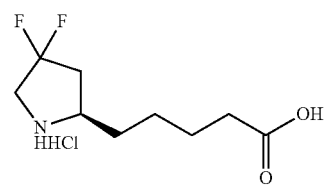

The title compound was prepared by the procedure described in step 6 of Example 4 using (R)-5-(1-(tert-butoxycarbonyl)-4,4-difluoropyrrolidin-2-yl)pentanoic acid (2.08 g, 6.77 mmol) and HCl in EtOAc (4 mol/L, 20 mL) to give the title compound as a white solid (1.44 g, 87%). The compound was characterized by the following spectroscopic data:

MS (ESI, pos.ion) m/z: 208.1 [M+H]⁺.

Step 7) 5-((R)-1-(((R)-6-(2-bromo-4-fluorophenyl)-5-(ethoxycarbonyl)-2-(thiazol-2-yl)-3,6-dihydropyrimidin-4-yl)methyl)-4,4-difluoropyrrolidin-2-yl)pentanoic acid

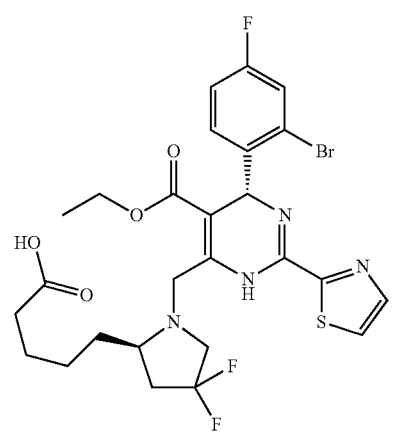 [SMILES: CCOC(=O)C1=C(CN2CC(F)(F)C[C@H]2CCCCC(=O)O)NC(c2nccs2)=N[C@H]1c1ccc(F)cc1Br]

The title compound was prepared by the procedure described in Example 2 using (R)-5-(4,4-difluoropyrrolidin-2-yl)pentanoic acid hydrochloride (0.56 g, 2.17 mmol), (R)-ethyl 4-(2-bromo-4-fluorophenyl)-6-(bromomethyl)-2-(thiazol-2-yl)-1,4-dihydropyrimidine-5-carboxylate (1.2 g, 2.39 mmol) and K₂CO₃ (0.6 g, 4.34 mmol) and anhydrous ethanol (12 mL) to give the title compound as a yellow solid (0.53 g, 39%). The compound was characterized by the following spectroscopic data:

MS (ESI, pos.ion) m/z: 629.0 [M+H]+; and
1H NMR (400 MHz, DMSO-d6): δ 12.21 (s, 1H), 9.51 (s, 1H), 8.01 (d, 1H), 7.94 (d, 1H), 7.57 (dd, 1H), 7.41 (dd, 1H), 7.24 (td, 1H), 6.02 (s, 1H), 4.19-4.04 (m, 2H), 3.96 (q, 2H), 3.59-3.48 (m, 1H), 3.03-2.91 (m, 2H), 2.61-2.52 (m, 1H), 2.13-2.05 (m, 2H), 2.03-1.96 (m, 1H), 1.70-1.60 (m, 1H), 1.50-1.40 (m, 2H), 1.33-1.25 (m, 3H), 1.06 (t, 3H).

Example 38

5-((S)-1-(((R)-6-(2-chloro-4-fluorophenyl)-5-(methoxycarbonyl)-2-(thiazol-2-yl)-3,6-dihydropyrimidin-4-yl)methyl)-4,4-difluoropyrrolidin-2-yl)pentanoic acid

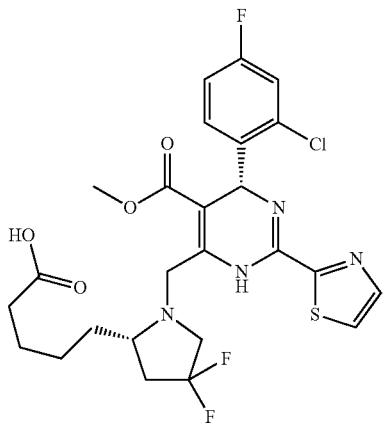 [SMILES: COC(=O)C1=C(CN2CC(F)(F)C[C@@H]2CCCCC(=O)O)NC(c2nccs2)=N[C@H]1c1ccc(F)cc1Cl]

Step 1) (S)-tert-butyl 4,4-difluoro-2-(3-hydroxypropyl)pyrrolidine-1-carboxylate

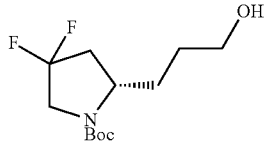 [SMILES: CC(C)(C)OC(=O)N1CC(F)(F)C[C@@H]1CCCO]

The title compound was prepared by the procedure described in step 37 of Example 1 using (S)-tert-butyl 2-(3-ethoxy-3-oxopropyl)-4,4-difluoropyrrolidine-1-carboxylate (3 g, 9.8 mmol), anhydrous THF (80 mL) and LiAlH4 (0.41 g, 10.74 mmol) to give the title compound as colorless oil (2.37 g, 91%). The compound was characterized by the following spectroscopic data:
MS (ESI, pos.ion) m/z: 210.1 [M+H-56].

Step 2) (S)-tert-butyl 4,4-difluoro-2-(3-oxopropyl)pyrrolidine-1-carboxylate

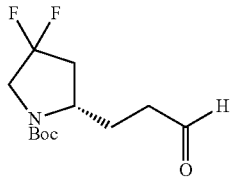 [SMILES: CC(C)(C)OC(=O)N1CC(F)(F)C[C@@H]1CCC=O]

The title compound was prepared by the procedure described in step 5 of Example 1 using (S)-tert-butyl 4,4-difluoro-2-(3-hydroxypropyl)pyrrolidine-1-carboxylate (2.3 g, 8.7 mmol), Dess-Martin periodinane (4.4 g, 10.4 mmol) and DCM (45 mL) as starting materials to give the title compound as colorless oil (1.58 g, 69%). The compound was characterized by the following spectroscopic data:
MS (ESI, pos.ion) m/z: 208.1 [M+H-56]+.

Step 3) (S)-tert-butyl 2-(5-ethoxy-5-oxopent-3-en-1-yl)-4,4-difluoropyrrolidine-1-carboxylate

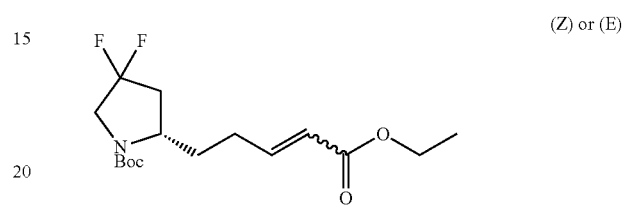

The title compound was prepared by the procedure described in step 6 of Example 1 using (S)-tert-butyl 4,4-difluoro-2-(3-oxopropyl)pyrrolidine-1-carboxylate (1.5 g, 5.7 mmol), ethyl (triphenylphosphoranylidene)acetate (1.99 g, 5.7 mmol) and DCM (30 mL) to give the title compound as colorless oil (1.24 g, 65%). The compound was characterized by the following spectroscopic data:
MS (ESI, pos.ion) m/z: 234.1 [M+H-100]+.

Step 4) (S)-tert-butyl 2-(5-ethoxy-5-oxopentyl)-4,4-difluoropyrrolidine-1-carboxylate

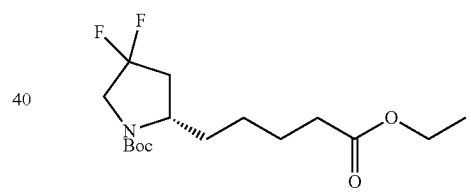

The title compound was prepared by the procedure described in step 6 of Example 2 using (S)-tert-butyl 2-(5-ethoxy-5-oxopent-3-en-1-yl)-4,4-difluoropyrrolidine-1-carboxylate (1.2 g, 3.6 mmol), Pd/C (10%, 0.5 g) and ethanol (24 mL) as starting materials to give the title compound as colourless oil (1.1 g, 93%). The compound was characterized by the following spectroscopic data:
MS (ESI, pos.ion) m/z: 236.3 [M+H-100]+.

Step 5) (S)-5-(1-(tert-butoxycarbonyl)-4,4-difluoropyrrolidin-2-yl)pentanoic acid

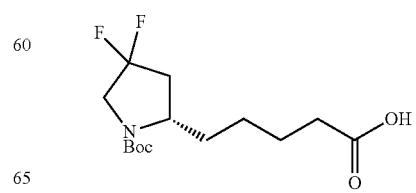

The title compound was prepared by the procedure described in step 6 of Example 3 using (S)-tert-butyl 2-(5-ethoxy-5-oxopentyl)-4,4-difluoropyrrolidine-1-carboxylate (1 g, 3 mmol), ethanol (20 mL) and a solution of LiOH.H₂O (1.26 g, 30 mmol) in water (25 mL) to give the title compound as colourless oil (0.83 g, 90%). The compound was characterized by the following spectroscopic data:

MS (ESI, pos.ion) m/z: 208.1 [M+H-100]⁺.

Step 6) (S)-5-(4,4-difluoropyrrolidin-2-yl)pentanoic acid hydrochloride

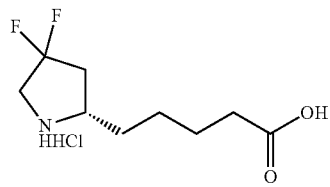

The title compound was prepared by the procedure described in step 6 of Example 4 using (S)-5-(1-(tert-butoxycarbonyl)-4,4-difluoropyrrolidin-2-yl)pentanoic acid (0.8 g, 2.6 mmol) and HCl in EtOAc (4 mol/L, 4 mL) to give the title compound as light yellow goo (0.54 g, 86%). The compound was characterized by the following spectroscopic data:

MS (ESI, pos.ion) m/z: 208.1 [M+H]⁺.

Step 7) 5-((S)-1-(((R)-6-(2-chloro-4-fluorophenyl)-5-(methoxycarbonyl)-2-(thiazol-2-yl)-3,6-dihydropyrimidin-4-yl)methyl)-4,4-difluoropyrrolidin-2-yl)pentanoic acid

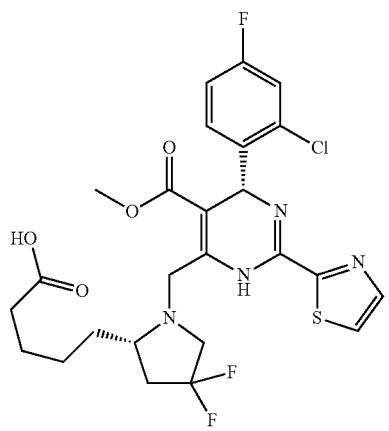 [SMILES: COC(=O)C1=C(CN2CC(F)(F)C[C@@H]2CCCCC(=O)O)NC(c2nccs2)=N[C@H]1c1ccc(F)cc1Cl]

The title compound was prepared by the procedure described in Example 2 using (S)-5-(4,4-difluoropyrrolidin-2-yl)pentanoic acid hydrochloride (0.5 g, 2.1 mmol), (R)-methyl 6-(bromomethyl)-4-(2-chloro-4-fluorophenyl)-2-(thiazol-2-yl)-1,4-dihydropyrimidine-5-carboxylate (0.93 g, 2.1 mmol) and potassium carbonate (0.29 g, 2.1 mmol) and ethanol (20 mL) to give the title compound as a yellow solid (0.5 g, 42%). The compound was characterized by the following spectroscopic data:

MS (ESI, pos.ion) m/z: 571.0 [M+H]⁺; and

¹H NMR (400 MHz, DMSO-d₆): δ 8.03 (d, 1H), 7.96 (d, 1H), 7.51-7.40 (m, 2H), 7.19 (td, 1H), 5.99 (s, 1H), 4.16-4.04 (m, 2H), 3.61-3.53 (m, 1H), 3.49 (s, 3H), 3.05-2.93 (m, 2H), 2.62-2.52 (m, 1H), 2.14-2.05 (m, 2H), 2.03-1.94 (m, 1H), 1.72-1.60 (m, 1H), 1.52-1.41 (m, 2H), 1.35-1.25 (m, 3H).

Example 39

3-(1-(((R)-6-(2-bromo-4-fluorophenyl)-5-(ethoxycarbonyl)-2-(thiazol-2-yl)-3,6-dihydropyrimidin-4-yl)methyl)-4-fluoro-3,3-dimethylpyrrolidin-2-yl)propanoic acid

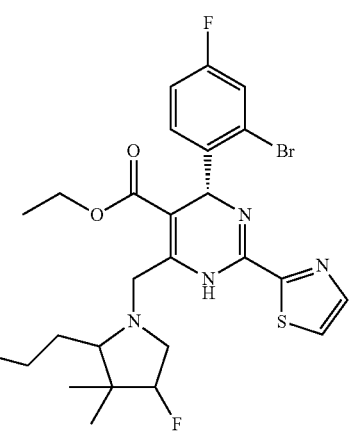

Step 1) 3-methylbut-2-en-1-yl 2-((tert-butoxycarbonyl)amino)acetate

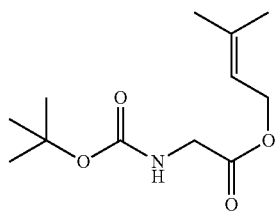 [SMILES: CC(C)=CCOC(=O)CNC(=O)OC(C)(C)C]

To a mixture of 3-methylbut-2-en-1-ol (10 g, 116.1 mmol), 2-((tert-butoxycarbonyl)amino)acetic acid (24.2 g, 138.1 mmol), DMAP (2.83 g, 23.2 mmol) and DCM (400 mL) was added a solution of DCC (35.9 g, 174.1 mmol) in DCM (200 mL) at −5° C. After the addition, the reaction was stirred at 25° C. for 8 hours. After the reaction was finished, the mixture was filtered and concentrated in vacuo. The residue was purified by silica column chromatography (PE/EtOAc (v/v)=3/1) to give the title compound as colourless oil (28 g, 99.15%). The compound was characterized by the following spectroscopic data:

¹H NMR (400 MHz, CDCl₃): δ 5.35 (t, 1H), 5.04 (s, 1H), 4.66 (d, 2H), 3.92 (d, 2H), 1.75 (d, 6H), 1.46 (s, 9H).

Step 2) 2-((tert-butoxycarbonyl)amino)-3,3-dimethylpent-4-enoic acid

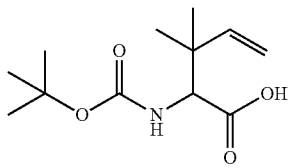 [SMILES: C=CC(C)(C)C(NC(=O)OC(C)(C)C)C(=O)O]

To a mixture of 3-methylbut-2-en-1-yl 2-((tert-butoxycarbonyl)amino)acetate (8.0 g, 32.8 mmol), zinc chloride (5.35 g, 39.3 mmol) and anhydrous THF (200 mL) was added a solution of LDA in THF (2 mol/L, 41 mL, 82.0 mmol) at −75° C. After the addition, the reaction was stirred −75° C. for 2 hours and then 25° C. for 12 hours. After the reaction was finished, the mixture was quenched with saturated aqueous ammonium chloride solution (100 mL), then saturated brine (100 mL) was added. The mixture was extracted with EtOAc (100 mL×3). The combined organic phases were washed with saturated brine (100 mL×2), and concentrated in vacuo. The residue was purified by silica column chromatography (PE/EtOAc (v/v)=1/1) to give the title compound as colorless oil (6.0 g, 75%). The compound was characterized by the following spectroscopic data:

MS (ESI, pos.ion) m/z: 188.2 [M+H-56]$^+$.

Step 3) tert-butyl (5-(iodomethyl)-4,4-dimethyl-2-oxotetrahydrofuran-3-yl)carbamate

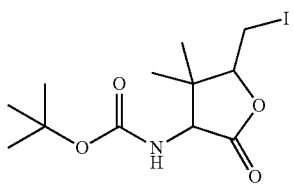 [SMILES: CC(C)(C)OC(=O)NC1C(=O)OC(CI)C1(C)C]

To a mixture of 2-((tert-butoxycarbonyl)amino)-3,3-dimethylpent-4-enoic acid (6.0 g, 24.6 mol), anhydrous THF (120 mL) and water (40 mL) was added a solution of iodize (18.7 g, 73.8 mmol) in THF (80 mL) at −5° C. After the addition, the reaction was stirred at 25° C. for 2 hours. After the reaction was finished, the mixture was quenched with saturated aqueous NaHCO$_3$ solution (60 mL). The resulted mixture was stirred for 30 min, and then poured into excess aqueous Na$_2$S$_2$O$_3$ solution (10%, 60 mL). The mixture was extracted with EtOAc (150 mL×3). The combined organic phases were concentrated in vacuo to give the title compound as brownness oil (8 g, 88%). The compound was characterized by the following spectroscopic data:

$^1$H NMR (400 MHz, CDCl$_3$): δ 4.87 (br, 1H), 4.54-4.39 (m, 2H), 3.34-3.14 (m, 2H), 1.48 (s, 9H), 1.33 (s, 3H), 0.86 (s, 3H).

Step 4) 3-amino-5-(iodomethyl)-4,4-dimethyldihydrofuran-2(3H)-one trifluoroacetic acid

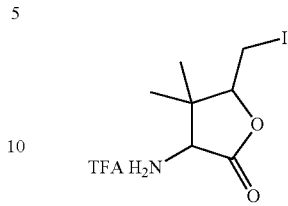

A mixture of tert-butyl (5-(iodomethyl)-4,4-dimethyl-2-oxotetrahydrofuran-3-yl)carbamate (4.0 g, 10.8 mmol), DCM (40 mL) and trifluoroacetic acid (12.3 g, 108 mmol) was stirred at 40 OC for 3 hours. After the reaction was finished, the mixture was concentrated in vacuo to give crude product which was used directly for the next step.

Step 5) 1-(tert-butoxycarbonyl)-4-hydroxy-3,3-dimethylpyrrolidine-2-carboxylic acid

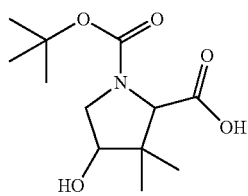 [SMILES: CC(C)(C)OC(=O)N1CC(O)C(C)(C)C1C(=O)O]

A mixture of 3-amino-5-(iodomethyl)-4,4-dimethyldihydrofuran-2(3H)-one trifluoroacetic acid (4.14 g, 10.8 mmol) and THF (40 mL) was adjusted to pH 9 with aqueous potassium hydroxide solution (0.5 mol/L). The resulted mixture was stirred at 25° C. for 4 hours. Then to the mixture was added Di-tert-butyl dicarbonate (2.35 g, 10.8 mmol) and aqueous sodium hydroxide solution (1 mol/L, 10.8 mL). The mixture was stirred was stirred at 25° C. for 12 hours. After the reaction was finished, the mixture was adjusted to pH 4 with 1 mol/L hydrochloric acid, and then concentrated in vacuo. The residue was purified by silica column chromatography (DCM/MeOH (v/v)=10/1) to give the title compound as a colorless solid (2.5 g, 89.3%). The compound was characterized by the following spectroscopic data:

MS (ESI, pos.ion) m/z: 204.1 [M+H-56]$^+$.

Step 6) 1-tert-butyl 2-methyl 4-hydroxy-3,3-dimethylpyrrolidine-1,2-dicarboxylate

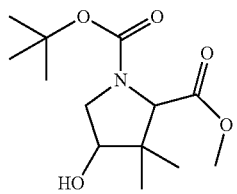 [SMILES: COC(=O)C1N(C(=O)OC(C)(C)C)CC(O)C1(C)C]

To a mixture of 1-(tert-butoxycarbonyl)-4-hydroxy-3,3-dimethylpyrrolidine-2-carboxylic acid (4.0 g, 15.4 mmol), cesium carbonate (15.0 g, 46.2 mmol) and DMF (150 mL) was added methyl iodide (4.37 g, 30.8 mmol) dropwise at 25° C. The reaction mixture was stirred at 25° C. for 12 hours. After the reaction was finished, the mixture was quenched with water. The mixture was extracted with EtOAc (150 mL×3). The combined organic phases were washed with saturated brine (100 mL×3), and concentrated in vacuo. The residue was purified by silica column chromatography (PE/EtOAc (v/v)=5/1) to give the title compound as colorless oil (3.5 g, 83.1%). The compound was characterized by the following spectroscopic data:

MS (ESI, pos.ion) m/z: 174.1 [M+H-100]$^+$.

Step 7) 1-tert-butyl 2-methyl 4-fluoro-3,3-dimethylpyrrolidine-1,2-dicarboxylate

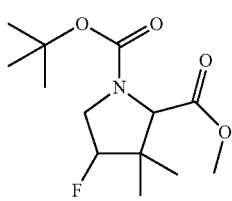 [SMILES: COC(=O)C1N(C(=O)OC(C)(C)C)CC(F)C1(C)C]

To a mixture of 1-tert-butyl 2-methyl 4-hydroxy-3,3-dimethylpyrrolidine-1,2-dicarboxylate (0.64 g, 2.34 mmol) and DCM (100 mL) was added DAST (1.13 g, 7.02 mmol) at 25° C. After the addition, the reaction mixture was stirred at 50° C. for 12 hours. After the reaction was finished, the mixture was quenched with saturated aqueous NaHCO$_3$ solution (50 mL). The mixture was extracted with DCM (60 mL×3). The combined organic phases were concentrated in vacuo. The residue was purified by silica column chromatography (PE/EtOAc (v/v)=5/1) to give the title compound as light yellow oil (0.51 g, 80%). The compound was characterized by the following spectroscopic data:

MS (ESI, pos.ion) m/z: 176.1 [M+H-100]$^+$.

Step 8) 1-(tert-butoxycarbonyl)-4-fluoro-2-(hydroxymethyl)-3,3-dimethylpyrrolidine

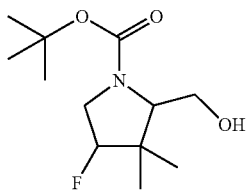 [SMILES: CC(C)(C)OC(=O)N1CC(F)C(C)(C)C1CO]

The title compound was prepared by the procedure described in step 1 of Example 37 using 1-tert-butyl 2-methyl 4-fluoro-3,3-dimethylpyrrolidine-1,2-dicarboxylate (0.51 g, 1.85 mmol), THF (150 mL) and LiAlH$_4$ (77.4 mg, 2.04 mmol) to give the title compound as light yellow oil (0.45 g, 98.2%). The compound was characterized by the following spectroscopic data:

MS (ESI, pos.ion) m/z: 192.1 [M+H-56]$^+$.

Step 9) 1-(tert-butoxycarbonyl)-4-fluoro-2-formyl-3,3-dimethylpyrrolidine

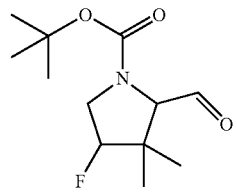 [SMILES: CC(C)(C)OC(=O)N1CC(F)C(C)(C)C1C=O]

The title compound was prepared by the procedure described in step 1 of Example 5 using (1-(tert-butoxycarbonyl)-4-fluoro-2-(hydroxymethyl)-3,3-dimethylpyrrolidine (0.45 g, 1.81 mmol), DCM (80 mL) and Dess-Martin periodinane (0.93 g, 2.18 mmol) to give the title compound as light yellow oil (0.4 g, 89.6%).

Step 10) 1-(tert-butoxycarbonyl)-2-(3-ethoxy-3-oxoprop-1-en-1-yl)-4-fluoro-3,3-dimethylpyrrolidine

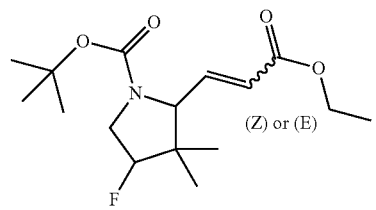 [SMILES: CCOC(=O)C=CC1N(C(=O)OC(C)(C)C)CC(F)C1(C)C]

The title compound was prepared by the procedure described in step 1 of Example 6 using 1-(tert-butoxycarbonyl)-4-fluoro-2-formyl-3,3-dimethylpyrrolidine (0.4 g, 1.63 mmol), DCM (80 mL) and ethyl (triphenylphosphoranylidene)acetate (0.68 g, 1.95 mmol) to give the title compound as light yellow oil (0.4 g, 77.7%). The compound was characterized by the following spectroscopic data:

MS (ESI, pos.ion) m/z: 216.3 [M+H-100]$^+$.

Step 11) 1-(tert-butoxycarbonyl)-2-(3-ethoxy-3-oxopropyl)-4-fluoro-3,3-dimethylpyrrolidine

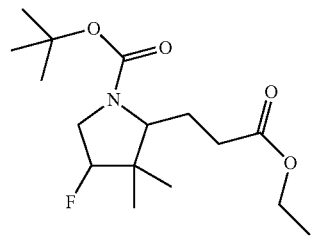 [SMILES: CCOC(=O)CCC1N(C(=O)OC(C)(C)C)CC(F)C1(C)C]

The title compound was prepared by the procedure described in step 2 of Example 6 using 1-(tert-butoxycarbonyl)-2-(3-ethoxy-3-oxoprop-1-en-1-yl)-4-fluoro-3,3-dimethylpyrrolidine (0.4 g, 1.27 mmol), methanol (50 mL) and Pd/C (10%, 0.1 g) to give the title compound as colourless oil (0.4 g, 99.4%). The compound was characterized by the following spectroscopic data:

MS (ESI, pos.ion) m/z: 262.2 [M+H-56]$^+$.

Step 12) 3-(1-(tert-butoxycarbonyl)-4-fluoro-3,3-dimethylpyrrolidin-2-yl)propanoic acid

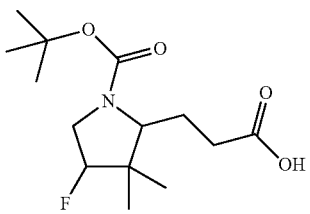 [SMILES: CC(C)(C)OC(=O)N1CC(F)C(C)(C)C1CCC(=O)O]

The title compound was prepared by the procedure described in step 3 of Example 6 using 1-(tert-butoxycarbonyl)-2-(3-ethoxy-3-oxopropyl)-4-fluoro-3,3-dimethylpyrrolidine (0.4 g, 1.26 mmol), ethanol (10 mL) and aqueous LiOH.H$_2$O solution (LiOH.H$_2$O (0.53 g, 12.6 mmol) in 10 mL of water) to give the title compound as light yellow oil (0.36 g, 98.7%). The compound was characterized by the following spectroscopic data:
MS (ESI, pos.ion) m/z: 234.2 [M+H-56]$^+$.

Step 13) 3-(4-fluoro-3,3-dimethylpyrrolidin-2-yl)propanoic acid hydrochloride

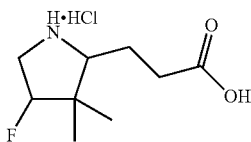

The title compound was prepared by the procedure described in step 4 of Example 6 using 3-(1-(tert-butoxycarbonyl)-4-fluoro-3,3-dimethylpyrrolidin-2-yl)propanoic acid (0.36 g, 1.24 mmol) and a solution of HCl in EtOAc (4 mol/L, 2 mL) to give the title compound as a sandy beige solid (0.28 g, 99.7%). The compound was characterized by the following spectroscopic data:
MS (ESI, pos.ion) m/z: 189.2 [M+H]$^+$.

Step 14) 3-(1-(((R)-6-(2-bromo-4-fluorophenyl)-5-(ethoxycarbonyl)-2-(thiazol-2-yl)-3,6-dihydropyrimidin-4-yl)methyl)-4-fluoro-3,3-dimethylpyrrolidin-2-yl)propanoic acid

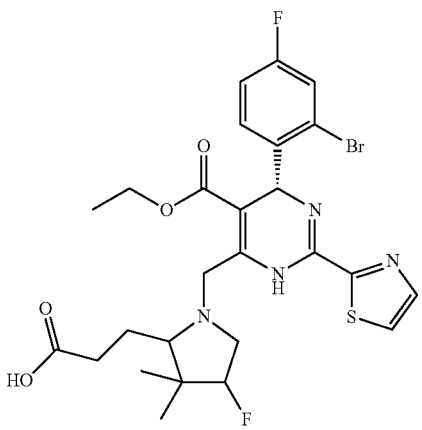 [SMILES: CCOC(=O)C1=C(CN2CC(F)C(C)(C)C2CCC(=O)O)NC(c2nccs2)=N[C@H]1c1ccc(F)cc1Br]

The title compound was prepared by the procedure described in Example 2 using 3-(4-fluoro-3,3-dimethylpyrrolidin-2-yl)propanoic acid hydrochloride (0.3 g, 1.33 mmol), (R)-ethyl 4-(2-bromo-4-fluorophenyl)-6-(bromomethyl)-2-(thiazol-2-yl)-1,4-dihydropyrimidine-5-carboxylate (0.81 g, 1.6 mmol), potassium carbonate (0.55 g, 4 mmol) and anhydrous ethyl alcohol (10 mL) to give the title compound as a yellow solid (53 mg, 6.5%). The compound was characterized by the following spectroscopic data:
MS (ESI, pos.ion) m/z: 611.3 [M+H]$^+$; and
$^1$H NMR (400 MHz, DMSO-d$_6$): δ 12.13 (br, 1H), 9.72 (s, s, 1H), 8.01-7.90 (m, 2H), 7.59-7.53 (m, 1H), 7.44-7.33 (m, 1H), 7.26-7.15 (m, 1H), 6.06 (s, s, 1H), 4.35-4.18 (m, 1H), 4.15-4.02 (m, 1H), 4.02-3.90 (m, 2H), 3.33-3.25 (m, 1H), 3.18-2.92 (m, 2H), 2.46-2.30 (m, 2H), 2.18-2.01 (m, 1H), 1.84-1.64 (m, 1H), 1.62-1.44 (m, 1H), 1.41-1.31 (m, 3H), 1.07-0.93 (m, 6H).

Example 40

3-((R)-1-(((R)-6-(2-bromo-4-fluorophenyl)-5-(ethoxycarbonyl)-2-(thiazol-2-yl)-3,6-dihydropyrimidin-4-yl)methyl)-5,5-difluoropiperidin-2-yl)propanoic acid

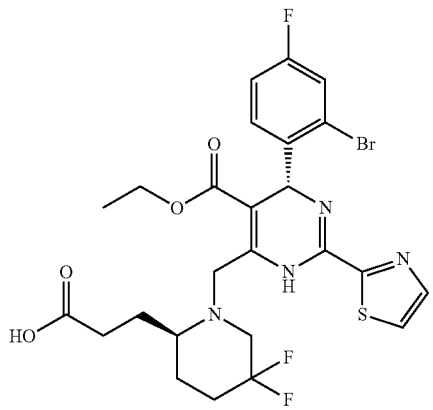 [SMILES: CCOC(=O)C1=C(CN2CC(F)(F)CC[C@H]2CCC(=O)O)NC(c2nccs2)=N[C@H]1c1ccc(F)cc1Br]

Step 1) (S)-ethyl 2-((tert-butoxycarbonyl)amino)-6-diazo-5-oxohexanoate

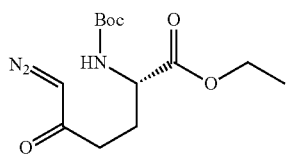

To a mixture of a solution of (trimethylsilyl)diazomethane solution in n-hexane (2 mol/L, 10.68 mL) and anhydrous THF (50 mL) was added a solution of n-Butyllithium in n-hexane (2.5 mol/L, 9.32 mL, 23.3 mmol) at −78° C. under nitrogen. The reaction mixture was stirred at −78° C. for 30 minutes, and then a solution of (S)-1-tert-butyl 2-ethyl 5-oxopyrrolidine-1,2-dicarboxylate (5 g, 19.43 mol) in THF (100 mL) was added dropwise. After the addition, the reaction mixture was stirred at −78° C. for further 45 minutes. After the reaction was finished, the reaction was quenched with saturated aqueous ammonium chloride solution (50 mL). The mixture was extracted with EtOAc (100 mL×2). The combined organic phases were washed with saturated brine (100 mL×2), dried with anhydrous Na₂SO₄, and concentrated in vacuo. The residue was purified by silica column chromatography (PE/EtOAc (v/v)=3/1) to give the title compound as light yellow oil (3.1 g, 53%). The compound was characterized by the following spectroscopic data:

MS (ESI, pos.ion) m/z: 200.1 [M+H-100]⁺.

Step 2) (S)-1-tert-butyl 2-ethyl
5-oxopiperidine-1,2-dicarboxylate

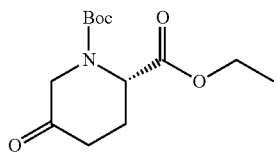 [SMILES: CCOC(=O)[C@@H]1CCC(=O)CN1C(=O)OC(C)(C)C]

To a mixture of (S)-ethyl 2-((tert-butoxycarbonyl)amino)-6-diazo-5-oxohexanoate (3.1 g, 10.4 mmol) and DCM (150 mL) was added Rhodium acetate (30 mg, 0.07 mmol) at 0° C. After the addition, the reaction was stirred at 0° C. for 1 hour, and then at 25° C. for 12 hours. After the reaction was finished, the reaction mixture was concentrated in vacuo. The residue was purified by silica column chromatography (PE/EtOAc (v/v)=3/1) to give the title compound as light yellow oil (1.25 g, 46%). The compound was characterized by the following spectroscopic data:

MS (ESI, pos.ion) m/z: 172.1 [M+H-100]⁺.

Step 3) (S)-1-tert-butyl 2-ethyl
5,5-difluoropiperidine-1,2-dicarboxylate

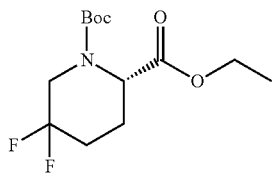

To a mixture of (S)-1-tert-butyl 2-ethyl 5-oxopiperidine-1,2-dicarboxylate (0.9 g, 3.3 mmol) and anhydrous DCM (90 mL) was added DAST (4.36 mL, 10 mmol) dropwise at 25° C. After the addition, the reaction was stirred at 25° C. for 12 hours. After the reaction was finished, the mixture was quenched with saturated aqueous sodium bicarbonate solution (30 mL). The resulted mixture was extracted with DCM (50 mL×2). The organic phases were dried with anhydrous Na₂SO₄, filtered and concentrated in vacuo. The residue was purified by silica column chromatography (PE/EtOAc (v/v) =4/1) to give the title compound as light yellow oil (0.75 g, 77%). The compound was characterized by the following spectroscopic data:

¹H NMR (600 MHz, DMSO-d₆): δ 4.77 (d, 1H), 4.23-4.12 (m, 2H), 4.11-3.98 (m, 1H), 3.30-3.03 (m, 1H), 2.20-2.08 (m, 2H), 1.96-1.71 (m, 2H), 1.44-1.35 (m, 9H), 1.21 (t, 3H).

Step 4) (S)-tert-butyl 5,5-difluoro-2-(hydroxymethyl)piperidine-1-carboxylate

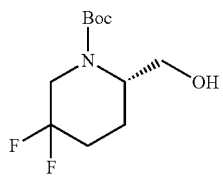

The title compound was prepared by the procedure described in step 1 of Example 37 using (S)-1-tert-butyl 2-ethyl 5,5-difluoropiperidine-1,2-dicarboxylate (0.9 g, 3.1 mmol), anhydrous THF (80 mL) and LiAlH₄ (0.12 g, 3.1 mmol) to give the title compound as colorless oil (0.71 g, 91%). The compound was characterized by the following spectroscopic data:

MS (ESI, pos.ion) m/z: 152.1 [M+H-100]⁺.

Step 5) (S)-tert-butyl
5,5-difluoro-2-formylpiperidine-1-carboxylate

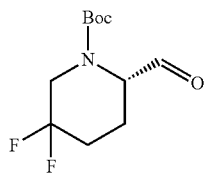

The title compound was prepared by the procedure described in step 1 of Example 5 using (S)-tert-butyl 5,5-difluoro-2-(hydroxymethyl)piperidine-1-carboxylate (0.7 g, 2.8 mmol), DCM (100 mL) and Dess-Martin periodinane (1.3 g, 3.06 mmol) to give the title compound as light yellow oil (0.6 g, 86%).

Step 6) (S)-tert-butyl 2-(3-ethoxy-3-oxoprop-1-en-1-yl)-5,5-difluoropiperidine-1-carboxylate

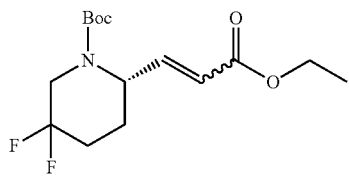

The title compound was prepared by the procedure described in step 1 of Example 6 using (S)-tert-butyl 5,5-difluoro-2-formylpiperidine-1-carboxylate (0.7 g, 2.81 mmol), DCM (30 mL) and ethyl (triphenylphosphoranylidene)acetate (1.1 g, 3.1 mmol) to give the title compound as colorless oil (0.7 g, 78.1%). The compound was characterized by the following spectroscopic data:

¹H NMR (400 MHz, CDCl₃): δ 6.84 (dd, 1H), 5.89 (dd, 1H), 5.08 (s, 1H), 4.36-4.15 (m, 3H), 3.16-2.93 (m, 1H), 2.37-2.20 (m, 2H), 2.15-2.08 (m, 1H), 1.96-1.87 (m, 1H), 1.50 (s, 9H), 1.33 (t, 3H).

Step 7) (R)-tert-butyl 2-(3-ethoxy-3-oxopropyl)-5,5-difluoropiperidine-1-carboxylate

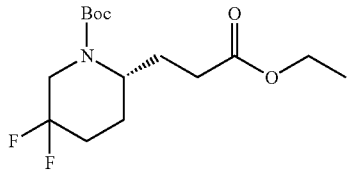 [SMILES: CCOC(=O)CC[C@@H]1CCC(F)(F)CN1C(=O)OC(C)(C)C]

The title compound was prepared by the procedure described in step 2 of Example 6 using (S)-tert-butyl 2-(3-ethoxy-3-oxoprop-1-en-1-yl)-5,5-difluoropiperidine-1-carboxylate (0.7 g, 2.2 mmol), methanol (40 mL) and Pd/C (10%, 0.1 g) to give the title compound as colourless oil (0.7 g, 99%). The compound was characterized by the following spectroscopic data:

MS (ESI, pos.ion) m/z: 222.1 [M+H-100]$^+$.

Step 8) (R)-3-(1-(tert-butoxycarbonyl)-5,5-difluoropiperidin-2-yl)propanoic acid

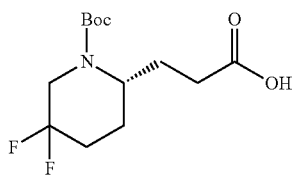

The title compound was prepared by the procedure described in step 3 of Example 6 using (R)-tert-butyl 2-(3-ethoxy-3-oxopropyl)-5,5-difluoropiperidine-1-carboxylate (0.7 g, 2.2 mmol), ethanol (50 mL) and aqueous LiOH.H$_2$O solution (LiOH.H$_2$O (0.73 g, 17.42 mmol) in 50 mL of water) to give the title compound as colourless oil (0.5 g, 78.3%). The compound was characterized by the following spectroscopic data:

MS (ESI, pos.ion) m/z: 194.1 [M+H-100]$^+$.

Step 9) (R)-3-(5,5-difluoropiperidin-2-yl)propanoic acid hydrochloride

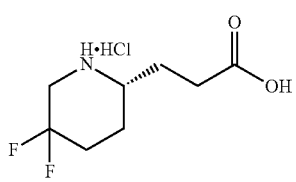

The title compound was prepared by the procedure described in step 3 of Example 6 using (R)-3-(1-(tert-butoxycarbonyl)-5,5-difluoropiperidin-2-yl)propanoic acid (0.5 g, 1.71 mmol) and a solution of HCl in EtOAc (4 mol/L, 5 mL) to give the title compound as white powder (0.4 g, 100%). The compound was characterized by the following spectroscopic data:

MS (ESI, pos.ion) m/z: 194.1 [M+H]$^+$.

Step 10) 3-((R)-1-(((R)-6-(2-bromo-4-fluorophenyl)-5-(ethoxycarbonyl)-2-(thiazol-2-yl)-3,6-dihydropyrimidin-4-yl)methyl)-5,5-difluoropiperidin-2-yl)propanoic acid

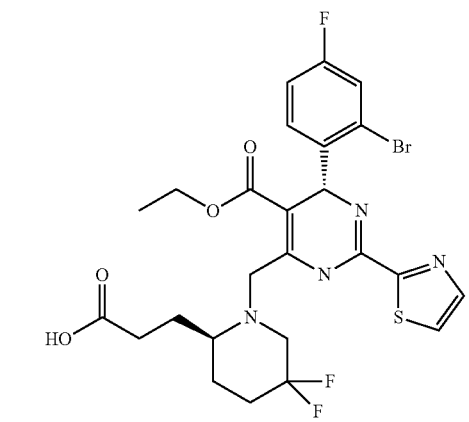 [SMILES: CCOC(=O)C1=C(CN2CC(F)(F)CC[C@H]2CCC(=O)O)NC(c2nccs2)=N[C@H]1c1ccc(F)cc1Br]

The title compound was prepared by the procedure described in Example 2 using (R)-3-(5,5-difluoropiperidin-2-yl)propanoic acid hydrochloride (0.36 g, 1.57 mmol), (R)-ethyl 4-(2-bromo-4-fluorophenyl)-6-(bromomethyl)-2-(thiazol-2-yl)-1,4-dihydropyrimidine-5-carboxylate (0.86 g, 1.71 mmol), potassium carbonate (0.43 g, 3.1 mmol) and anhydrous ethyl alcohol (30 mL) to give the title compound as a yellow solid (0.1 g, 10.5%). The compound was characterized by the following spectroscopic data:

MS (ESI, pos.ion) m/z: 615.2 [M+H]$^+$; and $^1$H NMR (400 MHz, DMSO-d$_6$): δ 12.03 (s, 1H), 9.58 (s, 1H), 8.04-7.88 (m, 2H), 7.60-7.51 (m, 1H), 7.45-7.37 (m, 1H), 7.27-7.18 (m, 1H), 6.02 (s, 1H), 4.36 (d, 1H), 4.03-3.91 (m, 3H), 3.21-3.10 (m, 1H), 3.02-2.86 (m, 1H), 2.76-2.62 (m, 1H), 2.30-2.19 (m, 2H), 2.13-2.02 (m, 1H), 1.98-1.81 (m, 3H), 1.68-1.50 (m, 2H), 1.05 (t, 3H).

Example 41

3-((S)-1-(((R)-6-(2,4-dichlorophenyl)-5-(ethoxycarbonyl)-2-(thiazol-2-yl)-3,6-dihydropyrimidin-4-yl)methyl)-5,5-difluoropiperidin-2-yl)propanoic acid

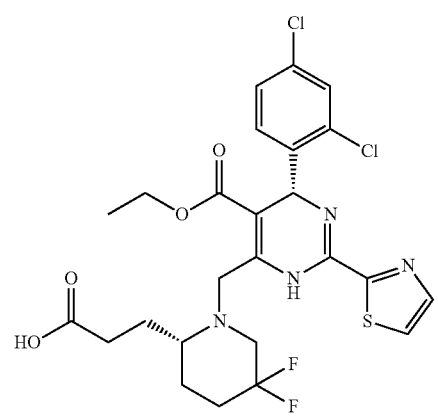 [SMILES: CCOC(=O)C1=C(CN2CC(F)(F)CC[C@@H]2CCC(=O)O)NC(c2nccs2)=N[C@H]1c1ccc(Cl)cc1Cl]

Step 1) (R)-ethyl 2-((tert-butoxycarbonyl)amino)-6-diazo-5-oxohexanoate

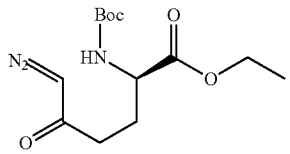

The title compound was prepared by the procedure described in step 1 of Example 40 using (trimethylsilyl)diazomethane solution in n-hexane (2 mol/L, 10.68 mL), anhydrous THF (50 mL), a solution of n-Butyllithium in n-hexane (2.5 mol/L, 9.32 mL, 23.3 mmol) and a solution of (R)-1-tert-butyl 2-ethyl 5-oxopyrrolidine-1,2-dicarboxylate (5.0 g, 19.43 mol) in THF (100 mL) to give the title compound as light yellow oil (2.73 g, 47%). The compound was characterized by the following spectroscopic data:

MS (ESI, pos.ion) m/z: 200.2 [M+H-100]$^+$.

Step 2) (R)-1-tert-butyl 2-ethyl 5-oxopiperidine-1,2-dicarboxylate

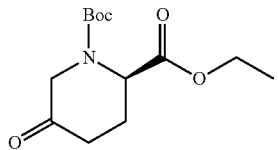 [SMILES: CCOC(=O)[C@H]1CCC(=O)CN1C(=O)OC(C)(C)C]

The title compound was prepared by the procedure described in step 2 of Example 40 using (R)-ethyl 2-((tert-butoxycarbonyl)amino)-6-diazo-5-oxohexanoate (3.1 g, 10.4 mmol), DCM (150 mL) and Rhodium acetate (30 mg, 0.07 mmol) to give the title compound as light yellow oil (1.41 g, 52%). The compound was characterized by the following spectroscopic data:

MS (ESI, pos.ion) m/z: 172.2 [M+H-100]$^+$.

Step 3) (R)-1-tert-butyl 2-ethyl 5,5-difluoropiperidine-1,2-dicarboxylate

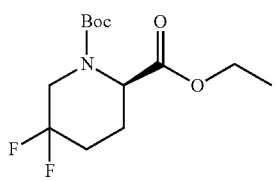 [SMILES: CCOC(=O)[C@H]1CCC(F)(F)CN1C(=O)OC(C)(C)C]

The title compound was prepared by the procedure described in step 3 of Example 40 using (R)-1-tert-butyl 2-ethyl 5-oxopiperidine-1,2-dicarboxylate (0.9 g, 3.3 mmol), anhydrous DCM (90 mL) and DAST (4.36 mL, 10 mmol) to give the title compound as colorless oil (0.59 g, 61%). The compound was characterized by the following spectroscopic data:

MS (ESI, pos.ion) m/z: 238.1 [M+H-56]$^+$.

Step 4) (R)-tert-butyl 5,5-difluoro-2-(hydroxymethyl)piperidine-1-carboxylate

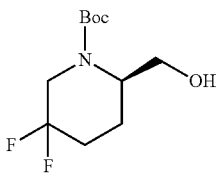 [SMILES: CC(C)(C)OC(=O)N1CC(F)(F)CC[C@@H]1CO]

The title compound was prepared by the procedure described in step 1 of Example 37 using (R)-1-tert-butyl 2-ethyl 5,5-difluoropiperidine-1,2-dicarboxylate (0.45 g, 1.55 mmol), anhydrous THF (40 mL) and LiAlH$_4$ (60 mg, 1.55 mmol) to give the title compound as colorless oil (0.34 g, 88%). The compound was characterized by the following spectroscopic data:

MS (ESI, pos.ion) m/z: 196.1 [M+H-56]$^+$.

Step 5) (R)-tert-butyl 5,5-difluoro-2-formylpiperidine-1-carboxylate

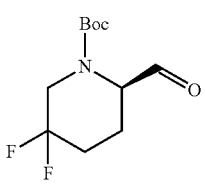 [SMILES: CC(C)(C)OC(=O)N1CC(F)(F)CC[C@@H]1C=O]

The title compound was prepared by the procedure described in step 1 of Example 5 using (R)-tert-butyl 5,5-difluoro-2-(hydroxymethyl)piperidine-1-carboxylate (0.35 g, 1.4 mmol), DCM (50 mL) and Dess-Martin periodinane (0.71 g, 1.68 mmol) to give the title compound as light yellow oil (0.26 g, 76%).

Step 6) (R)-tert-butyl 2-(3-ethoxy-3-oxoprop-1-en-1-yl)-5,5-difluoropiperidine-1-carboxylate

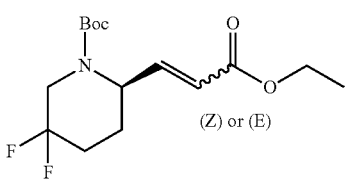 [SMILES: CCOC(=O)C=C[C@H]1CCC(F)(F)CN1C(=O)OC(C)(C)C]

(Z) or (E)

The title compound was prepared by the procedure described in step 1 of Example 6 using (R)-tert-butyl 5,5-difluoro-2-formylpiperidine-1-carboxylate (0.27 g, 1.1 mmol), DCM (30 mL) and ethyl (triphenylphosphoranylidene)acetate (0.38 g, 1.1 mmol) to give the title compound as colorless oil (0.31 g, 88%). The compound was characterized by the following spectroscopic data:

MS (ESI, pos.ion) m/z: 220.2 [M+H-100]$^+$.

Step 7) (S)-tert-butyl 2-(3-ethoxy-3-oxopropyl)-5,5-difluoropiperidine-1-carboxylate

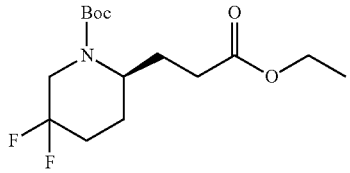 [SMILES: CCOC(=O)CC[C@H]1CCC(F)(F)CN1C(=O)OC(C)(C)C]

The title compound was prepared by the procedure described in step 2 of Example 6 using (R)-tert-butyl 2-(3-ethoxy-3-oxoprop-1-en-1-yl)-5,5-difluoropiperidine-1-carboxylate (0.31 g, 1 mmol), methanol (10 mL) and Pd/C (10%, 0.1 g) to give the title compound as colourless oil (0.31 g, 95%). The compound was characterized by the following spectroscopic data:

MS (ESI, pos.ion) m/z: 266.2 [M+H-56].

Step 8) (S)-3-(1-(tert-butoxycarbonyl)-5,5-difluoropiperidin-2-yl)propanoic acid

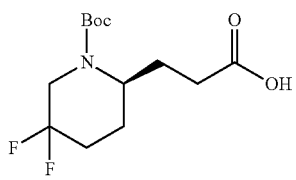 [SMILES: CC(C)(C)OC(=O)N1CC(F)(F)CC[C@@H]1CCC(=O)O]

The title compound was prepared by the procedure described in step 3 of Example 6 using (S)-tert-butyl 2-(3-ethoxy-3-oxopropyl)-5,5-difluoropiperidine-1-carboxylate (0.31 g, 1 mmol), ethanol (10 mL) and aqueous LiOH.H$_2$O solution (LiOH.H$_2$O (0.42 g, 10 mmol) in 10 mL of water) to give the title compound as colour oil (0.28 g, 94%). The compound was characterized by the following spectroscopic data:

MS (ESI, pos.ion) m/z: 194.1 [M+H-100]$^+$.

Step 9) (S)-3-(5,5-difluoropiperidin-2-yl)propanoic acid hydrochloride

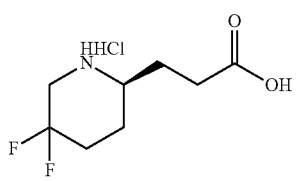

The title compound was prepared by the procedure described in step 4 of Example 6 using (S)-3-(1-(tert-butoxycarbonyl)-5,5-difluoropiperidin-2-yl)propanoic acid (0.28 g, 1 mmol) and a solution of HCl in EtOAc (4 mol/L, 3 mL) to give the title compound as white powder (0.18 g, 78%). The compound was characterized by the following spectroscopic data:

MS (ESI, pos.ion) m/z: 194.1 [M+H]$^+$.

Step 10) 3-((S)-1-(((R)-6-(2,4-dichlorophenyl)-5-(ethoxycarbonyl)-2-(thiazol-2-yl)-3,6-dihydropyrimidin-4-yl)methyl)-5,5-difluoropiperidin-2-yl)propanoic acid

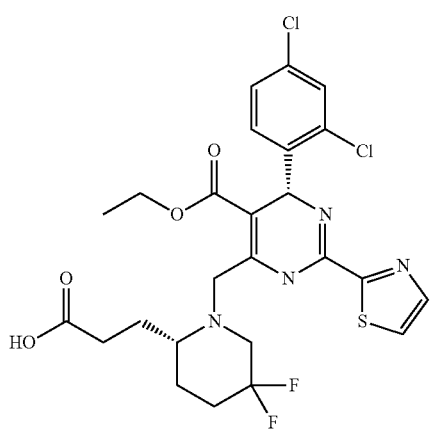 [SMILES: CCOC(=O)C1=C(CN2CC(F)(F)CC[C@@H]2CCC(=O)O)NC(c2nccs2)=N[C@H]1c1ccc(Cl)cc1Cl]

The title compound was prepared by the procedure described in Example 2 using (S)-3-(5,5-difluoropiperidin-2-yl)propanoic acid hydrochloride (0.21 g, 0.56 mmol), (R)-ethyl 6-(bromomethyl)-4-(2,4-dichlorophenyl)-2-(thiazol-2-yl)-1,4-dihydropyrimidine-5-carboxylate (0.37 g, 0.78 mmol), potassium carbonate (0.22 g, 1.56 mmol) and anhydrous ethyl alcohol (10 mL) to give the title compound as a yellow solid (69 mg, 15%). The compound was characterized by the following spectroscopic data:

MS (ESI, pos.ion) m/z: 587.1 [M+H]$^+$; and $^1$H NMR (400 MHz, DMSO-d$_6$): δ 8.01 (d, 1H), 7.94 (d, 1H), 7.56 (br, 1H), 7.40 (br, 2H), 6.01 (s, 1H), 4.34 (d, 1H), 4.01-3.91 (m, 3H), 3.22-3.10 (m, 1H), 3.05-2.87 (m, 1H), 2.74-2.62 (m, 1H), 2.29-2.18 (m, 2H), 2.11-2.02 (m, 1H), 1.99-1.81 (m, 3H), 1.68-1.52 (m, 2H), 1.06 (t, 3H).

Example 42

(R)-ethyl 4-(2-bromo-4-fluorophenyl)-6-(((S)-2-carbamoyl-4,4-difluoropyrrolidin-1-yl)methyl)-2-(thiazol-2-yl)-1,4-dihydropyrimidine-5-carboxylate

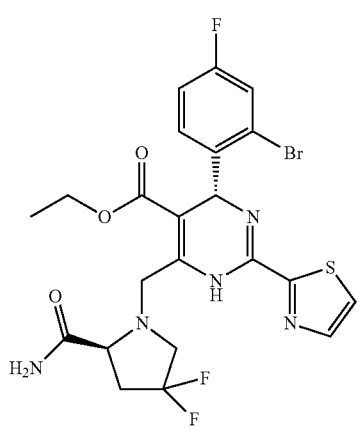 [SMILES: CCOC(=O)C1=C(CN2CC(F)(F)C[C@H]2C(N)=O)NC(c2nccs2)=N[C@H]1c1ccc(F)cc1Br]

Step 1) (S)-tert-butyl 2-carbamoyl-4,4-difluoropyrrolidine-1-carboxylate

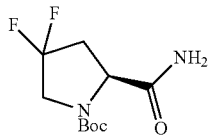 [SMILES: CC(C)(C)OC(=O)N1CC(F)(F)C[C@H]1C(N)=O]

A mixture of a NH$_3$-methanol solution (7 mol/L, 30 mL) and (S)-1-tert-butyl 2-methyl 4,4-difluoropyrrolidine-1,2-dicarboxylate (3.5 g, 13.2 mmol) was stirred at 25° C. for 12 hours in a sealed tube. After the reaction was finished, the mixture was concentrated in vacuo to give the title compound as a white solid (1.8 g, 54.3%). The compound was characterized by the following spectroscopic data:

MS (ESI, pos.ion) m/z: 195.1 [M+H-56]$^+$.

Step 2) (S)-4,4-difluoropyrrolidine-2-carboxamide hydrochloride

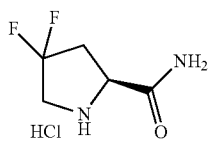

A mixture of (S)-tert-butyl 2-carbamoyl-4,4-difluoropyrrolidine-1-carboxylate (0.8 g, 3.2 mmol) and a solution of HCl in EtOAc (4 mol/L, 10 mL) was stirred at 25° C. for 2 hours. After the reaction was finished, the mixture filtered to give the title compound as a white solid (0.54 g, 90%). The compound was characterized by the following spectroscopic data:

$^1$H NMR (400 MHz, DMSO-d$_6$): δ 10.25 (s, 1H), 8.19 (s, 1H), 7.82 (s, 1H), 4.47 (t, 1H), 3.84-3.57 (m, 2H), 3.06-2.83 (m, 1H), 2.61-2.50 (m, 1H).

Step 3) (R)-ethyl 4-(2-bromo-4-fluorophenyl)-6-(((S)-2-carbamoyl-4,4-difluoropyrrolidin-1-yl)methyl)-2-(thiazol-2-yl)-1,4-dihydropyrimidine-5-carboxylate

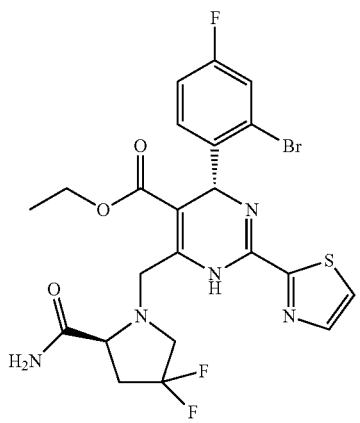 [SMILES: CCOC(=O)C1=C(CN2CC(F)(F)C[C@H]2C(N)=O)NC(c2nccs2)=N[C@H]1c1ccc(F)cc1Br]

A mixture of (S)-4,4-difluoropyrrolidine-2-carboxamide hydrochloride (0.2 g, 1.1 mmol), (R)-ethyl 4-(2-bromo-4-fluorophenyl)-6-(bromomethyl)-2-(thiazol-2-yl)-1,4-dihydropyrimidine-5-carboxylate (0.55 g, 1.1 mmol), potassium carbonate (0.3 g, 2.2 mmol) and ethyl alcohol (15 mL) was stirred at 25° C. for 10 hours. After the reaction was finished, the mixture was filtered, and the filtrate was concentrated in vacuo. The residue was purified by silica column chromatography (DCM/CH$_3$OH (v/v)=25/1) to give the title compound as yellow oil (0.2 g, 35%). The compound was characterized by the following spectroscopic data:

MS (ESI, pos.ion) m/z: 572.1 [M+H]$^+$; and
$^1$H NMR (600 MHz, DMSO-d$_6$): δ 8.17 (br, 1H), 8.12 (br, 1H), 8.05 (br, 1H), 7.72 (br, 1H), 7.61 (d, 1H), 7.58-7.49 (m, 1H), 7.34-7.24 (m, 1H), 6.04 (s, 1H), 4.49 (d, 2H), 4.26 (d, 2H), 3.65-3.53 (m, 3H), 2.96 (br, 2H), 1.07 (t, 3H).

Example 43

(S)-1-(((R)-6-(2-bromo-4-fluorophenyl)-5-(ethoxycarbonyl)-2-(thiazol-2-yl)-3,6-dihydropyrimidin-4-yl)methyl)-4-methylenepyrrolidine-2-carboxylic acid

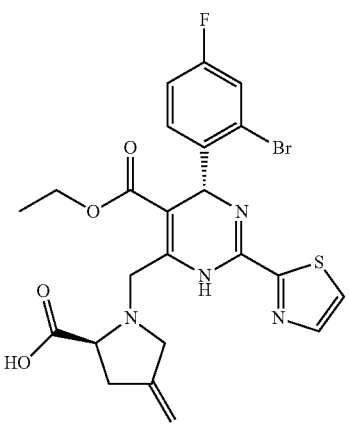 [SMILES: C=C1C[C@@H](C(=O)O)N(CC2=C(C(=O)OCC)[C@H](c3ccc(F)cc3Br)N=C(c3nccs3)N2)C1]

Step 1) (S)-1-tert-butyl 2-methyl 4-methylenepyrrolidine-1,2-dicarboxylate

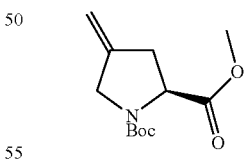

To a suspension of methyltriphenylphosphonium bromide potassium (5.9 g, 16.4 mmol) in anhydrous THF (30 mL) was added potassium tert-butoxide (1.8 g, 16.4 mmol) at −10° C. After the addition, the mixture was stirred at −10° C. for 15 min, and then stirred at 25° C. for 3 hours. Then the mixture was cooled to 0° C., and a solution of (S)-1-tert-butyl 2-methyl 4-oxopyrrolidine-1,2-dicarboxylate (2 g, 8.2 mmol) in THF (10 mL) was added slowly. After addition, the resulting mixture was stirred at 25° C. for 1 hour, cooled to 0° C., and then neutralized with hydrochloric acid (2 mol/L). The mixture was extracted with EtOAc (50 mL×2).

The combined organic phases were dried over anhydrous Na₂SO₄, and concentrated in vacuo. The residue was purified by silica column chromatography (PE/EtOAc (v/v)=10/1) to give the title compound as yellow oil (0.25 g, 12.6%). The compound was characterized by the following spectroscopic data:

MS (ESI, pos.ion) m/z: 142.2 [M+H-100]+; and

¹H NMR (400 MHz, CDCl₃): δ 5.11-4.92 (m, 2H), 4.60-4.37 (m, 1H), 4.16, 4.04 (s, s, 2H), 3.81, 3.63 (s, s, 3H), 3.11-2.85 (m, 1H), 2.78-2.42 (m, 1H), 1.53, 1.44 (s, s, 9H).

Step 2) (S)-1-(tert-butoxycarbonyl)-4-methylenepyrrolidine-2-carboxylic acid

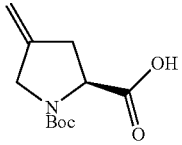 [SMILES: C=C1C[C@@H](C(=O)O)N(C(=O)OC(C)(C)C)C1]

A mixture of (S)-1-tert-butyl 2-methyl 4-methylenepyrrolidine-1,2-dicarboxylate (0.5 g, 2.1 mmol), ethanol (5 mL) and a solution of LiOH.H₂O (0.44 g, 10.5 mmol) in water (5 mL) was stirred at 25° C. for 3 hours. After the reaction was finished, the mixture was diluted with water (40 mL), and extracted with EtOAc (50 mL×3). The organic phases were discarded. The water phase was adjusted to pH 4-5, then extracted with EtOAc (50 mL×3), and the combined organic phases were washed with satured brine (80 mL), dried over anhydrous Na₂SO₄, and concentrated in vacuo to give the title compound as a white solid (0.2 g, 85%).

MS (ESI, pos.ion) m/z: 128.4 [M+H-100]⁺; and

¹H NMR (400 MHz, CDCl₃): δ 9.08 (br, 1H), 5.00 (s, 2H), 4.58-4.46 (m, 1H), 4.08-3.90 (m, 2H), 2.99-2.87 (m, 1H), 2.74-2.60 (m, 1H), 1.41 (s, 9H).

Step 3) (S)-4-methylenepyrrolidine-2-carboxylic acid hydrochloride

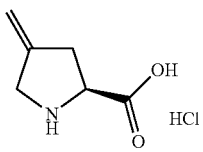

A mixture of (S)-1-(tert-butoxycarbonyl)-4-methylenepyrrolidine-2-carboxylic acid (0.45 g, 2 mmol) and a solution of HCl in EtOAc (4 mol/L, 5 mL) was stirred at 25° C. for 2 hours. After the reaction was finished, the mixture filtered to give the title compound as a white solid (0.27 g, 81%). The compound was characterized by the following spectroscopic data:

MS (ESI, pos.ion) m/z: 128.1 [M+H-100]⁺.

Step 4) (S)-1-(((R)-6-(2-bromo-4-fluorophenyl)-5-(ethoxycarbonyl)-2-(thiazol-2-yl)-3,6-dihydropyrimidin-4-yl)methyl)-4-methylenepyrrolidine-2-carboxylic acid

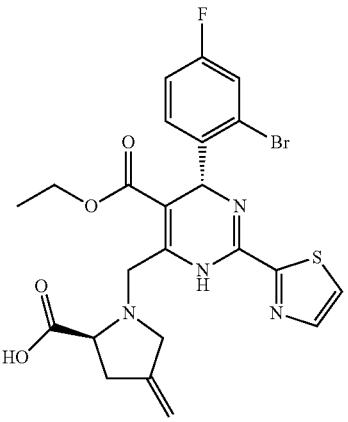 [SMILES: C=C1C[C@@H](C(=O)O)N(CC2=C(C(=O)OCC)[C@H](c3ccc(F)cc3Br)N=C(c3nccs3)N2)C1]

A mixture of (S)-4-methylenepyrrolidine-2-carboxylic acid hydrochloride (0.16 g, 1 mmol), (R)-ethyl 4-(2-bromo-4-fluorophenyl)-6-(bromomethyl)-2-(thiazol-2-yl)-1,4-dihydropyrimidine-5-carboxylate (0.5 g, 1 mmol), potassium carbonate (0.28 g, 2 mmol) and anhydrous ethyl alcohol (10 mL) was stirred at 25° C. for 10 hours. After the reaction was finished, the mixture was filtered, and the filtrate concentrated in vacuo. The residue was purified by silica column chromatography (DCM/CH₃OH (v/v)=25/1) to give the title compound as yellow oil (0.31 g, 56.3%). The compound was characterized by the following spectroscopic data:

MS (ESI, pos.ion) m/z: 549.1 [M+H]⁺; and

¹H-NMR (400 MHz, DMSO-d₆): δ 9.72 (s, 1H), 7.96-7.90 (m, 2H), 7.57-7.55 (m, 1H), 7.44-7.35 (m, 1H), 7.27-7.23 (m, 1H), 6.00 (s, 1H), 4.97 (s, 2H), 4.25 (d, 1H), 4.02 (d, 1H), 3.96-3.92 (m, 2H), 3.84-3.69 (m, 3H), 2.94-2.80 (m, 1H), 2.62-2.56 (m, 1H), 1.07-0.99 (m, 3H).

Example 44

(R)-ethyl-4-(2-bromo-4-fluorophenyl)-6-(((S)-4,4-difluoro-2-(methylcarbamoyl)pyrrolidin-1-yl)methyl)-2-(thiazol-2-yl)-1,4-dihydropyrimidine-5-carboxylate

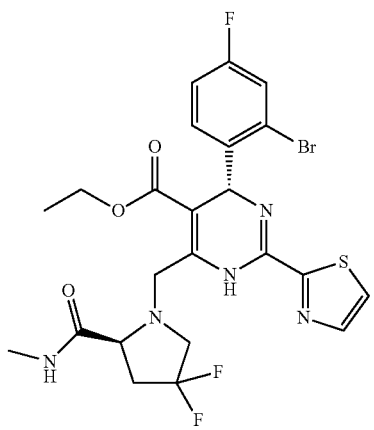 [SMILES: CCOC(=O)C1=C(CN2CC(F)(F)C[C@H]2C(=O)NC)NC(c2nccs2)=N[C@H]1c1ccc(F)cc1Br]

Step 1) (S)-tert-butyl 4,4-difluoro-2-(methylcarbamoyl)pyrrolidine 1-carboxylate

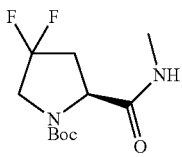

A mixture of (S)-1-(tert-butoxycarbonyl)-4,4-difluoropyrrolidine-2-carboxylic acid (0.4 g, 1.6 mmol), methylamine hydrochloride (0.26 g, 4 mmol), EDCI (0.61 g, 3.2 mmol), HOAT (0.1 g, 0.7 mmol) and DCM (15 mL) was stirred at 25° C. for 2 hours. After the reaction was finished, the mixture was concentrated in vacuo. The residue was purified by silica column chromatography (PE/EtOAc (v/v)=10/1) to give the title compound as colourless oil (0.25 g, 58%). The compound was characterized by the following spectroscopic data:

MS (ESI, pos.ion) m/z: 165.1 [M+H−100]+.

Step 2) (S)-4,4-difluoro-2-(methylcarbamoyl)pyrrolidine hydrochloride

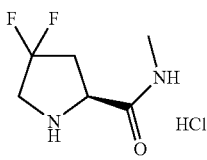

A mixture of (S)-tert-butyl 4,4-difluoro-2-(methylcarbamoyl)pyrrolidine-1-carboxylate (0.47 g, 1.8 mmol) and a solution of HCl in EtOAc (4 mol/L, 5 mL) was stirred at 25° C. for 2 hours. After the reaction was finished, the mixture was filtered to give the title compound as a white solid (0.27 g, 75%). The compound was characterized by the following spectroscopic data:

MS (ESI, pos.ion) m/z: 165.1 [M+H]+.

Step 3) (R)-ethyl-4-(2-bromo-4-fluorophenyl)-6-(((S)-4,4-difluoro-2-(methylcarbamoyl)pyrrolidin-1-yl)methyl)-2-(thiazol-2-yl)-1,4-dihydropyrimidine-5-carboxylate

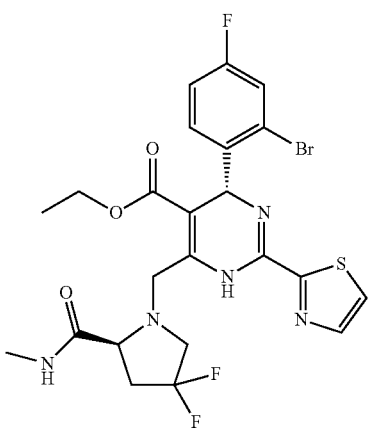 [SMILES: CCOC(=O)C1=C(CN2CC(F)(F)C[C@H]2C(=O)NC)NC(c2nccs2)=N[C@H]1c1ccc(F)cc1Br]

A mixture of (S)-4,4-difluoro-2-(methylcarbamoyl)pyrrolidine hydrochloride (0.2 g, 1 mmol), (R)-ethyl 4-(2-bromo-4-fluorophenyl)-6-(bromomethyl)-2-(thiazol-2-yl)-1,4-dihydropyrimidine-5-carboxylate (0.5 g, 1 mmol), potassium carbonate (0.28 g, 2 mmol) and anhydrous ethyl alcohol (10 mL) was stirred at 25° C. for 10 hours. After the reaction was finished, the mixture was filtered, and the filtrate was concentrated in vacuo. The residue was purified by silica column chromatography (DCM/CH$_3$OH (v/v)=100/1) to give the title compound as yellow oil (0.24 g, 41%). The compound was characterized by the following spectroscopic data:

MS (ESI, pos.ion) m/z: 586.1 [M+H]+; and $^1$H NMR (400 MHz, DMSO-d$_6$): δ 8.17 (s, 1H), 8.02 (d, 2H), 7.57 (d, 1H), 7.43 (d, 1H), 7.26 (s, 1H), 6.00 (s, 1H), 4.18 (d, 2H), 4.07 (s, 1H), 4.03 (d, 1H), 4.00-3.93 (m, 2H), 3.79 (s, 2H), 2.69 (s, 2H), 2.60 (d, 3H), 2.36 (dd, 1H), 1.05 (t, 3H).

Example 45

In-Vitro Anti-HBV Activity of Compounds in Stable HBV-Producing Cell Line (HepG2.2.15)

1. Assay Method

HBV DNA contents in cell culture fluid were detected by the qPCR-based assay and 50% effective concentration (EC$_{50}$) values of the compounds to HBV were calculated. Specific procedures are as follows:

HepG2.2.15 cells were seeded into each well of 96-well plates, 40,000 cells per well. Cells were treated with cell culture medium containing compounds with different concentrations 24 hours after cell seeding. The final concentration of each compound was 16.4 μM in each well and each compound was diluted to desired concentration using 3-fold gradient dilution protocol, 9 diluted points in duplicate. The culture mediums containing the compounds were refreshed on day 4 post cell seeding. Culture media were collected from the HepG2.2.15 plates on day 7 post cell seeding followed by HBV DNA extraction.

HBV DNA extraction: The HBV DNA extraction was performed using QIAamp 96 DNA Blood Kit (QIAGEN 51161).

PCR for quantification: PCR mix was prepared according to PCR system. PCR mix was dispensed to 96-well optical reaction plates (special for quantification). The standard diluted proportionally was added. Then the sample was added; The plates were sealed with optical adhesive film; PCR system was performed according to programs.

Percentage of HBV inhibition of DNA replication by compound was calculated using the following equation:

% Inh.=[1−HBV DNA quantity of sample/HBV DNA quantity of DMSO control]*100.

Calculating EC$_{50}$ value of compounds to HBV replication: the EC$_{50}$ values were calculated based on "four-parameter logistic equation" and using GraphPad Prism 5 analysis software.

2. Assay Results

Anti HBV activity of the compounds disclosed herein in HBV HepG2.2.15 cell lines were detected by the methods above. The results are shown in Table 2:

TABLE 2 anti-HBV activity of the compounds in HBV HepG2.2.15 cell line (HepG2.2.15)

| Example | EC$_{50}$ (μmol) |
|---|---|
| Example 1 | 0.0054 |
| Example 2 | 6.632 |
| Example 6 | 0.085 |
| Example 7 | 0.065 |
| Example 12 | 0.098 |
| Example 13 | 0.064 |
| Example 14 | 0.080 |
| Example 15 | 0.094 |
| Example 16 | 0.062 |

TABLE 2-continued anti-HBV activity of the compounds in HBV HepG2.2.15 cell line (HepG2.2.15)

| Example | EC$_{50}$ (μmol) |
|---|---|
| Example 17 | 0.012 |
| Example 18 | 0.014 |
| Example 19 | 0.020 |
| Example 20 | 0.017 |
| Example 21 | 0.009 |
| Example 22 | 0.011 |

3. Conclusions

The compounds disclosed herein showed potent inhibitory effect on HBV. Such compounds have surprising antiviral activity and can be applied in the treatment of various kinds of disorders caused by HBV infection

Example 46

Test Compounds' PK Assay in ICR Mice

I. Assay Method

The test compounds were poured into ICR mice stomach through mouth with 10 mg/kg or 5 mg/kg, or administered 2 mg/kg to ICR mice by tail-intravenous injection. Blood sample of orbital vein was taken at 0.083, 0.25, 0.5, 1, 2, 4, 6, 8 and 24 hours after administration, and collected in anticoagulation tube added with EDTA-K$_2$. The test compounds were extracted from plasma samples and chromatographed on a tandem mass spectrometer. Quantitation was performed using multiple reaction monitoring (MRM). Pharmacokinetic parameters were calculated using WinNonlin 6.3 software with non compartment model.

II. Assay Results

Test compounds' PK were detected with the methods above. The results are shown in Table 3:

TABLE 3

| E. | A.R | Dose mg/kg | T$_{max}$ h | C$_{max}$ ng/mL | t$_{1/2}$ h | AUC$_{last}$ hr * ng/mL | AUC$_{INF}$ hr * ng/mL | F % | CL L/h/Kg | Vss L/Kg |
|---|---|---|---|---|---|---|---|---|---|---|
| R | iv | 2 | 0.083 | 654.37 | 2.87 | 379.13 | 381.2 | N/A | 5.25 | 7.91 |
|   | po | 10 | 0.25 | 78.2 | 3.69 | 145.05 | 147.71 | 7.75 | N/A | N/A |
| Example 6 | iv | 2 | 0.08 | 6560 | 0.77 | 3270 | 3270 | N/A | 0.61 | 0.38 |
|   | po | 5 | 0.25 | 5410 | 3.14 | 4840 | 4850 | 59.3 | N/A | N/A |
| Example 8 | iv | 2 | 0.08 | 5790 | 1.35 | 2860 | 2870 | N/A | 0.69 | 0.39 |
|   | po | 5 | 0.25 | 4820 | 1.05 | 4960 | 4970 | 69.3 | N/A | N/A |
| Example 9 | iv | 2 | 0.08 | 6270 | 1.37 | 3230 | 3240 | N/A | 0.62 | 0.33 |
|   | po | 5 | 0.25 | 5460 | 1.06 | 4860 | 4870 | 60.2 | N/A | N/A |
| Example 39 | iv | 2 | 0.08 | 4260 | 3.22 | 5800 | 5810 | N/A | 0.34 | 0.73 |
|   | po | 5 | 0.5 | 4900 | 2.21 | 12500 | 12500 | 86.1 | N/A | N/A |

E.—Examples;
R.—Reference;
A.R.—Administration Routes;
Reference—Ethyl4-(2-bromo-4-fluorophenyl)-2-(thiazol-2-yl)-6-((4-morpholino)methyl)-1,4-dihydropyrimidine-5-carboxylate (The compound was synthesized according to the procedure as described in WO2008154817);
N/A—There is no detection;
AUC$_{last}$—AUC in 0-24 hours;
AUC$_{INF}$—AUC in 0 hour to infinite time.

III. Conclusions

After intragastric administration of drugs in ICR mice, the compound of Example 6, Example 8, Example 9 and the compound of Example 39 were rapidly absorbed and the peak time in plasma were 0.25 hour, 0.25 hour, 0.25 hour and 0.5 hour respectively. The AUC$_{last}$ of the compound of Example 6 was 4840 hr*ng/mL, the AUC$_{last}$ of the compound of Example 8 was 4960 hr*ng/mL, the AUC$_{last}$ of the compound of Example 9 was 4860 hr*ng/mL, and the AUC$_{last}$ of the compound of Example 39 was 12500 hr*ng/mL. The compounds have better exposure, which are apparently higher than reference. It showed that compounds were absorbed well in ICR mice. After administration by intravenous injection, the CL of the compound of Example 6, Example 8, Example 9 and the compound of Example 39 were 0.61 L/h/Kg, 0.69 L/h/Kg, 0.62 L/h/Kg and 0.34 L/h/Kg respectively, and Vss of the compound of Example 6, Example 8, Example 9 and the compound of Example 39 were 0.38 L/Kg, 0.39 L/Kg, 0.33 L/Kg and 0.73 L/Kg respectively. Calculated by the AUC$_{last}$ of the compound of Example 6, Example 8, Example 9 and the compound of Example 39, F were 59.3%, 69.3%, 60.2% and 96.1% respectively when the test compounds were poured into ICR mice stomach through mouth with 5 mg/kg. The compounds have better bioavailability, which are much higher than reference (7.75%).

Activity data comparison showed that the activity of most compounds disclosed herein were higher than reference, and thus it will show a good prospect in anti-HBV.

Although the present invention has been described by a way of a detailed description in which general description, examples and assays have been described, it will be obvious to one skilled in the art that certain changes and modifications may be made without departing from the invention, and therefore, all such changes and modifications are within the scope of the invention.

What is claimed is:

1. A compound having Formula (I) or (Ia), or an enantiomer, a diastereoisomer, a tautomer, a hydrate, a solvate, a stereoisomer, an N-oxide, or a pharmaceutically acceptable salt thereof,

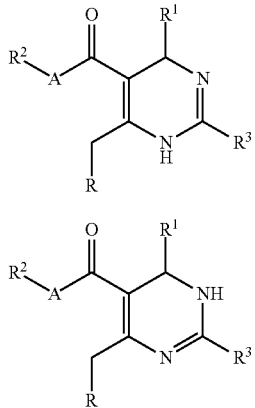

wherein
$R^1$ is $C_{6-10}$ aryl or $C_{1-9}$ heteroaryl;
$R^3$ is a 5-membered heteroaryl group;
A is a bond, —O—, —S— or —$NR^5$—;
R is

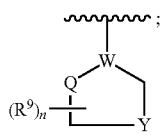

wherein, W is $CR^4$ or N;
each of $R^2$, $R^4$ and $R^5$ is independently hydrogen or $C_{1-4}$ alkyl;
Y is —$(CR^8R^{8a})_k$—S(=O)$_q$— or —$(CR^7R^6)_n$—;
Q is —$(CR^8R^{8a})_k$—;
each $R^7$ is independently hydrogen, F or alkyl;
each $R^6$ is independently F or alkyl;
or $R^6$ and $R^7$, together with the carbon atom to which they are attached, form —C(=CH$_2$)— or —C(=O)—;
each $R^8$ and $R^{8a}$ is independently hydrogen, cyano or alkyl;
each $R^9$ is independently —$(CR^{10}R^{10a})_t$—OH, triazolyl, tetrazolyl, —$(CR^{10}R^{10a})_m$—C(=O)O—$R^{11}$, —$(CR^{10}R^{10a})_k$—C(=O)O—$(CR^{10}R^{10a})_k$—OC(=O)O—$R^{11}$, —S(=O)$_q$O$R^{11}$, —$(CR^{10}R^{10a})_k$—S(=O)$_q$N($R^{11}$)$_2$, —$(CR^{10}R^{10a})_k$—C(=O)O—$(CR^{10}R^{10a})_k$—OC(=O)—$R^{11}$, —$(CR^{10}R^{10a})_k$—C(=O)O—$(CR^{10}R^{10a})_k$—C(=O)O—$R^{11}$, —$(CR^{10}R^{10a})_t$—N($R^{11}$)$_2$, —$(CR^{10}R^{10a})_t$—OC(=O)—$R^{11}$, or —$(CR^{10}R^{10a})_k$—C(=O)N($R^{11}$)$_2$;
each $R^{10}$ and $R^{10a}$ is independently hydrogen, halogen, haloalkyl or alkyl, or $R^{10}$ and $R^{10a}$, together with the carbon atom to which they are attached, form cycloalkyl, heterocyclyl or —C(=O)—;

each $R^{11}$ is independently hydrogen, alkyl, alkoxy, hydroxy, alkyl-S(=O)$_q$—, aryl, heteroaryl, cycloalkyl, heterocyclyl, arylalkyl, heterocyclyl-S(=O)$_q$—, heteroaryl-S(=O)$_q$—, cycloalkyl-S(=O)$_q$— or aryl-S(=O)$_q$—;
each n is independently 1, 2 or 3;
each t and m is independently 1, 2, 3 or 4;
each q is independently 1 or 2; and
each k is independently 0, 1, 2, 3 or 4;
wherein each alkoxy, alkyl-S(=O)$_q$—, aryl, heteroaryl, arylalkyl, heterocyclyl-S(=O)$_q$—, heteroaryl-S(=O)$_q$—, cycloalkyl-S(=O)$_q$— and aryl-S(=O)$_q$— described in $R^{11}$, alkyl described in $R^6$, $R^7$, $R^8$, $R^{8a}$, $R^{10}$, $R^{10a}$, and $R^{11}$, haloalkyl described in $R^{10}$ and $R^{10a}$, heterocyclyl and cycloalkyl described in $R^{10}$, $R^{10a}$, and $R^{11}$, triazolyl and tetrazolyl described in $R^9$, a 5-membered heteroaryl group described in $R^3$, $C_{1-4}$ alkyl described in $R^1$, $R^4$ and $R^5$, and $C_{6-10}$ aryl and $C_{1-9}$ heteroaryl described in $R^1$, is optionally and independently substituted with one or more substituents independently selected from hydrogen, fluoro, chloro, bromo, iodo, oxo (=O), methylene (=CH$_2$), alkyl, alkoxy, cyano, hydroxy, nitro, alkylamino, amino, aryl, heteroaryl, heterocyclyl, cycloalkyl, trifluoromethyl, trifluoromethoxy, haloalkyl-substituted aryl, halogen-substituted aryl or trifluoromethylsulfonyl.

2. The compound according to claim 1, wherein R is

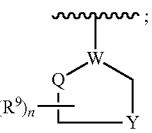

wherein, Y is —$(CR^8R^{8a})_k$—S(=O)$_q$— or —$(CR^7R^6)_n$—;
Q is —$(CR^8R^{8a})_k$—;
each $R^7$ is independently hydrogen, $C_{1-4}$ alkyl or F;
each $R^6$ is independently F or $C_{1-4}$ alkyl;
or $R^6$ and $R^7$, together with the carbon atom to which they are attached, form —C(=CH$_2$)— or —C(=O)—;
each $R^8$ and $R^{8a}$ is independently hydrogen or $C_{1-4}$ alkyl;
each $R^9$ is independently —$(CR^{10}R^{10a})_t$—OH, triazolyl, tetrazolyl, —$(CR^{10}R^{10a})_m$—C(=O)O—$R^{11}$, —$(CR^{10}R^{10a})_k$—C(=O)O—$(CR^{10}R^{10a})_k$—OC(=O)O—$R^{11}$, —S(=O)$_q$O$R^{11}$, —$(CR^{10}R^{10a})_k$—S(=O)$_q$N($R^{11}$)$_2$, —$(CR^{10}R^{10a})_k$—C(=O)O—$(CR^{10}R^{10a})_k$—OC(=O)—$R^{11}$, —$(CR^{10}R^{10a})_k$—C(=O)O—$R^{11}$, —$(CR^{10}R^{10a})_t$—N($R^{11}$)$_2$, —$(CR^{10}R^{10a})_t$—OC(=O)—$R^{11}$, or —$(CR^{10}R^{10a})_k$—C(=O)N($R^{11}$)$_2$;
each $R^{10}$ and $R^{10a}$ is independently hydrogen, halogen, $C_{1-4}$ haloalkyl or $C_{1-4}$ alkyl, or $R^{10}$ and $R^{10a}$, together with the carbon atom to which they are attached, form $C_{3-6}$ cycloalkyl, $C_{2-9}$ heterocyclyl or —C(=O)—; and
each $R^{11}$ is independently hydrogen, $C_{1-6}$ alkyl, $C_{1-6}$ alkoxy, $C_{1-6}$ alkyl-S(=O)$_q$—, $C_{6-10}$ aryl, $C_{1-9}$ heteroaryl, $C_{3-6}$ cycloalkyl, $C_{2-9}$ heterocyclyl, $C_{6-10}$ aryl-$C_{1-6}$-alkyl, $C_{2-9}$ heterocyclyl-S(=O)$_q$—, $C_{1-9}$ heteroaryl-S(=O)$_q$—, $C_{3-6}$ cycloalkyl-S(=O)$_q$— or $C_{6-10}$ aryl-S(=O)$_q$.

3. The compound according to claim 2, wherein R is

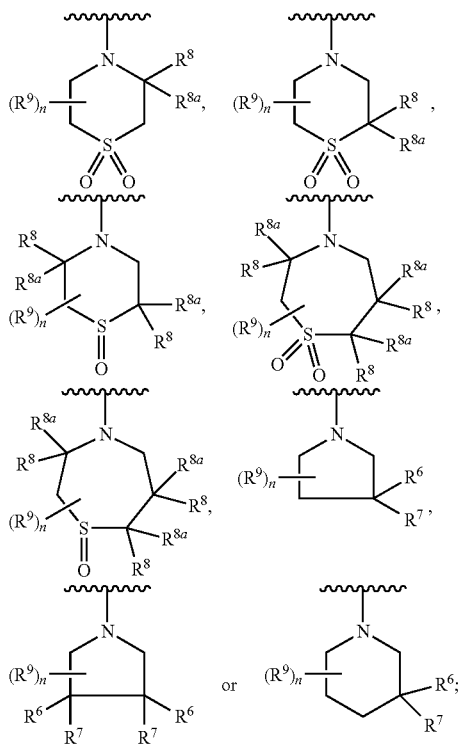

wherein, each $R^7$ is independently hydrogen, methyl, ethyl or F;

each $R^6$ is independently F, methyl or ethyl;

or $R^6$ and $R^7$, together with the carbon atom to which they are attached, form —C(=CH$_2$)— or —C(=O)—;

each $R^8$ and $R^{8a}$ is independently hydrogen, methyl, ethyl or propyl;

each $R^9$ is independently —(CR$^{10}$R$^{10a}$)$_t$—OH, triazolyl, tetrazolyl, —(CR$^{10}$R$^{10a}$)$_m$—C(=O)O—R$^{11}$, —(CR$^{10}$R$^{10a}$)$_k$—C(=O)O—(CR$^{10}$R$^{10a}$)$_k$—OC(=O) O—R$^{11}$, —S(=O)$_q$OR$^{11}$, —(CR$^{10}$R$^{10a}$)$_k$—S(=O)$_q$N (R$^{11}$)$_2$, —(CR$^{10}$R$^{10a}$)$_k$—C(=O)O—(CR$^{10}$R$^{10a}$)$_k$—OC (=O)—R$^{11}$, —(CR$^{10}$R$^{10a}$)$_k$—C(=O)O— (CR$^{10}$R$^{10a}$)$_k$—C(=O)O—R$^{11}$, —(CR$^{10}$R$^{10a}$)$_t$—N (R$^{11}$)$_2$, —(CR$^{10}$R$^{10a}$)$_t$—OC(=O)—R$^{11}$, or —(CR$^{10}$R$^{10a}$)$_k$—C(=O)N(R$^{11}$)$_2$;

each $R^{10}$ and $R^{10a}$ is independently hydrogen, fluoro, chloro, bromo, iodo, trifluoromethyl, methyl, ethyl, propyl, or $R^{10}$ and $R^{10a}$, together with the carbon atom to which they are attached, form cyclopropyl, cyclobutyl, cyclopentyl, cyclohexyl or —C(=O)—; and each $R^{11}$ is independently hydrogen, C$_{1-4}$ alkyl, C$_{1-4}$ alkoxyl, C$_{1-4}$ alkyl-S(=O)$_2$—, phenyl, pyridyl, thiazolyl, furyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S (=O)$_2$—, cyclobutyl-S(=O)$_2$—, cyclopentyl-S(=O)$_2$—, cyclohexyl-S(=O)$_2$—, naphthyl-S(=O)$_2$— or phenyl-S(=O)$_2$—.

4. The compound according to claim 1, wherein
$R^1$ is phenyl;
$R^3$ is thiazolyl or 1-methyl-1H-imidazolyl; and
each of $R^2$, $R^4$ and $R^5$ is independently hydrogen, methyl or ethyl;
wherein each thiazolyl and 1-methyl-1H-imidazolyl described in $R^3$, phenyl described in $R^1$, and methyl and ethyl described in $R^2$, $R^4$ and $R^5$, is optionally and independently substituted with one or more substituents independently selected from hydrogen, C$_{1-4}$ alkyl, fluoro, chloro or bromo.

5. The compound according to claim 1 having Formula (II) or (IIa), or an enantiomer, a diastereoisomer, a tautomer, a hydrate, a solvate, a stereoisomer, an N-oxide or a pharmaceutically acceptable salt thereof,

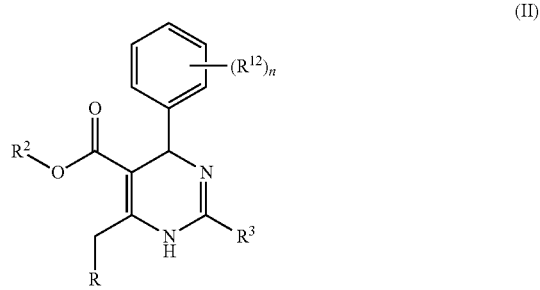

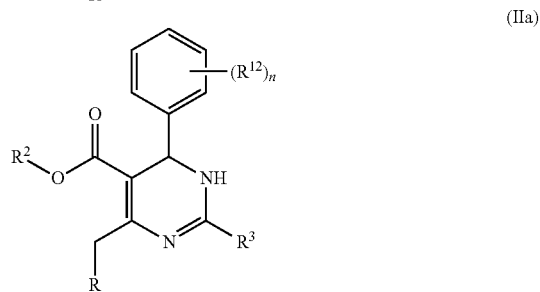

wherein
$R^2$ is hydrogen or C$_{1-4}$ alkyl;
$R^3$ is thiazolyl or 1-methyl-1H-imidazolyl;
R is

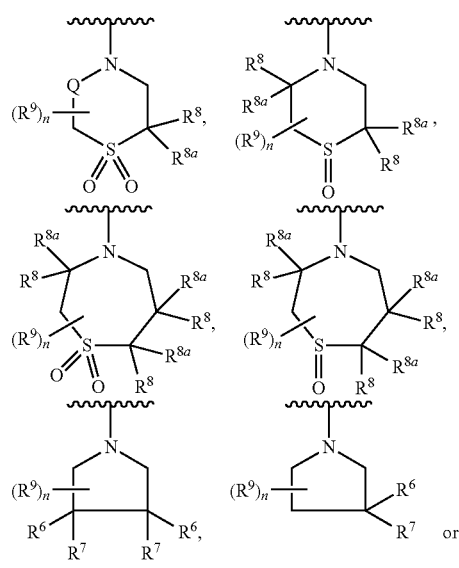

-continued

[structure: piperidine with (R⁹)ₙ, R⁶, R⁷]

wherein each R⁷ is independently hydrogen, C₁₋₄ alkyl or F;
each R⁶ is independently F or C₁₋₄ alkyl;
or R⁶ and R⁷, together with the carbon atom to which they are attached, form —C(=CH₂)— or —C(=O)—;
Q is —(CR⁸R⁸ᵃ)ₖ—;
each R⁸ and R⁸ᵃ is independently hydrogen or C₁₋₄ alkyl;
each R⁹ is independently —(CR¹⁰R¹⁰ᵃ)ₜ—OH, triazolyl, tetrazolyl, —(CR¹⁰R¹⁰ᵃ)ₘ—C(=O)O—R¹¹, —(CR¹⁰R¹⁰ᵃ)ₖ—C(=O)O—(CR¹⁰R¹⁰ᵃ)ₖ—OC(=O)O—R, —S(=O)_qOR¹¹, —(CR¹⁰R¹⁰ᵃ)ₖ—S(=O)_qN(R¹¹)₂, —(CR¹⁰R¹⁰ᵃ)ₖ—C(=O)O—(CR¹⁰R¹⁰ᵃ)ₖ—OC(=O)—R¹¹, —(CR¹⁰R¹⁰ᵃ)ₖ—C(=O)O—(CR¹⁰R¹⁰ᵃ)ₖ—C(=O)O—R¹¹, —(CR¹⁰R¹⁰ᵃ)ₜ—N(R¹¹)₂, —(CR¹⁰R¹⁰ᵃ)ₜ—OC(=O)—R¹¹, or —(CR¹⁰R¹⁰ᵃ)ₖ—C(=O)N(R¹¹)₂;
each R¹⁰ and R¹⁰ᵃ is independently hydrogen, fluoro, chloro, bromo, iodo, C₁₋₄ haloalkyl or C₁₋₄ alkyl, or R¹⁰ and R¹⁰ᵃ, together with the carbon atom to which they are attached, form C₃₋₆ cycloalkyl or —C(=O)—;
each R¹¹ is independently hydrogen, C₁₋₄ alkyl, C₁₋₄ alkoxy, hydroxy, C₁₋₄ alkyl-S(=O)_q—, C₆₋₁₀ aryl, C₁₋₉ heteroaryl, C₃₋₆ cycloalkyl, C₂₋₉ heterocyclyl, C₆₋₁₀ aryl-C₁₋₄-alkyl, C₂₋₉ heterocyclyl-S(=O)_q—, C₁₋₉ heteroaryl-S(=O)_q—, C₃₋₆ cycloalkyl-S(=O)_q— or C₆₋₁₀ aryl-S(=O)_q—;
each R¹² is independently hydrogen, fluoro, chloro or bromo;
each n is independently 1, 2 or 3;
each t and m is independently 1, 2, 3 or 4;
each q is independently 1 or 2; and
each k is independently 0, 1, 2, 3 or 4.

6. The compound according to claim 1 or 5, wherein R is

[structures of various pyrrolidine and related rings with (R⁹)ₙ substituents including F, F; CH₃ with F; F; =O (ketone); =CH₂; sulfone]

[continued structures: thiomorpholine sulfone with methyl; thiomorpholine sulfoxide with methyl; azepane sulfoxide; thiazepane sulfone; thiomorpholine sulfone with methyl; piperidine with F, F]

each R⁹ is independently —(CR¹⁰R¹⁰ᵃ)ₜ—OH, triazolyl, tetrazolyl, —(CR¹⁰R¹⁰ᵃ)ₘ—C(=O)O—R¹¹, —(CR¹⁰R¹⁰ᵃ)ₖ—C(=O)O—(CR¹⁰R¹⁰ᵃ)ₖ—OC(=O)O—R¹¹, —S(=O)_qOR¹¹, —(CR¹⁰R¹⁰ᵃ)ₖ—S(=O)_qN(R¹¹)₂, —(CR¹⁰R¹⁰ᵃ)ₖ—C(=O)O—(CR¹⁰R¹⁰ᵃ)ₖ—OC(=O)—R¹¹, —(CR¹⁰R¹⁰ᵃ)ₖ—C(=O)O—R¹¹, —(CR¹⁰R¹⁰ᵃ)ₜ—N(R¹¹)₂, —(CR¹⁰R¹⁰ᵃ)ₜ—OC(=O)—R¹¹, or —(CR¹⁰R¹⁰ᵃ)ₖ—C(=O)N(R¹¹)₂;
each R¹⁰ and R¹⁰ᵃ is independently hydrogen, fluoro, chloro, trifluoromethyl, methyl, ethyl, propyl, isopropyl, tert-butyl or n-butyl, or R¹⁰ and R¹⁰ᵃ together with the carbon atom to which they are attached, form cyclopropyl, cyclobutyl, cyclopentyl, cyclohexyl or —C(=O)—; and
each R¹¹ is independently hydrogen, methyl, ethyl, propyl, isopropyl, tert-butyl, n-butyl; methoxyl, ethoxy, propoxy, isopropoxy, tert-butoxy, n-butoxy, methyl-S(=O)₂—, ethyl-S(=O)₂—, propyl-S(=O)₂—, isopropyl-S(=O)₂—, pyridyl, thiazolyl, furyl, imidazolyl, isoxazolyl, oxazolyl, pyrrolyl, pyrimidinyl, pyridazinyl, diazolyl, triazolyl, tetrazolyl, thienyl, pyrazolyl, isothiazolyl, oxadiazolyl, thiadiazolyl, pyrazinyl, pyranyl, triazinyl, cyclopropyl, cyclobutyl, cyclopentyl, cyclohexyl, cyclopropyl-S(=O)₂—, cyclobutyl-S(=O)₂—, cyclopentyl-S(=O)₂—, cyclohexyl-S(=O)₂—, naphthyl-S(=O)₂— or phenyl-S(=O)₂—.

7. The compound according to claim 1 having one of the following structures, or an enantiomer, a diastereoisomer, a tautomer, a hydrate, a solvate, a stereoisomer, an N-oxide, or a pharmaceutically acceptable salt thereof, (1)

[structure of compound (1): dihydropyrimidine bearing 4-fluoro-2-bromophenyl, ethyl ester, thiazol-2-yl, and a pyrrolidine-2-carboxamide with 4,4-difluoro substitution]

193
-continued
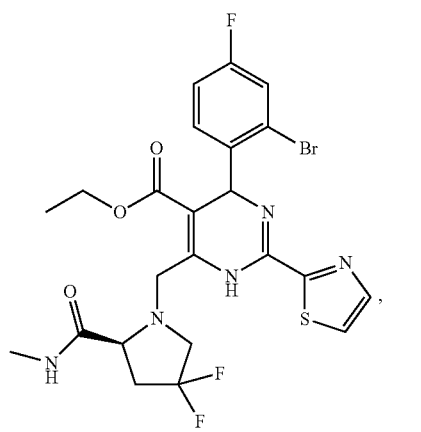
(2)
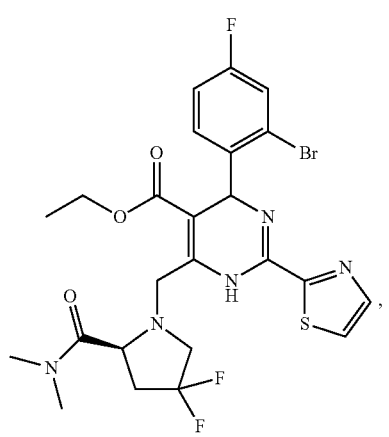
(3)
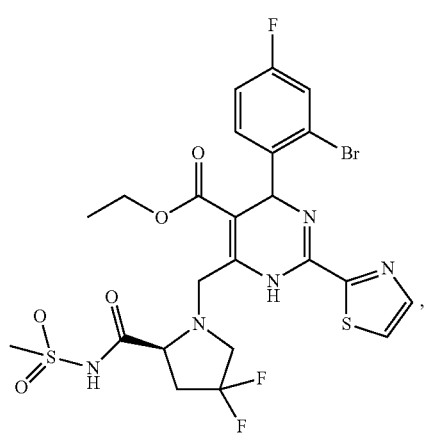
(4)
194
-continued
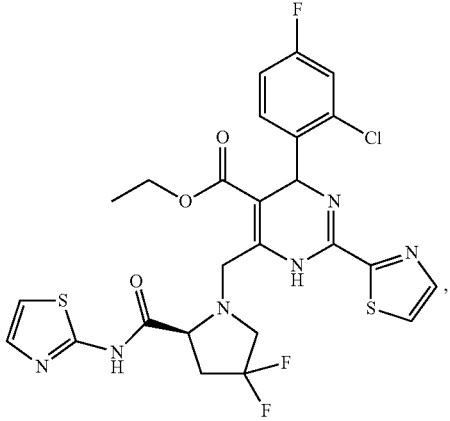
(5)
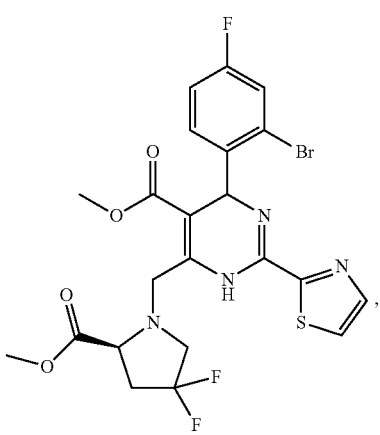
(6)
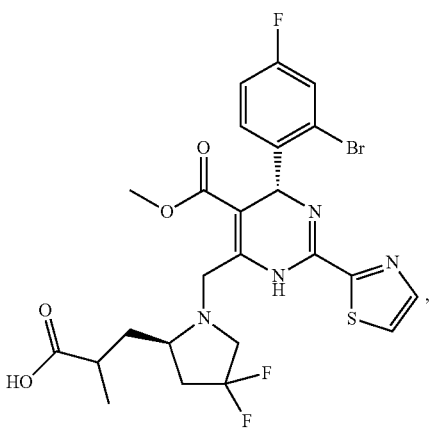
(7)
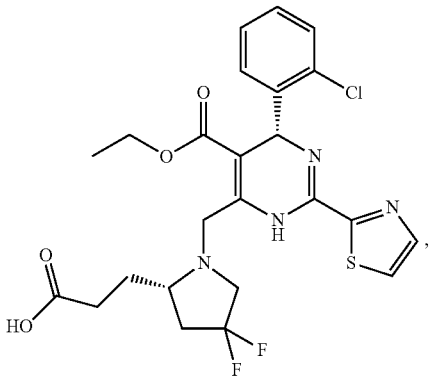
(8)

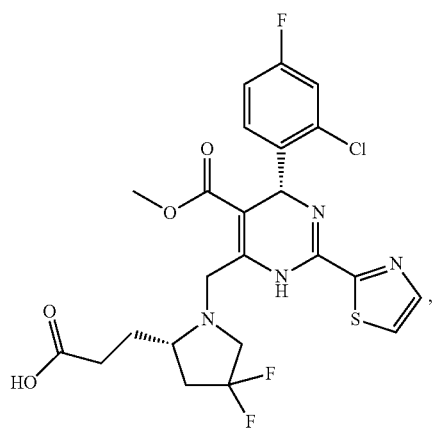
(9)
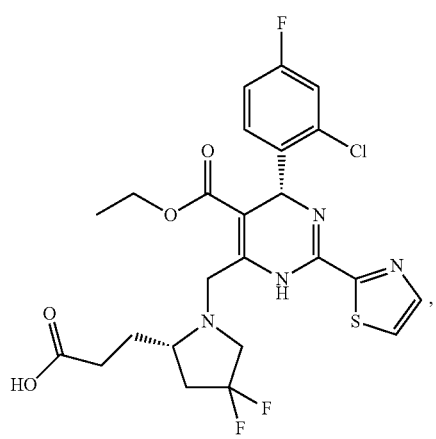
(10)
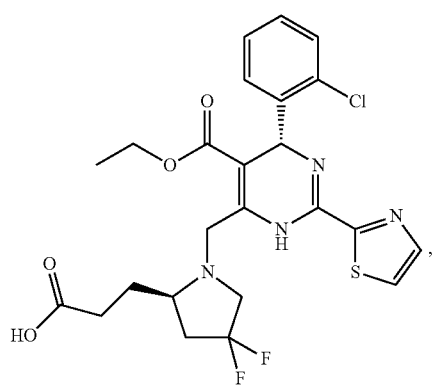
(11)
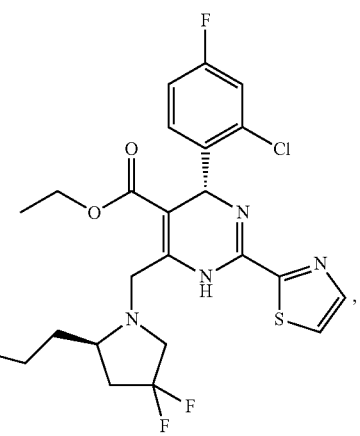
(12)
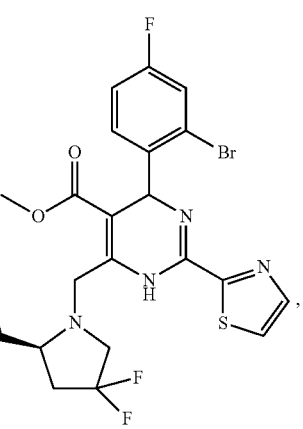
(13)
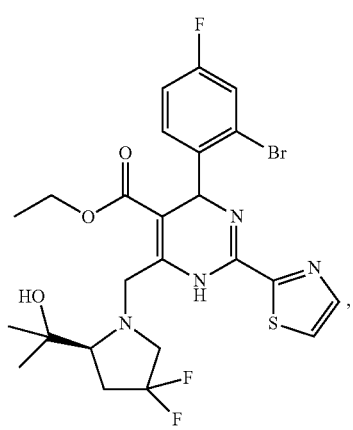
(14)

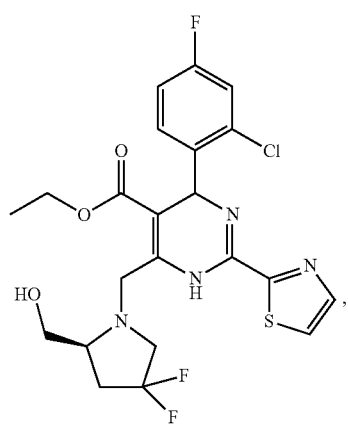
(15)
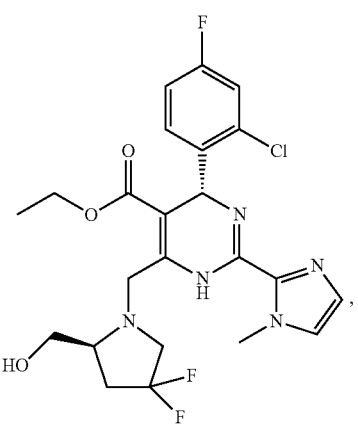
(18)
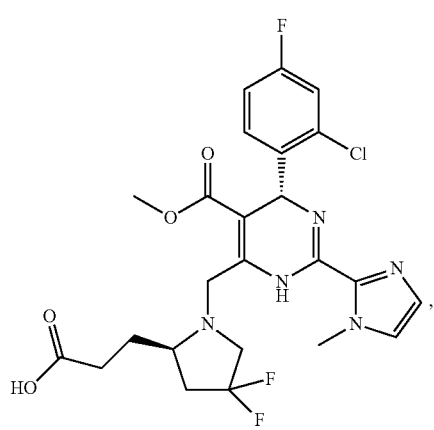
(16)
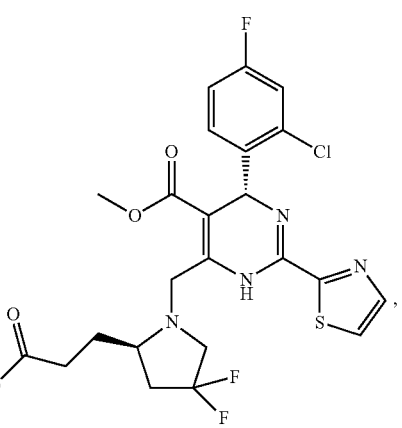
(19)
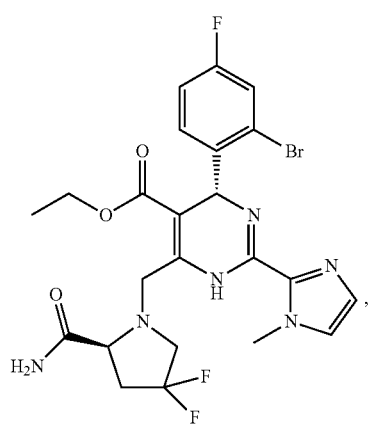
(17)
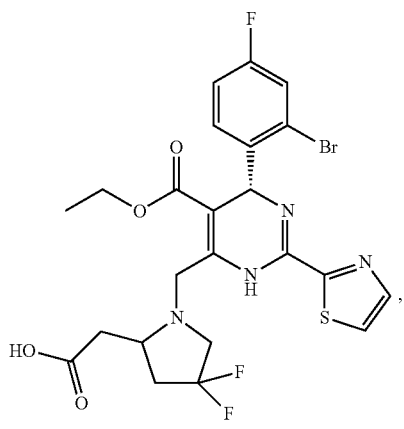
(20)

(21)
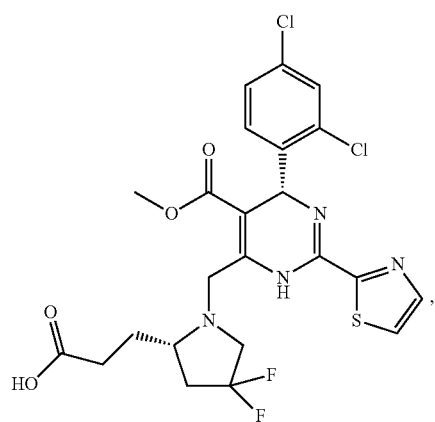
(22)
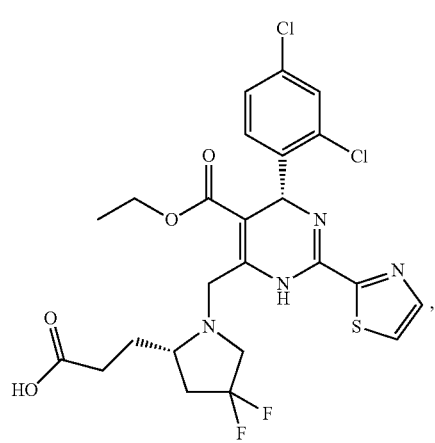
(23)
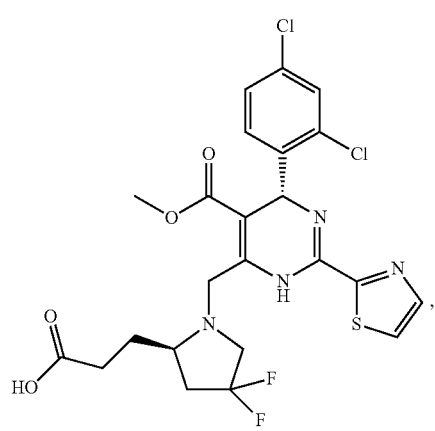
(24)
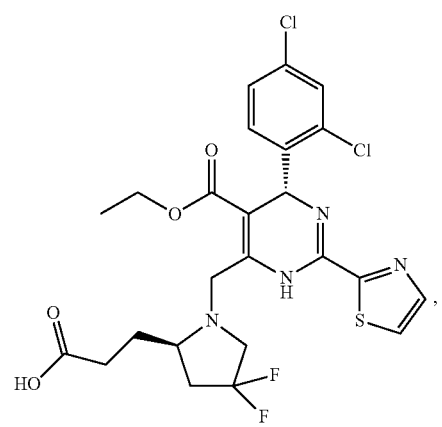
(25)
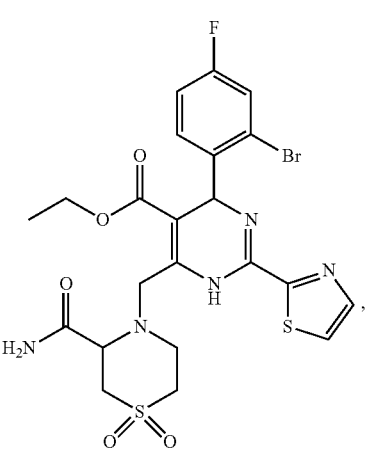
(26)
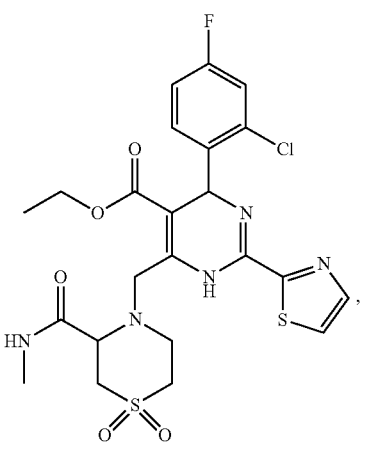

(27)
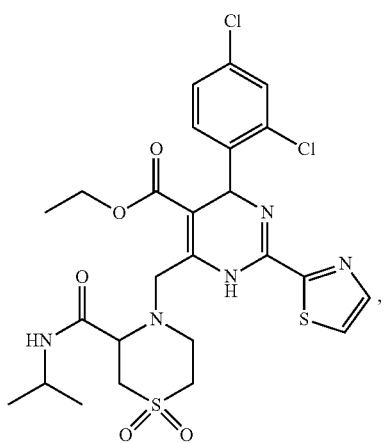
(28)
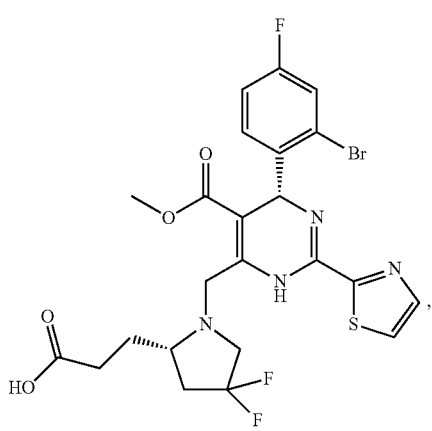
(29)
(30)
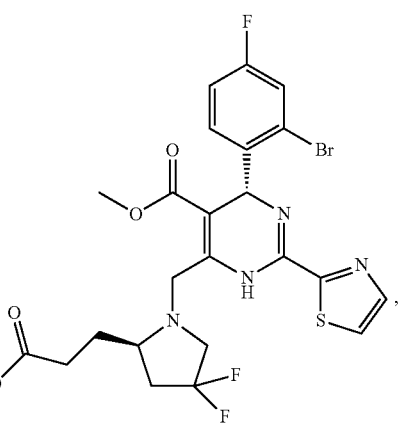
(31)
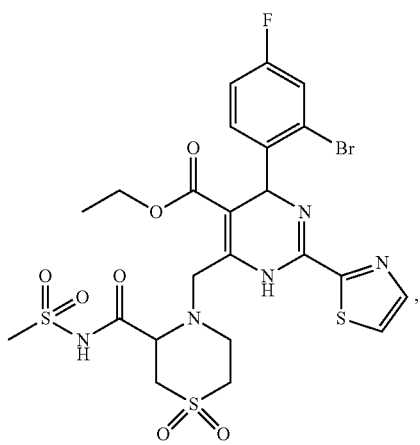
(32)
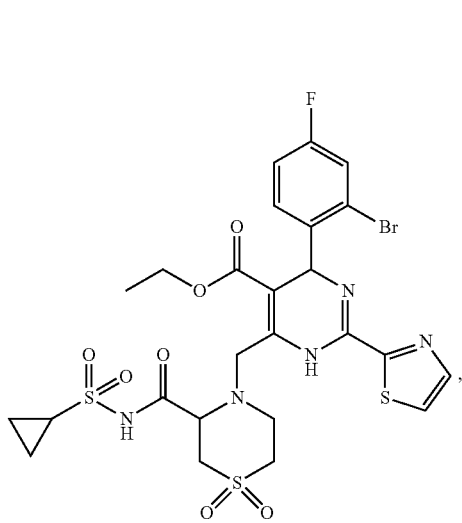

-continued
(33)
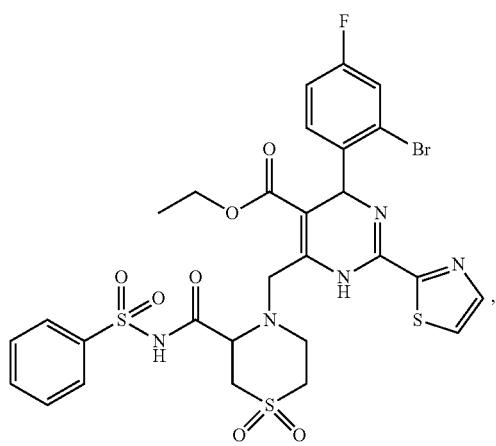
(34)
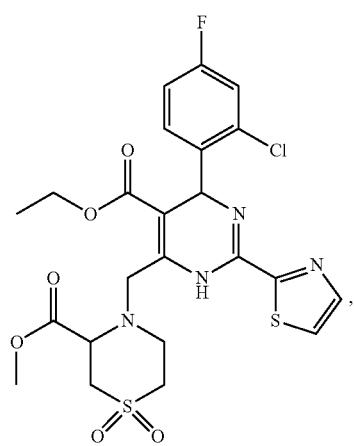
-continued
(36)
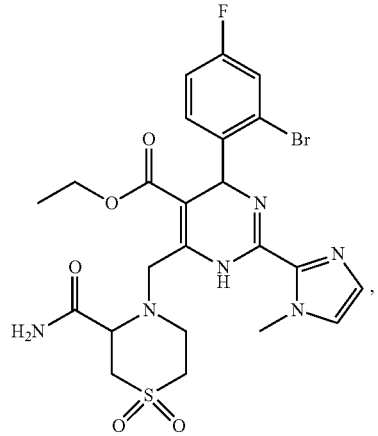
(37)
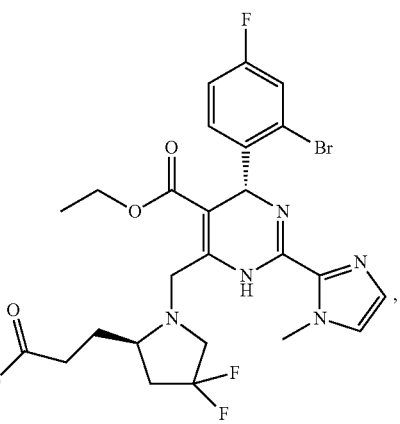
(35)
(38)
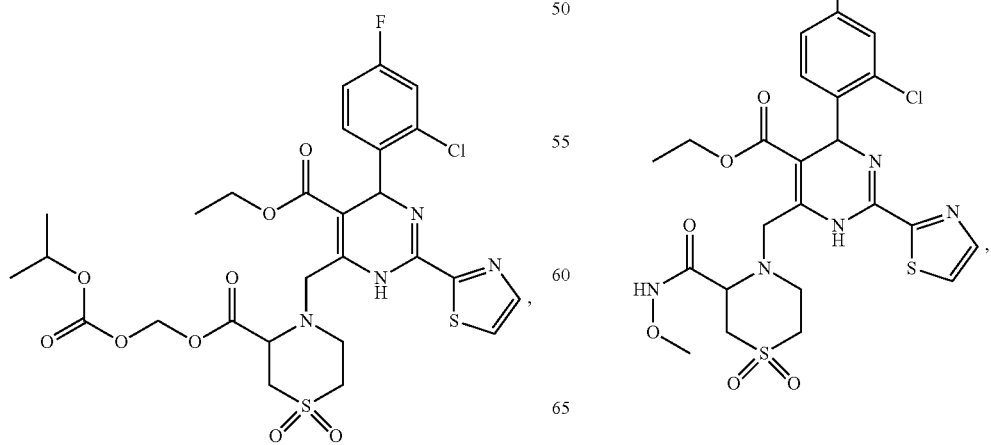

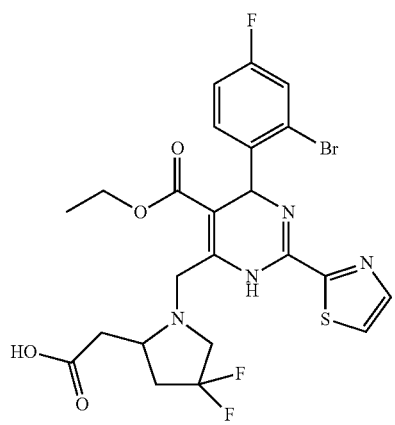
(39)
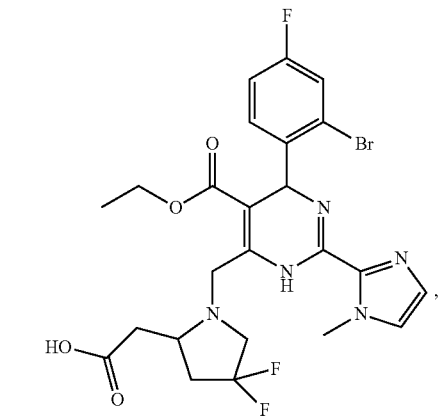
(42)
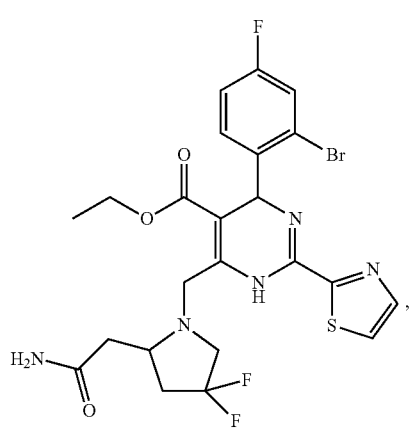
(40)
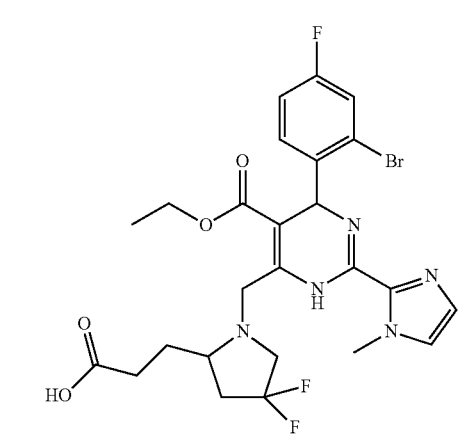
(43)
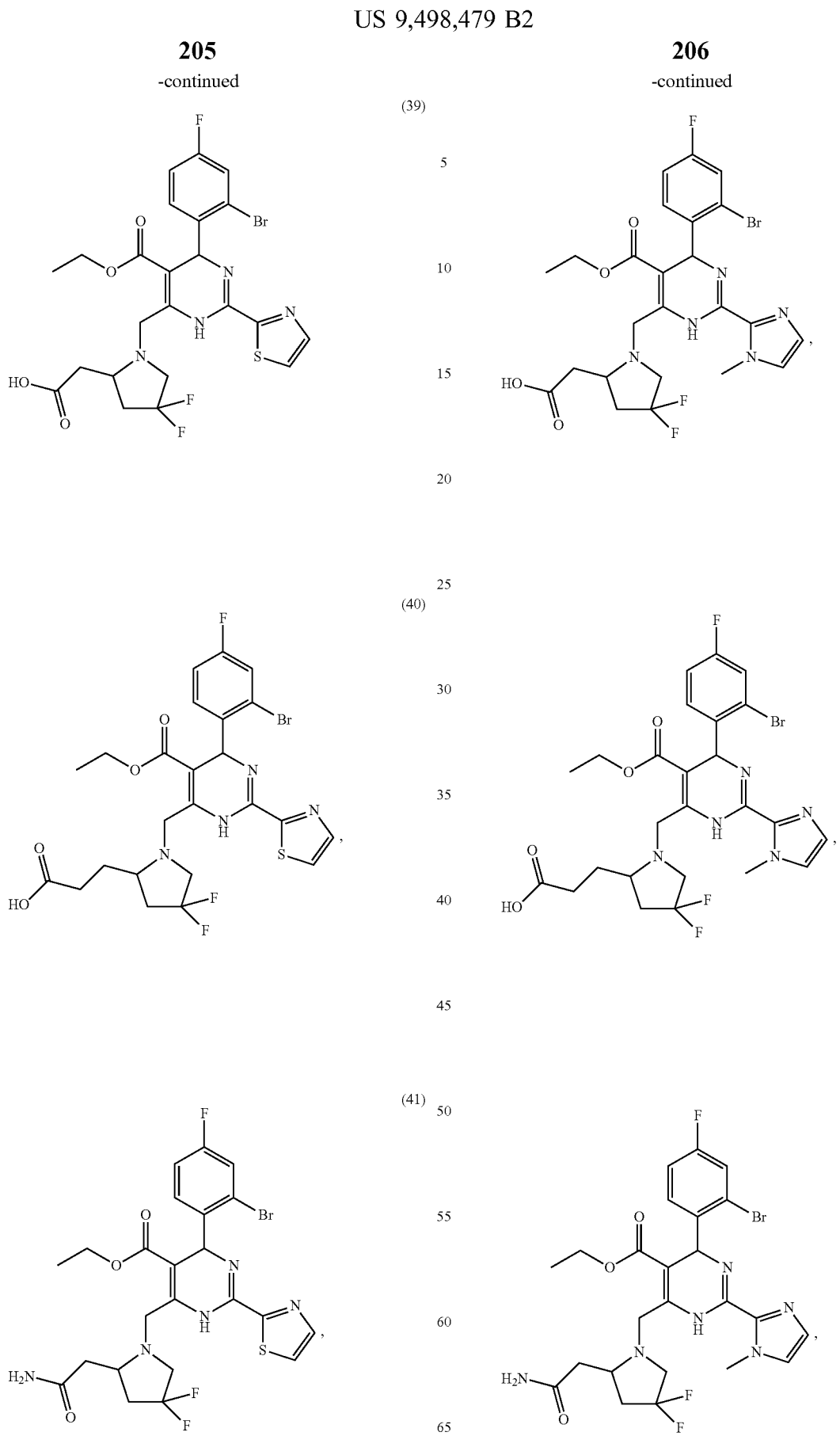
(41)
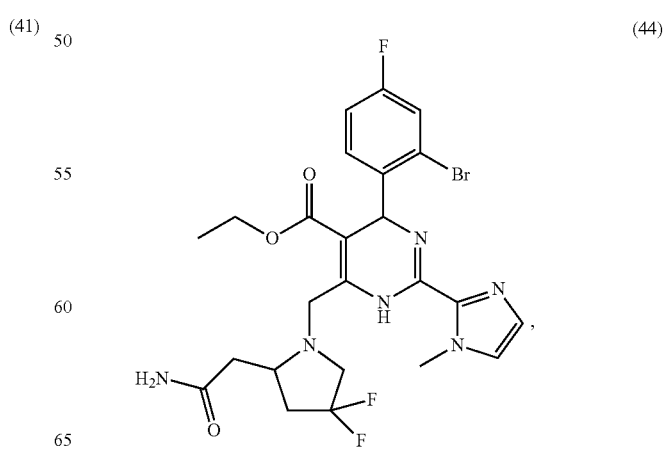
(44)

207
-continued
(45)
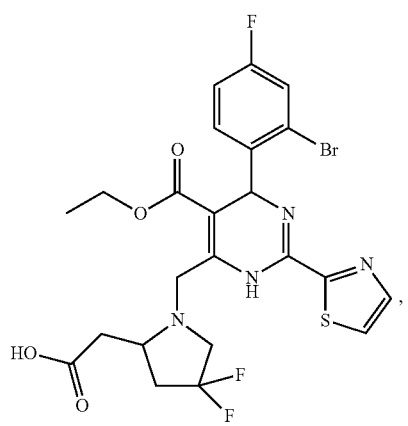
(46)
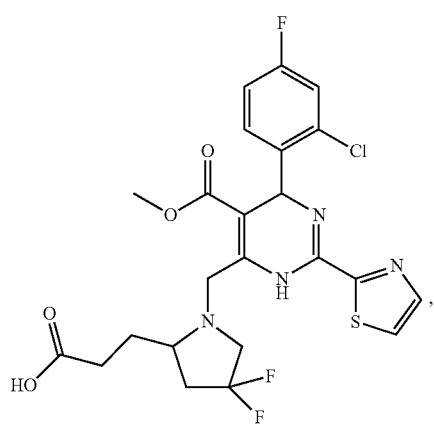
(47)
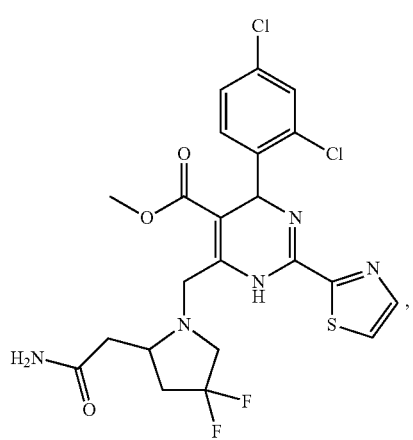
208
-continued
(48)
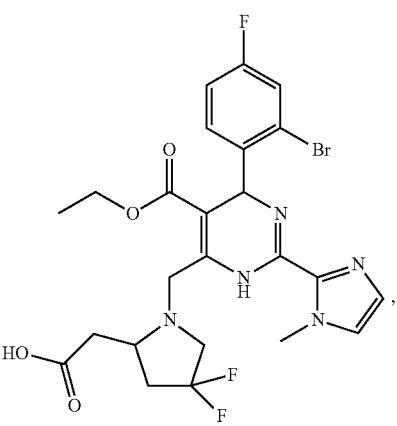
(49)
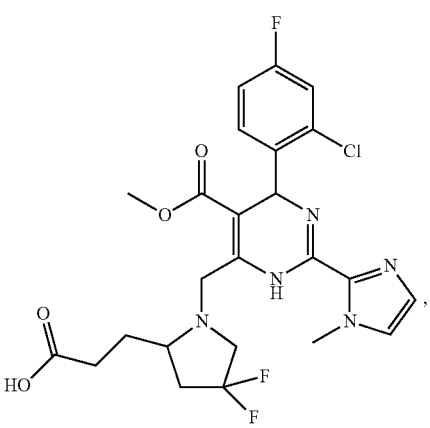
(50)
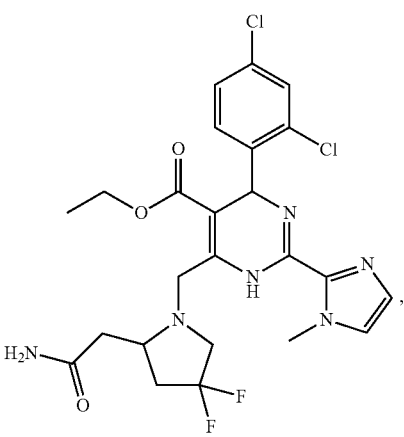

(51)
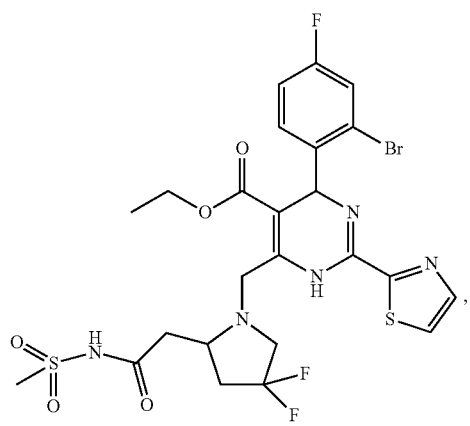
(54)
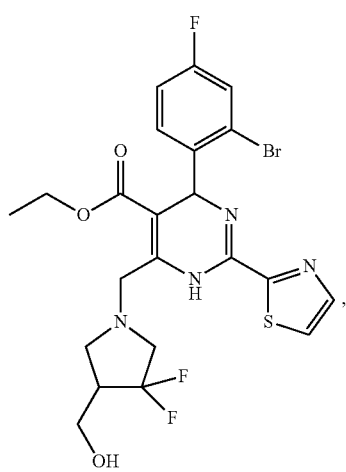
(52)
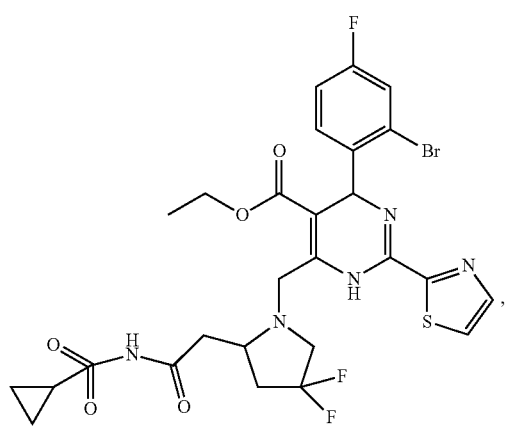
(55)
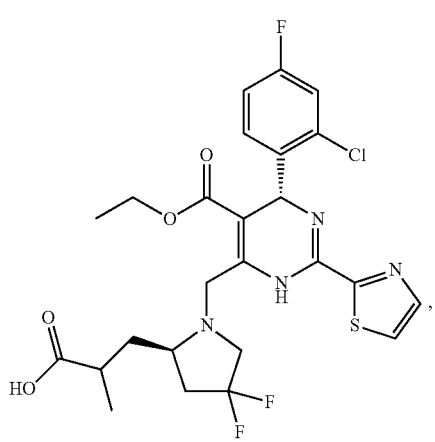
(53)
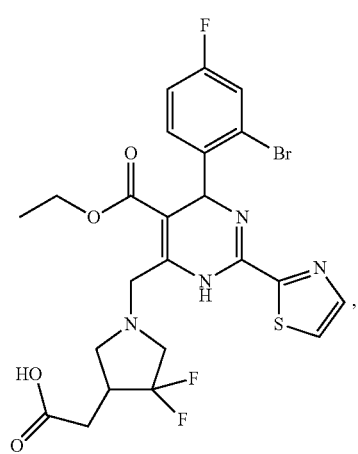
(56)
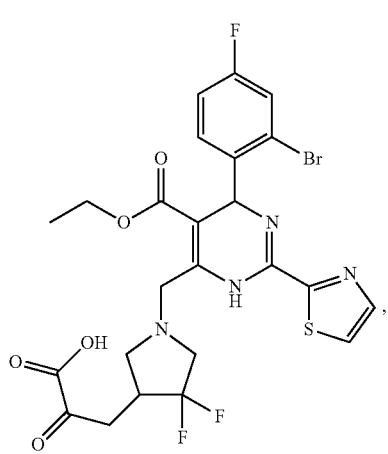

(57)
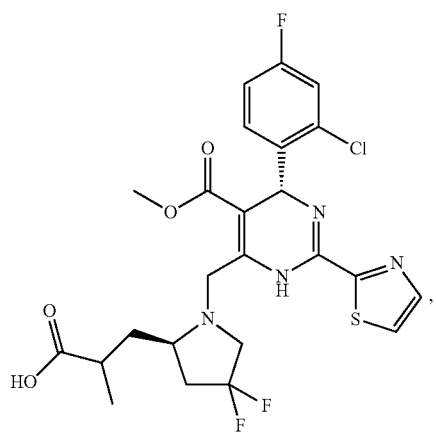
(58)
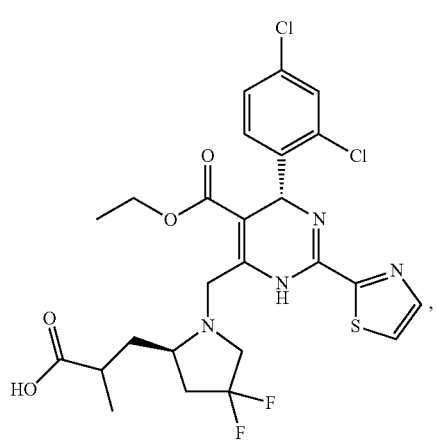
(59)
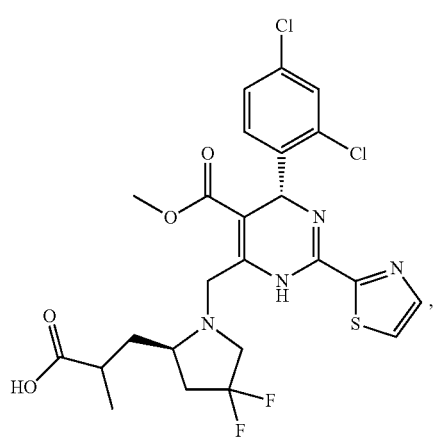
(60)
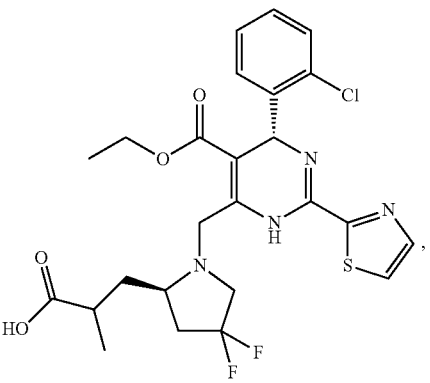
(61)
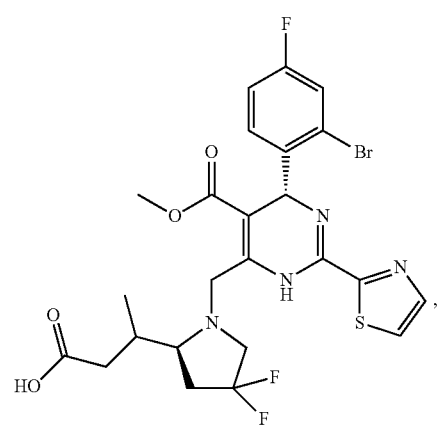
(62)
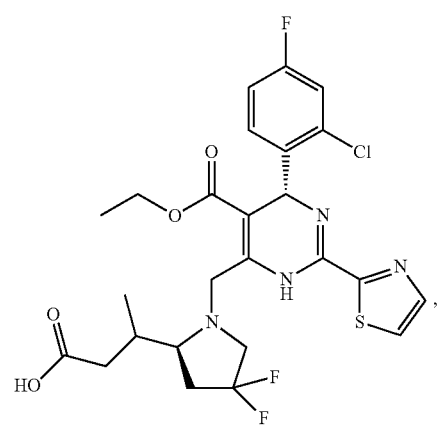
(63)
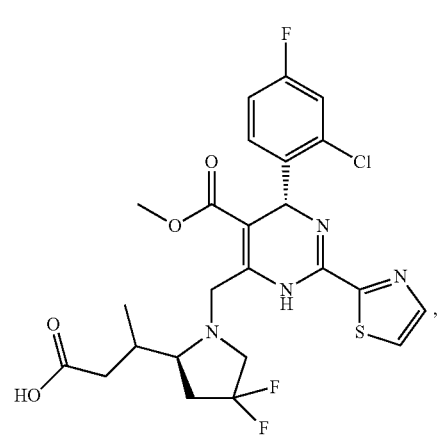

-continued
(64)
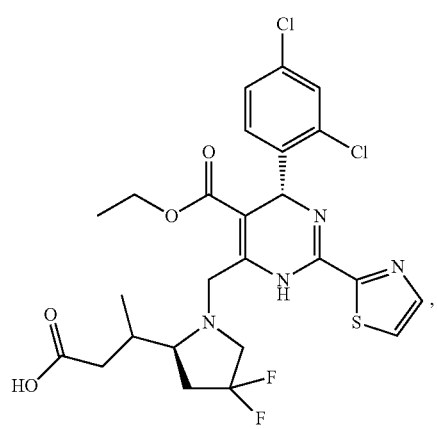
(65)
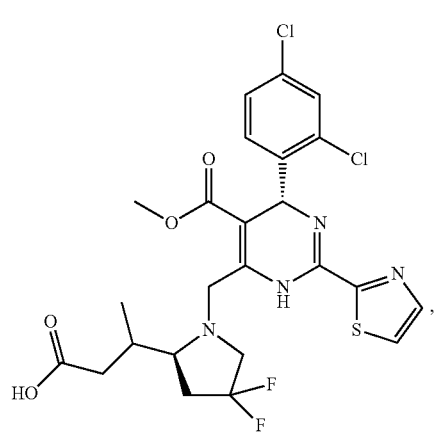
(66)
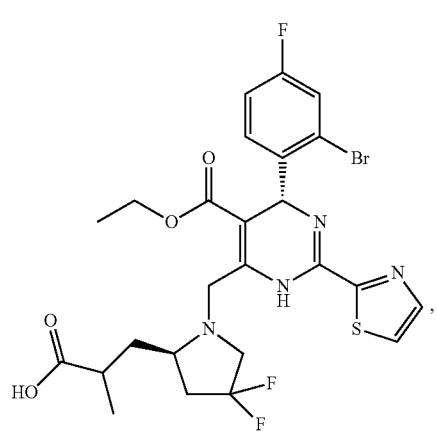
-continued
(67)
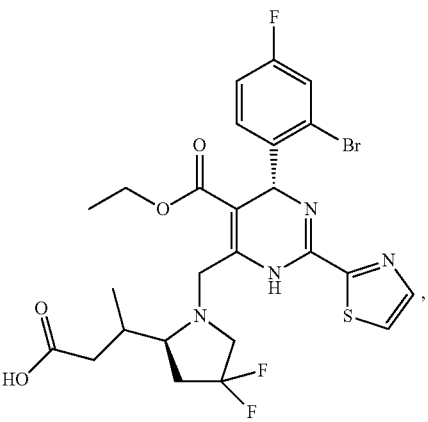
(68)
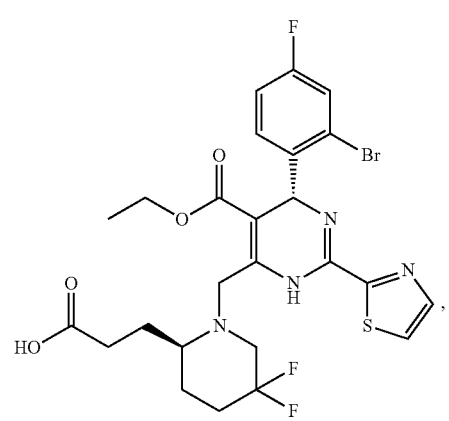
(69)
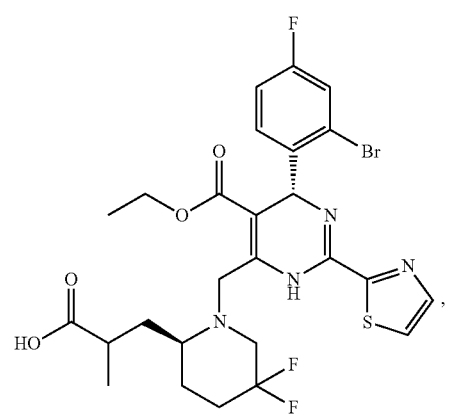
(70)
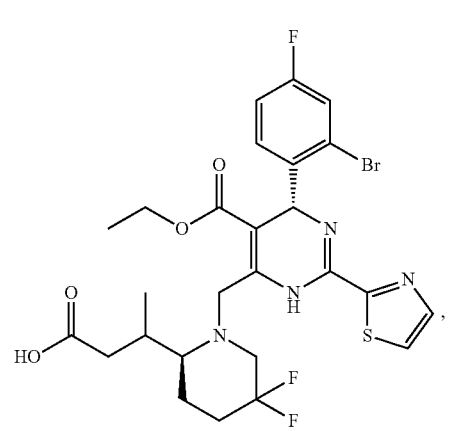

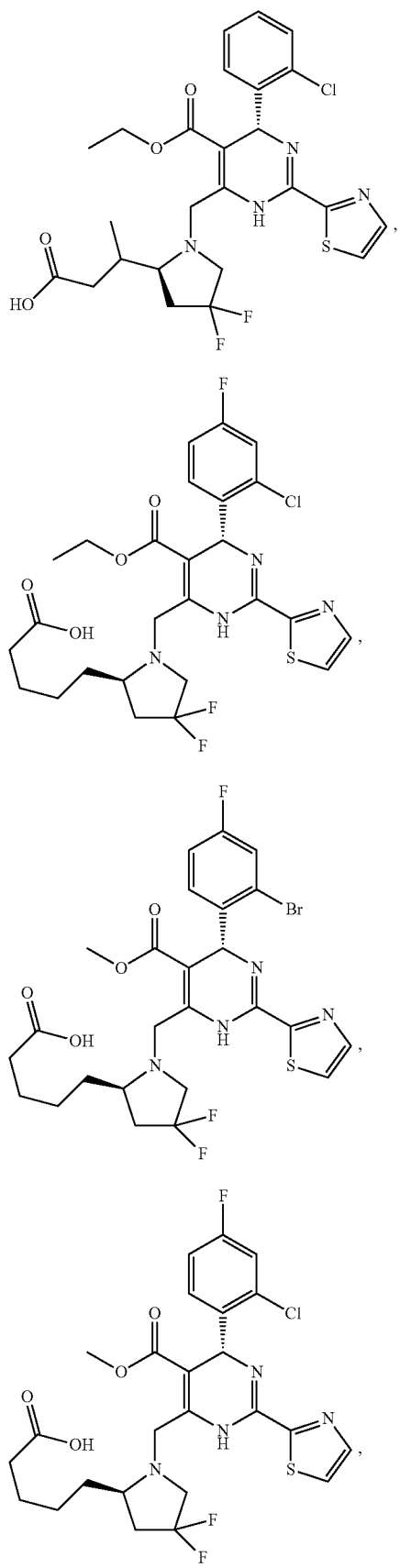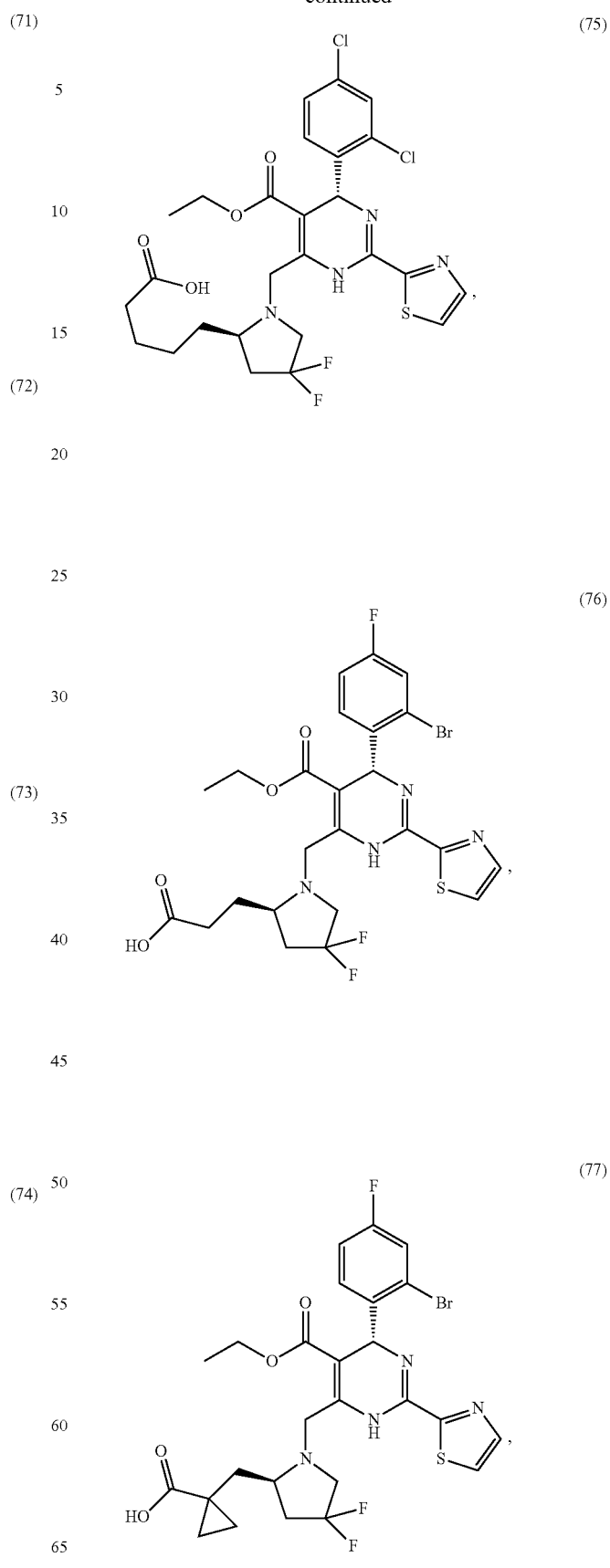

-continued
(78)
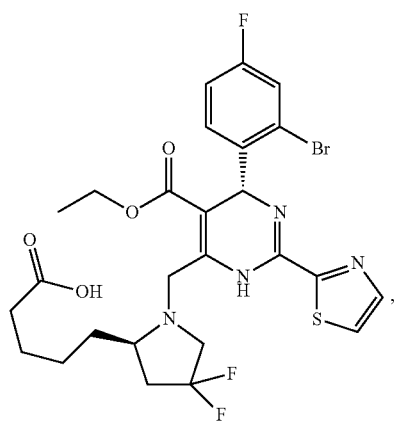
(79)
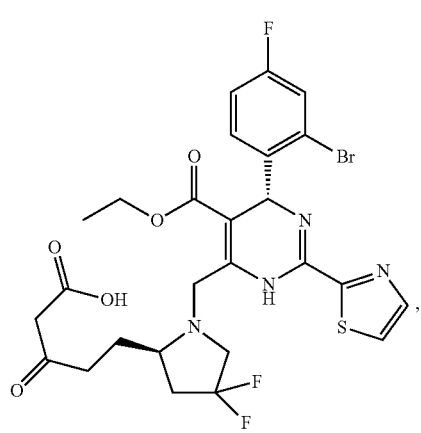
(80)
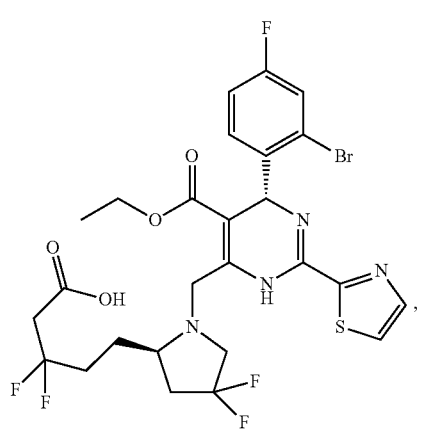
-continued
(81)
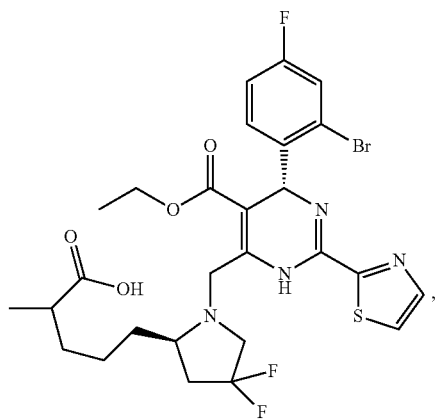
(82)
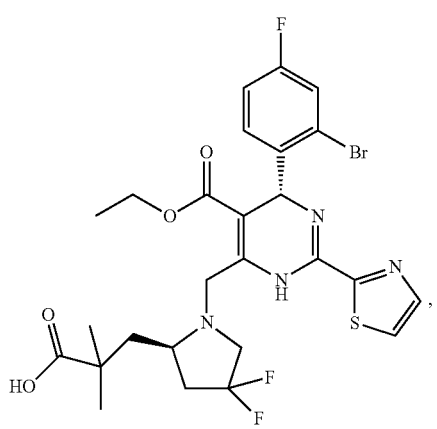
(83)
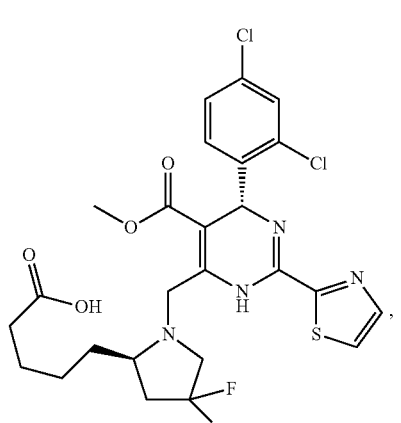
(84)
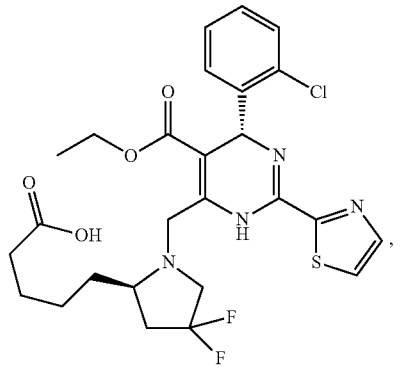

-continued
(85)
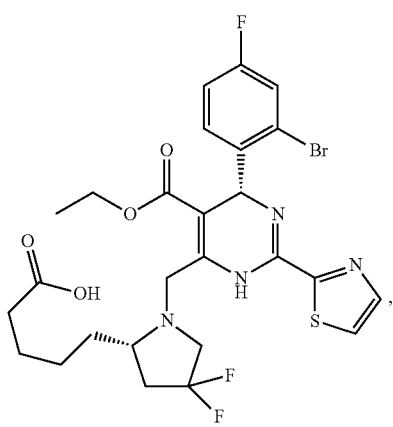
(86)
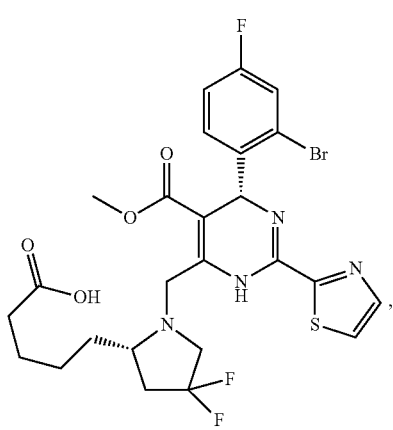
(87)
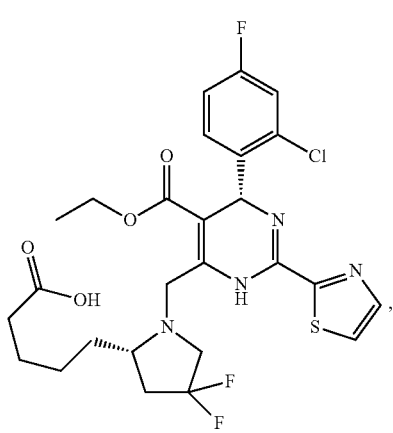
-continued
(88)
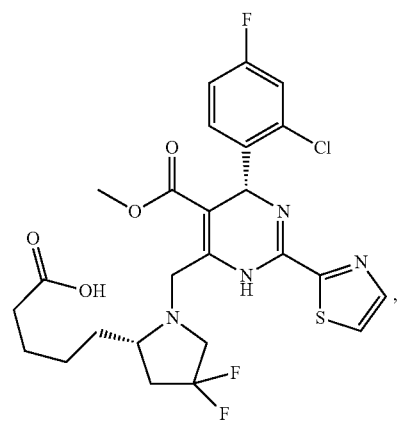
(89)
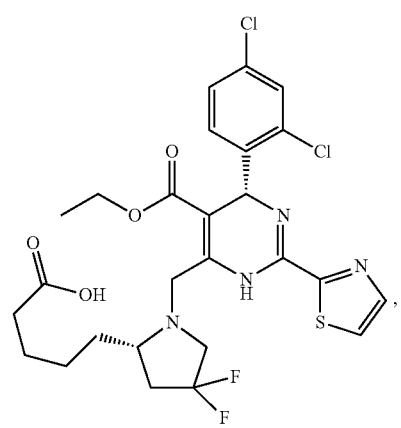
(90)
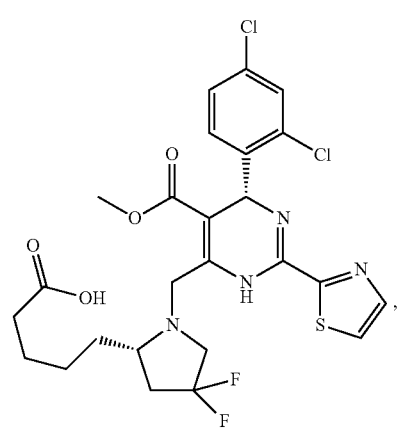
(91)
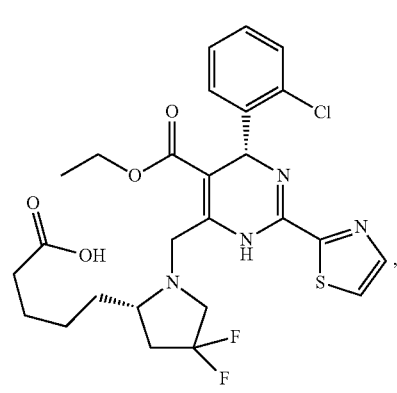

-continued
(92)
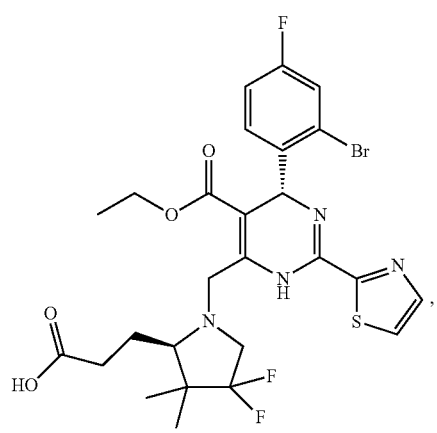
(93)
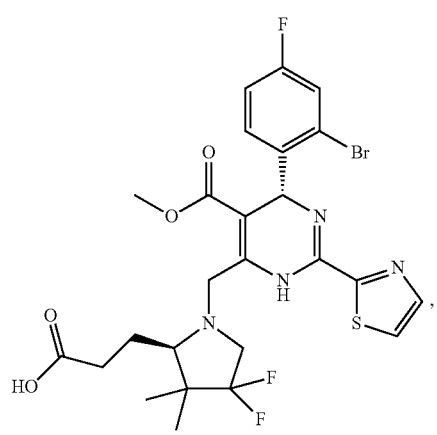
(94)
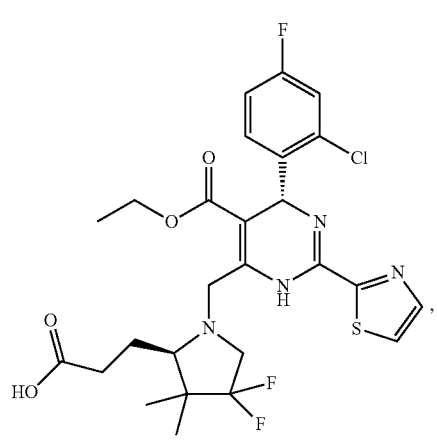
-continued
(95)
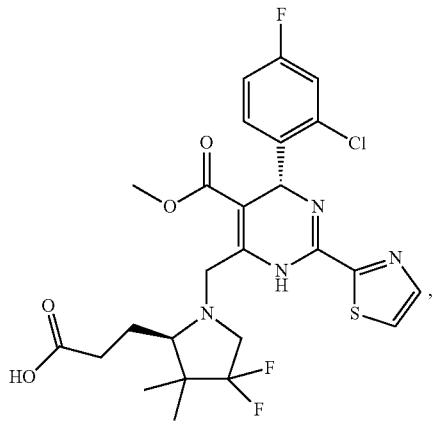
(96)
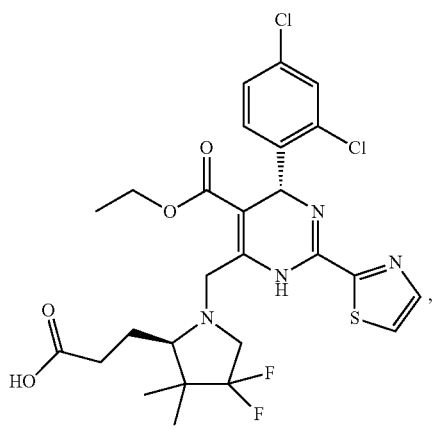
(97)
(98)
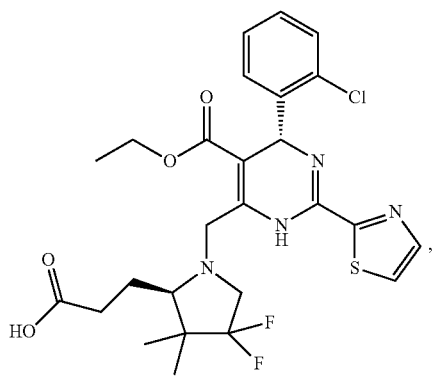

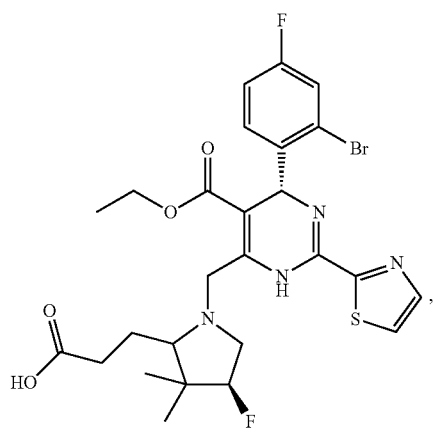
(99)
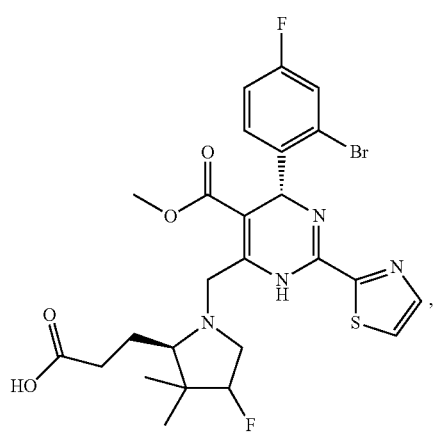
(100)
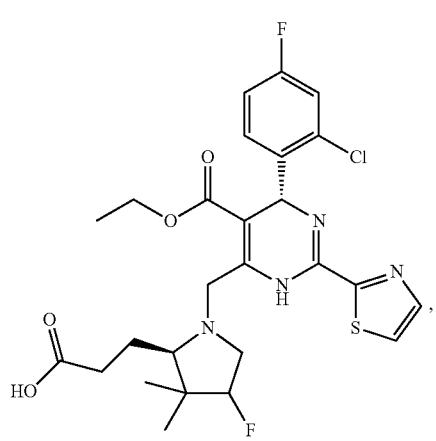
(101)
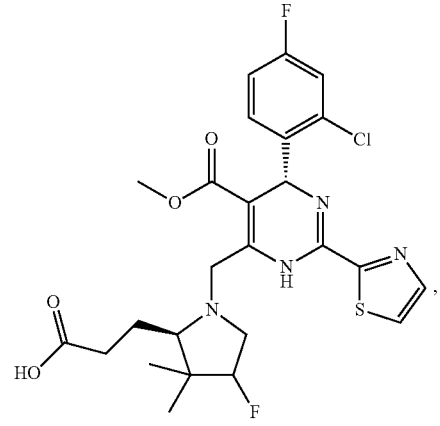
(102)
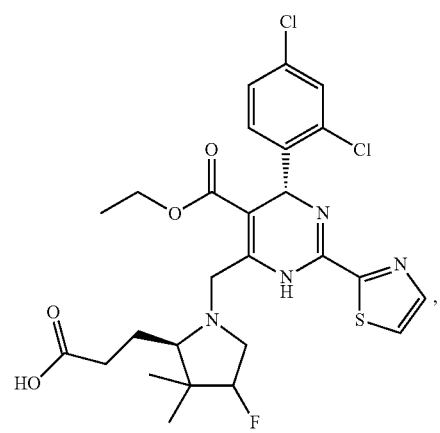
(103)
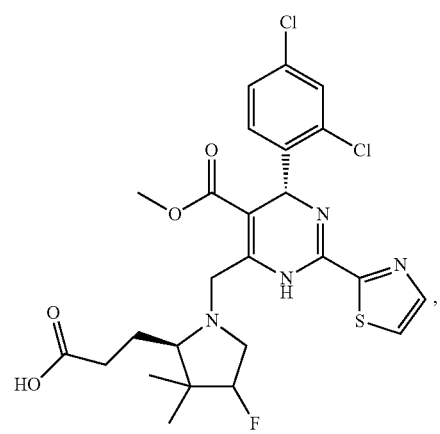
(104)
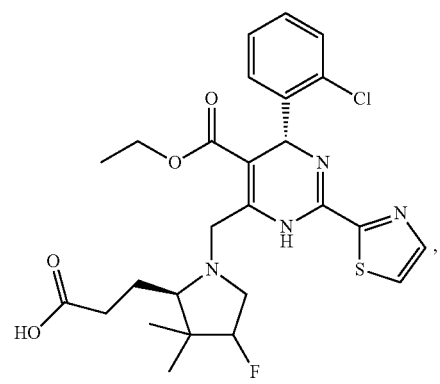
(105)

(106)
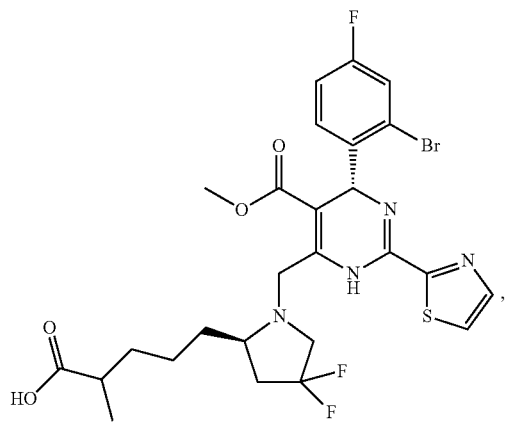
(109)
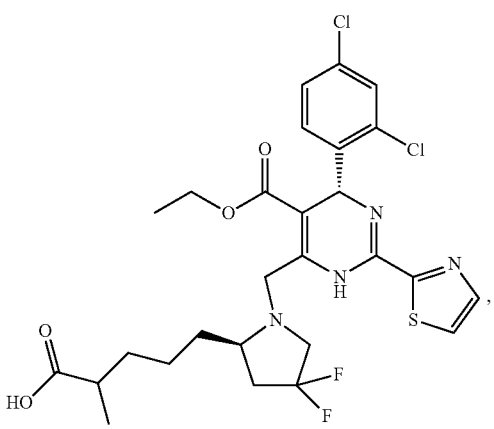
(107)
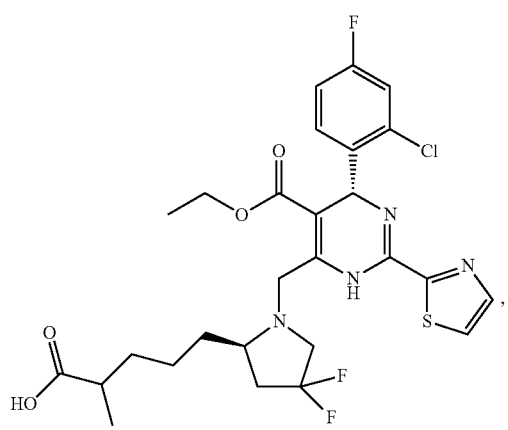
(110)
(108)
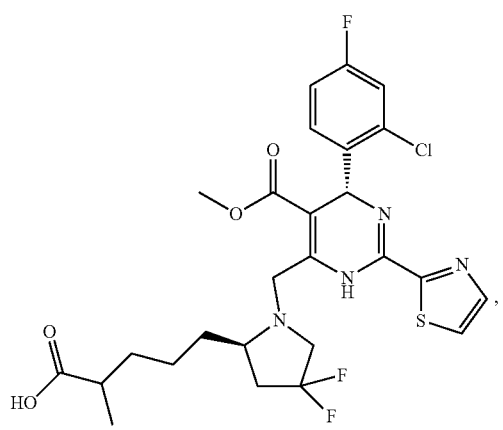
(111)
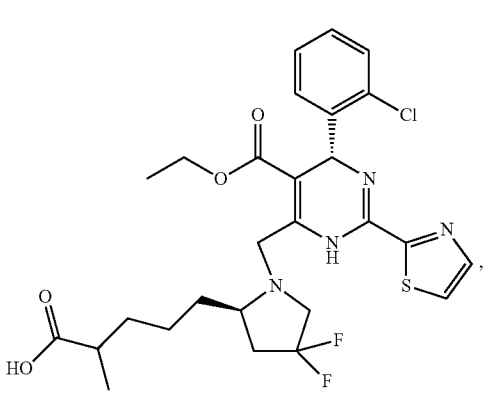

(112)
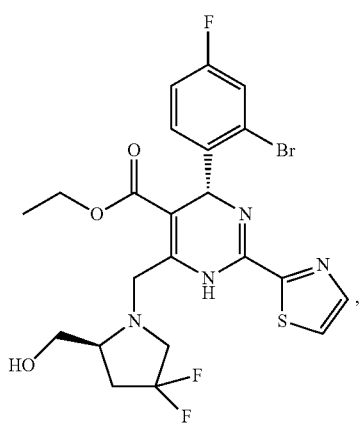
(113)
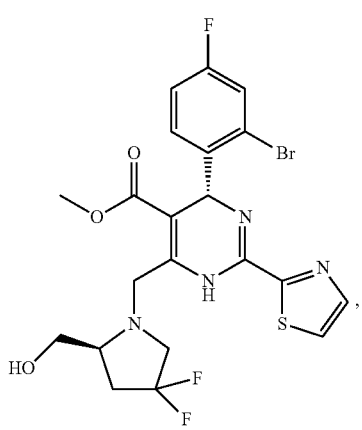
(114)
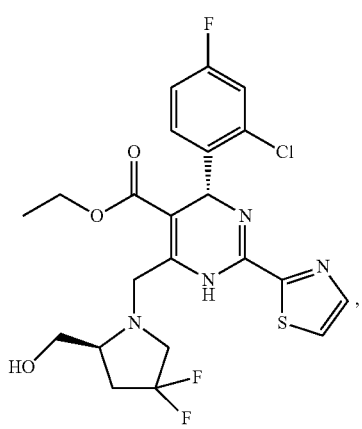
(115)
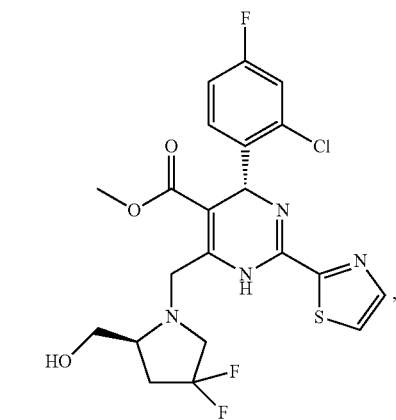
(116)
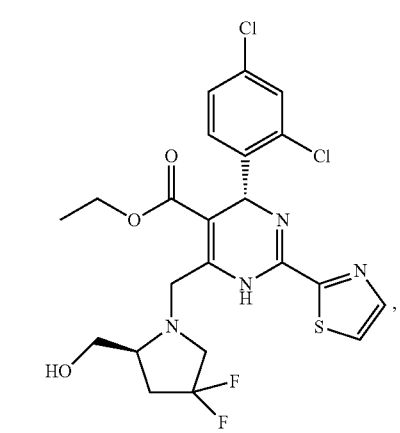
(117)
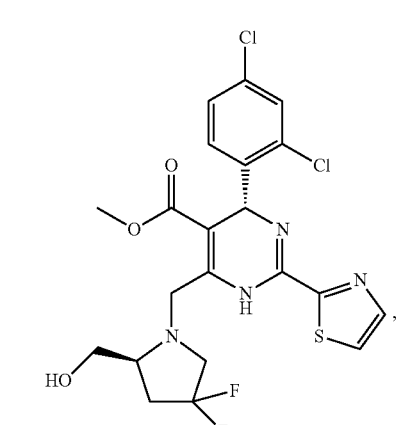
(118)
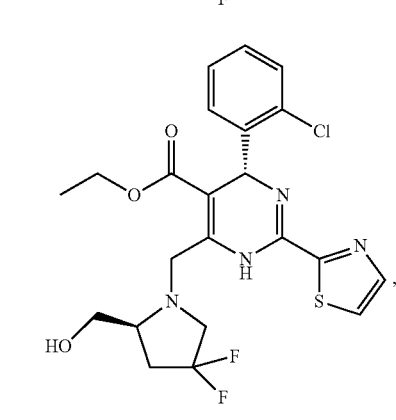

229
-continued
(119)
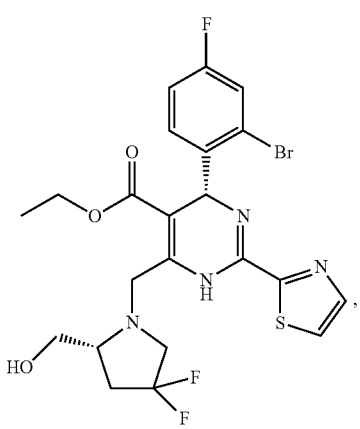
(120)
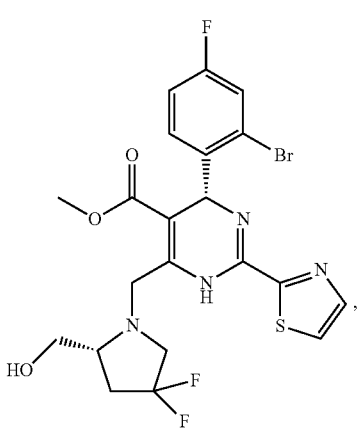
(121)
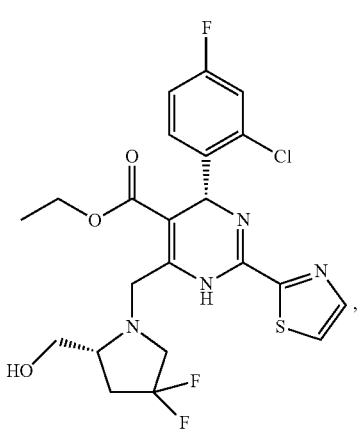
230
-continued
(122)
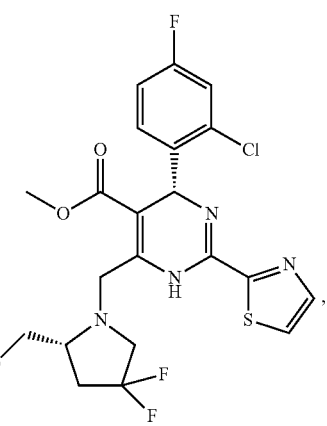
(123)
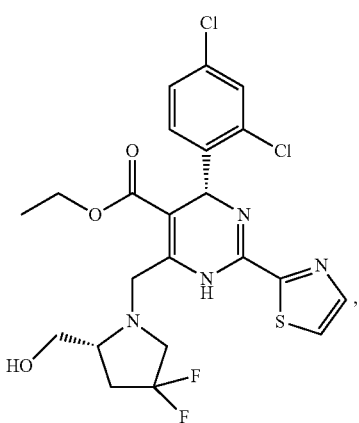
(124)
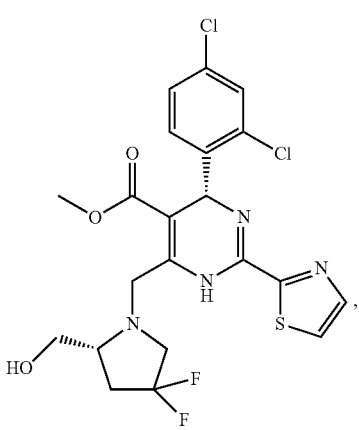
(125)
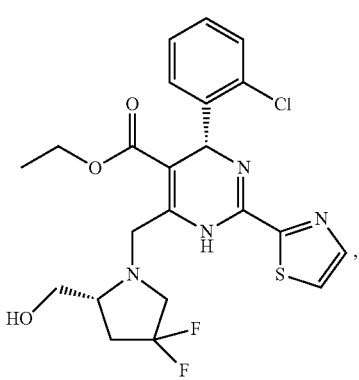

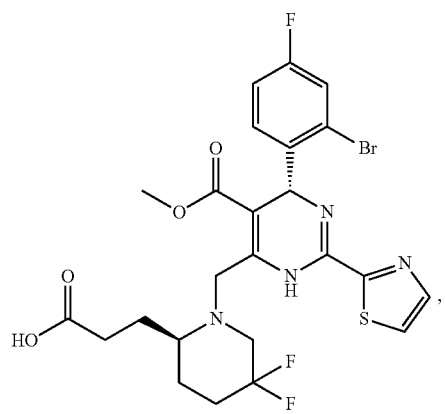
(126)
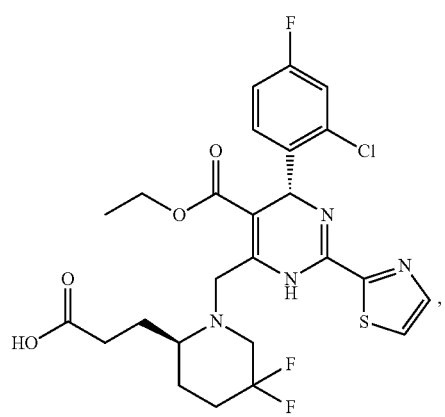
(127)
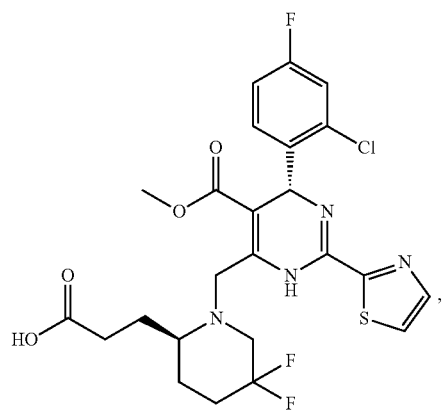
(128)
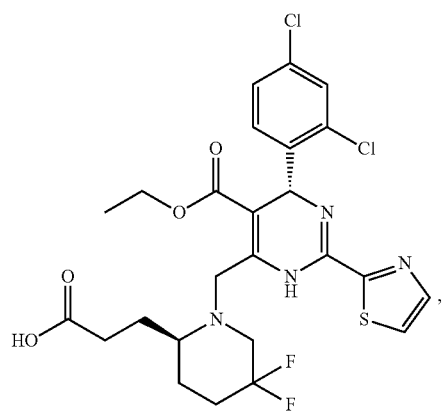
(129)
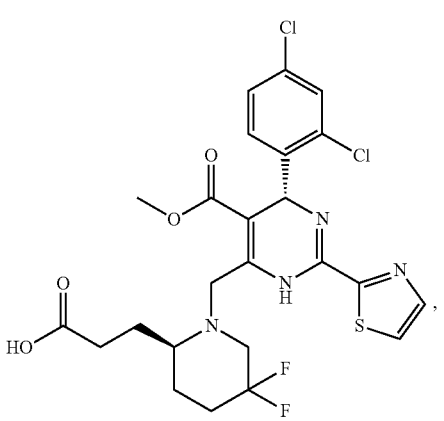
(130)
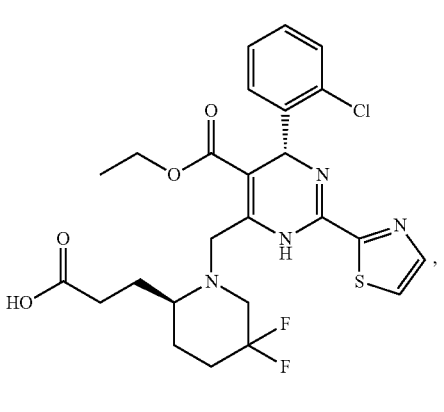
(131)
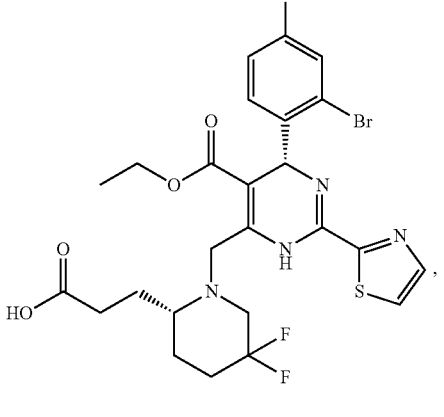
(132)
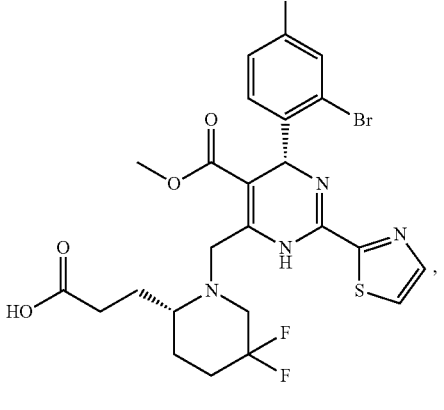
(133)

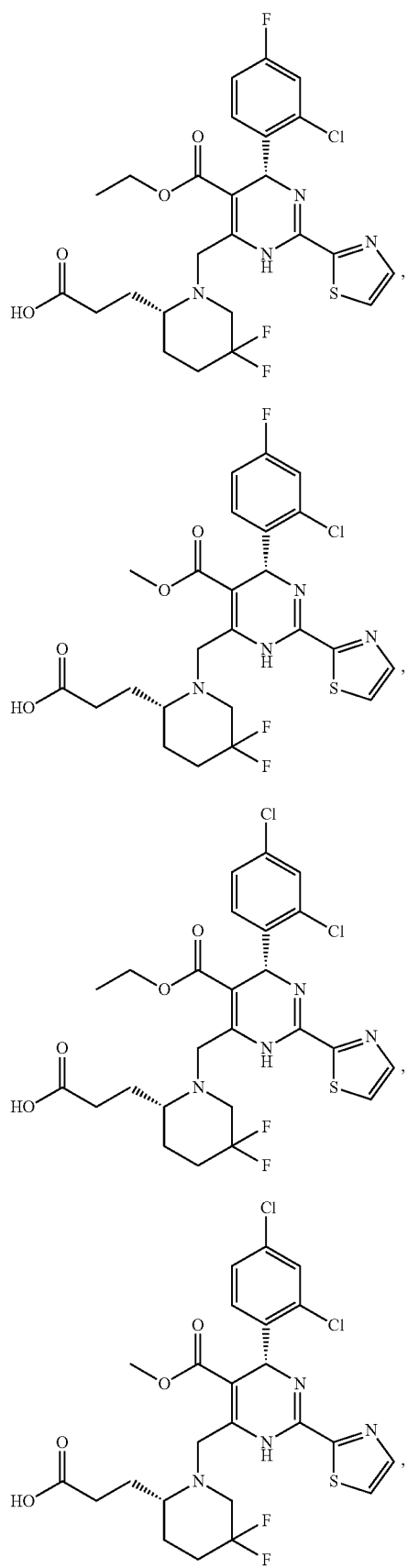

(142)
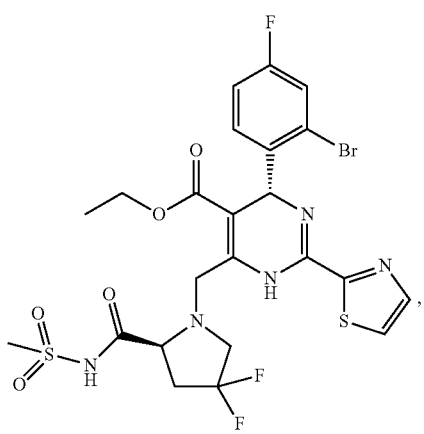
(143)
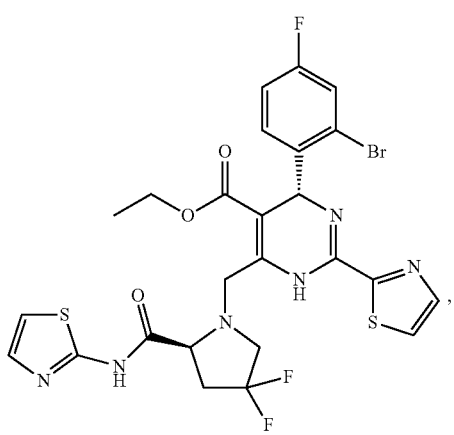
(144)
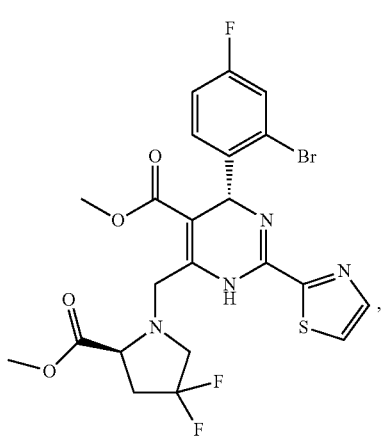
(145)
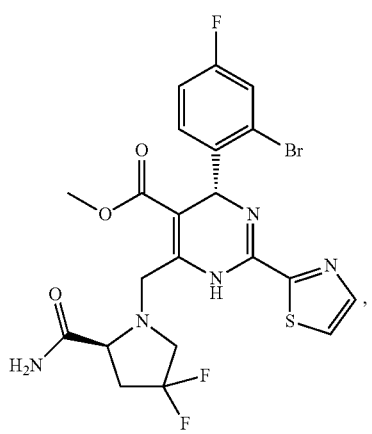
(146)
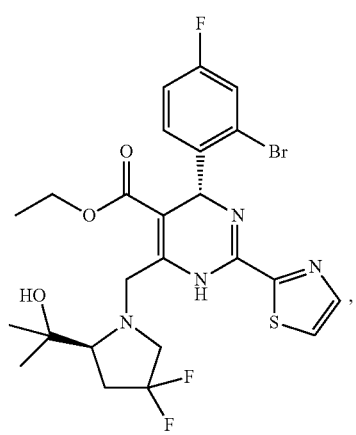
(147)
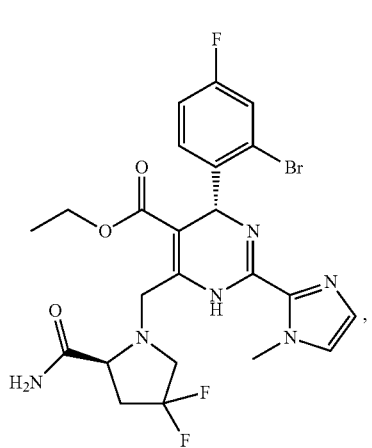

237
-continued
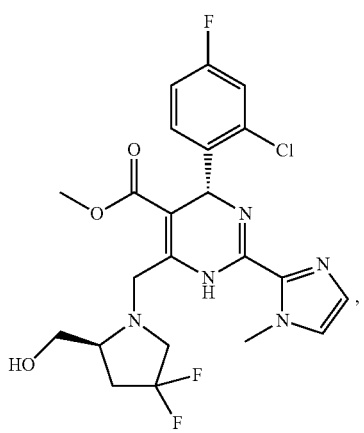
(148)
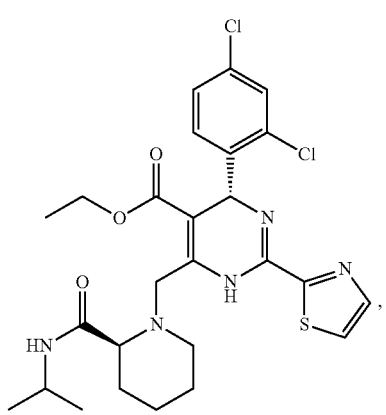
(151)
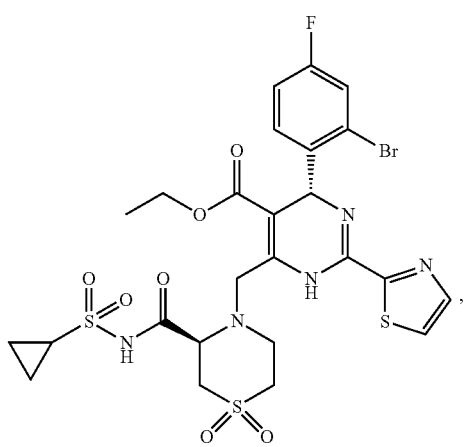
(149)
238
-continued
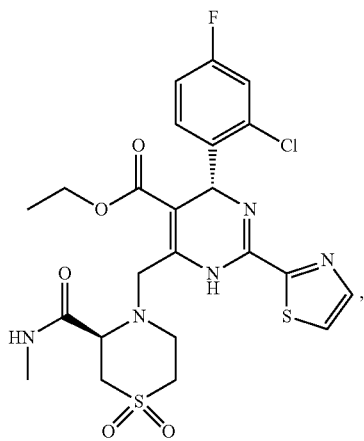
(150)
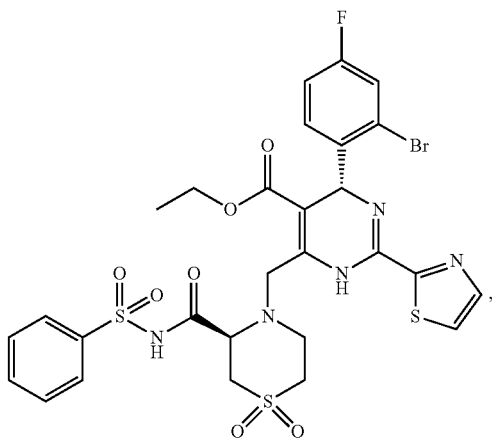
(152)
(153)

(154)
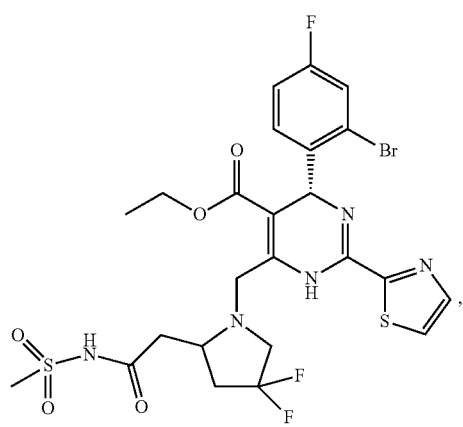
(156)
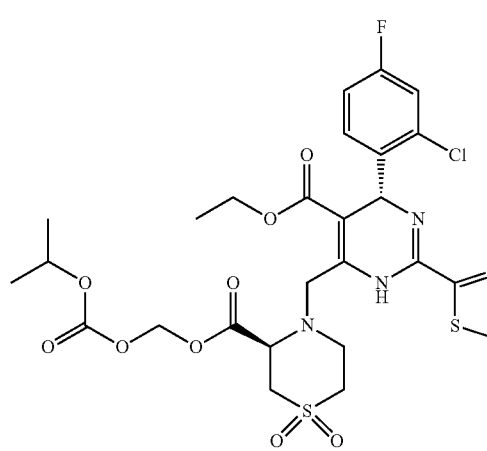
(157)
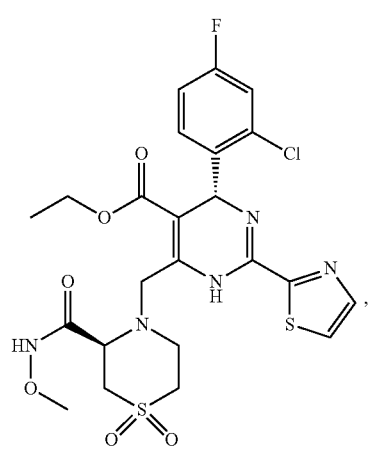
(158)
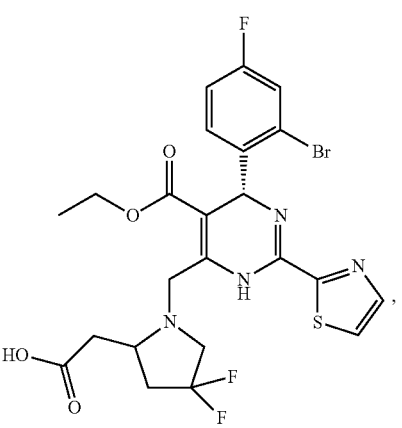
(159)
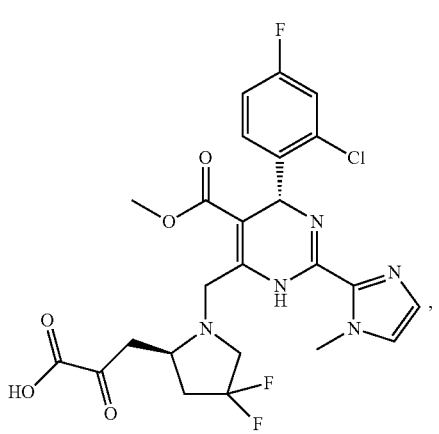
(160)
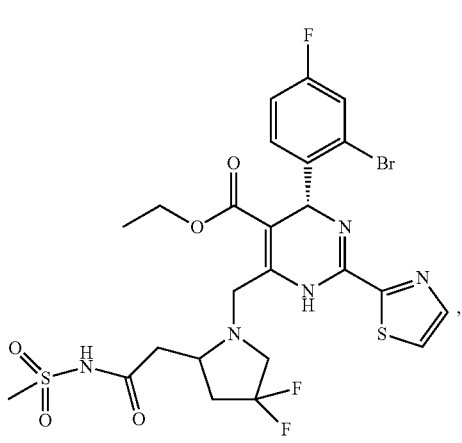

-continued (161), (162), (163), (164), (165), (166)

243
-continued
(167)
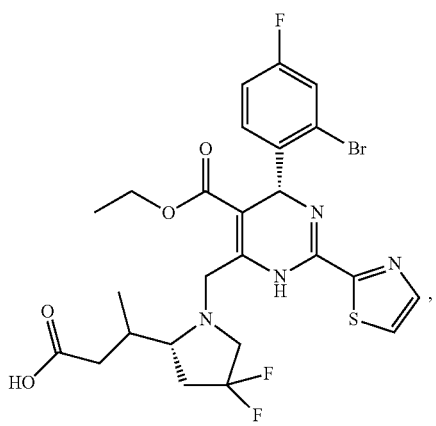
(168)
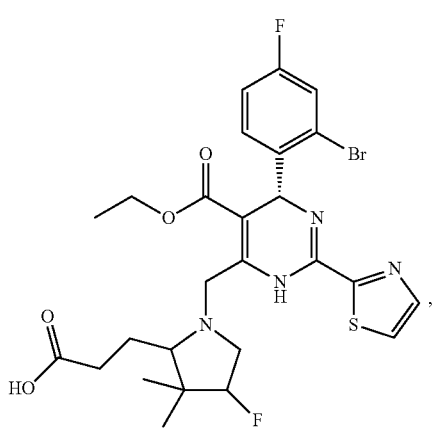
(169)
244
-continued
(170)
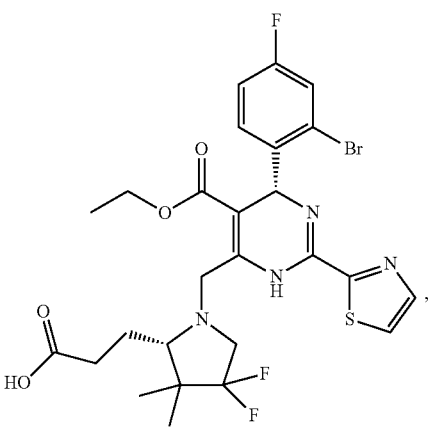
(171)
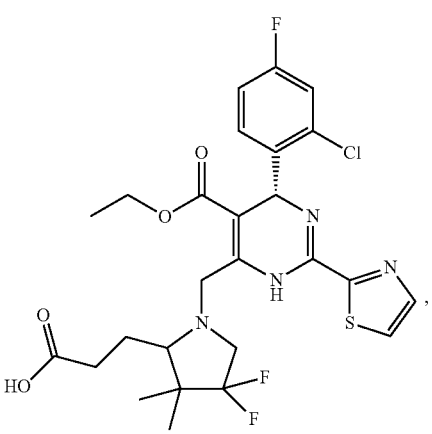
(172)

-continued
(173)
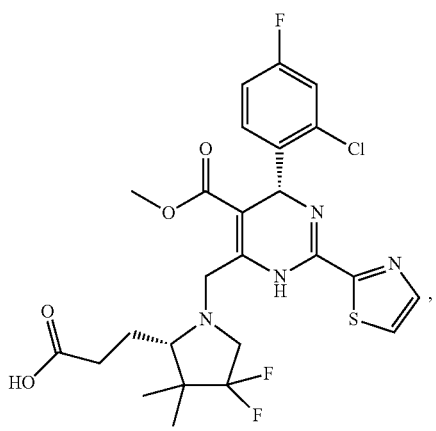
(174)
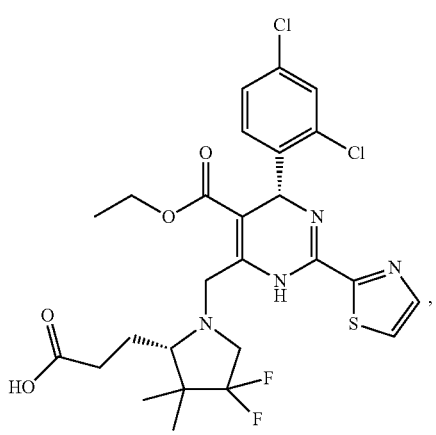
(175)
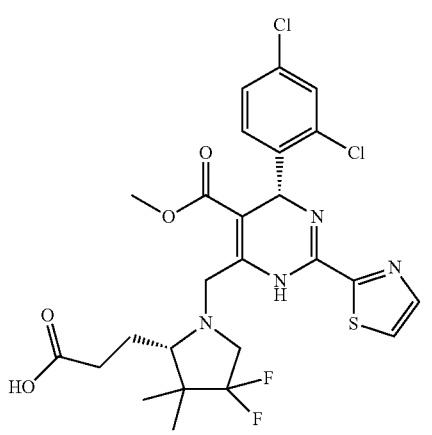
and
-continued
(176)
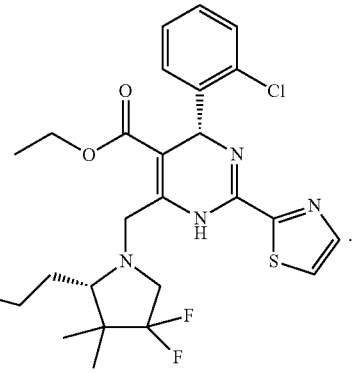
8. A compound having one of the following structures, or an enantiomer, a diastereoisomer, a tautomer, a hydrate, a solvate, a stereoisomer, an N-oxide, or a pharmaceutically acceptable salt thereof,
(8-9)
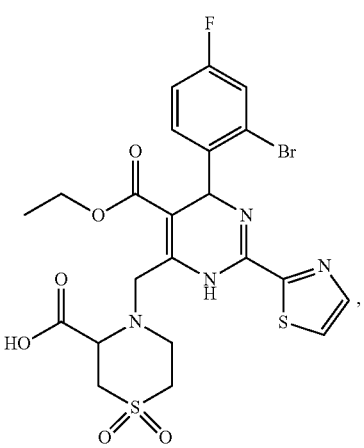
(8-10)
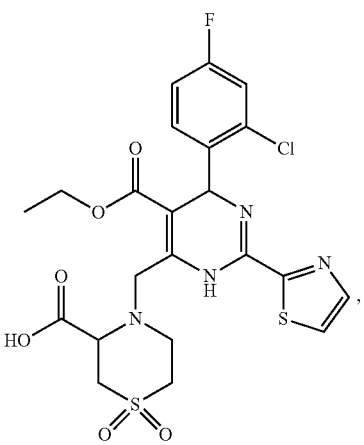

(8-11)
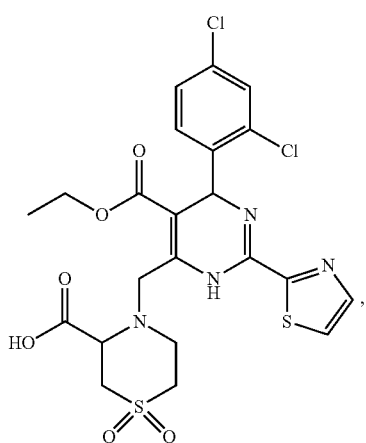
(8-12)
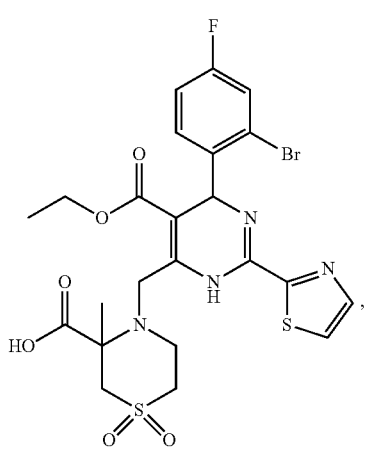
(8-14)
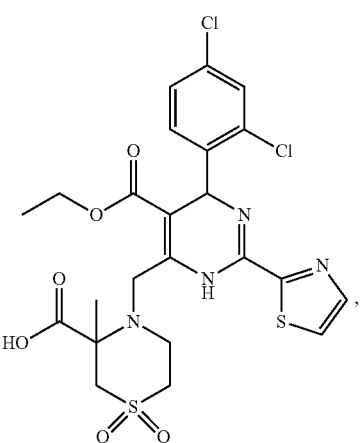
(8-15)
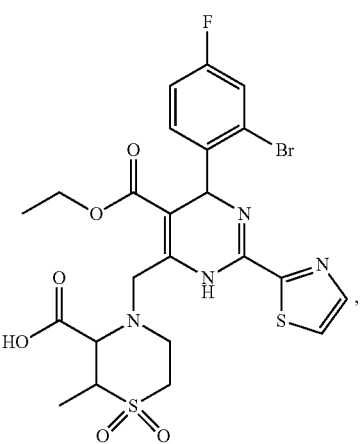
(8-16)
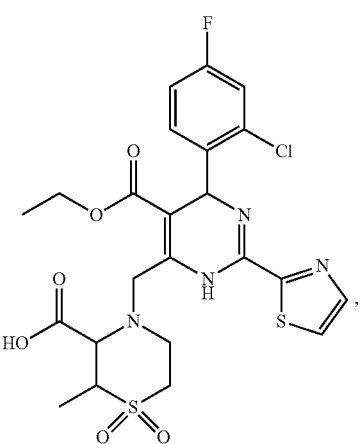

-continued
(8-17)
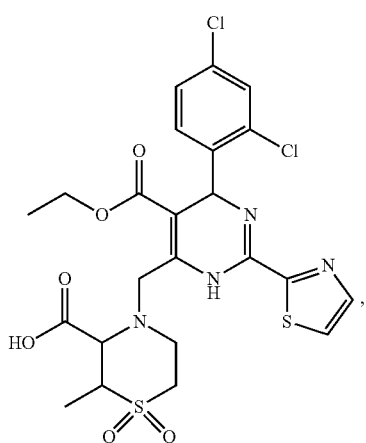
(8-18)
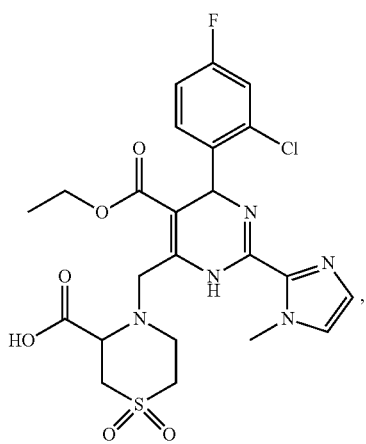
(8-19)
-continued
(8-22)
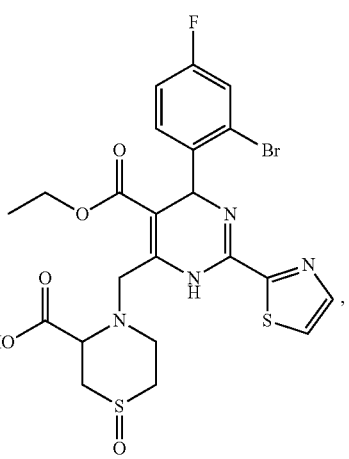
(8-23)
(8-24)
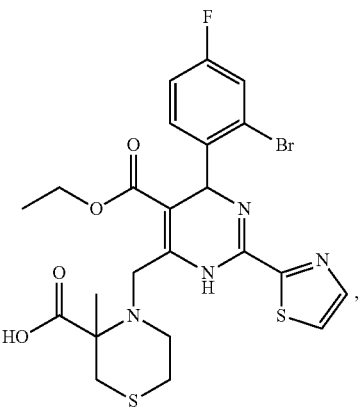

251
-continued
(8-25)
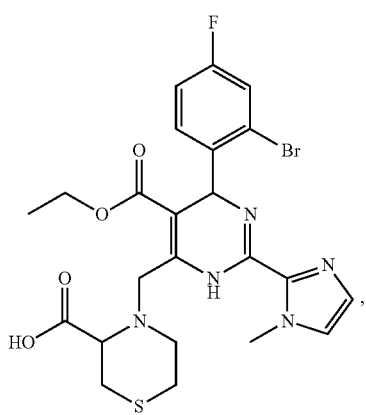
(8-30)
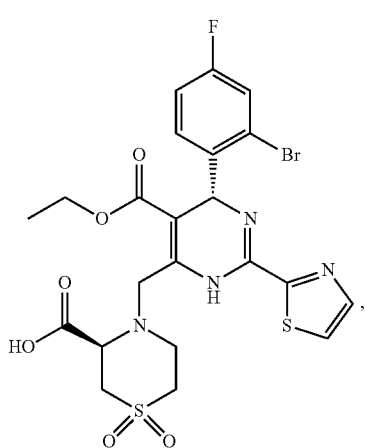
(8-31)
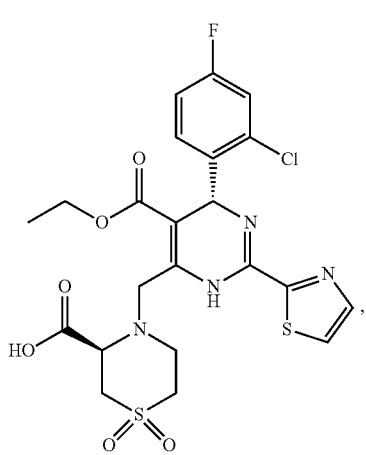
252
-continued
(8-31)
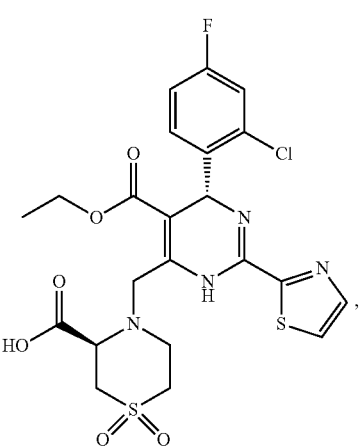
(8-32)
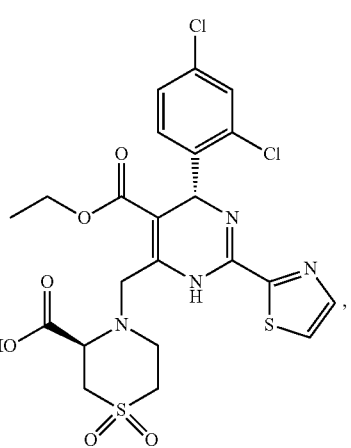
(8-33)
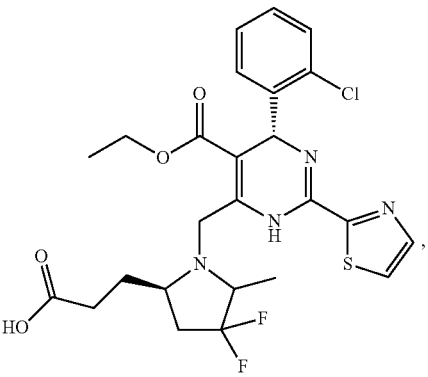

253
-continued
(8-34)
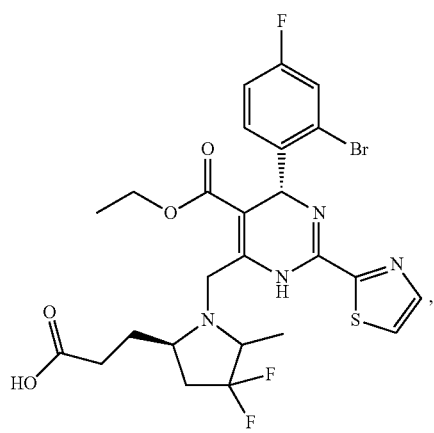
(8-35)
(8-36)
254
-continued
(8-37)
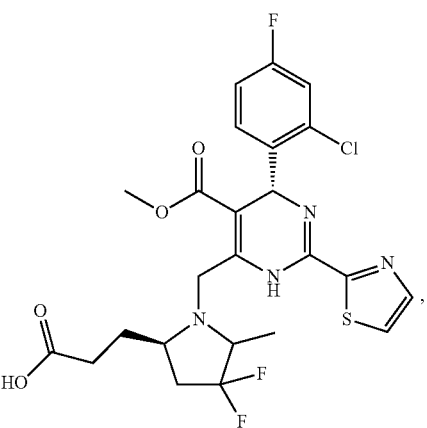
(8-38)
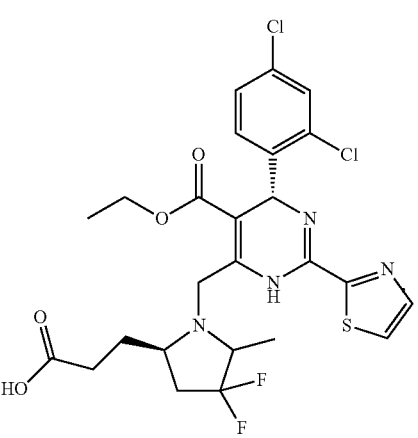
(8-39)
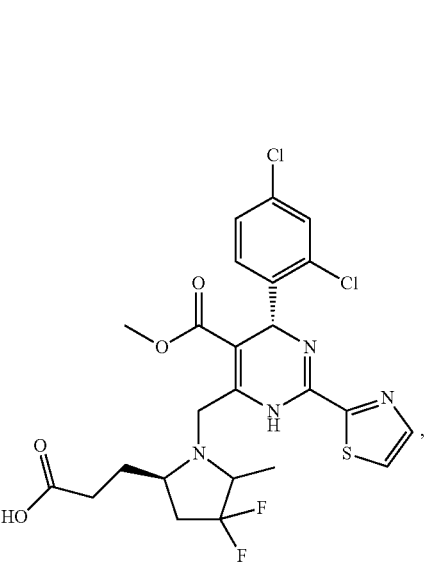

-continued
(8-40)
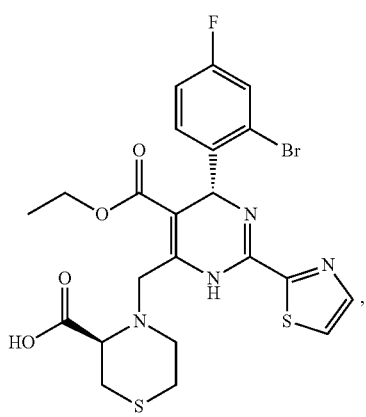
(8-48)
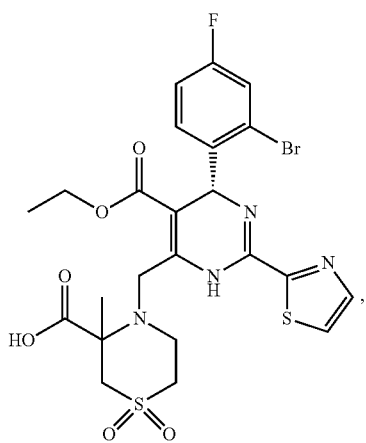
(8-49)
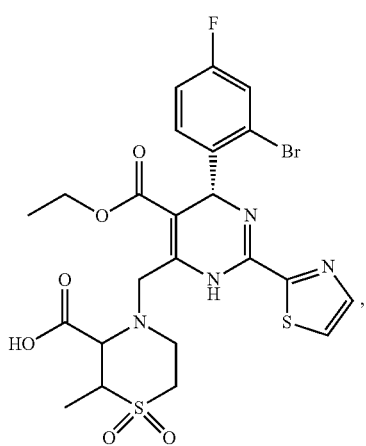
-continued
(8-49)
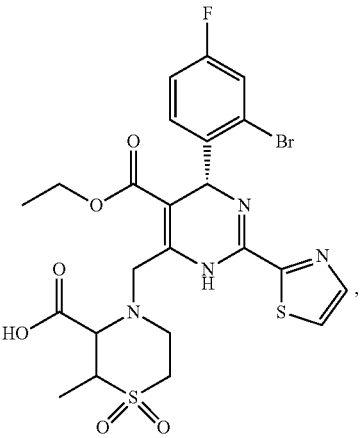
(8-50)
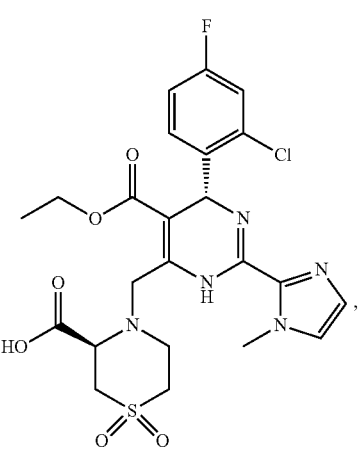
(8-51)
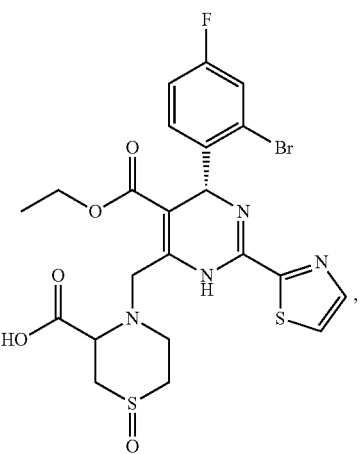

(8-52)

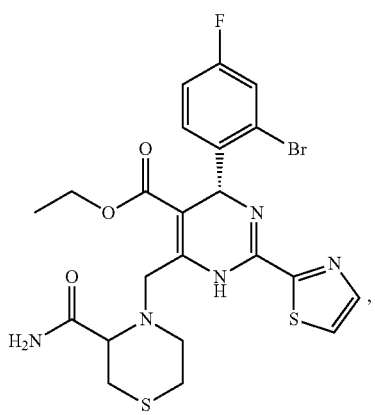

(8-55)

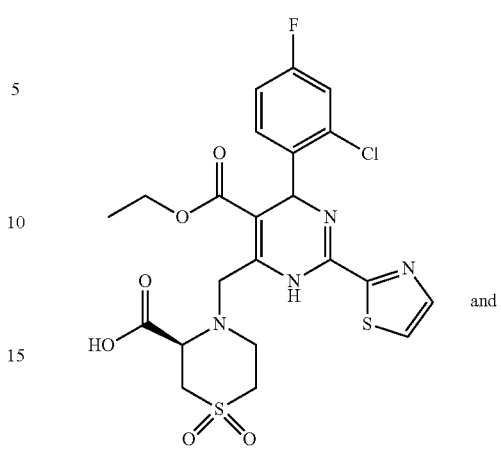

and

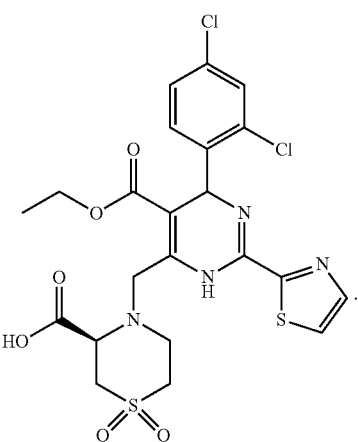

(8-55)

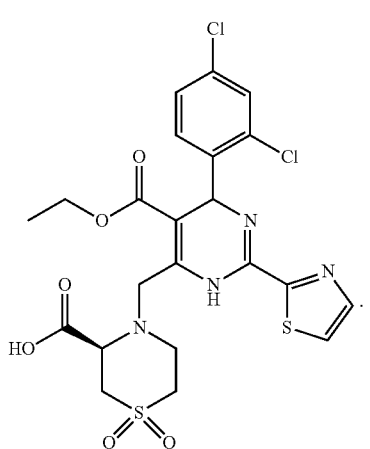

and

9. A pharmaceutical composition comprising the compound according to claim 1; and a pharmaceutically acceptable carrier, excipient, diluent, adjuvant, vehicle or a combination thereof.

10. The pharmaceutical composition according to claim 9 further comprising an anti-HBV agent.

11. The pharmaceutical composition according to claim 10, wherein the anti-HBV agent is a HBV polymerase inhibitor, immunomodulator or interferon.

12. The pharmaceutical composition according to claim 10, wherein the anti-HBV agent comprises at least one selected from the group consisting of lamivudine, telbivudine, tenofovir, entecavir, adefovir dipivoxil, alfaferone, alloferon, celmoleukin, clevudine, emtricitabine, famciclovir, interferon, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, euforavac, ampligen, phosphazid, heplisav, interferon α-2b, levamisole and propagermanium.

13. A method for treating a HBV disease comprising administering to a patient a therapeutically effective amount of the compound according to claim 1.

14. The method according to claim 13, wherein the viral disease or HBV disease is hepatitis B infection or a disease caused by hepatitis B infection.

15. The method according to claim 14, wherein the disease caused by hepatitis B infection is cirrhosis or hepatocellular carcinoma.

16. A method for treating a HBV disease comprising administering to a patient a therapeutically effective amount of the pharmaceutical composition according to claim 9.

17. The method according to claim 16, wherein the viral disease or HBV disease is hepatitis B infection or a disease caused by hepatitis B infection.

18. The method according to claim 17, wherein the disease caused by hepatitis B infection is cirrhosis or hepatocellular carcinoma.

* * * * *